(12) United States Patent  
Kono et al.

(10) Patent No.: US 9,663,514 B2  
(45) Date of Patent: *May 30, 2017

(54) SUBSTITUTED 6-AZA-ISOINDOLIN-1-ONE DERIVATIVES

(71) Applicant: Takeda Pharmaceutical Company Limited, Osaka (JP)

(72) Inventors: Mitsunori Kono, San Diego, CA (US); Zhe Nie, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/706,876

(22) Filed: May 7, 2015

(65) Prior Publication Data

US 2015/0274723 A1     Oct. 1, 2015

Related U.S. Application Data

(62) Division of application No. 14/128,576, filed as application No. PCT/US2012/043276 on Jun. 20, 2012, now Pat. No. 9,056,873.

(60) Provisional application No. 61/500,094, filed on Jun. 22, 2011.

(51) Int. Cl.

| C07D 471/04 | (2006.01) |
| C07D 519/00 | (2006.01) |
| A61K 31/4365 | (2006.01) |
| A61K 31/437 | (2006.01) |
| A61K 31/4985 | (2006.01) |
| A61K 31/519 | (2006.01) |
| A61K 31/5383 | (2006.01) |
| C07D 487/04 | (2006.01) |
| C07D 495/04 | (2006.01) |
| C07D 498/04 | (2006.01) |
| A61K 31/5365 | (2006.01) |

(52) U.S. Cl.  
CPC .......... *C07D 471/04* (2013.01); *A61K 31/437* (2013.01); *A61K 31/4365* (2013.01); *A61K 31/4985* (2013.01); *A61K 31/519* (2013.01); *A61K 31/5365* (2013.01); *A61K 31/5383* (2013.01); *C07D 487/04* (2013.01); *C07D 495/04* (2013.01); *C07D 498/04* (2013.01); *C07D 519/00* (2013.01)

(58) Field of Classification Search  
CPC .................................................. C07D 471/04  
USPC .......................................... 546/113; 514/300  
See application file for complete search history.

(56) References Cited

U.S. PATENT DOCUMENTS

| 5,238,950 A | 8/1993 | Clader et al. |
| 6,432,963 B1 | 8/2002 | Hisamichi et al. |
| 7,105,667 B2 | 9/2006 | Pitts et al. |
| 7,320,992 B2 | 1/2008 | Tegley et al. |
| 7,745,641 B2 | 6/2010 | Murakata et al. |
| 8,440,689 B2 | 5/2013 | Arikawa et al. |
| 2003/0092908 A1 | 5/2003 | Pitts et al. |
| 2003/0187261 A1 | 10/2003 | Havlicek et al. |
| 2003/0191143 A1 | 10/2003 | Pitts et al. |
| 2006/0116516 A1 | 6/2006 | Pitts et al. |
| 2010/0152159 A1 | 6/2010 | Mitchell et al. |
| 2010/0298557 A1 | 11/2010 | Yagi et al. |
| 2012/0027834 A1 | 2/2012 | Andre et al. |
| 2013/0116260 A1 | 5/2013 | Arikawa et al. |
| 2013/0245031 A1 | 9/2013 | Arikawa et al. |

FOREIGN PATENT DOCUMENTS

| CA | 2731926 | 2/2010 |
| CA | 2732087 | 2/2010 |
| EP | 0540334 | 1/1996 |
| EP | 1244668 | 1/2001 |
| EP | 1293213 | 2/2001 |

(Continued)

OTHER PUBLICATIONS

Bajpai, Malini "Fostamatinib, a Syk inhibitor prodrug for the treatment of inflammatory diseases," IDrugs 2009 12(3):174-185.

Braselmann, et al., "R406, an Orally Available Spleen Tyrosine Kinase Inhibitor Blocks Fc Receptor Signaling and Reduces Immune Complex-Mediated Inflammation," The Journal of Pharmacology and Experimental Therapeutics, vol. 319, No. 3 (2006) 998-1008.

(Continued)

*Primary Examiner* — Patricia L Morris  
(74) *Attorney, Agent, or Firm* — Matthew J. Russo

(57) ABSTRACT

Disclosed are compounds of Formula 1,

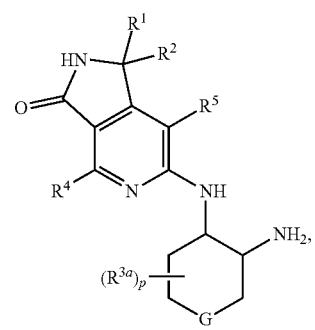

and pharmaceutically acceptable salts thereof, wherein G, p, $R^1$, $R^2$, $R^{3a}$, $R^4$, and $R^5$ are defined in the specification. This disclosure also relates to materials and methods for preparing compounds of Formula 1, to pharmaceutical compositions which contain them, and to their use for treating disorders, diseases, and conditions involving the immune system and inflammation, including rheumatoid arthritis, cancer, and other disorders, diseases, and conditions for which inhibition of SYK is indicated.

5 Claims, No Drawings

(56) References Cited

FOREIGN PATENT DOCUMENTS

| | | |
|---|---|---|
| EP | 1184376 | 2/2005 |
| EP | 2108642 | 10/2007 |
| EP | 1880993 | 1/2008 |
| JP | 63107966 | 5/1988 |
| JP | 2009067729 | 4/2009 |
| WO | 99/32479 | 7/1999 |
| WO | 01/09134 | 2/2001 |
| WO | 01/43731 | 6/2001 |
| WO | 01/49688 | 7/2001 |
| WO | 01/83485 | 11/2001 |
| WO | 02/087513 | 11/2002 |
| WO | 03/000688 | 1/2003 |
| WO | 03/009852 | 2/2003 |
| WO | 03/057695 | 7/2003 |
| WO | 03/063794 | 8/2003 |
| WO | 2004/016597 | 2/2004 |
| WO | 2004/037814 | 5/2004 |
| WO | 2004/041810 | 5/2004 |
| WO | 2004/087053 | 10/2004 |
| WO | 2004/087698 | 10/2004 |
| WO | 2004/087699 | 10/2004 |
| WO | 2005/012294 | 2/2005 |
| WO | 2005/021532 | 3/2005 |
| WO | 2005/039564 | 5/2005 |
| WO | 2005/056524 | 6/2005 |
| WO | 2006/028833 | 3/2006 |
| WO | 2006/062981 | 6/2006 |
| WO | 2006/068770 | 6/2006 |
| WO | 2006/108107 | 10/2006 |
| WO | 2006/129100 | 12/2006 |
| WO | 2007/002781 | 1/2007 |
| WO | 2007/023382 | 3/2007 |
| WO | 2007/025043 | 3/2007 |
| WO | 2007/053844 | 5/2007 |
| WO | 2007/070872 | 6/2007 |
| WO | 2007/084557 | 7/2007 |
| WO | 2008/033798 | 3/2008 |
| WO | 2008/051493 | 5/2008 |
| WO | 2008/057402 | 5/2008 |
| WO | 2008/064274 | 5/2008 |
| WO | 2008/118332 | 10/2008 |
| WO | 2008/151184 | 12/2008 |
| WO | 2009/026107 | 2/2009 |
| WO | 2009/062118 | 5/2009 |
| WO | 2009/080638 | 7/2009 |
| WO | 2009/102468 | 8/2009 |
| WO | 2009/105675 | 8/2009 |
| WO | 2009/123967 | 10/2009 |
| WO | 2009/136995 | 11/2009 |
| WO | 2009/145856 | 12/2009 |
| WO | 2009/150230 | 12/2009 |
| WO | 2010/027500 | 3/2010 |
| WO | 2010/068258 | 6/2010 |
| WO | 2010/146133 | 12/2010 |
| WO | 2011/075515 | 6/2011 |
| WO | 2011/075517 | 6/2011 |
| WO | 2011/075560 | 6/2011 |
| WO | 2011/134971 | 11/2011 |

OTHER PUBLICATIONS

Cywin, et al., "Discovery and SAR of Novel [1,6]Naphthyridines as Potent Inhibitors of Spleen Tyrosine Kinase (SYK)," Bioorganic & Medicinal Chemistry Letters 13 (2003) 1415-1418.

Farmer, et al., "Discovery and SAR of novel 4-thiazolyl-2-phenylaminopyrimidines as potent inhibitors of spleen tyrosine kinase (SYK)," Bioorganic & Medicinal Chemistry Letters 18 (2008) 6231-6235.

Hirabayashi et al., "Structure-activity relationship studies of 5-benzylaminoimidazo[1,2-c] pyrimidine-8-carboxamide derivatives as potent, highly selective ZAP-70 kinase inhibitors," Bioorganic & Medicinal Chemistry 17 (2009) 284-294.

Hirabayashi, et al. "A novel Syk family kinase inhibitor: Design, synthesis, and structure-activity relationship of 1,2,4-triazolo[4,3-c]pyrimidine and 1,2,4-triazolo[1,5-c]pyrimidine derivatives," Bioorganic & Medicinal Chemistry 16 (2008) 7347-7357.

Hirabayashi, et al. "Structure-activity relationship studies of imidazo[1,2-c]pyrimidine derivatives as potent and orally effective Syk family kinases inhibitors," Bioorganic & Medicinal Chemistry 16 (2008) 9247-9260.

Hisamichi, et al. "Synthentic studies on novel Syk inhibitors. Part 1: Synthesis and structure-activity relationships of pyrimidine-5-carboxamide derivatives," Bioorganic & Medicinal Chemistry 13 (2005) 4936-4951.

Lai, et al., "Potent Small Molecule Inhibitors of Spleen Tyrosine Kinase (Syk)," Bioorganic & Medicinal Chemistry Letters 13 (2003) 3111-3114.

Liddle, et al., "Discovery of GSK143, a highly potent, selective and orally efficacious spleen tyrosine kinase inhibitor," Bioorganic & Medicinal Chemistry Letters 21 (2011) 6188-6194.

Moore, et al., "An analysis of the diaminopyrimidine patent estates describing spleen tyrosine kinase inhibitors by Rigel and Portola," Export Opinion on Therapeutic Patents (2010) 20(12) 1703-17022.

Ruzza et al. "Therapeutic prospect of Syk inhibitors" Expert Opinion on Therapeutic Patents, 2009, Informa Healthcare GBR vol. 19, No. 10, pp. 1361-1376. XP002625888.

Xie, et al., "Pharmacophore modeling study based on known Spleen tyrosine kinase inhibitors together with virtual screening for identifying novel inhibitors," Bioorganic & Medicinal Chemistry Letters 19 (2009) 1944-1949.

Yamamoto, et al., "The Orally Available Spleen Tyrosine Kinase Inhibitor 2-[7-(3,4-Dimethoxyphenyl)-imidazo[1,2-c]pyrimidin-5-ylamino]-nicotinamide Dihydrochloride (BAY 61/3606) Blocks Antigen-Induced Airway Inflammation in Rodents," The Journal of Pharmacology and Experimental Therapeutics, vol. 306, No. 3 (2003) 1174-1181.

U.S. Appl. No. 12/972,333 Office Action mailed Oct. 12, 2012.

U.S. Appl. No. 12/972,333 Notice of Allowance mailed Jan. 22, 2013.

U.S. Appl. No. 13/518,806 Office Action mailed May 29, 2014.

U.S. Appl. No. 13/518,806 Notice of Allowance mailed Oct. 29, 2014.

U.S. Appl. No. 13/886,032 Notice of Allowance mailed Oct. 6, 2014.

SUBSTITUTED 6-AZA-ISOINDOLIN-1-ONE DERIVATIVES

CROSS-REFERENCE TO RELATED APPLICATIONS

This application is a divisional of U.S. Ser. No. 14/128,576, having a 371(c) date of Mar. 28, 2014, which is the U.S. National Stage entry under 35U.S.C.§371 of International Application PCT/US12/043276, filed Jun. 20, 2012, which claims the benefit of U.S. Provisional Application No. 61/500,094, filed Jun. 22, 2011, which are herein incorporated by reference.

FIELD OF THE INVENTION

This invention relates to substituted 6-aza-isoindolin-1-one derivatives, to pharmaceutical compositions containing them, and to their use for treating disorders and conditions involving the immune system and inflammation, including rheumatoid arthritis. The substituted 6-aza-isoindolin-1-one derivatives are inhibitors of spleen tyrosine kinase.

BACKGROUND OF THE INVENTION

Spleen tyrosine kinase (SYK) is a 72 kDa non-receptor cytoplasmic tyrosine kinase. SYK has a primary amino acid sequence similar to that of zeta-associated protein-70 (ZAP-70) and is involved in receptor-mediated signal transduction. The N-terminal domain of SYK contains two Src-homology 2 (SH2) domains, which bind to diphosphorylated immunoreceptor tyrosine-based activation motifs (ITAMs) found in the cytoplasmic signaling domains of many immunoreceptor complexes. The C-terminus contains the catalytic domain, and includes several catalytic loop autophosphorylation sites that are responsible for receptor-induced SYK activation and subsequent downstream signal propagation. SYK is expressed in many cell types involved in adaptive and innate immunity, including lymphocytes (B cells,Tcells, and NK cells), granulocytes (basophils, neutrophils, and eosinophils), monocytes, macrophages, dendritic cells, and mast cells. SYK is expressed in other cell types, including airway epithelium and fibroblasts in the upper respiratory system. See, e.g., Martin Turner et al., *Immunology Today* (2000) 21(3):148-54; and Michael P. Sanderson et al., *Inflammation & Allergy—Drug Targets* (2009) 8:87-95.

SYK's role in ITAM-dependent signaling and its expression in many cell types suggest that compounds which inhibit SYK activity may be useful for treating disorders involving the immune system and inflammation. Such disorders include Type I hypersensitivity reactions (allergic rhinitis, allergic asthma, and atopic dermatitis); autoimmune diseases (rheumatoid arthritis, multiple sclerosis, systemic lupus erythematosus, psoriasis, and immune thrombocytopenic purpura); and inflammation of the lung (chronic obstructive pulmonary disease). See, e.g., Brian R. Wong et al., *Expert Opin. Investig. Drugs* (2004) 13(7):743-62; Sanderson et al. (2009); Jane Denyer & Vipul Patel, *Drug News Perspective* (2009) 22(3):146-50; Esteban S. Masuda & Jochen Schmitz, *Pulmonary Pharmacology & Therapeutics* (2008) 21:461-67; Malini Bajpai et al., *Expert Opin. Investig. Drugs* (2008) 17(5):641-59; and Anna Podolanczuk et al., *Blood* (2009) 113:3154-60. Other disorders include hematological malignancies, such as acute myeloid leukemia, B-cell chronic lymphocytic leukemia, B-cell lymphoma (e.g., mantle cell lymphoma), and T-cell lymphoma (e.g., peripheral T-cell lymphoma); as well as epithelial cancers, such as lung cancer, pancreatic cancer, and colon cancer. See, e.g., Cynthia K. Hahn et al., *Cancer Cell* (2009) 16:281-294; D. H. Chu et al., *Immnol. Rev.* (1998) 165:167-180; A. L. Feldman et al., *Leukemia* (2008) 22:1139-43; A. Rinaldi et al., *Br. J. Haematol.* (2006) 132:303-316; B. Streubel et al., *Leukemia* (2006) 20:313-18; Maike Buchner et al., *Cancer Research* (2009) 69(13):5424-32; A. D. Baudot et al., *Oncogene* (2009) 28:3261-73; and Anurag Singh et al., *Cancer Cell* (2009) 15:489-500.

Various SYK inhibitors have been described in published patent applications. See, e.g., EP 1184376 A1; WO 01/83485 A1; WO 03/057695 A1; WO 2006/129100 A1; WO 01/09134 A1; WO 03/063794 A1; WO 2005/012294 A1; WO 2004/087699 A2; WO 2009/026107 A1; WO2009136995 A2; WO2009/145856 A1, and WO 2011/079051 A1.

SUMMARY OF THE INVENTION

This invention provides substituted 6-aza-isoindolin-1-one derivatives, and pharmaceutically acceptable complexes, salts, solvates, and hydrates of the compounds. This invention also provides pharmaceutical compositions containing the substituted 6-aza-isoindolin-1-one derivatives, and provides for the use of the compounds to treat disorders and conditions involving the immune system and inflammation, including rheumatoid arthritis.

One aspect of the invention provides a compound of Formula 1,

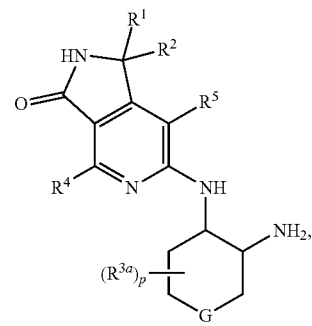

or a pharmaceutically acceptable salt thereof, wherein:

G is selected from 0 and $CH_2$;

$R^1$ and $R^2$ are each independently selected from hydrogen, halo, $C_{1-3}$ alkyl, and $C_{1-3}$ haloalkyl; or $R^1$ and $R^2$, together with the atom to which they are attached, form a $C_{3-6}$ cycloalkylidene;

each $R^{3a}$ is independently selected from halo, oxo, $-NO_2$, $-CN$, $R^6$, and $R^7$;

$R^4$ is selected from

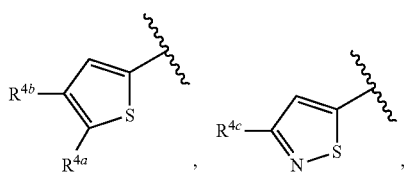

-continued

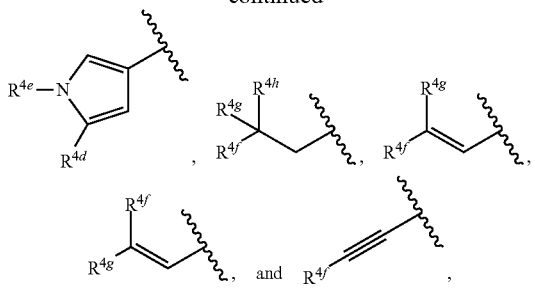

wherein ⌇ represents a point of attachment;

$R^{4a}$ and $R^{4b}$ are each independently selected from hydrogen, halo, —CN, $R^6$, and $R^7$, provided that (a) if $R^{4a}$ is hydrogen, then $R^{4b}$ is not unsubstituted methyl; (b) if $R^{4b}$ is hydrogen, then $R^{4a}$ is not hydrogen or unsubstituted methyl; and (c) if $R^{4b}$ is hydrogen and G is O, then $R^{4a}$ is not chloro; or $R^{4a}$ and $R^{4b}$, together with the atoms to which they are attached, form a phenylene or a $C_{3-5}$ heteroarylene, each optionally substituted with from one to four substituents independently selected from halo, oxo, —CN, $R^6$, and $R^7$, wherein the $C_{3-5}$ heteroarylene moiety has 5 or 6 ring atoms and 1 or 2 are heteroatoms, each of the heteroatoms being N;

$R^{4c}$ is selected from hydrogen, halo, —CN, $R^6$, and $R^7$, provided that when G is O, $R^{4c}$ is not unsubstituted methyl;

$R^{4d}$ and $R^{4e}$ are each independently selected from hydrogen, halo, —CN, $R^6$, and $R^7$; or $R^{4d}$ and $R^{4e}$, together with the atoms to which they are attached, form a $C_{3-5}$ heterocycle-diyl or a $C_{3-5}$ heteroarylene, each having 5 or 6 ring atoms, at least one heteroatom which is N, and optionally 1 or 2 additional heteroatoms independently selected from N, O, and S, and wherein the $C_{3-5}$ heterocycle-diyl or the $C_{3-5}$ heteroarylene is optionally substituted with from one to four substituents independently selected from halo, oxo, —CN, $R^6$, and $R^7$;

$R^{4f}$ is selected from $C_{3-8}$ cycloalkyl, $C_{2-5}$ heterocyclyl, $C_{6-14}$ aryl, and $C_{1-9}$ heteroaryl, each optionally substituted with from one to five substituents independently selected from halo, oxo, —CN, $R^6$, and $R^7$;

$R^{4g}$ and $R^{4h}$ are each independently selected from hydrogen, halo, $C_{1-3}$ alkyl, and $C_{1-3}$ haloalkyl; or $R^{4g}$ and $R^{4h}$, together with the atom to which they are attached, form a $C_{3-6}$ cycloalkylidene;

$R^5$ is selected from hydrogen, halo, —CN, $C_{1-4}$ alkyl, $C_{2-4}$ alkenyl, $C_{2-4}$ alkynyl, $C_{2-5}$ heterocyclyl, $C_{1-5}$ heteroaryl, and $R^{10}$, wherein the alkyl, alkenyl, and alkynyl moieties are each optionally substituted with from one to five substituents independently selected from halo, —CN, oxo, and $R^{10}$, and wherein the heterocyclyl moiety has 3 to 6 ring atoms and the heteroaryl moiety has 5 or 6 ring atoms, and the heterocyclyl and heteroaryl moieties are each optionally substituted with from one to four substituents independently selected from halo, —NO$_2$, —CN, $C_{1-4}$ alkyl, $C_{2-4}$ alkenyl, $C_{2-4}$ alkynyl, $C_{1-4}$ haloalkyl, and $R^{10}$;

each $R^6$ is independently selected from —OR$^8$, —N(R$^8$)R$^9$, —NR$^8$C(O)R$^9$, —C(O)R$^8$, —C(O)OR$^8$, —C(O)N(R$^8$)R$^9$, —C(O)N(R$^8$)OR$^9$, —C(O)N(R$^8$)S(O)$_2$R$^9$, —N(R$^8$)S(O)$_2$R$^9$, —S(O)$_n$R$^8$, and —S(O)$_2$N(R$^8$)R$^9$;

each $R^7$ is independently selected from $C_{1-6}$ alkyl, $C_{2-6}$ alkenyl, $C_{2-6}$ alkynyl, $C_{3-6}$ cycloalkyl-(CH$_2$)$_m$—, $C_{6-14}$ aryl-(CH$_2$)$_m$—, $C_{2-5}$ heterocyclyl-(CH$_2$)$_m$—, and $C_{1-6}$ heteroaryl-(CH$_2$)$_m$—, each optionally substituted with from one to five substituents independently selected from halo, oxo, —NO$_2$, —CN, $C_{1-6}$ alkyl, $C_{1-6}$ haloalkyl, and $R^{10}$;

each $R^8$ and $R^9$ is independently selected from hydrogen, $C_{1-6}$ alkyl, $C_{2-6}$ alkenyl, $C_{2-6}$ alkynyl, $C_{3-6}$ cycloalkyl-(CH$_2$)$_m$—, $C_{6-14}$ aryl-(CH$_2$)$_m$—, $C_{2-5}$ heterocyclyl-(CH$_2$)$_m$—, and $C_{1-9}$ heteroaryl-(CH$_2$)$_m$—, each non-hydrogen substituent optionally substituted with from one to five substituents independently selected from halo, oxo, —NO$_2$, —CN, $C_{1-6}$ alkyl, $C_{1-6}$ haloalkyl, and $R^{10}$;

each $R^{10}$ is independently selected from —OR$^{11}$, —N(R$^{11}$)R$^{12}$, —N(R$^{11}$)C(O)R$^{12}$, —C(O)R$^{11}$, —C(O)OR$^{11}$, —C(O)N(R$^{11}$)R$^{12}$, —C(O)N(R$^{11}$)OR$^{12}$, —C(O)N(R$^{11}$)S(O)$_2$R$^{12}$, —NR$^{11}$S(O)$_2$R$^{12}$, —S(O)—R$^{11}$, and —S(O)$_2$N(R$^{11}$)R$^{12}$;

each $R^{11}$ and $R^{12}$ is independently selected from hydrogen and $C_{1-6}$ alkyl;

each n is independently selected from 0, 1 and 2;

each m is independently selected from 0, 1, 2, 3, and 4;

each p is independently selected from 0, 1, 2, 3, 4, 5, and 6;

wherein each of the heteroaryl moieties recited for $R^{4f}$, $R^7$, $R^8$, and $R^9$ has 1 to 4 heteroatoms independently selected from N, O, and S, and each of the heterocyclyl moieties recited for $R^{4f}$, $R^7$, $R^8$, and $R^9$ has 1 or 2 heteroatoms independently selected from N, O, and S.

Another aspect of the invention provides a compound which is selected from the following group of compounds and their pharmaceutically acceptable salts:

6-((3R,4R)-3-Aminotetrahydro-2H-pyran-4-ylamino)-4-(3-(difluoromethyl)isothiazol-5-yl)-7-fluoro-1H-pyrrolo[3,4-c]pyridin-3(2H)-one;

6-((3R,4R)-3-Aminotetrahydro-2H-pyran-4-ylamino)-4-(3-ethylisothiazol-5-yl)-7-fluoro-1H-pyrrolo[3,4-c]pyridin-3(2H)-one;

6-((1R,2S)-2-Aminocyclohexylamino)-4-(3-ethylisothiazol-5-yl)-7-fluoro-1H-pyrrolo[3,4-c]pyridin-3(2H)-one;

6-((3R,4R)-3-Aminotetrahydro-2H-pyran-4-ylamino)-7-fluoro-4-(isothiazol-5-yl)-1H-pyrrolo[3,4-c]pyridin-3(2H)-one;

6-((1R,2S)-2-Aminocyclohexylamino)-7-fluoro-4-(isothiazol-5-yl)-1H-pyrrolo[3,4-c]pyridin-3(2H)-one;

6-((3R,4R)-3-Aminotetrahydro-2H-pyran-4-ylamino)-4-(3-cyclopropylisothiazol-5-yl)-7-fluoro-1H-pyrrolo[3,4-c]pyridin-3(2H)-one;

6-((3R,4R)-3-Aminotetrahydro-2H-pyran-4-ylamino)-7-fluoro-4-(5-fluorobenzo[b]thiophen-2-yl)-1H-pyrrolo[3,4-c]pyridin-3(2H)-one;

5-(6-((3R,4R)-3-Aminotetrahydro-2H-pyran-4-ylamino)-7-fluoro-3-oxo-2,3-dihydro-1H-pyrrolo[3,4-c]pyridin-4-yl)thiophene-2-carbonitrile;

6-((3R,4R)-3-Aminotetrahydro-2H-pyran-4-ylamino)-7-fluoro-4-(thieno[2,3-c]pyridin-2-yl)-1H-pyrrolo[3,4-c]pyridin-3(2H)-one;

5-(6-((3R,4R)-3-Aminotetrahydro-2H-pyran-4-ylamino)-7-fluoro-3-oxo-2,3-dihydro-1H-pyrrolo[3,4-c]pyridin-4-yl)thiophene-2-carbonitrile;

6-((3R,4R)-3-Aminotetrahydro-2H-pyran-4-ylamino)-7-fluoro-4-(5-fluorothiophen-2-yl)-1H-pyrrolo[3,4-c]pyridin-3(2H)-one;

6-((3R,4R)-3-Aminotetrahydro-2H-pyran-4-ylamino)-7-fluoro-4-(thieno[2,3-b]pyridin-2-yl)-1H-pyrrolo[3,4-c]pyridin-3(2H)-one;

6-((1R,2S)-2-Aminocyclohexylamino)-7-fluoro-4-(thieno[2,3-b]pyridin-2-yl)-1H-pyrrolo[3,4-c]pyridin-3(2H)-one;

6-((1R,2S)-2-Aminocyclohexylamino)-7-fluoro-4-(thieno[2,3-c]pyridin-2-yl)-1H-pyrrolo[3,4-c]pyridin-3(2H)-one;

6-(((1R,2S)-2-Aminocyclohexyl)amino)-7-fluoro-4-(5-fluorobenzo[b]thiophen-2-yl)-1H-pyrrolo[3,4-c]pyridin-3(2H)-one;

6-((3R,4R)-3-Aminotetrahydro-2H-pyran-4-ylamino)-7-fluoro-4-(thieno[3,2-c]pyridin-2-yl)-1H-pyrrolo[3,4-c]pyridin-3(2H)-one;

6-((1R,2S)-2-Aminocyclohexylamino)-7-fluoro-4-(thieno[3,2-c]pyridin-2-yl)-1H-pyrrolo[3,4-c]pyridin-3(2H)-one;

6-((3R,4R)-3-Aminotetrahydro-2H-pyran-4-ylamino)-7-fluoro-4-(6-fluorobenzo[b]thiophen-2-yl)-1H-pyrrolo[3,4-c]pyridin-3(2H)-one;

6-((1R,2S)-2-Aminocyclohexylamino)-7-fluoro-4-(6-fluorobenzo[b]thiophen-2-yl)-1H-pyrrolo[3,4-c]pyridin-3(2H)-one;

2-(6-((3R,4R)-3-Aminotetrahydro-2H-pyran-4-ylamino)-7-fluoro-3-oxo-2,3-dihydro-1H-pyrrolo[3,4-c]pyridin-4-yl)benzo[b]thiophene-5-carbonitrile;

2-(6-((1R,2S)-2-Aminocyclohexylamino)-7-fluoro-3-oxo-2,3-dihydro-1H-pyrrolo[3,4-c]pyridin-4-yl)benzo[b]thiophene-5-carbonitrile;

6-((3R,4R)-3-Aminotetrahydro-2H-pyran-4-ylamino)-7-fluoro-4-(4-fluorobenzo[b]thiophen-2-yl)-1H-pyrrolo[3,4-c]pyridin-3(2H)-one;

6-((1R,2S)-2-Aminocyclohexylamino)-7-fluoro-4-(4-fluorobenzo[b]thiophen-2-yl)-1H-pyrrolo[3,4-c]pyridin-3(2H)-one;

6-((3R,4R)-3-Aminotetrahydro-2H-pyran-4-ylamino)-7-fluoro-4-(thieno[3,2-b]pyridin-2-yl)-1H-pyrrolo[3,4-c]pyridin-3(2H)-one;

6-((1R,2S)-2-Aminocyclohexylamino)-7-fluoro-4-(thieno[3,2-b]pyridin-2-yl)-1H-pyrrolo[3,4-c]pyridin-3(2H)-one;

6-((3R,4R)-3-Aminotetrahydro-2H-pyran-4-ylamino)-7-fluoro-4-(4-fluorothiophen-2-yl)-1H-pyrrolo[3,4-c]pyridin-3(2H)-one;

6-((1R,2S)-2-Aminocyclohexylamino)-7-fluoro-4-(4-fluorothiophen-2-yl)-1H-pyrrolo[3,4-c]pyridin-3(2H)-one;

6-((1R,2S)-2-Aminocyclohexylamino)-7-fluoro-4-(1-methyl-1H-thieno[3,2-c]pyrazol-5-yl)-1H-pyrrolo[3,4-c]pyridin-3(2H)-one;

6-((3R,4R)-3-Aminotetrahydro-2H-pyran-4-ylamino)-7-fluoro-4-(1-methyl-1H-thieno[3,2-c]pyrazol-5-yl)-1H-pyrrolo[3,4-c]pyridin-3(2H)-one;

6-((1R,2S)-2-Aminocyclohexylamino)-4-(1,3-dimethyl-1H-thieno[3,2-c]pyrazol-5-yl)-7-fluoro-1H-pyrrolo[3,4-c]pyridin-3(2H)-one;

6-((3R,4R)-3-Aminotetrahydro-2H-pyran-4-ylamino)-4-(1,3-dimethyl-1H-thieno[3,2-c]pyrazol-5-yl)-7-fluoro-1H-pyrrolo[3,4-c]pyridin-3(2H)-one;

6-((1R,2S)-2-Aminocyclohexylamino)-4-(2,3-dimethyl-2H-thieno[3,2-c]pyrazol-5-yl)-7-fluoro-1H-pyrrolo[3,4-c]pyridin-3(2H)-one;

6-((3R,4R)-3-Aminotetrahydro-2H-pyran-4-ylamino)-4-(2,3-dimethyl-2H-thieno[3,2-c]pyrazol-5-yl)-7-fluoro-1H-pyrrolo[3,4-c]pyridin-3(2H)-one;

6-((1R,2S)-2-Aminocyclohexylamino)-4-(3,4-dihydro-1H-pyrrolo[2,1-c][1,4]oxazin-7-yl)-7-fluoro-1H-pyrrolo[3,4-c]pyridin-3(2H)-one;

6-((1R,2S)-2-Aminocyclohexylamino)-4-(1,3-dimethyl-1H-thieno[2,3-c]pyrazol-5-yl)-7-fluoro-1H-pyrrolo[3,4-c]pyridin-3(2H)-one;

6-((3R,4R)-3-Aminotetrahydro-2H-pyran-4-ylamino)-4-(1,3-dimethyl-1H-thieno[2,3-c]pyrazol-5-yl)-7-fluoro-1H-pyrrolo[3,4-c]pyridin-3(2H)-one;

Ethyl 2-(6-((3R,4R)-3-aminotetrahydro-2H-pyran-4-ylamino)-7-fluoro-3-oxo-2,3-dihydro-1H-pyrrolo[3,4-c]pyridin-4-yl)indolizine-7-carboxylate;

2-(6-((3R,4R)-3-Aminotetrahydro-2H-pyran-4-ylamino)-7-fluoro-3-oxo-2,3-dihydro-1H-pyrrolo[3,4-c]pyridin-4-yl)indolizine-7-carboxylic acid;

6-((3R,4R)-3-Aminotetrahydro-2H-pyran-4-ylamino)-7-fluoro-4-(1-oxo-2,3-dihydro-1H-pyrrolizin-6-yl)-1H-pyrrolo[3,4-c]pyridin-3(2H)-one;

6-((1R,2S)-2-Aminocyclohexylamino)-7-fluoro-4-(3-methylisothiazol-5-yl)-1H-pyrrolo[3,4-c]pyridin-3(2H)-one;

6-((1R,2S)-2-Aminocyclohexylamino)-7-fluoro-4-(phenylethynyl)-1H-pyrrolo[3,4-c]pyridin-3(2H)-one;

6-((3R,4R)-3-Aminotetrahydro-2H-pyran-4-ylamino)-7-fluoro-4-(phenylethynyl)-1H-pyrrolo[3,4-c]pyridin-3(2H)-one;

6-((1R,2S)-2-Aminocyclohexylamino)-7-fluoro-4-(4-fluorostyryl)-1H-pyrrolo[3,4-c]pyridin-3(2H)-one;

6-((3R,4R)-3-Aminotetrahydro-2H-pyran-4-ylamino)-7-fluoro-4-(4-fluorostyryl)-1H-pyrrolo[3,4-c]pyridin-3(2H)-one;

6-((1R,2S)-2-Aminocyclohexylamino)-7-fluoro-4-phenethyl-1H-pyrrolo[3,4-c]pyridin-3(2H)-one;

6-((1R,2S)-2-Aminocyclohexylamino)-7-fluoro-4-phenethyl-1H-pyrrolo[3,4-c]pyridin-3(2H)-one;

6-((3R,4R)-3-Aminotetrahydro-2H-pyran-4-ylamino)-4-(4-chlorophenethyl)-7-fluoro-1H-pyrrolo[3,4-c]pyridin-3(2H)-one;

6-((1R,2S)-2-Aminocyclohexylamino)-4-(4-chlorostyryl)-7-fluoro-1H-pyrrolo[3,4-c]pyridin-3(2H)-one;

6-((3R,4R)-3-Aminotetrahydro-2H-pyran-4-ylamino)-4-(4-chlorostyryl)-7-fluoro-1H-pyrrolo[3,4-c]pyridin-3(2H)-one;

6-(((3R,4R)-3-Aminotetrahydro-2H-pyran-4-yl)amino)-7-fluoro-4-(indolizin-2-yl)-1H-pyrrolo[3,4-c]pyridin-3(2H)-one;

2-(6-(((3R,4R)-3-Aminotetrahydro-2H-pyran-4-yl)amino)-7-fluoro-3-oxo-2,3-dihydro-1H-pyrrolo[3,4-c]pyridin-4-yl)indolizine-7-carbonitrile;

6-(((3R,4R)-3-Aminotetrahydro-2H-pyran-4-yl)amino)-7-fluoro-4-(7-fluoroindolizin-2-yl)-1H-pyrrolo[3,4-c]pyridin-3(2H)-one;

6-(((3R,4R)-3-Aminotetrahydro-2H-pyran-4-yl)amino)-7-fluoro-4-(1-oxo-1,2,3,4-tetrahydropyrrolo[1,2-a]pyrazin-7-yl)-1H-pyrrolo[3,4-c]pyridin-3(2H)-one;

6-(((3R,4R)-3-Aminotetrahydro-2H-pyran-4-yl)amino)-7-fluoro-4-(1-methyl-1H-pyrrolo[1,2-b]pyrazol-5-yl)-1H-pyrrolo[3,4-c]pyridin-3(2H)-one;

6-(((3R,4R)-3-Aminotetrahydro-2H-pyran-4-yl)amino)-7-fluoro-4-(3-oxo-1,2,3,4-tetrahydropyrrolo[1,2-a]pyrazin-7-yl)-1H-pyrrolo[3,4-c]pyridin-3(2H)-one;

6-(((3R,4R)-3-Aminotetrahydro-2H-pyran-4-yl)amino)-7-fluoro-4-(1-methyl-1H-pyrrolo[1,2-a]imidazol-6-yl)-1H-pyrrolo[3,4-c]pyridin-3(2H)-one;

6-(((3R,4R)-3-Aminotetrahydro-2H-pyran-4-yl)amino)-7-fluoro-4-(pyrrolo[2,1-b]oxazol-6-yl)-1H-pyrrolo[3,4-c]pyridin-3(2H)-one;

6-(((1R,2S)-2-Aminocyclohexyl)amino)-7-fluoro-4-(indolizin-2-yl)-1H-pyrrolo[3,4-c]pyridin-3(2H)-one;

2-(6-(((1R,2S)-2-Aminocyclohexyl)amino)-7-fluoro-3-oxo-2,3-dihydro-1H-pyrrolo[3,4-c]pyridin-4-yl)indolizine-7-carbonitrile;

6-(((1R,2S)-2-Aminocyclohexyl)amino)-7-fluoro-4-(7-fluoroindolizin-2-yl)-1H-pyrrolo[3,4-c]pyridin-3(2H)-one;

6-(((1R,2S)-2-Aminocyclohexyl)amino)-7-fluoro-4-(1-oxo-1,2,3,4-tetrahydropyrrolo[1,2-a]pyrazin-7-yl)-1H-pyrrolo[3,4-c]pyridin-3(2H)-one;

6-(((1R,2S)-2-Aminocyclohexyl)amino)-7-fluoro-4-(1-methyl-1H-pyrrolo[1,2-b]pyrazol-5-yl)-1H-pyrrolo[3,4-c]pyridin-3(2H)-one;

6-(((1R,2S)-2-Aminocyclohexyl)amino)-7-fluoro-4-(3-oxo-1,2,3,4-tetrahydropyrrolo[1,2-a]pyrazin-7-yl)-1H-pyrrolo[3,4-c]pyridin-3(2H)-one;

6-(((1R,2S)-2-Aminocyclohexyl)amino)-7-fluoro-4-(1-methyl-1H-pyrrolo[1,2-a]imidazol-6-yl)-1H-pyrrolo[3,4-c]pyridin-3(2H)-one;

6-(((1R,2S)-2-Aminocyclohexyl)amino)-7-fluoro-4-(pyrrolo[2,1-b]oxazol-6-yl)-1H-pyrrolo[3,4-c]pyridin-3(2H)-one;

6-(((1R,2S)-2-Aminocyclohexyl)amino)-7-fluoro-4-(8-oxo-5,6,7,8-tetrahydroindolizin-2-yl)-1H-pyrrolo[3,4-c]pyridin-3(2H)-one;

6-(((3R,4R)-3-Aminotetrahydro-2H-pyran-4-yl)amino)-7-fluoro-4-(8-oxo-5,6,7,8-tetrahydroindolizin-2-yl)-1H-pyrrolo[3,4-c]pyridin-3(2H)-one;

6-(((3R,4R)-3-Aminotetrahydro-2H-pyran-4-yl)amino)-7-fluoro-4-(3-methyl-3,4-dihydro-1H-pyrrolo[2,1-c][1,4]oxazin-7-yl)-1H-pyrrolo[3,4-c]pyridin-3(2H)-one;

6-(((3R,4R)-3-Aminotetrahydro-2H-pyran-4-yl)amino)-4-(3,3-dimethyl-3,4-dihydro-1H-pyrrolo[2,1-c][1,4]oxazin-7-yl)-7-fluoro-1H-pyrrolo[3,4-c]pyridin-3(2H)-one;

6-(((3R,4R)-3-Aminotetrahydro-2H-pyran-4-yl)amino)-4-(3-ethyl-3,4-dihydro-1H-pyrrolo[2,1-c][1,4]oxazin-7-yl)-7-fluoro-1H-pyrrolo[3,4-c]pyridin-3(2H)-one;

6-(((3R,4R)-3-Aminotetrahydro-2H-pyran-4-yl)amino)-7-fluoro-4-(3-isopropyl-3,4-dihydro-1H-pyrrolo[2,1-c][1,4]oxazin-7-yl)-1H-pyrrolo[3,4-c]pyridin-3(2H)-one;

6-(((3R,4R)-3-Aminotetrahydro-2H-pyran-4-yl)amino)-7-fluoro-4-(1,2,3,4-tetrahydropyrrolo[1,2-a]pyrazin-7-yl)-1H-pyrrolo[3,4-c]pyridin-3(2H)-one;

6-(((3R,4R)-3-Aminotetrahydro-2H-pyran-4-yl)amino)-7-fluoro-4-(2-methyl-1,2,3,4-tetrahydropyrrolo[1,2-a]pyrazin-7-yl)-1H-pyrrolo[3,4-c]pyridin-3(2H)-one;

6-(((3R,4R)-3-Aminotetrahydro-2H-pyran-4-yl)amino)-4-(2-ethyl-1,2,3,4-tetrahydropyrrolo[1,2-a]pyrazin-7-yl)-7-fluoro-1H-pyrrolo[3,4-c]pyridin-3(2H)-one;

6-(((1R,2S)-2-Aminocyclohexyl)amino)-7-fluoro-4-(3-methyl-3,4-dihydro-1H-pyrrolo[2,1-c][1,4]oxazin-7-yl)-1H-pyrrolo[3,4-c]pyridin-3(2H)-one;

6-(((1R,2S)-2-Aminocyclohexyl)amino)-4-(3,3-dimethyl-3,4-dihydro-1H-pyrrolo[2,1-c][1,4]oxazin-7-yl)-7-fluoro-1H-pyrrolo[3,4-c]pyridin-3(2H)-one;

6-(((1R,2S)-2-Aminocyclohexyl)amino)-4-(3-ethyl-3,4-dihydro-1H-pyrrolo[2,1-c][1,4]oxazin-7-yl)-7-fluoro-1H-pyrrolo[3,4-c]pyridin-3(2H)-one;

6-(((1R,2S)-2-Aminocyclohexyl)amino)-7-fluoro-4-(3-isopropyl-3,4-dihydro-1H-pyrrolo[2,1-c][1,4]oxazin-7-yl)-1H-pyrrolo[3,4-c]pyridin-3(2H)-one;

6-(((1R,2S)-2-Aminocyclohexyl)amino)-7-fluoro-4-(1,2,3,4-tetrahydropyrrolo[1,2-a]pyrazin-7-yl)-1H-pyrrolo[3,4-c]pyridin-3(2H)-one;

6-(((1R,2S)-2-Aminocyclohexyl)amino)-7-fluoro-4-(2-methyl-1,2,3,4-tetrahydropyrrolo[1,2-a]pyrazin-7-yl)-1H-pyrrolo[3,4-c]pyridin-3(2H)-one;

6-(((1R,2S)-2-Aminocyclohexyl)amino)-4-(2-ethyl-1,2,3,4-tetrahydropyrrolo[1,2-a]pyrazin-7-yl)-7-fluoro-1H-pyrrolo[3,4-c]pyridin-3(2H)-one;

6-(((3R,4R)-3-Aminotetrahydro-2H-pyran-4-ylamino)-4-(1-ethyl-1H-pyrazol-4-yl)-7-fluoro-1H-pyrrolo[3,4-c]pyridin-3(2H)-one;

a stereoisomer of any of the aforementioned compounds and their pharmaceutically acceptable salts.

A further aspect of the invention provides a pharmaceutical composition which includes: a compound of Formula 1, as defined above, or a pharmaceutically acceptable salt thereof, or a compound selected from the group of compounds defined in the preceding paragraph, or a pharmaceutically acceptable salt thereof; and a pharmaceutically acceptable excipient.

An additional aspect of the invention provides a use as a medicament of a compound of Formula 1 or a pharmaceutically acceptable salt thereof, or the use of a compound selected from the group of compounds defined above or a pharmaceutically acceptable salt thereof.

Another aspect of the invention provides a use of a compound of Formula 1 or a pharmaceutically acceptable salt thereof, or the use of a compound selected from the group of compounds defined above or a pharmaceutically acceptable salt thereof, for the manufacture of a medicament for the treatment of a disease or condition for which a SYK inhibitor is indicated.

A further aspect of the invention provides a method of treating a disease or condition in a subject for which a SYK inhibitor is indicated, the method comprising administering to the subject an effective amount of a compound of Formula 1 or a pharmaceutically acceptable salt thereof, or a compound selected from the group of compounds defined above or a pharmaceutically acceptable salt thereof.

An additional aspect of the invention provides a method of treating a disease or condition in a subject, the method comprising administering to the subject an effective amount of a compound of Formula 1 or a pharmaceutically acceptable salt thereof, or a compound selected from the group of compounds defined above or a pharmaceutically acceptable salt thereof, wherein the disease or condition is selected from allergic rhinitis, allergic asthma, atopic dermatitis, rheumatoid arthritis, multiple sclerosis, systemic lupus erythematosus, psoriasis, immune thrombocytopenic purpura, inflammatory bowel disease, Behcet's disease, graft versus host disease, chronic obstructive pulmonary disease, and thrombosis.

Another aspect of the invention provides a method of treating a disease or condition in a subject, the method comprising administering to the subject an effective amount of a compound of Formula 1 or a pharmaceutically acceptable salt thereof, or a compound selected from the group of compounds defined above or a pharmaceutically acceptable salt thereof, wherein the disease or condition is selected from cancer.

A further aspect of the invention provides a combination of an effective amount of a compound of Formula 1 or a pharmaceutically acceptable salt thereof, or a compound selected from the group of compounds defined above or a pharmaceutically acceptable salt thereof, and at least one additional pharmacologically active agent.

DETAILED DESCRIPTION OF THE INVENTION

Unless indicated otherwise, this disclosure uses definitions given below.

"Substituted," when used in connection with a chemical substituent or moiety (e.g., an alkyl group), means that one or more hydrogen atoms of the substituent or moiety have been replaced with one or more non-hydrogen atoms or groups, provided that valence requirements are met and that a chemically stable compound results from the substitution.

"About" or "approximately," when used in connection with a measurable numerical variable, refers to the indicated value of the variable and to all values of the variable that are within the experimental error of the indicated value or within ±10 percent of the indicated value, whichever is greater.

"Alkyl" refers to straight chain and branched saturated hydrocarbon groups, generally having a specified number of carbon atoms (e.g., $C_{1-3}$ alkyl refers to an alkyl group having 1 to 3 (i.e., 1, 2 or 3) carbon atoms, $C_{1-6}$ alkyl refers to an alkyl group having 1 to 6 carbon atoms, and so on). Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

"Alkenyl" refers to straight chain and branched hydrocarbon groups having one or more carbon-carbon double bonds, and generally having a specified number of carbon atoms. Examples of alkenyl groups include ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

"Alkynyl" refers to straight chain or branched hydrocarbon groups having one or more triple carbon-carbon bonds, and generally having a specified number of carbon atoms. Examples of alkynyl groups include ethynyl, 1-propyn-1-yl, 2-propyn-1-yl, 1-butyn-1-yl, 3-butyn-1-yl, 3-butyn-2-yl, 2-butyn-1-yl, and the like.

"Halo," "halogen" and "halogeno" may be used interchangeably and refer to fluoro, chloro, bromo, and iodo.

"Haloalkyl," "haloalkenyl," and "haloalkynyl," refer, respectively, to alkyl, alkenyl, and alkynyl groups substituted with one or more halogen atoms, where alkyl, alkenyl, and alkynyl are defined above, and generally having a specified number of carbon atoms. Examples of haloalkyl groups include fluoromethyl, difluoromethyl, trifluoromethyl, chloromethyl, dichloromethyl, trichloromethyl, and the like.

"Cycloalkyl" refers to saturated monocyclic and bicyclic hydrocarbon groups, generally having a specified number of carbon atoms that comprise the ring or rings (e.g., $C_{3-8}$ cycloalkyl refers to a cycloalkyl group having 3 to 8 carbon atoms as ring members). Bicyclic hydrocarbon groups may include isolated rings (two rings sharing no carbon atoms), spiro rings (two rings sharing one carbon atom), fused rings (two rings sharing two carbon atoms and the bond between the two common carbon atoms), and bridged rings (two rings sharing two carbon atoms, but not a common bond). The cycloalkyl group may be attached through any ring atom unless such attachment would violate valence requirements. In addition, the cycloalkyl group may include one or more non-hydrogen substituents unless such substitution would violate valence requirements.

Examples of monocyclic cycloalkyl groups include cyclopropyl, cyclobutyl, cyclopentyl, cyclohexyl, and the like. Examples of fused bicyclic cycloalkyl groups include bicyclo[2.1.0]pentanyl (i.e., bicyclo[2.1.0]pentan-1-yl, bicyclo[2.1.0]pentan-2-yl, and bicyclo[2.1.0]pentan-5-yl), bicyclo[3.1.0]hexanyl, bicyclo[3.2.0]heptanyl, bicyclo[4.1.0]heptanyl, bicyclo[3.3.0]octanyl, bicyclo[4.2.0]octanyl, bicyclo[4.3.0]nonanyl, bicyclo[4.4.0]decanyl, and the like. Examples of bridged cycloalkyl groups include bicyclo[2.1.1]hexanyl, bicyclo[2.2.1]heptanyl, bicyclo[3.1.1]heptanyl, bicyclo[2.2.2]octanyl, bicyclo[3.2.1]octanyl, bicyclo[4.1.1]octanyl, bicyclo[3.3.1]nonanyl, bicyclo[4.2.1]nonanyl, bicyclo[3.3.2]decanyl, bicyclo[4.2.2]decanyl, bicyclo[4.3.1]decanyl, bicyclo[3.3.3]undecanyl, bicyclo[4.3.2]undecanyl, bicyclo[4.3.3]dodecanyl, and the like. Examples of spiro cycloalkyl groups include spiro[3.3]heptanyl, spiro[2.4]heptanyl, spiro[3.4]octanyl, spiro[2.5]octanyl, spiro[3.5]nonanyl, and the like. Examples of isolated bicyclic cycloalkyl groups include those derived from bi(cyclobutane), cyclobutanecyclopentane, bi(cyclopentane), cyclobutanecyclohexane, cyclopentanecyclohexane, bi(cyclohexane), etc.

"Cycloalkylidene" refers to divalent monocyclic cycloalkyl groups, where cycloalkyl is defined above, which are attached through a single carbon atom of the group, and generally having a specified number of carbon atoms that comprise the ring (e.g., $C_{3-6}$ cycloalkylidene refers to a cycloalkylidene group having 3 to 6 carbon atoms as ring members). Examples include cyclopropylidene, cyclobutylidene, cyclopentylidene, and cyclohexylidene.

"Cycloalkenyl" refers to partially unsaturated monocyclic and bicyclic hydrocarbon groups, generally having a specified number of carbon atoms that comprise the ring or rings. As with cycloalkyl groups, the bicyclic cycloalkenyl groups may include isolated, spiro, fused, or bridged rings. Similarly, the cycloalkenyl group may be attached through any ring atom and may include one or more non-hydrogen substituents unless such attachment or substitution would violate valence requirements. Examples of cycloalkenyl groups include the partially unsaturated analogs of the cycloalkyl groups described above, such as cyclobutenyl (i.e., cyclobuten-1-yl and cyclobuten-3-yl), cyclopentenyl, cyclohexenyl, bicyclo[2.2.1]hept-2-enyl, and the like.

"Aryl" refers to fully unsaturated monocyclic aromatic hydrocarbons and to polycyclic hydrocarbons having at least one aromatic ring, both monocyclic and polycyclic aryl groups generally having a specified number of carbon atoms that comprise their ring members (e.g., $C_{6-14}$ aryl refers to an aryl group having 6 to 14 carbon atoms as ring members). The group may be attached through any ring atom and may include one or more non-hydrogen substituents unless such attachment or substitution would violate valence requirements. Examples of aryl groups include phenyl, biphenyl, cyclobutabenzenyl, indenyl, naphthalenyl, benzocycloheptanyl, biphenylenyl, fluorenyl, groups derived from cycloheptatriene cation, and the like.

"Arylene" refers to divalent aryl groups, where aryl is defined above. Examples of arylene groups include phenylene (i.e., benzene-1,2-diyl).

"Heterocycle" and "heterocyclyl" may be used interchangeably and refer to saturated or partially unsaturated monocyclic or bicyclic groups having ring atoms composed of carbon atoms and 1 to 4 heteroatoms independently selected from nitrogen, oxygen, and sulfur. Both the monocyclic and bicyclic groups generally have a specified number of carbon atoms in their ring or rings (e.g., $C_{2-5}$ heterocyclyl refers to a heterocyclyl group having 2 to 5 carbon atoms and 1 to 4 heteroatoms as ring members). As with bicyclic cycloalkyl groups, bicyclic heterocyclyl groups may include isolated rings, spiro rings, fused rings, and bridged rings. The heterocyclyl group may be attached through any ring atom and may include one or more non-hydrogen substituents unless such attachment or substitution would violate valence requirements or result in a chemically unstable compound. Examples of monocyclic heterocyclyl groups include oxiranyl, thiaranyl, aziridinyl (e.g., aziridin-1-yl and aziridin-2-yl), oxetanyl, thiatanyl, azetidinyl, tetrahydrofuranyl, tetrahydrothiopheneyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 5,6-dihydro-2H-pyranyl, 2H-pyranyl, 1,2,3,4-tetrahydropyridinyl, and 1,2,5,6-tetrahydropyridinyl.

"Heterocycle-diyl" refers to heterocyclyl groups which are attached through two ring atoms of the group, where heterocyclyl is defined above. They generally have a specified number of carbon atoms in their ring or rings (e.g., $C_{3-5}$ heterocycle-diyl refers to a heterocycle-diyl group having 3 to 5 carbon atoms and 1 to 4 heteroatoms as ring members). Examples of heterocycle-diyl groups include the multivalent analogs of the heterocycle groups described above, such as morpholine-3,4-diyl, pyrrolidine-1,2-diyl, 1-pyrrolidinyl-2-ylidene, 1-pyridinyl-2-ylidene, 1-(4H)-pyrazolyl-5-ylidene, 1-(3H)-imidazolyl-2-ylidene, 3-oxazolyl-2-ylidene, 1-piperidinyl-2-ylidene, 1-piperazinyl-6-ylidene, and the like.

"Heteroaromatic" and "heteroaryl" may be used interchangeably and refer to unsaturated monocyclic aromatic groups and to polycyclic groups having at least one aromatic ring, each of the groups having ring atoms composed of carbon atoms and 1 to 4 heteroatoms independently selected from nitrogen, oxygen, and sulfur. Both the monocyclic and polycyclic groups generally have a specified number of carbon atoms as ring members (e.g., $C_{1-9}$ heteroaryl refers to a heteroaryl group having 1 to 9 carbon atoms and 1 to 4 heteroatoms as ring members) and may include any bicyclic group in which any of the above-listed monocyclic heterocycles are fused to a benzene ring. The heteroaryl group may be attached through any ring atom (or ring atoms for fused rings) and may include one or more non-hydrogen substituents unless such attachment or substitution would violate valence requirements or result in a chemically unstable compound. Examples of heteroaryl groups include monocyclic groups such as pyrrolyl (e.g., pyrrol-1-yl, pyrrol-2-yl, and pyrrol-3-yl), furanyl, thiopheneyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, and pyrazinyl.

Examples of heteroaryl groups also include bicyclic groups such as benzofuranyl, isobenzofuranyl, benzothiopheneyl, benzo[c]thiopheneyl, indolyl, 3H-indolyl, isoindolyl, 1H-isoindolyl, indolinyl, isoindolinyl, benzimidazolyl, indazolyl, benzotriazolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl, 3H-imidazo[4,5-b]pyridinyl, 3H-imidazo[4,5-c]pyridinyl, 1H-pyrazolo[4,3-b]pyridinyl, 1H-pyrazolo[4,3-c]pyridinyl, 1H-pyrazolo[3,4-c]pyridinyl, 1H-pyrazolo[3,4-b]pyridinyl, 7H-purinyl, indolizinyl, imidazo[1,2-c]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, and pyrimido[4,5-d]pyrimidinyl.

"Heteroarylene" refers to heteroaryl groups which are attached through two ring atoms of the group, where heteroaryl is defined above. They generally have a specified number of carbon atoms in their ring or rings (e.g., $C_{3-5}$ heteroarylene refers to a heteroarylene group having 3 to 5 carbon atoms and 1 to 4 heteroatoms as ring members). Examples of heteroarylene groups include the multivalent analogs of the heteroaryl groups described above, such as pyridine-2,3-diyl, pyridine-3,4-diyl, pyrazole-4,5-diyl, pyrazole-3,4-diyl, and the like.

"Oxo" refers to a double bonded oxygen (=O).

"Leaving group" refers to any group that leaves a molecule during a fragmentation process, including substitution reactions, elimination reactions, and addition-elimination reactions. Leaving groups may be nucleofugal, in which the group leaves with a pair of electrons that formerly served as the bond between the leaving group and the molecule, or may be electrofugal, in which the group leaves without the pair of electrons. The ability of a nucleofugal leaving group to leave depends on its base strength, with the strongest bases being the poorest leaving groups. Common nucleofugal leaving groups include nitrogen (e.g., from diazonium salts); sulfonates, including alkylsulfonates (e.g., mesylate), fluoroalkylsulfonates (e.g., triflate, hexaflate, nonaflate, and tresylate), and arylsulfonates (e.g., tosylate, brosylate, closylate, and nosylate). Others include carbonates, halide ions, carboxylate anions, phenolate ions, and alkoxides. Some stronger bases, such as $NH_2^-$ and $OH^-$ can be made better leaving groups by treatment with an acid. Common electrofugal leaving groups include the proton, $CO_2$, and metals.

"Opposite enantiomer" refers to a molecule that is a non-superimposable mirror image of a reference molecule, which may be obtained by inverting all of the stereogenic centers of the reference molecule. For example, if the reference molecule has S absolute stereochemical configuration, then the opposite enantiomer has R absolute stereochemical configuration. Likewise, if the reference molecule has S,S absolute stereochemical configuration, then the opposite enantiomer has R,R stereochemical configuration, and so on.

"Stereoisomer" and "stereoisomers" of a compound with given stereochemical configuration refer to the opposite enantiomer of the compound and to any diastereoisomers, including geometrical isomers (Z/E) of the compound. For example, if a compound has S,R,Z stereochemical configuration, its stereoisomers would include its opposite enantiomer having R,S,Z configuration, and its diastereomers having S,S,Z configuration, R,R,Z configuration, S,R,E configuration, R,S,E configuration, S,S,E configuration, and R,R,E configuration. If the stereochemical configuration of a compound is not specified, then "stereoisomer" refers to any one of the possible stereochemical configurations of the compound.

"Substantially pure stereoisomer" and variants thereof refer to a sample containing a compound having a specific stereochemical configuration and which comprises at least about 95% of the sample.

"Pure stereoisomer" and variants thereof refer to a sample containing a compound having a specific stereochemical configuration and which comprises at least about 99.5% of the sample.

"Subject" refers to a mammal, including a human.

"Pharmaceutically acceptable" substances refers to those substances which are within the scope of sound medical judgment suitable for use in contact with the tissues of subjects without undue toxicity, irritation, allergic response, and the like, commensurate with a reasonable benefit-to-risk ratio, and effective for their intended use.

"Treating" refers to reversing, alleviating, inhibiting the progress of, or preventing a disorder, disease or condition to which such term applies, or to reversing, alleviating, inhibiting the progress of, or preventing one or more symptoms of such disorder, disease or condition.

"Treatment" refers to the act of "treating," as defined immediately above.

"Drug," "drug substance," "active pharmaceutical ingredient," and the like, refer to a compound (e.g., compounds of Formula 1 and compounds specifically named above) that may be used for treating a subject in need of treatment.

"Therapeutically effective amount" of a drug refers to the quantity of the drug that may be used for treating a subject and may depend on the weight and age of the subject and the route of administration, among other things.

"Excipient" refers to any substance that may influence the bioavailability of a drug, but is otherwise pharmacologically inactive.

"Pharmaceutical composition" refers to the combination of one or more drug substances and one or more excipients.

"Drug product," "pharmaceutical dosage form," "dosage form," "final dosage form" and the like, refer to a pharmaceutical composition that is administered to a subject in need of treatment and generally may be in the form of tablets, capsules, sachets containing powder or granules, liquid solutions or suspensions, patches, films, and the like.

The following abbreviations are used throughout the specification: Ac (acetyl); ACN (acetonitrile); AIBN (azo-bis-isobutyronitrile); API (active pharmaceutical ingredient); aq (aqueous); Boc (tert-butoxycarbonyl); BSA (bovine serum albumin); Cbz (carbobenzyloxy); dba (dibenzylideneacetone); COD (1,5-cyclooctadiene); DCC (1,3-dicyclohexylcarbodiimide); DCM (dichloromethane); DIPEA (N,N-diisopropylethylamine, Hünig's Base); DMA (N,N-dimethylacetamide); DMAP (4-dimethylaminopyridine); DMARD (disease modifying antirheumatic drug); DME (1,2-dimethoxyethane); DMF (N,N-dimethylformamide); DMSO (dimethylsulfoxide); dppf (1,1'-bis(diphenylphosphino)ferrocene); DTT (dithiothreitol); EDA ethoxylated dodecyl alcohol, Brj®35); EDCI (N-(3-dimethylaminopropyl)-N'-ethylcarbodiimide); EDTA (ethylenediaminetetraacetic acid); ee (enantiomeric excess); eq (equivalents); Et (ethyl); Et$_3$N (triethyl-amine); EtOAc (ethyl acetate); EtOH (ethanol); FAM (5-carboxyfluorescein); HATU (2-(3H-[1,2,3]triazolo[4,5-b]pyridin-3-yl)-1,1,3,3-tetramethyluronium hexafluorophosphate(V)); HEPES (4-(2-hydroxyethyl)piperazine-1-ethanesulfonic acid); HOAc (acetic acid); HOBt (1H-benzo[d][1,2,3]triazol-1-ol); IC$_{50}$ (concentration at 50% inhibition); IPA (isopropanol); IPAc (isopropyl acetate); IPE (isopropylether); LDA (lithium diisopropylamide); LiHMDS (lithium bis(trimethylsilyl)amide); mCPBA (m-chloroperoxybenzoic acid); Me (methyl); MeOH (methanol); MTBE (methyl tert-butyl ether); MOI (multiplicity of infection); mp (melting point); NaOt-Bu (sodium tertiary butoxide); NBS (N-bromosuccinimide); NCS (N-chlorosuccinimide); NIS (N-iodosuccinimide); PE (petroleum ether); Ph (phenyl); pIC$_{50}$ ($-\log_{10}$(IC$_{50}$), where IC$_{50}$ is given in molar (M) units); Pr (propyl); i-Pr (isopropyl); PTFE (polytetrafluoroethylene); RT (room temperature, approximately 20° C. to 25° C.); SYK (spleen tyrosine kinase); TCEP (tris(2-carboxyethyl)phosphine); TFA (trifluoroacetic acid); TFAA (2,2,2-trifluoroacetic anhydride); THF (tetrahydrofuran); Ts (tosyl); and Tris buffer (2-amino-2-hydroxymethyl-propane-1,3-diol buffer).

This disclosure concerns compounds of Formula 1, which includes compounds specifically named above, and their pharmaceutically acceptable complexes, salts, solvates and hydrates. This disclosure also concerns materials and methods for preparing compounds of Formula 1, pharmaceutical compositions containing them, and their use for treating disorders, diseases, and conditions involving the immune system and inflammation, including rheumatoid arthritis, cancer, including hematological malignancies, epithelial cancers (i.e., carcinomas), and other disorders, diseases, and conditions for which inhibition of SYK is indicated.

Compounds of Formula 1 also include those in which (a) R$^1$ is hydrogen and R$^2$ is C$_{1-3}$ alkyl, in particular, methyl or ethyl; (b) R$^1$ and R$^2$ are both C$_{1-3}$ alkyl groups, in particular methyl; (c) R$^1$ and R$^2$, together with the carbon atom to which they are attached, form a cyclopropyl group; or (d) R$^1$ and R$^2$ are both hydrogen atoms.

In addition, or as an alternative to one or more of embodiments (a) through (d) in the preceding paragraph, compounds of Formula 1 include those in which: (e) R$^5$ is hydrogen, halo, or C$_{1-4}$ alkyl, in particular, methyl or ethyl; (f) R$^5$ is hydrogen or halo, or more particularly, chloro or fluoro; or R$^5$ is fluoro.

In addition, or as an alternative to one or more of embodiments (a) through (f) in the preceding paragraphs, compounds of Formula 1 include those in which: (g) p is 0.

In addition, or as an alternative to one or more of embodiments (a) through (g) in the preceding paragraphs, compounds of Formula 1 include those in which: (h) R$^4$ is selected from

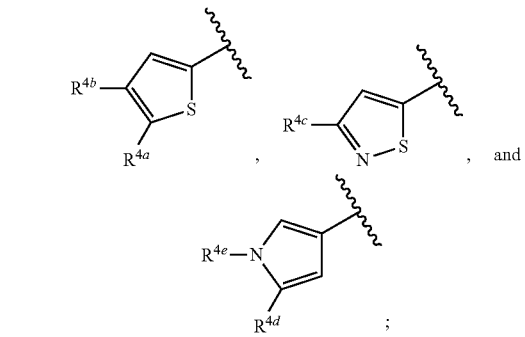

(i) R$^4$ is

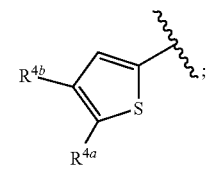

(j) R$^4$ is

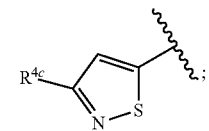

or (k)

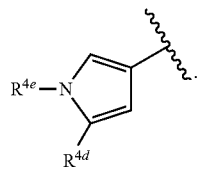

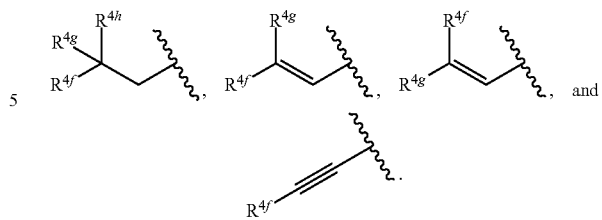

In addition, or as an alternative to one or more of embodiments (a) through (i) in the preceding paragraphs, compounds of Formula 1 include those in which: (1) $R^{4a}$ is hydrogen, halo, —CN, $C_{1-4}$ alkyl, in particular methyl, ethyl, propyl or isopropyl, or is $C_{3-8}$ cycloalkyl, in particular cyclopropyl, and $R^{4b}$ is halo, —CN, $C_{2-4}$ alkyl, in particular ethyl, propyl or isopropyl, or is $C_{3-8}$ cycloalkyl, in particular cyclopropyl; (m) $R^{4a}$ is hydrogen, halo, —CN, methyl, ethyl, propyl, isopropyl or cyclopropyl, and $R^{4b}$ is halo, —CN, ethyl, propyl, isopropyl or cyclopropyl; (n) $R^{4a}$ is fluoro, bromo, —CN, $C_{2-4}$ alkyl, in particular ethyl, propyl or isopropyl, or is $C_{3-8}$ cycloalkyl, in particular cyclopropyl, and $R^{4b}$ is hydrogen, halo, —CN, $C_{1-4}$ alkyl, in particular methyl, ethyl, propyl or isopropyl, or is $C_{3-8}$ cycloalkyl, in particular cyclopropyl; (o) $R^{4a}$ is fluoro, bromo, —CN, ethyl, propyl, isopropyl or cyclopropyl, and $R^{4b}$ is hydrogen, halo, —CN, methyl, ethyl, propyl, isopropyl or cyclopropyl.

In addition, or as an alternative to one or more of embodiments (a) through (i) in the preceding paragraphs, compounds of Formula 1 include those in which: (p) $R^{4a}$ and $R^{4b}$, together with the atoms to which they are attached, form a phenylene or a $C_{3-5}$ heteroarylene, each optionally substituted with from one to four substituents independently selected from halo, oxo, —CN, $R^6$, and $R^7$, wherein the $C_{3-5}$ heteroarylene moiety has 5 or 6 ring atoms and 1 or 2 are heteroatoms, each of the heteroatoms being N.

In addition, or as an alternative to one or more of embodiments (a) through (h) and (j) in the preceding paragraphs, compounds of Formula 1 include those in which: (q) $R^{4c}$ is hydrogen, halo, —CN, $C_{1-4}$ alkyl, in particular methyl, ethyl, propyl, isopropyl, or is $C_{3-8}$ cycloalkyl, in particular cyclopropyl, provided that when G is O, $R^{4c}$ is not unsubstituted methyl.

In addition, or as an alternative to one or more of embodiments (a) through (h) and (k) in the preceding paragraphs, compounds of Formula 1 include those in which: (r) $R^{4d}$ and $R^{4e}$ are each independently hydrogen, halo, —CN, $C_{1-4}$ alkyl, in particular methyl, ethyl, propyl or isopropyl, or $C_{3-8}$ cycloalkyl, in particular cyclopropyl.

In addition, or as an alternative to one or more of embodiments (a) through (h) and (k) in the preceding paragraphs, compounds of Formula 1 include those in which: (s) $R^{4d}$ and $R^{4e}$, together with the atoms to which they are attached, form a $C_{3-5}$ heterocycle-diyl or a $C_{3-5}$ heteroarylene, each having 5 or 6 ring atoms, at least one heteroatom which is N, and optionally 1 or 2 additional heteroatoms independently selected from N, O, and S, and wherein the $C_{3-5}$ heterocycle-diyl or the $C_{3-5}$ heteroarylene is optionally substituted with from one to four substituents independently selected from halo, oxo, —CN, $R^6$, and $R^7$.

In addition, or as an alternative to one or more of embodiments (a) through (g) in the preceding paragraphs, compounds of Formula 1 include those in which (t) $R^4$ is selected from:

In addition, or as an alternative to one or more of embodiments (a) through (t) in the preceding paragraphs, compounds of Formula 1 include those in which (u) G is $CH_2$.

In addition, or as an alternative to one or more of embodiments (a) through (t) in the preceding paragraphs, compounds of Formula 1 include those in which (v) G is O.

Compounds of Formula 1 also include any of the above embodiments in which (w) one or more of the $R^{3a}$, $R^{4a}$, $R^{4b}$, $R^{4c}$, $R^{4d}$, $R^{4f}$, $R^{4e}$, $R^5$, $R^7$, $R_8$, and $R^9$ substituents have no optional substituents.

Compounds of Formula 1 include (x) those having stereochemical configuration given by Formula 1A:

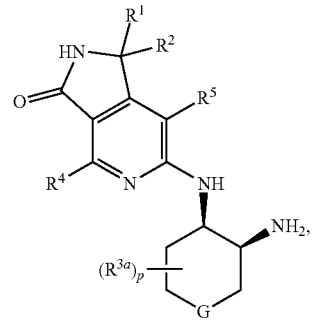

1A wherein G, p, $R^1$, $R^2$, $R^{3a}$, $R^4$, and $R^5$ in Formula 1A are as defined for Formula 1 or as defined in one or more of embodiments (a) through (w) in the preceding paragraphs.

Compounds of Formula 1 include embodiments (a) through (x) described in the preceding paragraphs and all compounds specifically named above and in the examples, and generally include all salts, complexes, solvates, hydrates, and liquid crystals of the compounds of Formula 1. Likewise, references to compounds of Formula 1 include all complexes, solvates, hydrates, and liquid crystals of the salts of the compounds of Formula 1.

Compounds of Formula 1, which include compounds specifically named above, may form pharmaceutically acceptable complexes, salts, solvates and hydrates. These salts include acid addition salts (including di-acids) and base salts. Pharmaceutically acceptable acid addition salts include nontoxic salts derived from inorganic acids such as hydrochloric acid, nitric acid, phosphoric acid, sulfuric acid, hydrobromic acid, hydroiodic acid, hydrofluoric acid, and phosphorous acids, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

Pharmaceutically acceptable base salts include nontoxic salts derived from bases, including metal cations, such as an alkali or alkaline earth metal cation, as well as amines Examples of suitable metal cations include sodium ($Na^+$), potassium ($K^+$), magnesium ($Mg^{2+}$), calcium ($Ca^{2+}$), zinc ($Zn^{2+}$), and aluminum ($Al^{3+}$). Examples of suitable amines include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2002).

Pharmaceutically acceptable salts may be prepared using various methods. For example, one may react a compound of Formula 1 with an appropriate acid or base to give the desired salt. One may also react a precursor of the compound of Formula 1 with an acid or base to remove an acid- or base-labile protecting group or to open a lactone or lactam group of the precursor. Additionally, one may convert a salt of the compound of Formula 1 to another salt through treatment with an appropriate acid or base or through contact with an ion exchange resin. Following reaction, one may then isolate the salt by filtration if it precipitates from solution, or by evaporation to recover the salt. The degree of ionization of the salt may vary from completely ionized to almost non-ionized.

Compounds of Formula 1 may exist in a continuum of solid states ranging from fully amorphous to fully crystalline. The term "amorphous" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

Compounds of Formula 1 may also exist in unsolvated and solvated forms. The term "solvate" describes a molecular complex comprising the compound and one or more pharmaceutically acceptable solvent molecules (e.g., EtOH). The term "hydrate" is a solvate in which the solvent is water. Pharmaceutically acceptable solvates include those in which the solvent may be isotopically substituted (e.g., $D_2O$, acetone-$d_6$, DMSO-$d_6$).

A currently accepted classification system for solvates and hydrates of organic compounds is one that distinguishes between isolated site, channel, and metal-ion coordinated solvates and hydrates. See, e.g., K. R. Morris (H. G. Brittain ed.) *Polymorphism in Pharmaceutical Solids* (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

Compounds of Formula 1 may also exist as multi-component complexes (other than salts and solvates) in which the compound (drug) and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together. See, e.g., O. Almarsson and M. J. Zaworotko, *Chem. Commun.* (2004) 17:1889-1896. For a general review of multi-component complexes, see J. K. Haleblian, *J. Pharm. Sci.* (1975) 64(8):1269-88.

When subjected to suitable conditions, compounds of Formula 1 may exist in a mesomorphic state (mesophase or liquid crystal). The mesomorphic state lies between the true crystalline state and the true liquid state (either melt or solution). Mesomorphism arising as the result of a change in temperature is described as "thermotropic" and mesomorphism resulting from the addition of a second component, such as water or another solvent, is described as "lyotropic." Compounds that have the potential to form lyotropic mesophases are described as "amphiphilic" and include molecules which possess a polar ionic moiety (e.g., —$COO^-Na^+$, —$COO^-K^+$, —$SO_3^-Na^+$) or polar non-ionic moiety (such as —$N^-N^+(CH_3)_3$). See, e.g., N. H. Hartshorne and A. Stuart, *Crystals and the Polarizing Microscope* (4th ed, 1970).

Compounds of Formula 1 generally include all polymorphs and crystal habits, prodrugs, metabolites, stereoisomers, and tautomers thereof, as well as all isotopically-labeled compounds thereof.

"Prodrugs" refer to compounds having little or no pharmacological activity that can, when metabolized in vivo, undergo conversion to compounds having desired pharmacological activity. Prodrugs may be prepared by replacing appropriate functionalities present in pharmacologically active compounds with "pro-moieties" as described, for example, in H. Bundgaar, *Design of Prodrugs* (1985). Examples of prodrugs include ester, ether or amide derivatives of compounds of Formula 1 having carboxylic acid, hydroxy, or amino functional groups, respectively. For further discussions of prodrugs, see e.g., T. Higuchi and V. Stella "Pro-drugs as Novel Delivery Systems," *ACS Symposium Series* 14 (1975) and E. B. Roche ed., *Bioreversible Carriers in Drug Design* (1987).

"Metabolites" refer to compounds formed in vivo upon administration of pharmacologically active compounds. Examples include hydroxymethyl, hydroxy, secondary amino, primary amino, phenol, and carboxylic acid derivatives of compounds of Formula 1 having methyl, alkoxy, tertiary amino, secondary amino, phenyl, and amide groups, respectively.

Certain compounds described herein may have stereoisomers. These compounds may exist as single enantiomers (enantiopure compounds) or mixtures of enantiomers (enriched and racemic samples), which depending on the relative excess of one enantiomer over another in a sample, may exhibit optical activity. Such stereoisomers, which are non-superimposable mirror images, possess a stereogenic axis or one or more stereogenic centers (i.e., chirality). Other compounds may be stereoisomers that are not mirror images. Such stereoisomers, which are known as diastereoisomers, may be chiral or achiral (contain no stereogenic centers). They include molecules containing an alkenyl or cyclic group, so that cis/trans (or Z/E) stereoisomers are possible, or molecules containing two or more stereogenic centers, in which inversion of a single stereogenic center generates a corresponding diastereoisomer. Unless stated or otherwise clear (e.g., through use of stereobonds, stereocenter descriptors, etc.) the scope of the invention and disclosure generally includes the reference compound and its stereoisomers, whether they are each pure (e.g., enantiopure) or mixtures (e.g., enantiomerically enriched or racemic).

Geometrical (cis/trans) isomers may be separated by conventional techniques such as chromatography and fractional crystallization.

Individual enantiomers of compounds may be prepared via chiral synthesis from a suitable optically pure precursor or isolated via resolution of the racemate (or the racemate of a salt or derivative) using, for example, chiral HPLC. Alternatively, the racemate (or a racemic precursor) may be reacted with a suitable enantiomerically pure compound (e.g., acid or base) to yield a pair of diastereoisomers, each composed of a single enantiomer, which are separated via, say, fractional recrystallization or chromatography. The desired enantiomer is subsequently regenerated from the appropriate diastereoisomer. Often, the desired enantiomer may be further enriched by recrystallization in a suitable solvent (e.g., ACN) when it is it available in sufficient quantity (e.g., typically not much less than about 85% ee, and in some cases, not much less than about 90% ee). For a further discussion of techniques for separating stereoisomers, see E. L. Eliel and S. H. Wilen, *Stereochemistry of Organic Compounds* (1994).

"Tautomers" refer to structural isomers that are interconvertible via a low energy barrier. Tautomeric isomerism (tautomerism) may take the form of proton tautomerism in which the compound contains, for example, an imino, keto, or oxime group, or valence tautomerism in which the compound contains an aromatic moiety.

Compounds described herein also include all pharmaceutically acceptable isotopic variations, in which at least one atom is replaced by an atom having the same atomic number, but an atomic mass different from the atomic mass usually found in nature. Isotopes suitable for inclusion in compounds of Formula 1 include, for example, isotopes of hydrogen, such as $^2H$ and $^3H$; isotopes of carbon, such as $^{11}C$ $^{13}C$ and $^{14}C$; isotopes of nitrogen, such as $^{13}N$ and $^{15}N$; isotopes of oxygen, such as $^{15}O$, $^{17}O$ and $^{18}O$; isotopes of sulfur, such as $^{35}S$; isotopes of fluorine, such as $^{18}F$; isotopes of chlorine, such as $^{36}Cl$, and isotopes of iodine, such as $^{123}I$ and $^{125}I$. Use of isotopic variations (e.g., deuterium, $^2H$) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^3H$, or $^{14}C$), which may be useful in drug and/or substrate tissue distribution studies. Substitution with positron emitting isotopes, such as $^{11}C$, $^{18}F$, $^{15}O$ and $^{13}N$ may be useful in Positron Emission Topography (PET) studies for examining substrate receptor occupancy. Isotopically-labeled compounds may be prepared by processes analogous to those described elsewhere in the disclosure using an appropriate isotopically-labeled reagent in place of a non-labeled reagent.

The compounds of Formula 1 may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in a number of treatises, including Richard Larock, *Comprehensive Organic Transformations* (1999), and the multi-volume series edited by Michael B. Smith and others, *Compendium of Organic Synthetic Methods* (1974 et seq.). Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a diacid, etc.). In addition, in some instances, reaction intermediates may be used in subsequent steps without isolation or purification (i.e., in situ).

Starting materials and reagents may be obtained from commercial sources or may be prepared using literature methods. For a description of useful starting materials and intermediates, see co-pending and commonly assigned US and PCT published patent applications US 2011-0152273 A1 and WO 2011/079051 A1, both filed 17 Dec. 2010, which are herein incorporated by reference.

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry* (1999) and P. Kocienski, *Protective Groups* (2000).

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure to a stoichiometric range, a temperature range, a pH range, etc., whether or not expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric triamide).

In the schemes, below, substituent identifiers (e.g., $R^1$, $R^2$, $R^{3a}$, $R^4$, $R^5$, p, G, etc.) are as defined above for Formula 1. As mentioned earlier, however, some of the starting materials and intermediates may include protecting groups, which are removed prior to the final product. In such cases, the substituent identifier refers to moieties defined in Formula 1 and to those moieties with appropriate protecting groups. For example, a starting material or intermediate in the schemes may include a substituent identifier (e.g., $R^4$) having a potentially reactive amine. In such cases, the substituent identifier would include the protected moiety (e.g., with, say, a Boc or Cbz group attached to the amine) as well as the unprotected moiety.

Scheme 1 shows a method for preparing compound 1-9. Starting material 1-0 (2-chloro-3-iodopyridine) undergoes ortho-directed lithiation via treatment with LDA in THF at −78° C. Quenching with dry ice gives 1-1, which is subsequently esterified at RT using iodomethane and a base (e.g., potassium carbonate). The iodo group of intermediate 1-2 is converted to a nitrile group via palladium-catalyzed cyanation or through treatment with cyanocopper or zinc cyanide in a suitable solvent (e.g., DMF, DMA, etc.) at elevated temperature. The $R^4$ substituent is installed on 1-3 using a Suzuki reaction, which gives intermediate 1-4. N-oxidation of the pyridine moiety via treatment with hydrogen peroxide/urea complex gives an activated intermediate 1-5, which is chlorinated through reaction with phosphorus oxychloride at an elevated temperature (e.g., 90-100° C.). Displacement of the chloro group on 1-6 via reaction with an appropriately-substituted amine 1-7 gives intermediate 1-8. Subsequent reduction through palladium-catalyzed hydrogenation and cyclization gives compound 1-9. Here, and in the schemes below, $R^{3b}$ is an amine protecting group. Depending on the nature of the protecting group, hydrogenation may effect removal of $R^{3b}$ (e.g., when $R^{3b}$ is Cbz, benzyl, etc.) while in others, a separate deprotection step may be necessary (e.g., treatment with acid when $R^{3b}$ is a Boc group).

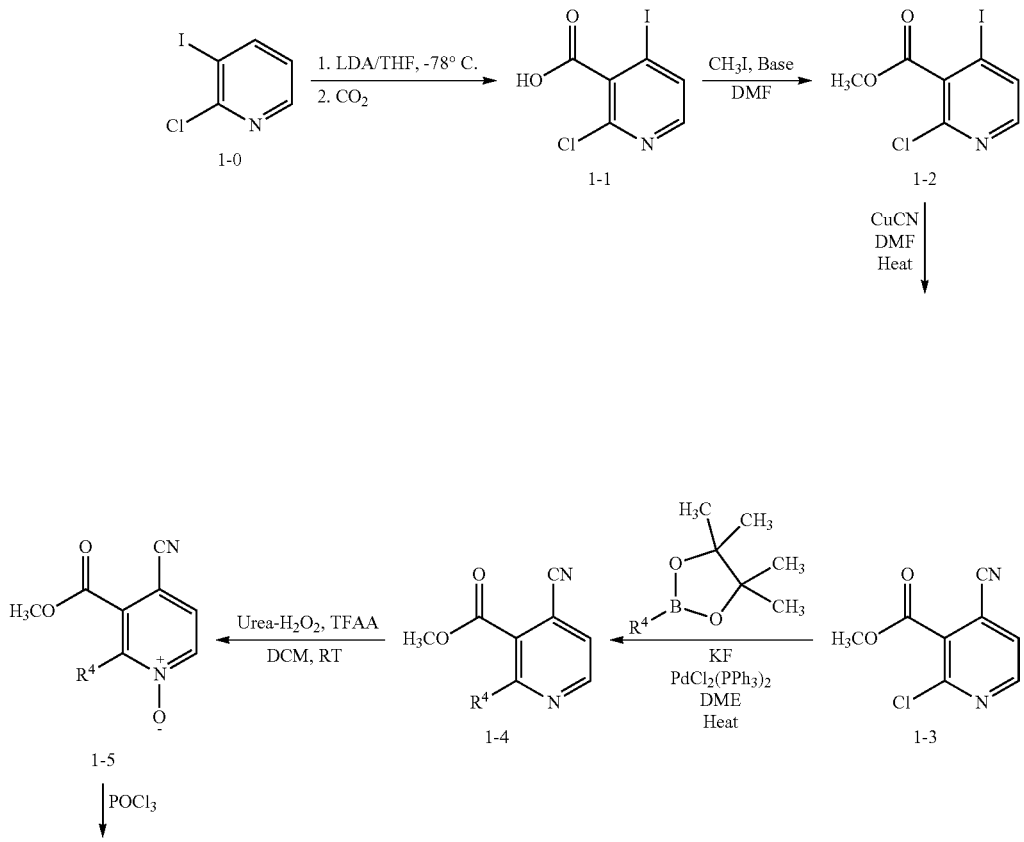

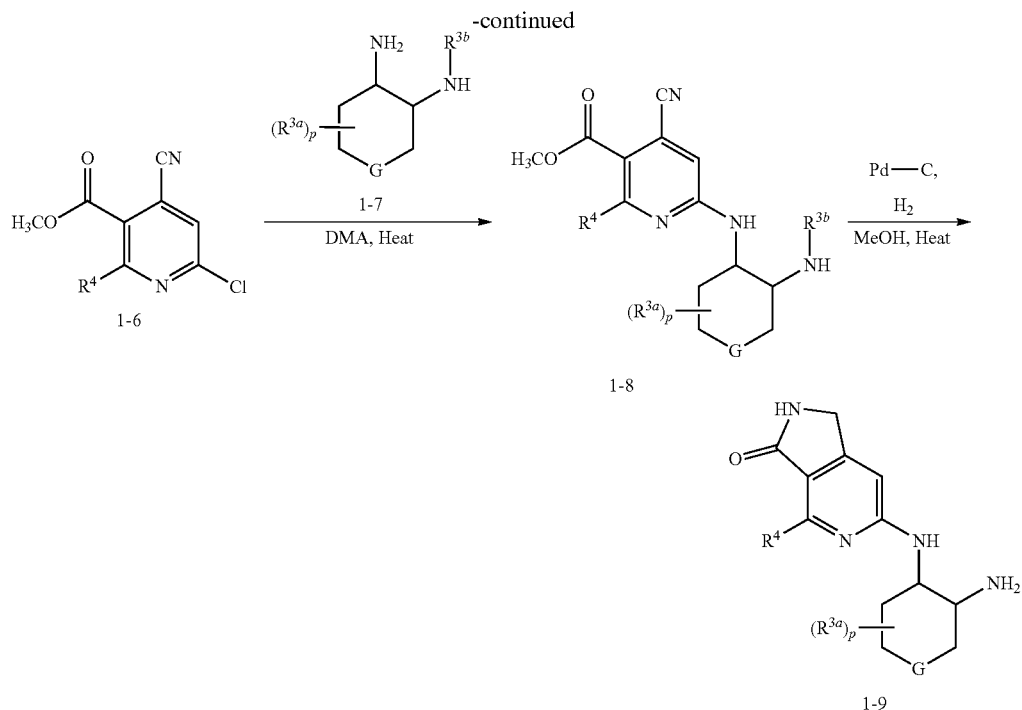

Scheme 2 depicts the synthesis of compound 2-5. Starting material 2-0 (2,6-dichloro-5-fluoronicotinic acid) is lithiated via treatment with LDA in THF at −78° C. Quenching with DMF gives an aldehyde intermediate 2-1, which undergoes reductive amination through reaction with an amine (e.g., (2,4-dimethoxyphenyl)methanamine) and reducing agent (e.g., NaBH(OAc)$_3$). The resulting amino acid (not shown) is cyclized via amide coupling, which employs a suitable coupling agent (e.g., EDCI, DCC, etc.), catalyst (HOBt, DMAP, etc.), and solvent (e.g., DMF, DMSO, ACN, THF, DCM, etc.). As in the previous scheme, displacement of the chloro group of compound 2-2 with an appropriate amine 1-7 gives intermediate 2-3, which is subsequently reacted with a boronic acid or borate (e.g., $R^4$—B(OR$^{13}$)$_2$, where each $R^{13}$ is H or $C_{1-4}$ alkyl) in the presence of a palladium catalyst (e.g., Pd(PPh$_3$)$_4$, (PPh$_3$)$_2$PdCl$_2$, etc.), base (e.g., KF or Na$_2$CO$_3$), and organic solvent (e.g., dioxane, DMF, etc.) at elevated temperature (e.g., about 90° C.) to give 2-4. Following the Suzuki coupling, deprotection of the amine and the lactam nitrogen via treatment of 2-4, e.g. with TFA at elevated temperature (e.g., 40-60° C.) when $R^{3b}$ is a Boc group, generates 2-5.

Scheme 2

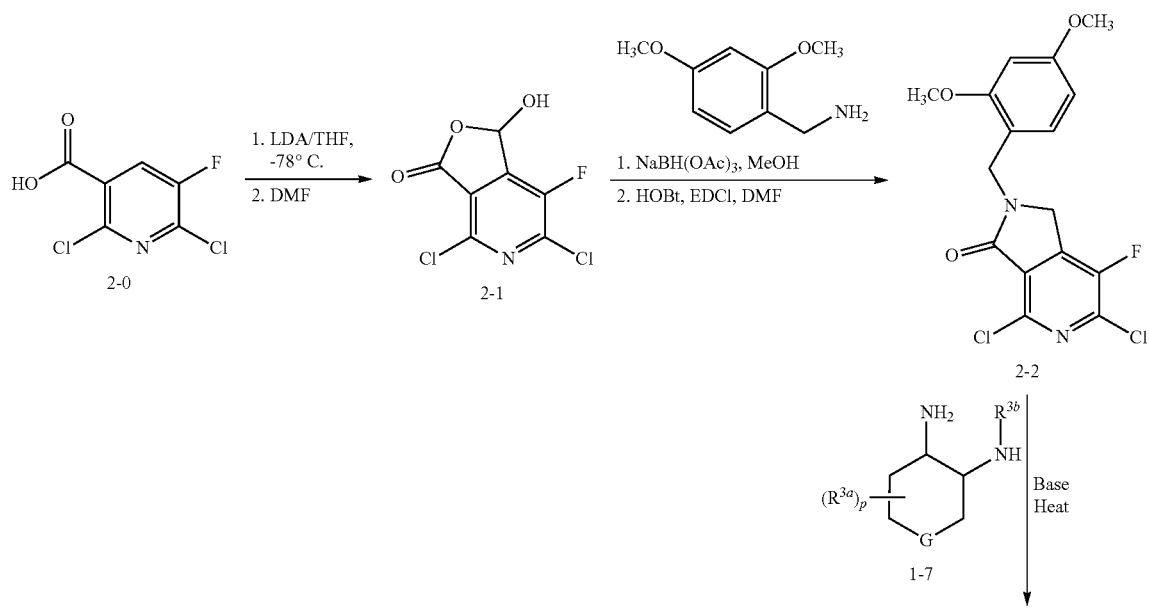

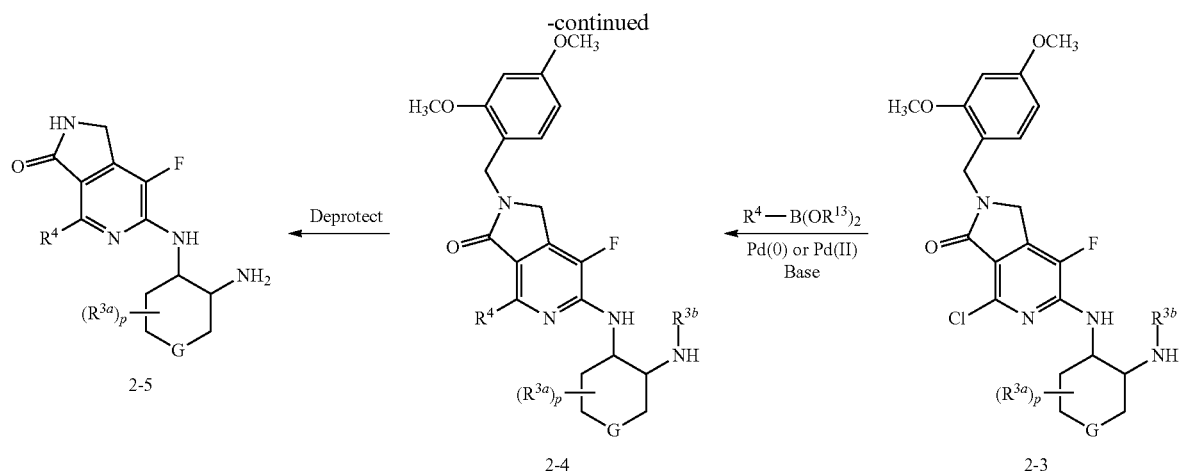

Scheme 3 depicts an alternate synthesis of compound 2-5. Starting material 3-0 (2,6-dichloro-5-fluoronicotinonitrile) is hydrolyzed by treatment with concentrated sulfuric acid at elevated temperature (e.g., about 65° C.) to give amide 3-1, which is lithiated via treatment with LiHMDS at about 0° C. or reaction with LDA in THF at −78° C. Reaction with DMF gives upon acid workup (e.g., treatment with aqueous HCl) an aldehyde (not shown) that cyclizes to form intermediate 3-2. The intermediate 3-2 is reduced to lactam 3-3 by treatment with a reducing agent (e.g., triethyl silane) and an acid (e.g., TFA) in an organic solvent (e.g., DCM). Following installation of a Boc protecting group on lactam 3-3, displacement of a chloro group on compound 3-4 via reaction with an appropriate amine 1-7 gives intermediate 3-5. The intermediate is subsequently reacted with a boronic acid or borate (e.g., $R^4$—$B(OR^{13})_2$ in the presence of a palladium catalyst (e.g., $Pd(PPh_3)_4$, $(PPh_3)_2PdCl_2$, $Pd_2(dba)_3$, etc.), an optional ligand (e.g., 2-(dicyclohexylphosphino)biphenyl), a base (e.g., KF or $Na_2CO_3$), and an organic solvent (e.g., dioxane, DMF, etc.) to give compound 3-6. The Suzuki reaction is carried out at elevated temperature (e.g., 90-160° C.), either by conventional heating or via microwave irradiation. Alternatively, compound 3-5 may be reacted with an aromatic tin reagent (e.g., $R^4$—Sn(n-Bu)$_3$) in the presence of a palladium catalyst (e.g., $Pd(PPh_3)_4$) and an organic solvent (e.g., toluene) at elevated temperature (e.g., about 100° C.). Following the Suzuki or Stille coupling, deprotection of the amine and the lactam nitrogen via treatment of 3-6, e.g. with an acid (e.g., TFA or HCl) at RT or above (e.g., 20-60° C.) when $R^{3b}$ is a Boc group, generates 2-5.

Scheme 3

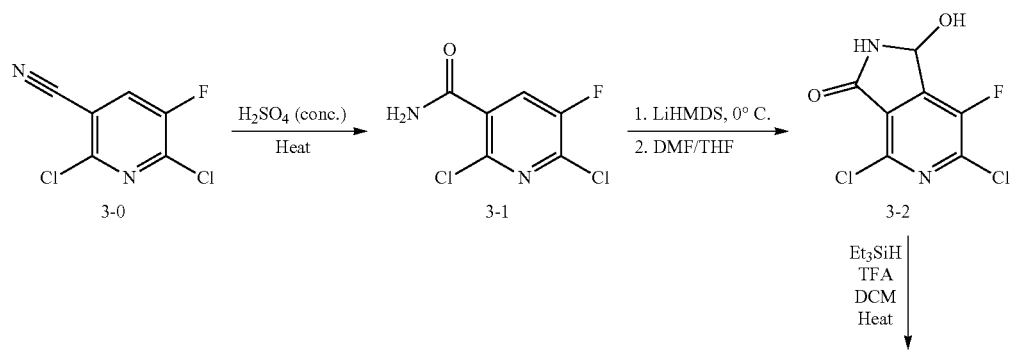

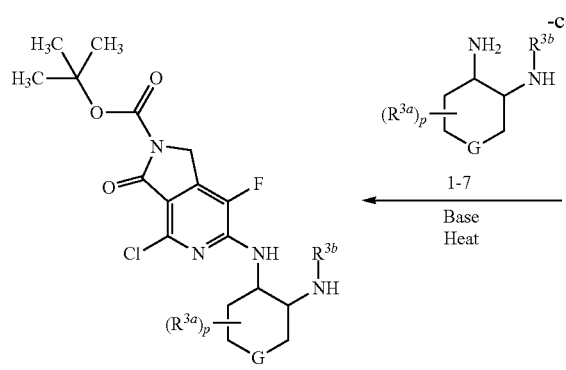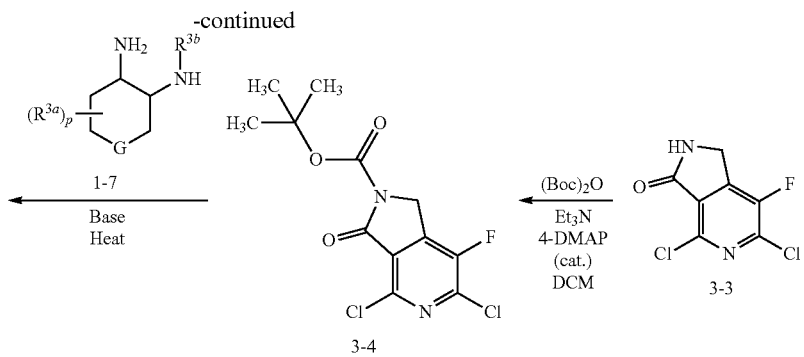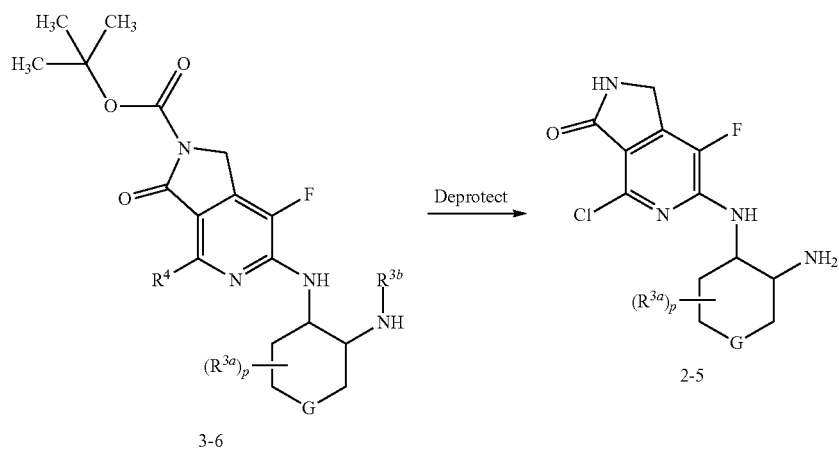

Scheme 4 depicts an alternate synthesis of intermediate 3-5. Starting material 3-0 (2,6-dichloro-5-fluoronicotinonitrile) is reacted with potassium fluoride in anhydrous DMSO to give difluoro intermediate 4-1, which is reacted with a palladium (II) catalyst (e.g., PdCl$_2$) and acetamide in THF/water at elevated temperature (e.g., about 60° C.). The resulting amide 4-2 is lithiated via treatment with LiHMDS in THF at about 0° C. or reaction with LDA in THF at −78° C. Reaction with DMF followed by acid workup gives intermediate 4-3, which is reduced to lactam 4-4 by treatment with a reducing agent (e.g., triethyl silane) and an acid (e.g., TFA) in an organic solvent (e.g., DCM). Following installation of a Boc protecting group on lactam 4-4, displacement of a fluoro group on compound 4-5 via reaction with an appropriate amine 1-7 in the presence of a base (e.g., N-methylmorpholine) and at elevated temperature (e.g., about 60° C.) gives intermediate 3-5.

Scheme 4

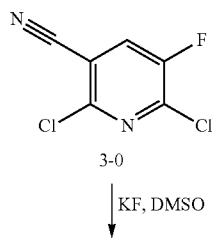

3-0

KF, DMSO

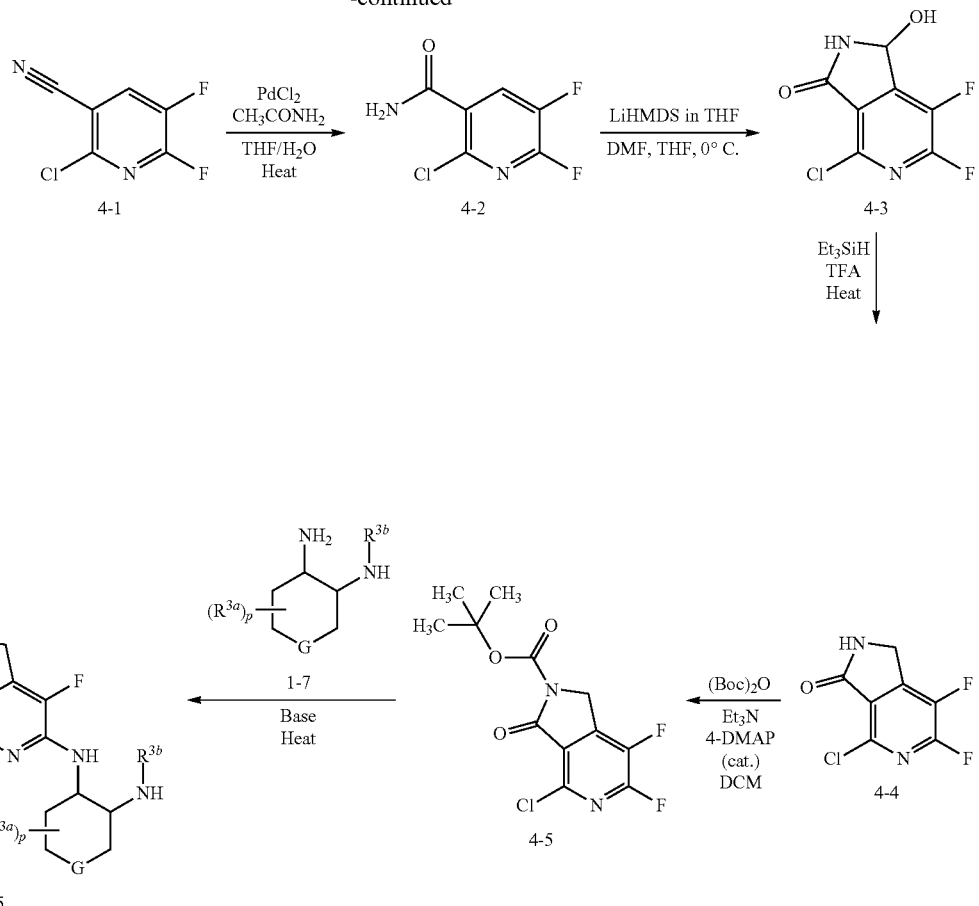

Schemes 5 and 6 show methods for preparing compound 5-7. Starting material 2-1, which may be prepared in accordance with Scheme 2, is reacted with (2,4-dimethoxyphenyl) methanamine in MeOH at room temperature. The resulting immine 5-1 is reacted with an organolithium reagent ($R^1$—Li) in THF at −78° C. Subsequent treatment with acid gives lactam 5-2, which is reacted with a reducing agent (e.g., triethyl silane) and an acid (e.g., TFA) at reflux conditions to give compound 5-3. Following installation of a Boc protecting group on the lactam nitrogen, displacement of a chloro on intermediate 5-4 via reaction with an appropriate amine 1-7 gives intermediate 5-5. The intermediate is subsequently reacted with a boronic acid or borate (e.g., $R^4$—B$(OR^{13})_2$ in the presence of a palladium catalyst (e.g., Pd(PPh$_3$)$_4$, (PPh$_3$)$_2$PdCl$_2$, Pd$_2$(dba)$_3$, etc.), an optional ligand (e.g., 2-(dicyclohexylphosphino)biphenyl), a base (e.g., KF or Na$_2$CO$_3$), and an organic solvent (e.g., dioxane, DMF, etc.) to give compound 5-6. The Suzuki reaction is carried out at elevated temperature (e.g., 90-160° C.), either by conventional heating or via microwave irradiation. Following the Suzuki coupling, deprotection of the amine and lactam nitrogen via treatment of 5-6, e.g. with an acid (e.g., TFA or HCl) at RT or above (e.g., 20-60° C.) when $R^{3b}$ is a Boc group, gives 5-7.

Scheme 5

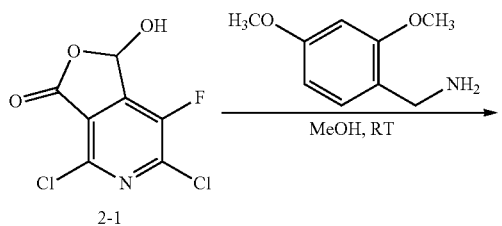

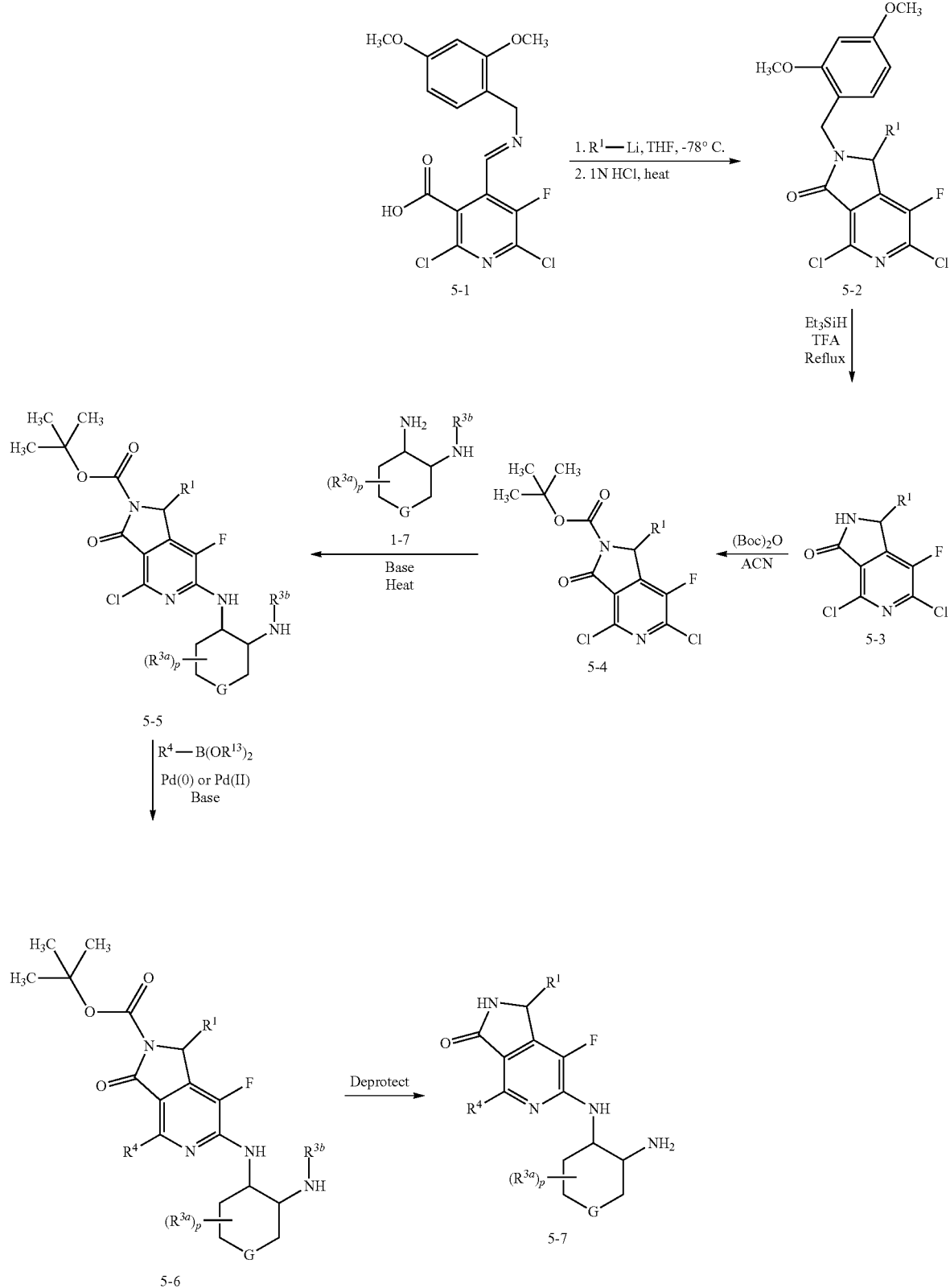
Alternatively, intermediate 5-2 may be reacted with amine 1-7 as shown in Scheme 6 to give intermediate 6-1, which is subsequently reacted with a boronic acid or borate under Suzuki conditions to give compound 6-2. Deprotection yields desired compound 5-7.

Scheme 6

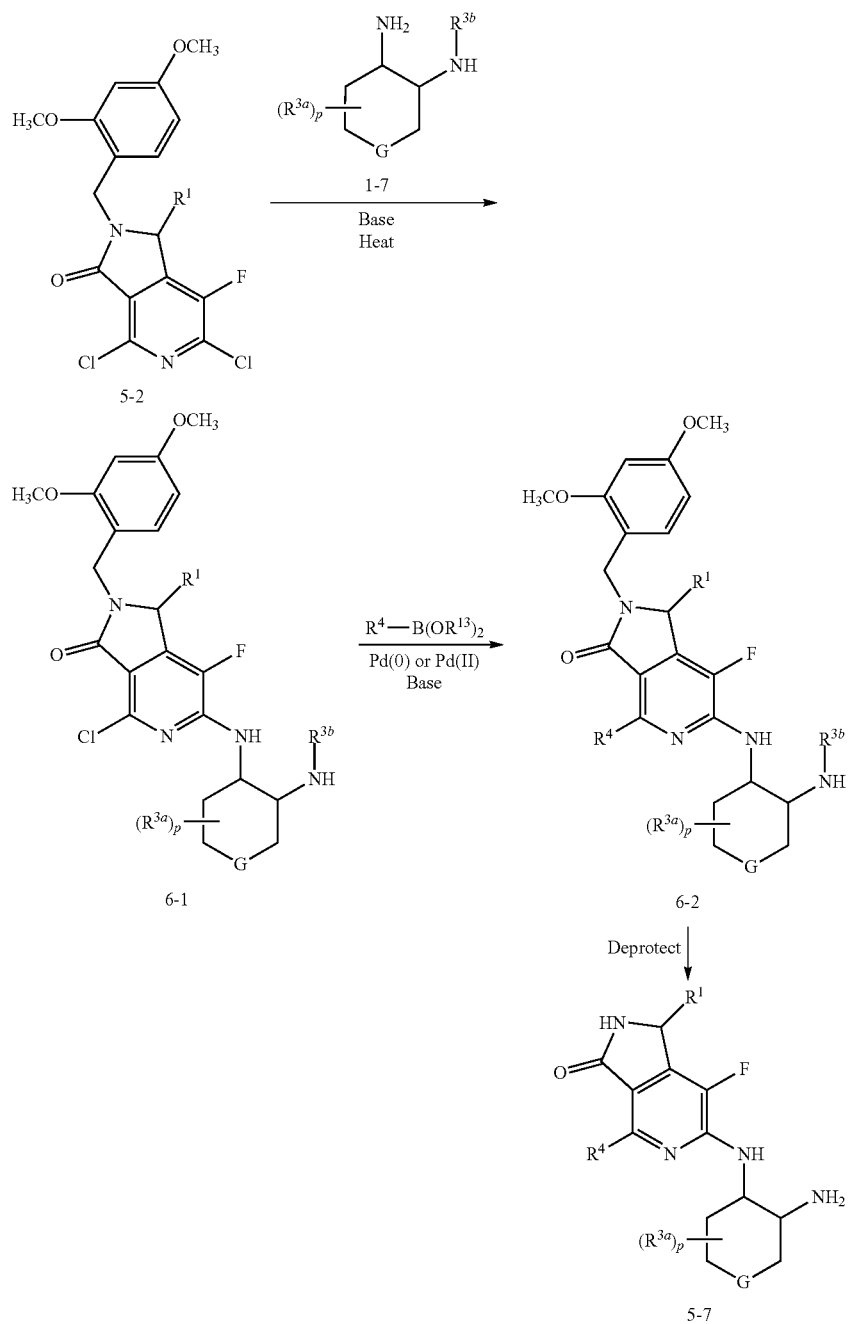

Scheme 7 illustrates methods for preparing compounds 7-2, 7-3, 7-4, 7-5, and 7-6. Starting material 7-0, which may be prepared using the methods described above, may be reacted with NBS or NIS to give halo-pyridine intermediate 7-1 ($Y^1$ is Br or I). The halo group of 7-1 may be converted to a nitrile group via palladium-catalyzed cyanation to give 7-2. Compound 7-2 may be subsequently reacted with a Grignard reagent ($R^7$—MgBr) to give an imine intermediate (not shown), which upon acid hydrolysis, yields compound 7-3. Alternatively, halo-pyridine intermediate 7-1 may be reacted with $NHR^8R^9$ in the presence of a palladium (II) catalyst (e.g., $PdCl_2$(dppf)), a stoichiometric amount of base (e.g., NaOt—Bu), and an organic solvent (e.g., dioxane, toluene, etc.), at elevated temperature (e.g., about 100° C.). The Buchwald-Hartwig coupling gives heteroaryl amine 7-4. In addition, 7-1 may be reacted with a terminal alkyne ($HCR^{13}$, e.g., $R^{13}$ is H or $C_{1-4}$ alkyl) in the presence of a palladium (II) catalyst (e.g., $(PPh_3)_2PdCl_2$), a copper (I) co-catalyst (e.g., CuI), and an amine base (e.g. $Et_3N$), at RT. Following the Sonogashira coupling, reduction of the alkyne moiety yields compound 7-5 with $R^5$ being, e.g., $C_{1-5}$ alkyl. Compound 7-1 may be reacted with a boronic acid or borate (e.g., $R^5$—$B(OR^{13})_2$, where $R^5$ is $C_{1-9}$ heteroaryl and e.g., $R^{13}$ is H or $C_{1-4}$ alkyl) in the presence of a palladium catalyst (e.g., Pd(PPh$_3$)$_4$, (PPh$_3$)$_2$PdCl$_2$, etc.), a base (e.g., KF or Na$_2$CO$_3$), and an organic solvent (e.g., dioxane, DMF, etc.). The Suzuki-type coupling is carried out at elevated temperature (e.g., about 90° C.) and gives compound 7-5 with R$^5$ being C$_{1-9}$ heteroaryl.

As shown in Scheme 7, compound 7-0 may alternatively be treated with a fluorinating agent, such as SELECT-FLUOR® (1-(chloromethyl)-4-fluoro-1,4-diazoniabicyclo[2.2.2]octane ditetrafluoroborate), in an organic solvent (e.g., DCM) or a mixture of organic solvents (e.g., DCM and MeOH), to give a fluoro-pyridine derivative 7-6 (Y$^2$ is F). Similarly, 7-0 may be treated with a chlorinating agent, such as NCS, in an aprotic solvent (e.g., DCM) to give a chloro-pyridine derivative 7-6 (Y$^2$ is Cl).

and may be obtained, for example, as solid plugs, powders, or films by methods such as precipitation, crystallization, freeze drying, spray drying, evaporative drying, microwave drying, or radio frequency drying.

Compounds of Formula 1 may be administered alone or in combination with one another or with one or more pharmacologically active compounds which are different than the compounds of Formula 1. Generally, one or more these compounds are administered as a pharmaceutical composition (a formulation) in association with one or more pharmaceutically acceptable excipients. The choice of excipients depends on the particular mode of administration, the effect of the excipient on solubility and stability, and the nature of the dosage form, among other things. Useful

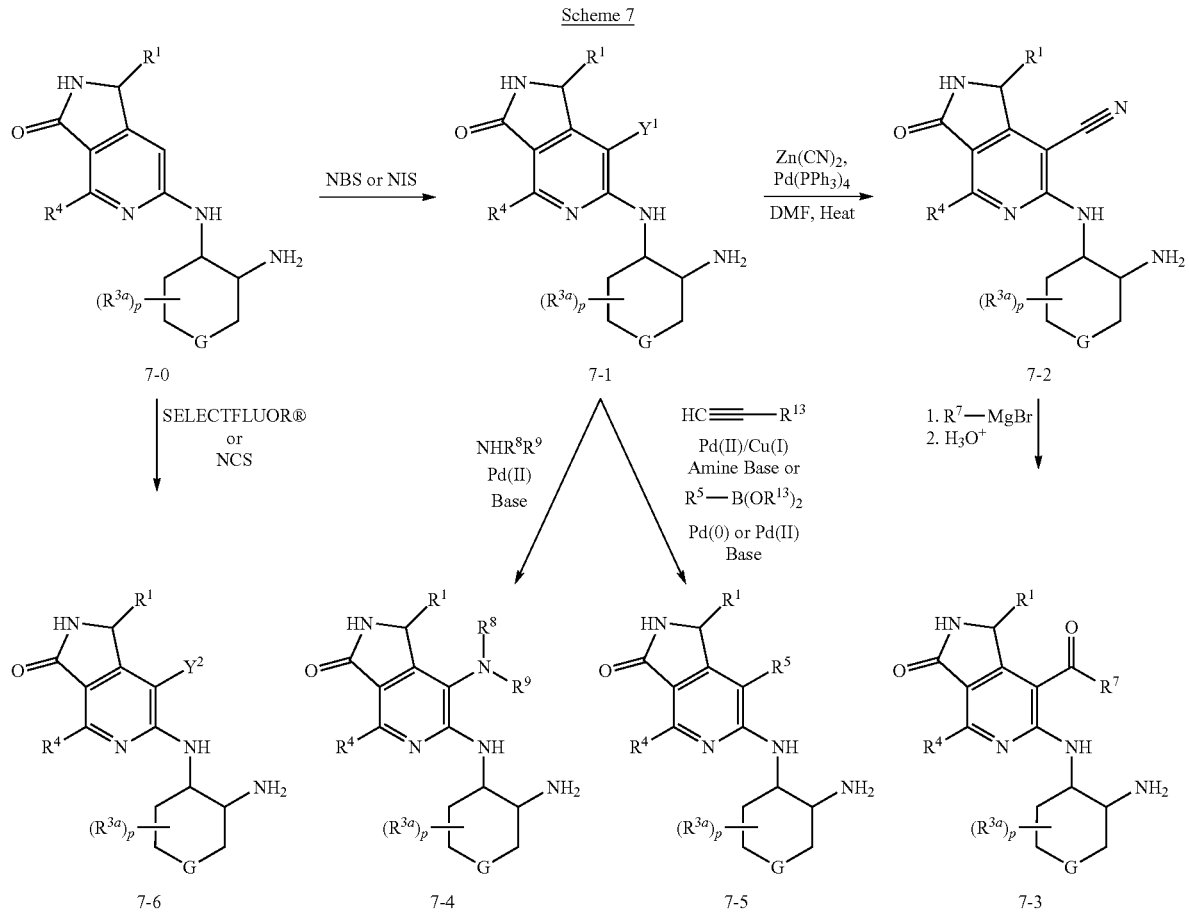

Scheme 7

The methods depicted in Schemes 1-7 may be varied as desired. For example, protecting groups may be added or removed at various steps in the routes. In addition, the intermediates may be further elaborated via, for example, alkylation, acylation, hydrolysis, oxidation, reduction, amidation, sulfonation, alkynation, alkyenation, and the like to give the desired final product.

Compounds of Formula 1, which include compounds named above, and their pharmaceutically acceptable complexes, salts, solvates and hydrates, should be assessed for their biopharmaceutical properties, such as solubility and solution stability across pH, permeability, and the like, to select an appropriate dosage form and route of administration. Compounds that are intended for pharmaceutical use may be administered as crystalline or amorphous products, pharmaceutical compositions and methods for their preparation may be found, for example, in A. R. Gennaro (ed.), Remington: The Science and Practice of Pharmacy (20th ed., 2000).

Compounds of Formula 1 may be administered orally. Oral administration may involve swallowing in which case the compound enters the bloodstream via the gastrointestinal tract. Alternatively or additionally, oral administration may involve mucosal administration (e.g., buccal, sublingual, supralingual administration) such that the compound enters the bloodstream through the oral mucosa.

Formulations suitable for oral administration include solid, semi-solid and liquid systems such as tablets; soft or hard capsules containing multi- or nano-particulates, liquids, or powders; lozenges which may be liquid-filled; chews;

gels; fast dispersing dosage forms; films; ovules; sprays; and buccal or mucoadhesive patches. Liquid formulations include suspensions, solutions, syrups and elixirs. Such formulations may be employed as fillers in soft or hard capsules (made, e.g., from gelatin or hydroxypropylmethylcellulose) and typically comprise a carrier (e.g., water, ethanol, polyethylene glycol, propylene glycol, methylcellulose, or a suitable oil) and one or more emulsifying agents, suspending agents or both. Liquid formulations may also be prepared by the reconstitution of a solid (e.g., from a sachet).

Compounds of Formula 1 may also be used in fast-dissolving, fast-disintegrating dosage forms such as those described in Liang and Chen, *Expert Opinion in Therapeutic Patents* (2001) 11(6):981-986.

For tablet dosage forms, depending on dose, the active pharmaceutical ingredient (API) may comprise from about 1 wt % to about 80 wt % of the dosage form or more typically from about 5 wt % to about 60 wt % of the dosage form. In addition to the API, tablets may include one or more disintegrants, binders, diluents, surfactants, glidants, lubricants, anti-oxidants, colorants, flavoring agents, preservatives, and taste-masking agents. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, $C_{1-6}$ alkyl-substituted hydroxypropylcellulose, starch, pregelatinized starch, and sodium alginate. Generally, the disintegrant will comprise from about 1 wt % to about 25 wt % or from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropylcellulose and hydroxypropylmethylcellulose. Tablets may also contain diluents, such as lactose (monohydrate, spray-dried monohydrate, anhydrous), mannitol, xylitol, dextrose, sucrose, sorbitol, microcrystalline cellulose, starch and dibasic calcium phosphate dihydrate.

Tablets may also include surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets may also contain lubricants such as magnesium stearate, calcium stearate, zinc stearate, sodium stearyl fumarate, and mixtures of magnesium stearate with sodium lauryl sulfate. Lubricants may comprise from about 0.25 wt % to about 10 wt % or from about 0.5 wt % to about 3 wt % of the tablet.

Tablet blends may be compressed directly or by roller compaction to form tablets. Tablet blends or portions of blends may alternatively be wet-, dry-, or melt-granulated, melt congealed, or extruded before tableting. If desired, prior to blending one or more of the components may be sized by screening or milling or both. The final dosage form may comprise one or more layers and may be coated, uncoated, or encapsulated. Exemplary tablets may contain up to about 80 wt % of API, from about 10 wt % to about 90 wt % of binder, from about 0 wt % to about 85 wt % of diluent, from about 2 wt % to about 10 wt % of disintegrant, and from about 0.25 wt % to about 10 wt % of lubricant. For a discussion of blending, granulation, milling, screening, tableting, coating, as well as a description of alternative techniques for preparing drug products, see A. R. Gennaro (ed.), *Remington: The Science and Practice of Pharmacy* (20th ed., 2000); H. A. Lieberman et al. (ed.), *Pharmaceutical Dosage Forms: Tablets*, Vol. 1-3 (2d ed., 1990); and D. K. Parikh & C. K. Parikh, *Handbook of Pharmaceutical Granulation Technology*, Vol. 81 (1997).

Consumable oral films for human or veterinary use are pliable water-soluble or water-swellable thin film dosage forms which may be rapidly dissolving or mucoadhesive. In addition to the API, a typical film includes one or more film-forming polymers, binders, solvents, humectants, plasticizers, stabilizers or emulsifiers, viscosity-modifying agents, and solvents. Other film ingredients may include anti-oxidants, colorants, flavorants and flavor enhancers, preservatives, salivary stimulating agents, cooling agents, co-solvents (including oils), emollients, bulking agents, anti-foaming agents, surfactants, and taste-masking agents. Some components of the formulation may perform more than one function.

In addition to dosing requirements, the amount of API in the film may depend on its solubility. If water soluble, the API would typically comprise from about 1 wt % to about 80 wt % of the non-solvent components (solutes) in the film or from about 20 wt % to about 50 wt % of the solutes in the film. A less soluble API may comprise a greater proportion of the composition, typically up to about 88 wt % of the non-solvent components in the film.

The film-forming polymer may be selected from natural polysaccharides, proteins, or synthetic hydrocolloids and typically comprises from about 0.01 wt % to about 99 wt % or from about 30 wt % to about 80 wt % of the film.

Film dosage forms are typically prepared by evaporative drying of thin aqueous films coated onto a peelable backing support or paper, which may carried out in a drying oven or tunnel (e.g., in a combined coating-drying apparatus), in lyophilization equipment, or in a vacuum oven.

Useful solid formulations for oral administration may include immediate release formulations and modified release formulations. Modified release formulations include delayed-, sustained-, pulsed-, controlled-, targeted-, and programmed-release. For a general description of suitable modified release formulations, see U.S. Pat. No. 6,106,864. For details of other useful release technologies, such as high energy dispersions and osmotic and coated particles, see Verma et al, *Pharmaceutical Technology On-line* (2001) 25(2):1-14.

Compounds of Formula 1 may also be administered directly into the blood stream, muscle, or an internal organ of the subject. Suitable techniques for parenteral administration include intravenous, intraarterial, intraperitoneal, intrathecal, intraventricular, intraurethral, intrasternal, intracranial, intramuscular, intrasynovial, and subcutaneous administration. Suitable devices for parenteral administration include needle injectors, including microneedle injectors, needle-free injectors, and infusion devices.

Parenteral formulations are typically aqueous solutions which may contain excipients such as salts, carbohydrates and buffering agents (e.g., pH of from about 3 to about 9). For some applications, however, compounds of Formula 1 may be more suitably formulated as a sterile non-aqueous solution or as a dried form to be used in conjunction with a suitable vehicle such as sterile, pyrogen-free water. The preparation of parenteral formulations under sterile conditions (e.g., by lyophilization) may be readily accomplished using standard pharmaceutical techniques.

The solubility of compounds which are used in the preparation of parenteral solutions may be increased through appropriate formulation techniques, such as the incorporation of solubility-enhancing agents. Formulations for parenteral administration may be formulated to be immediate or modified release. Modified release formulations include delayed, sustained, pulsed, controlled, targeted, and programmed release. Thus, compounds of Formula 1 may be formulated as a suspension, a solid, a semi-solid, or a thixotropic liquid for administration as an implanted depot providing modified release of the active compound. Examples of such formulations include drug-coated stents and semi-solids and suspensions comprising drug-loaded poly(DL-lactic-coglycolic)acid (PGLA) microspheres.

Compounds of Formula 1 may also be administered topically, intradermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers may include alcohol, water, mineral oil, liquid petrolatum, white petrolatum, glycerin, polyethylene glycol and propylene glycol. Topical formulations may also include penetration enhancers. See, e.g., Finnin and Morgan, *J. Pharm. Sci.* 88(10): 955-958 (1999).

Other means of topical administration include delivery by electroporation, iontophoresis, phonophoresis, sonophoresis and microneedle or needle-free (e.g. Powderject™ and Bioject™) injection. Formulations for topical administration may be formulated to be immediate or modified release as described above.

Compounds of Formula 1 may also be administered intranasally or by inhalation, typically in the form of a dry powder, an aerosol spray, or nasal drops. An inhaler may be used to administer the dry powder, which comprises the API alone, a powder blend of the API and a diluent, such as lactose, or a mixed component particle that includes the API and a phospholipid, such as phosphatidylcholine. For intranasal use, the powder may include a bioadhesive agent, e.g., chitosan or cyclodextrin. A pressurized container, pump, sprayer, atomizer, or nebulizer, may be used to generate the aerosol spray from a solution or suspension comprising the API, one or more agents for dispersing, solubilizing, or extending the release of the API (e.g., EtOH with or without water), one or more solvents (e.g., 1,1,1,2-tetrafluoroethane or 1,1,1,2,3,3,3-heptafluoropropane) which serve as a propellant, and an optional surfactant, such as sorbitan trioleate, oleic acid, or an oligolactic acid. An atomizer using electrohydrodynamics may be used to produce a fine mist.

Prior to use in a dry powder or suspension formulation, the drug product is usually comminuted to a particle size suitable for delivery by inhalation (typically 90% of the particles, based on volume, having a largest dimension less than 5 microns). This may be achieved by any appropriate size reduction method, such as spiral jet milling, fluid bed jet milling, supercritical fluid processing, high pressure homogenization, or spray drying.

Capsules, blisters and cartridges (made, for example, from gelatin or hydroxypropylmethyl cellulose) for use in an inhaler or insufflator may be formulated to contain a powder mixture of the active compound, a suitable powder base such as lactose or starch, and a performance modifier such as L-leucine, mannitol, or magnesium stearate. The lactose may be anhydrous or monohydrated. Other suitable excipients include dextran, glucose, maltose, sorbitol, xylitol, fructose, sucrose, and trehalose.

A suitable solution formulation for use in an atomizer using electrohydrodynamics to produce a fine mist may contain from about 1 µg to about 20 mg of the API per actuation and the actuation volume may vary from about 1 µL to about 100 µL. A typical formulation may comprise one or more compounds of Formula 1, propylene glycol, sterile water, EtOH, and NaCl. Alternative solvents, which may be used instead of propylene glycol, include glycerol and polyethylene glycol.

Formulations for inhaled administration, intranasal administration, or both, may be formulated to be immediate or modified release using, for example, PGLA. Suitable flavors, such as menthol and levomenthol, or sweeteners, such as saccharin or sodium saccharin, may be added to formulations intended for inhaled/intranasal administration.

In the case of dry powder inhalers and aerosols, the dosage unit is determined by means of a valve that delivers a metered amount. Units are typically arranged to administer a metered dose or "puff" containing from about 10 µg to about 1000 µg of the API. The overall daily dose will typically range from about 100 µg to about 10 mg which may be administered in a single dose or, more usually, as divided doses throughout the day.

The active compounds may be administered rectally or vaginally, e.g., in the form of a suppository, pessary, or enema. Cocoa butter is a traditional suppository base, but various alternatives may be used as appropriate. Formulations for rectal or vaginal administration may be formulated to be immediate or modified release as described above.

Compounds of Formula 1 may also be administered directly to the eye or ear, typically in the form of drops of a micronized suspension or solution in isotonic, pH-adjusted, sterile saline. Other formulations suitable for ocular and aural administration include ointments, gels, biodegradable implants (e.g. absorbable gel sponges, collagen), non-biodegradable implants (e.g. silicone), wafers, lenses, and particulate or vesicular systems, such as niosomes or liposomes. The formulation may include one or more polymers and a preservative, such as benzalkonium chloride. Typical polymers include crossed-linked polyacrylic acid, polyvinylalcohol, hyaluronic acid, cellulosic polymers (e.g., hydroxypropylmethylcellulose, hydroxyethylcellulose, methyl cellulose), and heteropolysaccharide polymers (e.g., gelan gum). Such formulations may also be delivered by iontophoresis. Formulations for ocular or aural administration may be formulated to be immediate or modified release as described above.

To improve their solubility, dissolution rate, taste-masking, bioavailability, or stability, compounds of Formula 1 may be combined with soluble macromolecular entities, including cyclodextrin and its derivatives and polyethylene glycol-containing polymers. For example, API-cyclodextrin complexes are generally useful for most dosage forms and routes of administration. Both inclusion and non-inclusion complexes may be used. As an alternative to direct complexation with the API, the cyclodextrin may be used as an auxiliary additive, i.e. as a carrier, diluent, or solubilizer. Alpha-, beta- and gamma-cyclodextrins are commonly used for these purposes. See, e.g., WO 91/11172, WO 94/02518, and WO 98/55148.

As noted above, one or more compounds of Formula 1, including compounds specifically named above, and their pharmaceutically active complexes, salts, solvates and hydrates, may be combined with each other or with one or more other active pharmaceutically active compounds to treat various diseases, conditions and disorders. In such cases, the active compounds may be combined in a single dosage form as described above or may be provided in the form of a kit which is suitable for coadministration of the compositions. The kit comprises (1) two or more different pharmaceutical compositions, at least one of which contains a compound of Formula 1; and (2) a device for separately retaining the two pharmaceutical compositions, such as a divided bottle or a divided foil packet. An example of such a kit is the familiar blister pack used for the packaging of tablets or capsules. The kit is suitable for administering different types of dosage forms (e.g., oral and parenteral) or for administering different pharmaceutical compositions at separate dosing intervals, or for titrating the different pharmaceutical compositions against one another. To assist with patient compliance, the kit typically comprises directions for administration and may be provided with a memory aid.

For administration to human patients, the total daily dose of the claimed and disclosed compounds is typically in the range of about 0.1 mg to about 3000 mg depending on the route of administration. For example, oral administration may require a total daily dose of from about 1 mg to about 3000 mg, while an intravenous dose may only require a total daily dose of from about 0.1 mg to about 300 mg. The total daily dose may be administered in single or divided doses and, at the physician's discretion, may fall outside of the typical ranges given above. Although these dosages are based on an average human subject having a mass of about 60 kg to about 70 kg, the physician will be able to determine the appropriate dose for a patient (e.g., an infant) whose mass falls outside of this weight range.

As noted above, the compounds of Formula 1 may be used to treat disorders, diseases, and conditions for which inhibition of SYK is indicated. Such disorders, diseases, and conditions generally relate to any unhealthy or abnormal state in a subject for which the inhibition of SYK provides a therapeutic benefit. More particularly, such disorders, diseases, and conditions may involve the immune system and inflammation, including Type I hypersensitivity (allergic) reactions (allergic rhinitis, allergic asthma, and atopic dermatitis); autoimmune diseases (rheumatoid arthritis, multiple sclerosis, systemic lupus erythematosus, psoriasis, and immune thrombocytopenic purpura); inflammation of the lung (chronic obstructive pulmonary disease) and thrombosis. The compounds of Formula 1 may also be used to treat disorders, diseases, and conditions related to abnormal cell growth, including hematological malignancies, such as acute myeloid leukemia, B-cell chronic lymphocytic leukemia, B-cell lymphoma (e.g., mantle cell lymphoma), and T-cell lymphoma (e.g., peripheral T-cell lymphoma), as well as epithelial cancers (i.e., carcinomas), such as lung cancer (small cell lung cancer and non-small cell lung cancer), pancreatic cancer, and colon cancer.

In addition to the hematological malignancies and epithelial cancers noted above, the compounds of Formula 1 may also be used to treat other types of cancer, including leukemia (chronic myelogenous leukemia and chronic lymphocytic leukemia); breast cancer, genitourinary cancer, skin cancer, bone cancer, prostate cancer, and liver cancer; brain cancer; cancer of the larynx, gall bladder, rectum, parathyroid, thyroid, adrenal, neural tissue, bladder, head, neck, stomach, bronchi, and kidneys; basal cell carcinoma, squamous cell carcinoma, metastatic skin carcinoma, osteosarcoma, Ewing's sarcoma, veticulum cell sarcoma, and Kaposi's sarcoma; myeloma, giant cell tumor, islet cell tumor, acute and chronic lymphocytic and granulocytic tumors, hairy-cell tumor, adenoma, medullary carcinoma, pheochromocytoma, mucosal neuromas, intestinal ganglioneuromas, hyperplastic corneal nerve tumor, marfanoid habitus tumor, Wilms' tumor, seminoma, ovarian tumor, leiomyomater tumor, cervical dysplasia, neuroblastoma, retinoblastoma, myelodysplastic syndrome, rhabdomyosarcoma, astrocytoma, non-Hodgkin's lymphoma, malignant hypercalcemia, polycythermia vera, adenocarcinoma, glioblastoma multiforma, glioma, lymphomas, and malignant melanomas, among others.

In addition to cancer, the compounds of Formula 1 may also be used to treat other diseases related to abnormal cell growth, including non-malignant proliferative diseases such as benign prostatic hypertrophy, restinosis, hyperplasia, synovial proliferation disorder, retinopathy or other neovascular disorders of the eye, among others.

The compounds of Formula 1 may also be used to treat autoimmune disorders in addition to those listed above. Such disorders, diseases, and conditions include Crohns disease, dermatomyositis, diabetes mellitus type 1, Goodpasture's syndrome, Graves' disease, Guillain-Barré syndrome, Hashimoto's disease, mixed connective tissue damage, myasthenia gravis, narcolepsy, *pemphigus vulgaris*, pernicious anemia, polymyositis, primary biliary cirrhosis, Sjögren's syndrome, temporal arteritis, ulcerative colitis, vasculitis, and Wegener's granulomatosis, among others.

Furthermore, compounds of Formula 1 may be used to treat inflammatory disorders including asthma, chronic inflammation, chronic prostatitis, glomerulonephritis, hypersensitivities, inflammatory bowel diseases (ulcerative colitis in addition to Crohn's disease), pelvic inflammatory disease, reperfusion injury, transplant rejection, graft versus host disease, vasculitis, and systemic inflammatory response syndrome.

The compounds of Formula 1 may also be used to treat specific diseases that may fall within one or more general disorders described above, including arthritis. In addition to rheumatoid arthritis, Sjögren's syndrome, systemic lupus erythematosus, SLE in children and adolescents, compounds of Formula 1 may also be used to treat other arthritis diseases, including ankylosing spondylitis, avascular necrosis, Behcet's disease, bursitis, calcium pyrophosphate dihyrate crystal deposition disease (pseudo gout), carpal tunnel syndrome, Ehlers-Danlos syndrome, fibromyalgia, Fifth disease, giant cell arteritis, gout, juvenile dermatomyositis, juvenile rheumatoid arthritis, juvenile spondyloarthopathy, Lyme disease, Marfan syndrome, myositis, osteoarthritis, osteogenesis imperfect, osteoporosis, Paget's disease, psoriatic arthritis, Raynaud's phenomenon, reactive arthritis, reflex sympathetic dystrophy syndrome, scleroderma, spinal stenosis, Still's disease, and tendinitis, among others.

The claimed and disclosed compounds may be combined with one or more other pharmacologically active compounds or therapies for the treatment of one or more disorders, diseases or conditions for which SYK is indicated, including disorders, diseases, and conditions involving the immune system, inflammation, and abnormal cell growth. For example, compounds of Formula 1, which include compounds specifically named above, and their pharmaceutically acceptable complexes, salts, solvates and hydrates, may be administered simultaneously, sequentially or separately in combination with one or more compounds or therapies for treating arthritis, including rheumatoid arthritis and osteoarthritis, or for treating cancer, including hematological malignancies, such as acute myeloid leukemia, B-cell chronic lymphocytic leukemia, B-cell lymphoma, and T-cell lymphoma, and carcinomas, such as lung cancer, pancreatic cancer, and colon cancer. Such combinations may offer significant therapeutic advantages, including fewer side effects, improved ability to treat underserved patient populations, or synergistic activity.

For example, when used to treat arthritis, the compounds of Formula 1 may be combined with one or more nonsteroidal anti-inflammatory drugs (NSAIDs), analgesics, corticosteroids, biological response modifiers, and protein-A immunoadsorption therapy. Alternatively or additionally, when treating rheumatoid arthritis, the compounds of Formula 1 may be combined with one or more disease modifying antirheumatic drugs (DMARDs), and when treating osteoarthritis, the compounds of Formula 1 may be combined with one or more osteoporosis agents.

Representative NSAIDs include apazone, aspirin, celecoxib, diclofenac (with and without misoprostol), diflunisal, etodolac, fenoprofen, flurbiprofen, ibuprofen, indomethacin, ketoprofen, meclofenamate sodium, mefenamic acid, meloxicam, nabumetone, naproxen, oxaprozin, phenylbutazone, piroxicam, choline and magnesium salicylates, salsalate, and sulindac. Representative analgesics include acetaminophen and morphine sulfate, as well as codeine, hydrocodone, oxycodone, propoxyphene, and tramadol, all with or without acetaminophen. Representative corticosteroids include betamethasone, cortisone acetate, dexamethasone, hydrocortisone, methylprednisolone, prednisolone, and prednisone. Representative biological response modifiers include TNF-α inhibitors, such as adalimumab, etanercept, and infliximab; selective B-cell inhibitors, such as rituximab; IL-1 inhibitors, such as anakinra, and selective costimulation modulators, such as abatacept.

Representative DMARDs include auranofin (oral gold), azathioprine, chlorambucil, cyclophosamide, cyclosporine, gold sodium thiomalate (injectable gold), hydroxychloroquine, leflunomide, methotrexate, minocycline, myophenolate mofetil, penicillamine, and sulfasalazine. Representative osteoporosis agents include bisphosphonates, such as alendronate, ibandronate, risedronate, and zoledronic acid; selective estrogen receptor modulators, such as droloxifene, lasofoxifene, and raloxifene; hormones, such as calcitonin, estrogens, and parathyroid hormone; and immunosuppressant agents such as azathioprine, cyclosporine, and rapamycin.

Particularly useful combinations for treating rheumatoid arthritis include a compound of Formula 1 and methotrexate; a compound of Formula 1 and one or more biological response modifiers, such as lefluonomide, etanercept, adalimumab, and infliximab; or a compound of Formula 1, methotrexate, and one or more biological response modifiers, such as lefluonomide, etanercept, adalimumab, and infliximab.

For the treatment of thrombis and restenosis, the compounds of Formula 1 may be combined with one or more cardiovascular agents such as calcium channel blockers, statins, fibrates, beta-blockers, ACE inhibitors, and platelet aggregation inhibitors.

The compounds of Formula 1 may also be combined with one or more compounds or therapies for treating cancer. These include chemotherapeutic agents (i.e., cytotoxic or antineoplastic agents) such as alkylating agents, antibiotics, antimetabolic agents, plant-derived agents, and topoisomerase inhibitors, as well as molecularly targeted drugs which block the growth and spread of cancer by interfering with specific molecules involved in tumor growth and progression. Molecularly targeted drugs include both small molecules and biologics.

Representative alkylating agents include bischloroethylamines (nitrogen mustards, e.g., chlorambucil, cyclophosphamide, ifosfamide, mechlorethamine, melphalan, and uracil mustard); aziridines (e.g., thiotepa); alkyl alkone sulfonates (e.g., busulfan); nitrosoureas (e.g., carmustine, lomustine, and streptozocin); nonclassical alkylating agents (e.g., altretamine, dacarbazine, and procarbazine); and platinum compounds (e.g., carboplatin, cisplatin, nedaplatin, oxaliplatin, satraplatin, and triplatin tetranitrate).

Representative antibiotic agents include anthracyclines (e.g., aclarubicin, amrubicin, daunorubicin, doxorubicin, epirubicin, idarubicin, pirarubicin, valrubicin, and zorubicin); anthracenediones (e.g., mitoxantrone and pixantrone); and *streptomyces* (e.g., actinomycin, bleomycin, dactinomycin, mitomycin C, and plicamycin).

Representative antimetabolic agents include dihydrofolate reductase inhibitors (e.g., aminopterin, methotrexate, and pemetrexed); hymidylate synthase inhibitors (e.g., raltitrexed and pemetrexed); folinic acid (e.g., leucovorin); adenosine deaminase inhibitors (e.g., pentostatin); halogenated/ribonucleotide reductase inhibitors (e.g., cladribine, clofarabine, and fludarabine); thiopurines (e.g., thioguanine and mercaptopurine); thymidylate synthase inhibitors (e.g., fluorouracil, capecitabine, tegafur, carmofur, and floxuridine); DNA polymerase inhibitors (e.g., cytarabine); ribonucleotide reductase inhibitors (e.g., gemcitabine); hypomethylating agent (e.g., azacitidine and decitabine); and ribonucleotide reductase inhibitor (e.g., hydroxyurea); and an asparagine depleter (e.g., asparaginase)

Representative plant-derived agents include *vinca* alkaloids (e.g., vincristine, vinblastine, vindesine, vinzolidine, and vinorelbine), podophyllotoxins (e.g., etoposide and teniposide), and taxanes (e.g., docetaxel, larotaxel, ortataxel, paclitaxel, and tesetaxel).

Representative type I topoisomerase inhibitors include camptothecins, such as belotecan, irinotecan, rubitecan, and topotecan. Representative type II topoisomerase inhibitors include amsacrine, etoposide, etoposide phosphate, and teniposide, which are derivatives of epipodophyllotoxins.

Molecularly targeted therapies include biologic agents such as cytokines and other immune-regulating agents. Useful cytokines include interleukin-2 (IL-2, aldesleukin), interleukin 4 (IL-4), interleukin 12 (IL-12), and interferon, which includes more than 23 related subtypes. Other cytokines include granulocyte colony stimulating factor (CSF) (filgrastim) and granulocyte macrophage CSF (sargramostim). Other immuno-modulating agents include *bacillus* Calmette-Guerin, levamisole, and octreotide; monoclonal antibodies against tumor antigens, such as trastruzumab and rituximab; and cancer vaccines, which induce an immune response to tumors.

In addition, molecularly targeted drugs that interfere with specific molecules involved in tumor growth and progression include inhibitors of epidermal growth factor (EGF), transforming growth factor-alpha (TGF$_\alpha$), TGF$_\beta$, heregulin, insulin-like growth factor (IGF), fibroblast growth factor (FGF), keratinocyte growth factor (KGF), colony stimulating factor (CSF), erythropoietin (EPO), interleukin-2 (IL-2), nerve growth factor (NGF), platelet-derived growth factor (PDGF), hetaptocyte growth factor (HGF), vascular endothelial growth factor (VEGF), angiopoietin, epidermal growth factor receptor (EGFR), human epidermal growth factor receptor 2 (HER2), HER4, insulin-like growth factor 1 receptor (IGF1R), IGF2R, fibroblast growth factor 1 receptor (FGF1R), FGF2R, FGF3R, FGF4R, vascular endothelial growth factor receptor (VEGFR), tyrosine kinase with immunoglobulin-like and epidermal growth factor-like domains 2 (Tie-2), platelet-derived growth factor receptor (PDGFR), Abl, Bcr-Abl, Raf, FMS-like tyrosine kinase 3 (FLT3), c-Kit, Src, protein kinase c (PKC), tropomyosin receptor kinase (Trk), Ret, mammalian target of rapamycin (mTOR), Aurora kinase, polo-like kinase (PLK), mitogen activated protein kinase (MAPK), mesenchymal-epithelial transition factor (c-MET), cyclin-dependant kinase (CDK), Akt, extracellular signal-regulated kinases (ERK), poly(ADP) ribose polymerase (PARP), and the like.

Specific molecularly targeted drugs include selective estrogen receptor modulators, such as tamoxifen, toremifene, fulvestrant, and raloxifene; antiandrogens, such as bicalutamide, nilutamide, megestrol, and flutamide; and aromatase inhibitors, such as exemestane, anastrozole, and letrozole. Other specific molecularly targeted drugs include agents which inhibit signal transduction, such as imatinib, dasatinib, nilotinib, trastuzumab, gefitinib, erlotinib, cetuximab, lapatinib, panitumumab, and temsirolimus; agents that induce apoptosis, such as bortezomib; agents that block angiogensis, such as bevacizumab, sorafenib, and sunitinib; agents that help the immune system destroy cancel cells, such as rituximab and alemtuzumab; and monoclonal antibodies which deliver toxic molecules to cancer cells, such as gemtuzumab ozogamicin, tositumomab, 131I-tositumoab, and ibritumomab tiuxetan.

Biological Activity: SYK Inhibition

The ability of compounds to inhibit SYK activity may be assessed using a variety of methods, including in vitro and in vivo assays. The following in vitro assay measures a test compound's ability to inhibit SYK-mediated phosphorylation of a FAM-labeled SYK-specific substrate (5FAM-KKKKEEIYFFFG-$NH_2$).

SYK protein is prepared from cDNA encoding human spleen tyrosine kinase and is expressed in insect cells using a baculovirus expression vector. The cDNA (IMAGE: 3542895) is purchased from Open Biosystems. The SYK kinase domain (residues 356-635) is amplified via PCR and cloned into plasmid pFastBacl (Invitrogen) at BamHI/XbaI sites. Recombinant plasmid encoding Met-Ala-Lys-SYK (356-635)-HHHHHH is sequenced and transformed into *E. coli* DH10Bac strain. The recombinant bacmid DNA is isolated and transfected into Sf9 insect cells. Recombinant virus is harvested 72 h after transfection. High titer viral stock is prepared by infecting Sf9 cells at a multiplicity of infection (MOI) of approximately 0.01. A suspension of Sf9 cells (10 L) is infected with recombinant virus (MOI=5) and is incubated in a Wave Bioreactor (GE-Healthcare) for 48 h. The cells are harvested and stored at −80° C.

To purify the expressed protein, the frozen Sf9 cells (10 L) are broken into small (<1 cm) particles and suspended in a lysis buffer (300 mL) containing 20 mM Tris (pH 7.6), 0.25 mM TCEP, 100 mM NaCl, 5% glycerol and a protease inhibitor. The suspension is stirred at RT until completely thawed, lysed an additional 2-4 min on a rotary blade homogenizer, and then centrifuged at 4200 g for 1 h. Following centrifugation, the supernatant is poured through cheese cloth and combined with a nickel chelating resin (Probond Resin™, Invitrogen) which is pre-equilibrated in a wash buffer containing 10 mM Tris (pH 7.6), 0.25 mM TCEP, 300 mM NaCl, 5% glycerol, and 20 mM imidazole. The mixture is agitated for 3 h in a cold room and then centrifuged at 900 g for 10 min. The resin is dispersed in wash buffer (50 mL), centrifuged for 10 min at 900 g, re-dispersed in a small amount of wash buffer (5 mL), and then pour into a disposable Poly-Prep chromatography column, through which wash buffer is passed by gravity until no protein is observed in coomassie buffer (about 120 mL of wash buffer). An elution buffer (30 mL) containing 10 mM HEPES (pH 7.4), 150 mM NaCl, 10% glycerol, 5 mM DTT, and 400 mM imidazole is used to elute the SYK protein from the resin. The eluate is concentrated (5 mL) and further purified on a Superdex 200 column (1.2 mL/min for 160 min, 10 mM HEPES (pH 7.4), 10 mM NaCl, 10 mM MgCl, 0.1 mM EDTA, and 0.25 mM TCEP). The chromatographed fractions are run on SDS-PAGE and the requisite fractions are pooled and concentrated. Final delivery buffer is 10 mM HEPES (pH 7.4), 10 mM Methione, 150 mM NaCl, 10% glycerol, 5 mM DTT.

SYK inhibition is determined using a black 384 well plate format in buffer containing 50 mM HEPES, 10 mM NaCl, 10 mM $MgCl_2$, 0.2 mM EDTA, 0.01% EDA (Brij®35), 1 mM DTT, and 0.1 mg/ml BSA at pH 7.3. Each test compound is prepared in DMSO using 2-fold serial dilutions for 11 data points, which are added to the buffer so that each dilution contains 3% DMSO. To each well is added 2 μL of 3 μM SFAM-KKKKEEIYFFFG-$NH_2$ (in buffer), 2 μL of diluted test compound (3% DMSO in buffer), and 2 μL of 2.4 nM SYK and 45 μM ATP (in buffer). The reaction mixture is incubated at RT for 60 min, and quenched by adding 50 mM Hepes, 30 mM EDTA, 0.1% Triton X-100 (pH 7.3). To quantify the fluorescent-labeled substrate and product following reaction, the test plate is loaded on a Caliper LC-3000, which measures percent of conversion by microfluidic-based separation. Corresponding $IC_{50}$ values are calculated by non-linear curve fitting of the compound concentrations and percent of inhibition to the standard $IC_{50}$ equation and reported as $pIC_{50}$, i.e., $-\log(IC_{50})$, where $IC_{50}$ is molar concentration.

EXAMPLES

The following examples are intended to be illustrative and non-limiting, and represent specific embodiments of the present invention.

$^1$H nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), spt (septet) and br (broad). The mass spectra (m/z) were recorded using either electrospray ionization (ESI) or atmospheric pressure chemical ionization (APCI). The following abbreviations are used for common solvents: $CDCl_3$ (deuterochloroform), DMSO-$d_6$ (deuterodimethylsulfoxide), $CD_3OD$ (deuteromethanol), and THF-$d_8$ (deuterotetrahydrofuran). "Ammonia" refers to a concentrated solution of ammonia in water possessing a specific gravity of 0.88.

Where indicated, products of certain preparations and examples are purified by mass-triggered HPLC (e.g., Pump: Waters™ 2525; MS: ZQ™; Software: MassLynx™) flash chromatography or preparative thin layer chromatography (TLC). Preparative HPLC is carried out using either acidic or basic conditions. Acid conditions are typically gradients in Solvent A (water with 0.05% TFA) and Solvent B (acetonitrile with 0.035% TFA); basic conditions are typically gradients in Solvent A (10 mM $NH_4HCO_3$ in water) and Solvent B (10 mM $NH_4HCO_3$ in 20/80 (v/v) water/acetonitrile). The mentioned preparative HPLC conditions use acidic conditions unless indicated as basic. Preparative TLC is typically carried out on silica gel 60 $F_{254}$ plates. After isolation by chromatography, the solvent is removed and the product is obtained by drying in a centrifugal evaporator (e.g., GeneVac™) rotary evaporator, evacuated flask, lyophilizer, etc. Reactions in an inert (e.g., nitrogen) or reactive (e.g., $H_2$) atmosphere are typically carried out at a pressure of about 1 atmosphere (14.7 psi) or greater.

Preparation 1

3-(Difluoromethyl)-5-(tributylstannyl)isothiazole

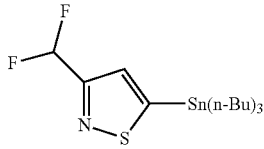

Step A: Isothiazol-3-ylmethanol

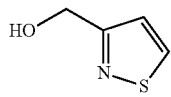

To a stirred suspension of isothiazole-3-carboxylic acid (500 mg, 3.87 mmol) in THF (10 mL) was added BH$_3$.THF (15.49 mL, 15.49 mmol) dropwise at 0° C. The reaction mixture was stirred at 70° C. for 1 h, then cooled to 0° C., quenched with MeOH, and concentrated in vacuo. Water was added to the residue and the mixture was extracted with EtOAc. The extracts were dried over anhydrous sodium sulfate, filtered, and concentrated in vacuo. The resulting residue was purified by silica gel chromatography (Biotage™ Flash 60 column) eluting with hexane/EtOAc (1:1) to give the title compound as a yellow oil (149.9 mg, 33.6%). $^1$H NMR (500 MHz, CDCl$_3$) δ ppm 2.45-2.76 (m, 1 H), 4.86 (s, 2 H), 7.22 (d, J=4.64 Hz, 1 H), 8.67 (d, J=4.64 Hz, 1 H).

Step B: Isothiazole-3-carbaldehyde

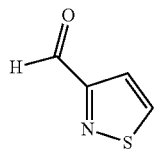

To a stirred suspension of isothiazol-3-ylmethanol (140 mg, 1.23 mmol) in EtOAc (5.0 mL) was added manganese dioxide (700 mg, 8.05 mmol). The reaction mixture was stirred at room temperature overnight. The mixture was subsequently filtered through Celite and the filtrate was concentrated in vacuo. The resulting residue was purified by silica gel chromatography (Biotage™ Flash 60 column) eluting with hexane/EtOAc (4:1) to give the title compound as colorless oil (39.8 mg, 29%). $^1$H NMR (500 MHz, CDCl$_3$) δ ppm 7.82 (d, J=4.64 Hz, 1 H), 8.74 (d, J=4.60 Hz, 1 H), 10.08 (s, 1 H).

Step C: 3-(Difluoromethyl)isothiazole

To a stirred solution of isothiazole-3-carbaldehyde (77.6 mg, 0.686 mmol) in CH$_2$Cl$_2$ (5.0 mL) was added N,N-diethylaminosulfur trifluoride (0.272 mL, 2.06 mmol) dropwise at 0° C. The reaction mixture was stirred at 0° C. for 1 h, quenched with saturated aq NaHCO$_3$, and extracted with EtOAc. The extracts were dried over anhydrous sodium sulfate, passed through a short pad of silica gel (eluting with EtOAc) and evaporated in vacuo to give the title compound, which was used without further purification.

Step D: 3-(Difluoromethyl)-5-(tributylstannyl)isothiazole

To a cold (−78° C.) solution of 3-(difluoromethyl)isothiazole (93 mg, 0.688 mmol) in anhydrous THF (2.0 mL) was added n-butyllithium (0.473 mL, 0.757 mmol) dropwise. The reaction mixture was stirred for 60 minutes at −78° C. A solution of tributylchlorostannane (0.223 mL, 0.826 mmol) in anhydrous THF (0.5 mL) was added and the reaction mixture was stirred for 30 minutes at −78° C. The solution was subsequently allowed to warm to room temperature over a period of about one hour. Saturated aq NaHCO$_3$ was added, and the aqueous phase was extracted with EtOAc. The organic phases were combined, dried over anhydrous sodium sulfate, passed through a short pad of silica gel (eluting with EtOAc) and evaporated in vacuo to give the title compound, which was used without further purification.

Preparation 2

5-(Tributylstannyl)-3-vinylisothiazole

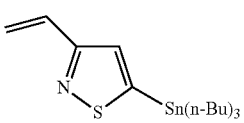

Step A: 3-Vinylisothiazole

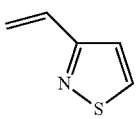

A solution of 3-bromoisothiazole (100 mg, 0.610 mmol), tributyl(vinyl)stannane (580 mg, 1.829 mmol), tetrakis(triphenylphosphine)palladium(0) (352 mg, 0.305 mmol) in toluene (2 mL) was heated to 120° C. for 45 minutes via microwave irradiation. The reaction mixture was poured into water and was extracted with EtOAc. The extracts were dried over Na₂SO, and concentrated in vacuo. The residue was purified by silica gel chromatography (Flash 60 column) eluting with hexane/EtOAc (19:1) to give the title compound as a colorless oil (26.3 mg, 39%). ¹H NMR (500 MHz, CDCl₃) δ ppm 5.54 (d, J=10.25 Hz, 1 H), 5.98 (d, J=18.55 Hz, 1 H), 6.86-6.95 (m, 1 H), 7.37 (d, J=4.88 Hz, 1 H), 8.59 (d, J=4.90 Hz, 1 H).

Step B: 5-(Tributylstannyl)-3-vinylisothiazole

To a cold (−78° C.) solution of 3-vinylisothiazole (300 mg, 2.70 mmol) in anhydrous THF (6.0 mL) was added n-butyllithium (1.855 mL, 2.97 mmol) dropwise. After stirring the reaction mixture for 60 minutes at −78° C., a solution of tributylchlorostannane (0.873 mL, 3.24 mmol) in anhydrous THF (1.5 mL) was added. The reaction mixture was stirred for 30 minutes at −78° C. and then allowed to warm to room temperature over a 1 hour period. Saturated aqueous sodium bicarbonate was added and the aqueous phase was extracted with EtOAc. The organic phases were combined, dried over anhydrous sodium sulfate, filtered, and evaporated in vacuo. The residue was purified by silica gel chromatography (Flash 60 column) eluting with hexane/EtOAc (19:1) to give the title compound as a pale yellow oil (472.8 mg, 44%). ¹H NMR (500 MHz, CDCl₃) δ ppm 0.90 (t, J=7.32 Hz, 9 H), 1.13-1.18 (m, 6 H), 1.34 (sextet, J=7.42 Hz, 6 H), 1.52-1.61 (m, 6 H), 5.50 (dd, J=11.23, 0.98 Hz, 1H), 6.00 (dd, J=17.60, 0.98 Hz, 1 H), 6.96 (dd, J=17.57, 11.23 Hz, 1 H), 7.33 (s, 1 H).

Preparation 3

5-(Tributylstannyl)isothiazole

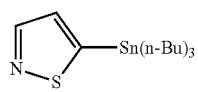

To a cold (−78° C.) solution of isothiazole (100 mg, 1.175 mmol) in anhydrous THF (2.0 mL) was added n-butyllithium (0.808 mL, 1.292 mmol) dropwise. The reaction mixture was stirred for 60 minutes at −78° C. A solution of tributylchlorostannane (0.380 mL, 1.410 mmol) in anhydrous THF (0.5 mL) was added, and the reaction mixture was stirred for 30 minutes at −78° C. The solution was allowed to warm to room temperature over a 1 hour period. Saturated aqueous sodium bicarbonate was added and the aqueous phase was extracted with EtOAc. The combined organic phase was dried over anhydrous sodium sulfate, filtered, and evaporated in vacuo. The residue was purified by silica gel chromatography (Flash 60 column) eluting with hexane/EtOAc (19:1) to give the title compound as a pale yellow oil (139.3 mg, 32%). ¹H NMR (500 MHz, CDCl₃) δ ppm 0.90 (t, J=7.32 Hz, 9 H), 1.14-1.20 (m, 6 H), 1.28-1.39 (m, 6 H), 1.51-1.62 (m, 6 H), 7.27-7.32 (m, 1 H), 8.66 (d, J=1.46 Hz, 1 H).

Preparation 4

3-Cyclopropyl-5-(tributylstannyl)isothiazole

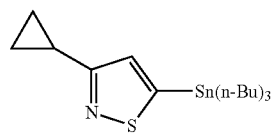

Step A: 3-cyclopropyl-5-iodoisothiazole

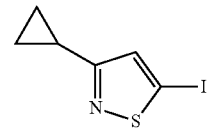

To a water (1.4 mL) and ice (5.0 cc) suspension was added 3-cyclopropylisothiazol-5-amine (500 mg, 3.57 mmol) followed by concentrated sulfuric acid (1.4 mL). A solution of sodium nitrite (258 mg, 3.74 mmol) in water (5.0 mL) was added dropwise at 0° C., and the mixture was stirred at 0° C. for 1 hour. Next, a solution of potassium iodide (622 mg, 3.74 mmol) in water (3.5 mL) was added dropwise at 0° C., and the mixture was heated at 80° C. for 1 hour. Ethyl acetate at 0° C. was added and the mixture was neutralized with potassium carbonate. The organic layer was separated, dried over magnesium sulfate, concentrated under reduced pressure, and purified by silica gel chromatography (Flash 60 column) eluting with hexane/EtOAc (19:1) to give the title compound as green oil (356.5 mg, 40%). ¹H NMR (500 MHz, CDCl₃) δ ppm 0.92-0.98 (m, 2 H), 0.98-1.04 (m, 2 H), 2.13-2.20 (m, 1 H), 7.06 (s, 1 H).

Step B: 3-Cyclopropyl-5-(tributylstannyl)isothiazole

To a cold (−78° C.) solution of 3-cyclopropyl-5-iodoisothiazole (100 mg, 0.398 mmol) in anhydrous THF (2.0 mL) was added n-butyllithium (0.299 mL, 0.478 mmol) dropwise. The reaction mixture was stirred for 60 minutes at −78° C. A solution of tributylchlorostannane (0.129 mL, 0.478 mmol) in anhydrous THF (2.0 mL) was added to the reaction mixture, which was stirred for 30 minutes −78° C. and subsequently allowed to warm to ambient temperature over a 1 hour period. Saturated aqueous sodium bicarbonate was added to the reaction mixture. The aqueous phase was extracted with EtOAc and the combined organic phase was dried over anhydrous sodium sulfate, filtered, and evaporated in vacuo. The residue was purified by silica gel chromatography (Flash 60 column) eluting with hexane/EtOAc (19:1) to give the title compound as a colorless oil (142.8 mg, 87%). ¹H NMR (500 MHz, CDCl₃) δ ppm 0.85-0.93 (m, 9 H), 0.95-1.05 (m, 4 H), 1.09-1.17 (m, 6 H), 1.28-1.38 (m, 6 H), 1.47-1.61 (m, 6 H), 2.20-2.29 (m, 1 H), 6.93 (s, 1 H).

Preparation 5

3-Methyl-5-(tributylstannyl)isothiazole

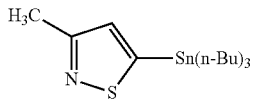

To a cold (−78° C.) solution of 3-methylisothiazole (100 mg, 1.0 mmol) in anhydrous THF (2.0 mL) was added n-butyllithium (0.693 mL, 1.1 mmol) dropwise. After stirring for 60 minutes at −78° C., a solution of tributylchlorostannane (0.326 mL, 1.210 mmol) in anhydrous THF (0.5 mL) was added to the reaction mixture. The reaction mixture was stirred for 30 minutes at −78° C. and then allowed to warm to RT over a 2 to 3 hour period. Saturated aq NaHCO₃ was added and the aqueous phase was extracted with EtOAc (3×50 mL). The combined organic phase was dried over anhydrous Na₂SO₄, filtered, and evaporated in vacuo. The residue was purified by silica gel chromatography (Flash 60 column) eluting with hexane/EtOAc (9:1) to give the title compound. $^1$H NMR (500 MHz, CDCl₃) δ ppm 0.86-0.94 (m, 9 H), 1.05-1.21 (m, 6 H), 1.26-1.38 (m, 6 H), 1.44-1.65 (m, 6 H), 2.56 (s, 3 H), 6.97-7.04 (m, 1 H).

Preparation 6

3-Methyl-5-(4,4,5,5-tetramethyl-1,3,2-dioxaborolan-2-yl)isothiazole

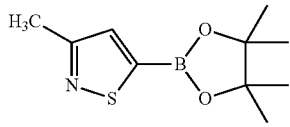

To a cooled (−25° C.) solution of 5-iodo-3-methylisothiazole (59.5 g, 264 mmol) and 2-isopropoxy-4,4,5,5-tetramethyl-1,3,2-dioxaborolane (50.2 g, 270 mmol) in anhydrous THF (300 mL) was added dropwise 1.3 M isopropylmagnesium lithium chloride in THF (218 mL, 283 mmol) at a rate which maintained the temperature at −15° C. to −25° C. The reaction mixture was stirred at −10° C. for 5 minutes after the addition was completed. HPLC analysis indicated that the starting material was consumed. A solution of acetic acid (16.19 mL, 283 mmol) in THF (40 mL) was added slowly to the reaction solution at 0° C. Hexanes (250 mL) and MTBE (150 mL) were sequentially added to the reaction mixture. A solid precipitate was formed, which was filtered off by passing the reaction mixture through a pad of Celite. The filtrate was concentrated via rotary evaporation to afford an oil residue, which was dispersed in MTBE (500 mL) through vigorous stirring. Additional precipitate was formed, which was filtered off using a pad of Celite. The filtrate was again concentrated to an oil, and MTBE (200 mL) was added, which formed additional solid precipitate that was filtered off using a pad of Celite. The process was repeated two more times until no more solid was formed when MTBE was added to the oil residue. The oil was dried in a rotary evaporator under high vacuum overnight with a bath temperature of 20° C., which afforded the title compound as an oil (49.55 g, 83%). $^1$H NMR (400 MHz, CDCl₃) δ ppm 1.37 (s, 12H), 2.56 (s, 3H), 7.41 (s, 1H).

Preparation 7

Thieno[2,3-c]pyridin-2-ylboronic acid

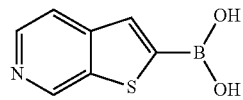 [SMILES: OB(O)c1cc2ccncc2s1]

To a cold (−78° C.) solution of thieno[2,3-c]pyridine (2.040 g, 15.09 mmol) in anhydrous THF (50 mL) was added n-butyllithium (6.64 mL, 16.60 mmol) dropwise. The reaction mixture was stirred for 60 minutes at −78° C. A solution of triisopropyl borate (4.16 mL, 18.11 mmol) was added and the reaction mixture was stirred for 30 minutes at −78° C. The solution was allowed to warm to room temperature over a 2 hour period. TLC showed the reaction was complete. Aqueous HCl (1N, 1000 mL) and DCM (500 mL) were added to the reaction mixture. The aqueous and organic layers were separated. The aqueous layer was concentrated to a volume of 500 mL and a solid precipitate was filtered and dried to give the title compound as off-white, needle-shaped crystals (2.4 g, 74%). $^1$H NMR (400 MHz, DMSO-d₆) δ ppm 8.24 (s, 1 H), 8.41 (d, J=4.80 Hz, 1 H), 8.66 (d, J=6.32 Hz, 1 H), 9.10 (br s, 2 H), 9.72 (br s, 1 H).

Preparation 8

2-(Tributylstannyl)thieno[2,3-c]pyridine

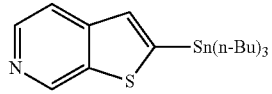

To a cold (−78° C.) solution of thieno[2,3-c]pyridine (524 mg, 3.88 mmol) in anhydrous THF (50 mL) was added n-butyllithium (2.66 mL, 4.26 mmol) dropwise. The mixture was stirred for 60 minutes at −78° C. A solution of tributylchlorostannane (1.254 mL, 4.65 mmol) in anhydrous THF (10 mL) was added, and the reaction mixture was stirred for 30 minutes at −78° C. The solution was allowed to warm to room temperature over a period of 2 to 3 hours. Saturated aqueous sodium bicarbonate was added. The aqueous phase was extracted with diethyl ether (3×200 mL). The combined organic phase was dried over anhydrous sodium sulfate, filtered, and evaporated in vacuo. The crude product was purified by silica gel column chromatography, eluting with a gradient of 10-50% EtOAc and hexane over a period of 60 minutes. The desired fractions were collected to give the title compound as a clear oil (1.1 g, 67%). $^1$H NMR (500 MHz, DMSO-d₆) δ ppm 0.86 (t, J=7.32 Hz, 9 H), 1.08-1.38 (m, 12 H), 1.45-1.71 (m, 6 H), 7.59 (s, 1 H), 7.76-7.93 (m, 1 H), 8.41 (s, 1 H), 9.23 (s, 1 H).

Preparation 9

2-(5-Fluorothiophen-2-yl)-4,4,5,5-tetramethyl-1,3,2-dioxaborolane

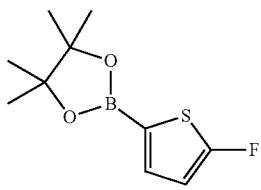

To a solution of thiophene (252 mg, 2.99 mmol) in THF (3.5 mL) at −78° C. was added n-butyllithium (2.5M, 1.3 mL, 3.2 mmol) dropwise to keep the temperature below −70° C. The solution was stirred for 40 minutes at −78° C. A solution of N-fluorobenzenesulfonimide (987 mg, 3.1 mmol) in THF (5 mL) was added over a period of 20 minutes. The temperature of the mixture was allowed to rise to −10° C. and was subsequently cooled to −78° C. To the mixture was added n-butyllithium (2.5M, 1.3 mL, 3.2 mmol) and 2-isopropoxy-4,4,5,5-tetramethyl-1,3,2-dioxaborolane (580 mg, 3.1 mmol) in THF (2 mL). The reaction was allowed to continue at −78° C. for 30 min and then quenched with saturated aqueous ammonium chloride (10 mL). The organic layer was separated and the aqueous phase was extracted with EtOAc (3×15 mL). The organic layers were combined and dried over sodium sulfate. After removal of solvent, the residue was purified by flash chromatography (petroleum ether/ethyl acetate=20:1) to give the title compound (143 mg, 21%). $^1$H NMR (400 MHz, CDCl$_3$) δ ppm 1.32 (s, 12 H), 6.55 (d, J=3.6 Hz, 1 H), 7.27 (d, J=3.6 Hz, 1H).

Preparation 10

2-(Tributylstannyl)thieno[2,3-b]pyridine

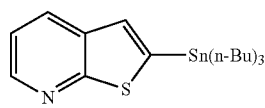

To a cold (−78° C.) solution of thieno[2,3-b]pyridine (2.000 g, 14.79 mmol) in anhydrous THF (50 mL) was added n-butyllithium (10.17 mL, 16.27 mmol) dropwise. The reaction mixture was stirred for 60 minutes at −78° C. A solution of tributylchlorostannane (4.79 mL, 17.75 mmol) in anhydrous THF (10 mL) was added and the reaction mixture was stirred for 30 minutes at −78° C. The solution was allowed to warm to room temperature over a period of 2 to 3 hours. Saturated aqueous sodium bicarbonate was added. The aqueous phase was extracted with ether (3×200 mL). The organic layers were combined, dried over anhydrous sodium sulfate, filtered, and evaporated in vacuo. The crude product was purified by silica gel column chromatography, eluting with a gradient of 10-50% EtOAc and hexane over a period of 60 minutes. The desired fractions were collected and the solvent removed in vacuo to give the title compound (4.5 g, 72%) $^1$H NMR (500 MHz, DMSO-d$_6$) δ ppm 0.87 (t, J=7.32 Hz, 9 H), 1.13-1.20 (m, 6 H), 1.32 (dq, J=14.64, 7.32 Hz, 6 H), 1.52-1.64 (m, 6 H), 7.34-7.42 (m, 1 H), 7.51 (s, 1 H), 8.25 (dd, J=7.81, 1.46 Hz, 1 H), 8.50 (dd, J=4.39, 1.46 Hz, 1 H).

Preparation 11

2-(Tributylstannyl)thieno[3,2-c]pyridine

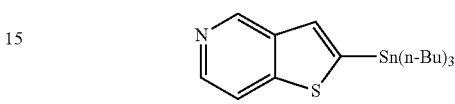

To a cold (−78° C.) solution of thieno[3,2-c]pyridine (2.000 g, 14.79 mmol) in anhydrous THF (50 mL) was added n-butyllithium (10.17 mL, 16.27 mmol) dropwise. The reaction mixture was stirred at −78° C. for 60 minutes. A solution of tributylchlorostannane (4.79 mL, 17.75 mmol) in anhydrous THF (10 mL) was added. The reaction mixture was stirred at −78° C. for 30 minutes and the solution was allowed to warm to room temperature over a period of 2 to 3 hours. Saturated aqueous NaHCO$_3$ was added. The aqueous phase was extracted with ether (3×200 mL). The organic layers were combined, dried over anhydrous sodium sulfate, filtered, and evaporated in vacuo. The crude product was purified by silica gel column chromatography, eluting with a gradient of 10-50% EtOAc and hexane over a period of 60 minutes. The desired fractions were collected to give the title compound as a clear oil (4.2 g, 67%). $^1$H NMR (500 MHz, DMSO-d$_6$) δ ppm 0.79-0.94 (m, 9 H), 1.10-1.24 (m, 6 H), 1.32 (sextet, J=7.32 Hz, 6 H), 1.51-1.66 (m, 6 H), 7.63-7.70 (m, 1 H), 8.04 (d, J=5.37 Hz, 1 H), 8.35 (d, J=5.86 Hz, 1 H), 9.16 (d, J=0.98 Hz, 1 H).

Preparation 12

5-Cyanobenzo[b]thiophen-2-ylboronic acid

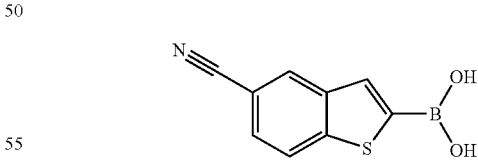

To a cold (−78° C.) solution of benzo[b]thiophene-5-carbonitrile (276 mg, 1.734 mmol) in anhydrous THF (5 mL) was added n-butyllithium (0.763 mL, 1.907 mmol) dropwise. The reaction mixture was stirred at −78° C. for 60 minutes. Next, a solution of triisopropyl borate (0.478 mL, 2.080 mmol) was added. The reaction mixture was stirred for 30 minutes stirring at −78° C. and then was allowed to warm to room temperature over a 2 hour period. Solvent was removed to give the title compound, which was used without purification or work up.

Preparation 13

4-Fluorobenzo[b]thiophen-2-ylboronic acid

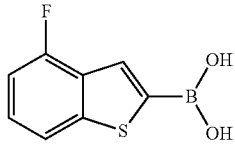 [SMILES: OB(O)c1cc2c(F)cccc2s1]

Step A: 4-Fluorobenzo[b]thiophene

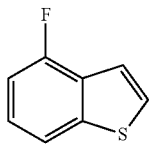

A mixture of 4-fluorobenzo[b]thiophene-2-carboxylic acid (200 mg, 1.019 mmol) and 1,8-diazabicyclo[5.4.0]undec-7-ene (0.457 mL, 3.06 mmol) in DMA (1 mL) was heated at 200° C. for 1 hour. The reaction mixture was allowed to cool and was poured into water (100 mL). The product was extracted with hexane (2×20 mL) and washed with 1N HCl (100 mL) and 1N NaOH (50 mL). The organic layers were combined, dried over Na$_2$SO$_4$ and the solvent was removed in vacuo to give the title compound as a yellow oil, which was used without further purification.

Step B: 4-Fluorobenzo[b]thiophen-2-ylboronic acid

To a cold (−78° C.) solution of 4-fluorobenzo[b]thiophene (80.4 mg, 0.528 mmol) in anhydrous THF (1 mL) was added n-butyllithium (0.363 mL, 0.581 mmol) dropwise. The reaction mixture was stirred at −78° C. for 60 minutes. A solution of triisopropyl borate (0.146 mL, 0.634 mmol) was added. The reaction mixture was stirred at −78° C. for 30 minutes and was then allowed to warm to room temperature over a 2 hour period. TLC showed completion of reaction. 1N HCl (100 mL) and DCM (50 mL) were added to the reaction mixture. The aqueous and organic layers were separated. The aqueous layer was concentrated to 50 mL, yielding a solid precipitate that was filtered and dried to give the title compound as off-white, needle-shaped crystals. The product was used without further purification.

Preparation 14

Thieno[3,2-b]pyridin-2-ylboronic acid hydrochloride

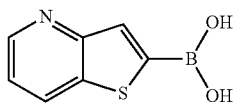 [SMILES: OB(O)c1cc2ncccc2s1]

Step A: Thieno[3,2-b]pyridine

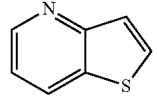

A solution of 7-chlorothieno[3,2-b]pyridine (500 mg, 2.95 mmol) and zinc (193 mg, 2.95 mmol) in acetic acid (5 mL) was stirred at room temperature for 3 days, followed by stirring at 50° C. for 5 hours. The solvent was removed in vacuo and the residue was dissolved in DCM (200 mL) and extracted with 1N NaOH (500 mL). The aqueous layer was washed again with DCM (2×200 mL). The organic layers were combined, dried over Na$_2$SO$_4$, and the solvent was removed in vacuo to yield the title compound as a yellow oil, which was used without further purification. ESI-MS m/z [M+H]$^+$calc'd for C$_7$H$_5$NS, 136. found, 136.

Step B: Thieno[3,2-b]pyridin-2-ylboronic acid hydrochloride

To a cold (−78° C.) solution of thieno[3,2-b]pyridine (404 mg, 2.99 mmol) in anhydrous THF (1 mL) was added n-butyllithium (2.055 mL, 3.29 mmol) dropwise. The reaction mixture was stirred at −78° C. for 60 minutes, after which a solution of triisopropyl borate (0.825 mL, 3.59 mmol) was added. The reaction mixture was stirred at −78° C. for 30 minutes and was then allowed to warm to room temperature over a period of 2 hours. UPLC showed completion of reaction. The solvent was removed and DCM (50 mL) and aqueous 1N HCl (50 mL) were added to the residue. The organic layer was separated, and the aqueous layer was collected and concentrated to yield an HCl salt of the title compound as a yellow solid, which was used without further purification.

Preparation 15

2-(4-Fluorothiophen-2-yl)-4,4,5,5-tetramethyl-1,3,2-dioxaborolane

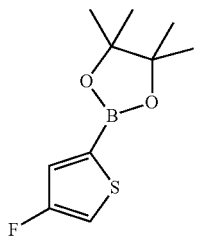

Step A: 3-Fluorothiophene

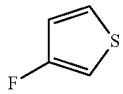

To a single neck round bottom flask containing 3-fluoro-thiophene-2-carboxylic acid (1.68 g, 11.50 mmol) dissolved in quinoline (12 mL) was added copper chromite (1.789 g, 5.75 mmol). The round bottom flask was connected to a distillation unit fitted with a thermometer and a receiving flask maintained at about 0° C. The reaction mixture was initially heated at 150° C. for 1 hour and then at 185° C. Volatile 3-fluorothiophene started slowly distilling into the receiving flask as a colorless liquid. After 20 minutes, a slight vacuum was applied to ensure complete distillation of 3-fluorothiophene, while taking care to ensure that no quinoline was distilled into the receiving flask. Once the distillation was complete, the receiving flask was sealed and the title compound was stored in a refrigerator until it was used (580 mg, 99%). $^1$H NMR (400 MHz, CDCl$_3$) δ ppm 6.72 (dt, J=3.47, 1.29 Hz, 1 H), 6.81-6.92 (m, 1 H), 7.19 (dt, J=5.43, 3.35 Hz, 1 H).

Step B: 2-(4-Fluorothiophen-2-yl)-4,4,5,5-tetramethyl-1,3,2-dioxaborolane

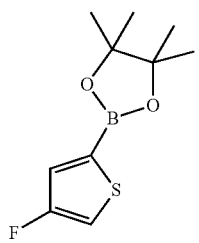

To a mixture of [Ir(μ-OMe(COD)] (50 mg, 0.015 mmol, 3 mol %) and 4,4,5,5-tetramethyl-1,3,2-dioxaborolane (1.292 g, 9.79 mmol) was added a solution of 4,4'-di-tert-butyl-2,2'-bipyridine (0.039 g, 0.147 mmol) in n-hexane (3 mL). The reaction mixture was stirred for 1 minute and then added to a vessel containing 3-fluorothiophene (0.5 g, 4.90 mmol) dissolved in hexane (3 mL). The mixture was allowed to react at room temperature for 1 hour. The mixture was subsequently evaporated and used without further work up.

Preparation 16

1-Methyl-5-(tributylstannyl)-1H-thieno[3,2-c]pyrazole

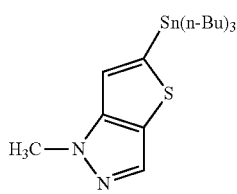

Step A: (E)-1-((3-Bromothiophen-2-yl)methylene)-2-(diphenylmethylene) hydrazine

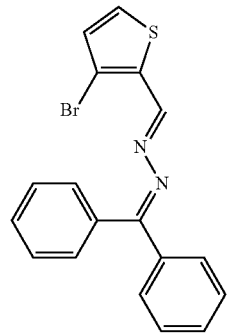 [SMILES: Brc1ccsc1/C=N/N=C(c1ccccc1)c1ccccc1]

3-Bromothiophene-2-carbaldehyde (8.0 g, 41.9 mmol) and (diphenylmethylene)hydrazine (9.45 g, 48.2 mmol) were dissolved in ethanol (60 mL) and the solution was heated at 80° C. overnight. Volatiles from the reaction mixture were removed via rotary evaporation and the crude product was purified by normal phase silica gel chromatography (ISCO-Combiflash) eluting with a gradient of 0-30% hexane and EtOAc. The pure fractions were combined and evaporated to give the title compound as a mixture of cis/trans isomers (15.0 g, 97%). ESI-MS m/z [M+H]$^+$calc'd for C$_{18}$H$_{13}$BrN$_2$S, 370. found, 370.

Step B: (E)-1-(Diphenylmethylene)-2-((3-(2-(diphenylmethylene)hydrazinyl) thiophen-2-yl)methylene) hydrazine

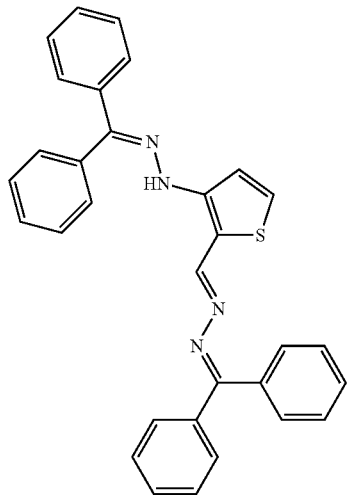 [SMILES: C(=N\N=C(c1ccccc1)c1ccccc1)/c1sccc1NN=C(c1ccccc1)c1ccccc1]

To a mixture of (E)-1-((3-bromothiophen-2-yl)methylene)-2-(diphenylmethylene)hydrazine (15 g, 40.6 mmol, including its Z isomer) and (diphenylmethylene)hydrazine (9.57 g, 48.7 mmol) in toluene (125 mL) was added palladium(II) acetate (0.120 g, 2.031 mmol), 1,1'-bis(diphenylphosphino)ferrocene (2.252 g, 4.06 mmol) and Cs$_2$CO$_3$ (26.5 g, 81 mmol). The reaction mixture was stirred at 85° C. for 14 hours and was subsequently diluted with toluene (25 mL) and filtered to remove undissolved solids. The filtrate was purified by flash column chromatography. The pure product fractions were evaporated to give the title compound (15.5 g, 79%). ESI-MS m/z [M+H]+calc'd for $C_{31}H_{24}N_4S$, 485. found, 485.

Step C: 1H-thieno[3,2-c]pyrazole

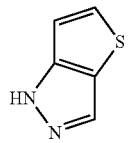

To a solution of (E)-1-(diphenylmethylene)-2-((3-(2-(diphenylmethylene)hydrazinyl)thiophen-2-yl)methylene)hydrazine (15 g, 31.0 mmol) in EtOH (125 mL) was added concentrated HCl (50 mL). The reaction mixture was heated at 80° C. for 2 hours. The mixture was then basified with saturated aqueous NaHCO$_3$ (20 mL) and solid NaHCO$_3$ to pH 8-9 and the aqueous solution was extracted with EtOAc (2×250 mL). The organic layers were combined, dried over sodium sulfate, and evaporated. The resulting mixture was purified by silica gel column chromatography, eluting with a gradient of 0-20% dichloromethane and methanol. The pure product fractions were combined and evaporated to give the title compound (2.8 g, 73%). ESI-MS m/z [M+H]+ calc'd for $C_5H_4N_2S$, 125. found, 125.

Step D: (a) 1-Methyl-1H-thieno[3,2-c]pyrazole and (b) 2-methyl-2H-thieno[3,2-c]pyrazole

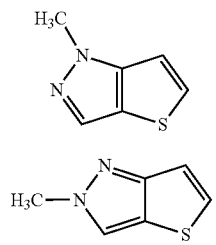

1H-thieno[3,2-c]pyrazole (2500 mg, 20.13 mmol) was dissolved in THF (45 mL) under nitrogen and cooled to 0° C. in an ice bath. Sodium hydride (966 mg, 24.16 mmol) was slowly added. After 20 minutes, iodomethane (1.511 mL, 24.16 mmol) was added dropwise, and the mixture was allowed to react at room temperature for an hour. The reaction was subsequently quenched with water (20 mL) and extracted with EtOAc (2×60 mL). The organic layers were combined, dried over sodium sulfate, and evaporated. The resulting gummy liquid was purified by silica gel column (80 g) chromatography, eluting with a gradient of 0-100% hexane and EtOAc and yielding two clean separate product fractions. The fractions corresponding to one of the two products were combined and the solvent evaporated to give title compound (a) as a light green liquid (1.45 g, 53%). $^1$H NMR (400 MHz, CDCl$_3$) δ ppm 4.03 (s, 3 H), 6.90 (dd, J=5.31, 0.76 Hz, 1 H), 7.38 (d, J=5.31 Hz, 1 H), 7.65 (s, 1 H). ESI-MS m/z [M+H]+ calc'd for $C_6H_6N_2S$, 139. found, 139. The fractions corresponding to the second of the two products were combined and the solvent evaporated to give title compound (b) as a light green liquid (1.32 g, 47%). ESI-MS m/z [M+H]+ calc'd for $C_6H_6N_2S$, 139. found, 139.

Step E: 1-Methyl-5-(tributylstannyl)-1H-thieno[3,2-c]pyrazole

To a cold (−78° C.) mixture of 1-methyl-1H-thieno[3,2-c]pyrazole (200 mg, 1.447 mmol) in THF (10 mL) was added n-butyllithium (0.637 mL, 1.592 mmol) dropwise under a nitrogen atmosphere. The reaction mixture was stirred at −78° C. for 60 minutes. Tributylchlorostannane (0.471 mL, 1.737 mmol) was added, and the reaction mixture was stirred at −78° C. for 60 minutes and then warmed to room temperature over a period of 2 hours. The reaction was quenched with brine (20 mL) and extracted with ethyl acetate (2×30 mL). The organic layers were combined, dried over sodium sulfate, concentrated, and purified via flash chromatography, eluting with 20% EtOAc and hexane to give the title compound as a clear oil (420 mg, 68%). $^1$H NMR (400 MHz, CDCl$_3$) δ ppm 0.76-0.99 (m, 9 H), 0.99-1.22 (m, 6 H), 1.22-1.51 (m, 6 H), 1.51-1.72 (m, 6 H), 4.02 (s, 3 H), 6.87 (d, J=0.51 Hz, 1 H), 7.58 (s, 1 H).

Preparation 17

(a) 1,3-Dimethyl-1H-thieno[3,2-c]pyrazole and (b) 2,3-dimethyl-2H-thieno[3,2-c]pyrazole

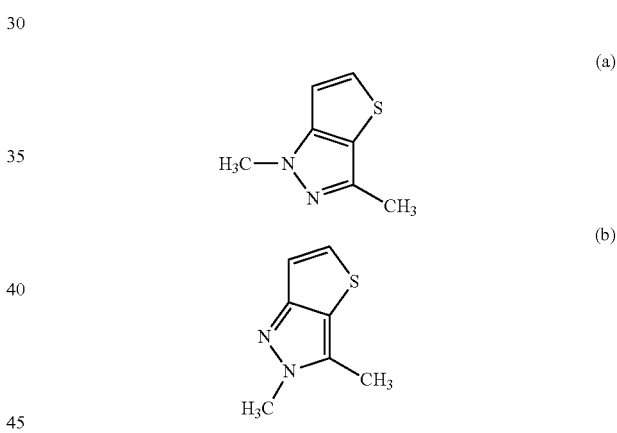

Step A: (E)-1-(1-(3-Bromothiophen-2-yl)ethylidene)-2-(diphenylmethylene) hydrazine

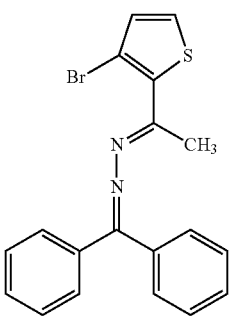 [SMILES: C/C(=N\N=C(c1ccccc1)c1ccccc1)c1sccc1Br]

1-(3-Bromothiophen-2-yl)ethanone (8.0 g, 39.0 mmol) and (diphenylmethylene)hydrazine (8.42 g, 42.9 mmol)

were dissolved in ethanol (75 mL). The reaction mixture was heated in an oil bath at 80° C. for 16 hours. Following reaction, the volatiles were evaporated, and the condensed mixture was purified via silica gel column chromatography, eluting with a gradient of 0-100% hexane and EtOAc. The pure fractions were combined and evaporated to give the title compound as a yellow solid (12.5 g, 84%). ESI-MS m/z [M+H]$^+$calc'd for $C_{19}H_{15}BrN_2S$, 384. found, 384.

Step B: (E)-1-(Diphenylmethylene)-2-(1-(3-(2-(diphenylmethylene)hydrazinyl) thiophen-2-yl)ethylidene)hydrazine

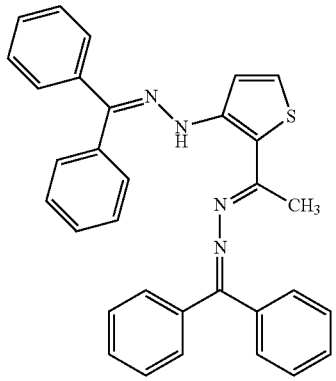 [SMILES: C/C(=N\N=C(c1ccccc1)c1ccccc1)c1sccc1NN=C(c1ccccc1)c1ccccc1]

To a mixture of (E)-1-(1-(3-bromothiophen-2-yl)ethylidene)-2-(diphenylmethylene)hydrazine (12.5 g, 32.6 mmol, including its Z isomer) and (diphenylmethylene)hydrazine (7.68 g, 39.1 mmol) in toluene (25 mL) was added palladium (II) acetate (0.385 g, 6.52 mmol), 1,1'-bis(diphenylphosphino)ferrocene (1.808 g, 3.26 mmol) and $Cs_2CO_3$ (21.25 g, 65.2 mmol). The reaction mixture was heated at 80° C. for 14 hours. The mixture was subsequently diluted with toluene (25 mL) and filtered to remove solids. The filtrate was evaporated and chromatographed using a gradient of 0-100% hexane and EtOAc. The pure product fractions were combined and evaporated to give the title compound (12.5 g, 77%). ESI-MS m/z [M+H]$^+$calc'd for $C_{32}H_{26}N_4S$, 499. found, 499.

Step C: 3-Methyl-1H-thieno[3,2-c]pyrazole

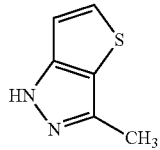

To a mixture of (E)-1-(diphenylmethylene)-2-(1-(3-(2-(diphenylmethylene)hydrazinyl)thiophen-2-yl)ethylidene) hydrazine (12.5 g, 25.07 mmol) in EtOH (75 mL) was added concentrated HCl (40 mL). The reaction mixture was heated at 80° C. for 2 hours, then basified with saturated aqueous $NaHCO_3$ (50 mL) and solid $NaHCO_3$ to pH 8-9. The reaction mixture was extracted with EtOAc (2×250 mL). The organic layers were combined, dried over sodium sulfate, and evaporated. The resulting mixture was purified by silica gel column chromatography, eluting with a gradient of 0-20% dichloromethane and methanol. The pure product fractions were combined and evaporated to give the title compound as a tan solid (2.6 g, 75%). $^1$H NMR (400 MHz, $CDCl_3$) δ ppm 2.42-2.57 (m, 3 H), 6.97 (d, J=5.05 Hz, 1 H), 7.40 (d, J=5.31 Hz, 1 H), 9.04 (br s, 1 H). ESI-MS m/z [M+H]$^+$calc'd for $C_6H_6N_2S$, 139. found, 139.

Step D: (a) 1,3-Dimethyl-1H-thieno[3,2-c]pyrazole and (b) 2,3-dimethyl-2H-thieno[3,2-c]pyrazole 3-Methyl-1H-thieno[3,2-c]pyrazole (2 g, 14.47 mmol) was dissolved in THF (45 mL) under nitrogen and was cooled to 0° C. in an ice bath. Sodium hydride (695 mg, 17.37 mmol) was slowly added. After 20 minutes, iodomethane (1.086 mL, 17.37 mmol) was added dropwise. The mixture was allowed to react at room temperature for 1 hour. The reaction mixture was quenched with water (20 mL) and extracted with EtOAc (2×60 mL). The organic layers were combined, dried over sodium sulfate, and evaporated. The resulting gummy liquid was purified by silica gel column (80 g) chromatography, eluting with a gradient of 0-100% hexane and EtOAc and yielding two clean separate product fractions. The fractions corresponding to one of the two products were combined and the solvent evaporated to give the title compound (a) as black liquid (1.0 g, 45%). $^1$H NMR (400 MHz, $CDCl_3$) δ ppm 2.43 (s, 3 H), 3.95 (s, 3 H), 6.84 (d, J=5.31 Hz, 1 H), 7.34 (d, J=5.31 Hz, 1 H). ESI-MS m/z [M+H]$^+$calc'd for $C_7H_8N_2S$, 153. found, 153. The fractions corresponding to the second of the two products were combined and the solvent evaporated to give title compound (b) as a black liquid (1.354 g, 62%). $^1$H NMR (400 MHz, $CDCl_3$) δ ppm 2.48 (s, 3 H), 3.97 (s, 3 H), 7.03 (d, J=5.31 Hz, 1 H), 7.28 (d, J=5.31 Hz, 1 H). ESI-MS m/z [M+H]$^+$ calc'd for $C_7H_8N_2S$, 153. found, 153.

Preparation 18

1,3-Dimethyl-5-(tributylstannyl)-1H-thieno[3,2-c]pyrazole

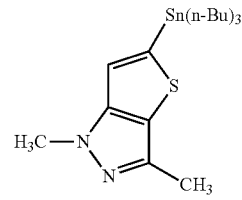

To a cold (−78° C.) mixture of 1,3-dimethyl-1H-thieno [3,2-c]pyrazole (400 mg, 2.63 mmol) and THF (15 mL) under a nitrogen atmosphere was added n-butyllithium (1.156 mL, 2.89 mmol) dropwise. The reaction mixture was stirred at −78° C. for 60 minutes. Tributylchlorostannane (0.855 mL, 3.15 mmol) was added, and the reaction mixture was stirred at −78° C. for 60 minutes and then warmed to room temperature with stirring over a period of 1 hour. The reaction mixture was quenched with brine (15 mL) and extracted with EtOAc (2×25 mL). The organic layers were combined, dried over sodium sulfate, and evaporated. The resulting residue was purified by normal-phase silica gel column (80 g) chromatography, eluting with a gradient of 0-100% hexane and EtOAc. The pure product fractions were combined and evaporated to give the title compound as a clear oil (1.060 g, 91%). $^1$H NMR (400 MHz, $CDCl_3$) δ ppm 0.77-0.98 (m, 9 H), 1.04-1.20 (m, 6 H), 1.25-1.47 (m, 6 H), 1.49-1.70 (m, 6 H), 2.41 (s, 3 H), 3.94 (s, 3 H), 6.82 (s, 1 H). ESI-MS m/z [M+H]$^+$calc'd for $C_{19}H_{34}N_2SSn$, 443. found, 443.

Preparation 19

2,3-Dimethyl-5-(tributylstannyl)-2H-thieno[3,2-c]pyrazole

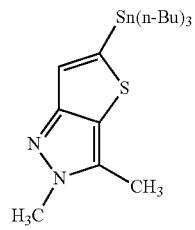

To a cold (−78° C.) mixture of 2,3-dimethyl-2H-thieno[3,2-c]pyrazole (400 mg, 2.63 mmol) and THF (15 mL) under a nitrogen atmosphere was added n-butyllithium (1.156 mL, 2.89 mmol) dropwise. The reaction mixture was stirred at −78° C. for 60 minutes. Tributylchlorostannane (0.855 mL, 3.15 mmol) was added, and the reaction mixture was stirred at −78° C. for 60 minutes and then warmed to room temperature with stirring over a period of 1 hour. The reaction mixture was quenched with brine (15 mL) and extracted with EtOAc (2×25 mL). The organic layers were combined, dried over sodium sulfate, and evaporated. The resulting residue was purified by silica gel column (80 g) chromatography, eluting with a gradient of 0-100% hexane and EtOAc. The pure product fractions were combined and evaporated to give the title compound as a gray solid (1.060 g, 2.402 mmol, 91%). $^1$H NMR (400 MHz, CDCl$_3$) δ ppm 0.78-0.99 (m, 9 H), 1.06-1.22 (m, 6 H), 1.23-1.46 (m, 6 H), 1.48-1.70 (m, 6 H), 2.46 (s, 3 H), 3.96 (s, 3 H), 7.03 (s, 1 H). ESI-MS m/z [M+H]$^+$calc'd for $C_{19}H_{34}N_2SSn$, 443. found, 443.

Preparation 20

7-(Tributylstannyl)-3,4-dihydro-1H-pyrrolo[2,1-c][1,4]oxazine

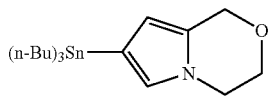

Step A: 4-Iodo-1H-pyrrole-2-carbaldehyde

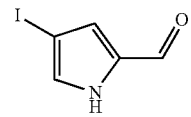

To a cold (−78° C.) solution of 1H-pyrrole-2-carbaldehyde (7.0 g, 73.6 mmol) and THF (50 mL) was added 1-iodopyrrolidine-2,5-dione (19.87 g, 88 mmol) portion wise over a period of 20 minutes. The temperature of the mixture was maintained at −78° C. for 2 hours. The reaction was subsequently quenched with water (20 mL) and hexanes (100 mL) and the mixture was allowed warm to room temperature. The organic and aqueous layers were separated. The aqueous layer was extracted with hexanes (100 mL). The organic layers were combined, dried over sodium sulfate, and evaporated to give the title compound (14 g, 86%). ESI-MS m/z [M+H]$^+$calc'd for $C_5H_4INO$, 221. found, 221.

Step B: 1-(2-Hydroxyethyl)-4-iodo-1H-pyrrole-2-carbaldehyde

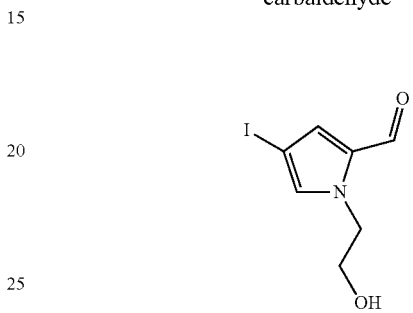

To a solution of 4-iodo-1H-pyrrole-2-carbaldehyde (5 g, 22.62 mmol) and dioxane (25 mL) was added KOH (3.81 g, 67.9 mmol), followed by 2-bromoethanol (3.31 mL, 45.2 mmol). The mixture was allowed to react at 60° C. for 16 hours and was then cooled to room temperature. The pH was adjusted to ~6 by the addition of acetic acid. The reaction mixture was then concentrated in vacuo to give a residue, which was partitioned between water and ethyl acetate. The organic phase was washed with water, brine, dried over anhydrous sodium sulfate, and concentrated in vacuo to give a residue. The residue was purified by silica gel column chromatography, eluting with a 0-100% gradient of hexane and EtOAc. The pure product fractions were combined and evaporated to give the title compound (3.4 g, 57%). $^1$H NMR (400 MHz, CDCl$_3$) δ ppm 3.84-3.96 (m, 2 H), 4.39-4.54 (m, 2 H), 6.99-7.15 (m, 2H), 9.38-9.53 (m, 1 H). ESI-MS m/z [M+H]$^+$calc'd for $C_7H_8INO_2$, 266. found, 266.

Step C: 2-(2-Formyl-4-iodo-1H-pyrrol-1-yl)ethyl 4-methylbenzenesulfonate

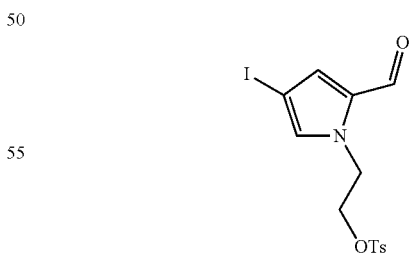

To a cooled (0° C.) solution of 1-(2-hydroxyethyl)-4-iodo-1H-pyrrole-2-carbaldehyde (3.4 g, 12.83 mmol) and dichloromethane (25 mL) was added Et$_3$N (7.15 mL, 51.3 mmol). After 5 minutes, 4-methylbenzene-1-sulfonyl chloride (2.81 g, 14.75 mmol) was added portion wise over a period of 15 minutes, and the reaction mixture was allowed to warm to room temperature. Following reaction at room temperature overnight, water was added and the resulting layers were separated. The aqueous layer was extracted with dichloromethane (50 mL). The organic layers were combined, washed with saturated aqueous NaHCO$_3$ and brine, dried over sodium sulfate, and evaporated to give a brown residue. The residue was purified with petroleum ether to give the title compound as a brown solid, which was used without further purification (3.8 g, 71%). ESI-MS m/z [M+H]$^+$calc'd for C$_{14}$H$_{14}$INO$_4$S, 420. found, 420.

Step D: 2-(2-(Hydroxymethyl)-4-iodo-1H-pyrrol-1-yl)ethyl 4-methyl benzenesulfonate

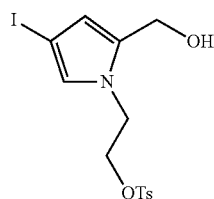 [SMILES: Cc1ccc(S(=O)(=O)OCCn2cc(I)cc2CO)cc1]

To a cooled (0° C.) solution of 2-(2-formyl-4-iodo-1H-pyrrol-1-yl)ethyl 4-methylbenzenesulfonate (3.5 g, 8.35 mmol) and EtOH (25 mL) was slowly added sodium borohydride (0.164 g, 4.34 mmol). After 30 minutes, the reaction mixture was allowed to warm to room temperature and to react for an additional hour. The pH of the reaction mixture was adjusted to ~6. The solvent was removed using a rotary evaporator and the resulting residue was partitioned between water and dichloromethane. The organic phase was washed with water, brine, dried over sodium sulfate, and concentrated. The resulting residue was suspended in a mixture of ether and hexane and then filtered to give the title compound as an off-white solid (2.75 g, 78%). $^1$H NMR (400 MHz, DMSO-d$_6$) δ ppm 2.42 (s, 3 H), 4.05-4.21 (m, 2 H), 4.21-4.36 (m, 4 H), 5.00 (t, J=5.18 Hz, 1 H), 6.00 (d, J=1.77 Hz, 1 H), 6.75 (d, J=1.77 Hz, 1 H), 7.43 (m, J=8.34 Hz, 2 H), 7.64 (m, J=8.34 Hz, 2 H). ESI-MS m/z [M+H]$^+$calc'd for C$_{14}$H$_{16}$I NO$_4$S, 422. found, 404.

Step E: 7-Iodo-3,4-dihydro-1H-pyrrolo[2,1-c][1,4]oxazine

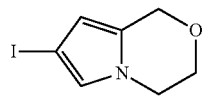

To a stirred mixture of sodium hydride (0.261 g, 6.53 mmol) and THF (10 mL) was slowly added a solution of 2-(2-(hydroxymethyl)-4-iodo-1H-pyrrol-1-yl)ethyl 4-methylbenzenesulfonate (2.75 g, 6.53 mmol) and THF (25 mL). The reaction mixture was stirred at room temperature for 30 hours, then diluted with water (20 mL) and extracted with EtOAc (2×60 mL). The organic phase was dried over sodium sulfate, evaporated, and purified using silica gel column (80 g) chromatography, eluting with a gradient of 0-100% hexane and EtOAc. The pure compound fractions were combined and evaporated to give the title compound as a tan solid, which turned green on standing (1.02 g, 63%). ESI-MS m/z [M+H]$^+$calc'd for C$_7$H$_8$INO, 250. found, 250.

Step F: 7-(Tributylstannyl)-3,4-dihydro-1H-pyrrolo[2,1-c][1,4]oxazine

To a cold (−78° C.) mixture of 7-iodo-3,4-dihydro-1H-pyrrolo[2,1-c][1,4]oxazine (300 mg, 1.205 mmol) and THF (10 mL) was added n-butyllithium (0.530 mL, 1.325 mmol) dropwise under a nitrogen atmosphere. The reaction mixture was stirred at −78° C. for 60 minutes, after which tributylchlorostannane (0.392 mL, 1.445 mmol) was added. The reaction mixture was stirred at −78° C. 60 minutes, then warmed to room temperature and stirred for 1 hour. The reaction was quenched with brine (10 mL) and extracted with EtOAc (2×25 mL). The organic phase was separated, dried over sodium sulfate, concentrated, and purified via flash column chromatography to give the title compound as an oil, which was used without further purification (300 mg, 60%).

Preparation 21

1,3-Dimethyl-5-(tributylstannyl)-1H-thieno[2,3-c]pyrazole

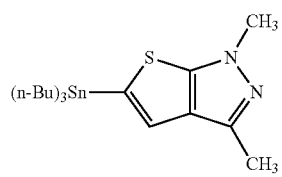

Step A: 1,3-Dimethyl-1H-thieno[2,3-c]pyrazole

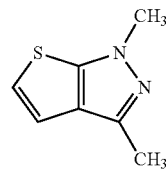

A mixture of 1,3-dimethyl-1H-thieno[2,3-c]pyrazole-5-carboxylic acid (2 g, 10.19 mmol), copper (1.943 g, 30.6 mmol) and quinoline (10 mL, 85 mmol) were heated to 200° C. for 1 hour in a Biotage Initiator microwave. Following heating, the mixture was extracted with ethyl acetate (3×100 mL) and 3N HCl (200 mL). The organic layers were combined, dried over sodium sulfate, concentrated, and purified via silica gel flash chromatography, eluting with a gradient of 10-40% EtOAc and hexane to give the title compound as a clear oil (1.07 g, 69%). $^1$H NMR (400 MHz, DMSO-d$_6$) δ ppm 2.32 (s, 9H), 3.83 (s, 3H), 6.98 (d, J=5.40 Hz, 1H), 7.09 (d, J=4.90 Hz, 1H). ESI-MS m/z [M+H]$^+$ calc'd for C$_7$H$_8$N$_2$S, 153. found, 153.

Step B: 1,3-Dimethyl-5-(tributylstannyl)-1H-thieno[2,3-c]pyrazole

To a cold (−78° C.) mixture of 1,3-dimethyl-1H-thieno[2,3-c]pyrazole (1.0 g, 6.57 mmol) and THF (50 mL) was added n-butyllithium (4.52 mL, 7.23 mmol) dropwise and allowed under a nitrogen atmosphere. The reaction mixture was stirred at −78° C. for 1 hour. To this solution was added tributylchlorostannane (2.13 mL, 7.88 mmol) and the mixture was stirred at −78° C. for 1 hour and then warmed to room temperature over a period of 2 hours. The reaction was quenched with brine (100 mL) and extracted with ethyl acetate (2×100 mL). The organic layers were combined, dried over sodium sulfate, concentrated, and purified via silica gel flash chromatography, eluting with 20% EtOAc and hexane to give the title compound as a clear oil (1.60 g, 55%). $^1$H NMR (400 MHz, DMSO-d$_6$) δ ppm 0.86 (t, J=7.33 Hz, 9H), 1.02-1.06 (m, 6H), 1.30 (dq, J=7.29, 14.75 Hz, 6H), 1.44-1.64 (m, 6H), 2.31 (s, 3H), 3.80 (s, 3H), 6.94 (s, 1H).

Preparation 22

Ethyl 2-(4,4,5,5-tetramethyl-1,3,2-dioxaborolan-2-yl)indolizine-7-carboxylate

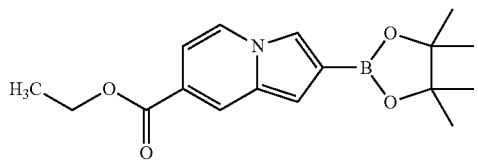 [SMILES: CCOC(=O)c1ccn2cc(B3OC(C)(C)C(C)(C)O3)cc2c1]

Step A: Ethyl 2-bromoindolizine-7-carboxylate

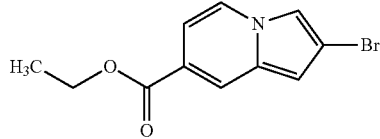

A mixture of 4-bromo-1H-pyrrole-2-carbaldehyde (1.00 g, 5.75 mmol), (E)-ethyl 4-bromobut-2-enoate (1.555 mL, 11.49 mmol), and potassium carbonate (1.74 g, 12.6 mmol) in DMF (20 mL) was stirred overnight at room temperature under a nitrogen atmosphere. Following reaction, the solution was extracted with ethyl acetate (2×100 mL) and water (100 mL). The organic layers were combined, dried over sodium sulfate, concentrated, and purified via silica gel flash chromatography, eluting with a gradient of 10-30% EtOAc and hexane to give, upon removal of solvent, the title compound as a purple solid (350 mg, 23%). $^1$H NMR (400 MHz, DMSO-d$_6$) δ ppm 1.32 (t, J=7.40 Hz, 3H), 4.31 (q, J=5.40 Hz, 2H), 6.92 (s, 1H), 7.02-7.03 (m, 1H), 7.93 (s, 1H), 8.13 (s, 1H), 8.28-8.29 (m, 1H). ESI-MS m/z [M+H]$^+$ calc'd for C$_{11}$H$_{10}$BrNO$_2$, 268. found, 268.

Step B: Ethyl 2-(4,4,5,5-tetramethyl-1,3,2-dioxaborolan-2-yl)indolizine-7-carboxylate A mixture of ethyl 2-bromoindolizine-7-carboxylate (100 mg, 0.373 mmol), bis(pinacolato)diboron (227 mg, 0.895 mmol), PdCl$_2$(dppf) (13.65 mg, 0.019 mmol), and potassium acetate (110 mg, 1.12 mmol) in DMSO (3 mL) was heated to 80° C. in an oil bath overnight. The solution was extracted with diethyl ether (2×20 mL) and water (30 mL). The organic layers were combined, dried over magnesium sulfate, and concentrated to give the title compound, which was used without further purification (328 mg). ESI-MS m/z [M+H]$^+$calc'd for C$_{12}$H$_{22}$BNO$_4$, 316. found, 316.

Preparation 23

6-(4,4,5,5-Tetramethyl-1,3,2-dioxaborolan-2-yl)-2,3-dihydro-1H-pyrrolizin-1-one

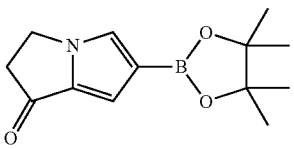 [SMILES: CC1(C)OB(c2cc3n(c2)CCC3=O)OC1(C)C]

Step A: 6-Bromo-2,3-dihydro-1H-pyrrolizin-1-one

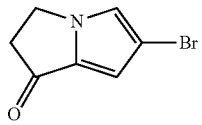

A mixture of 2,3-dihydro-1H-pyrrolizin-1-one (300 mg, 2.48 mmol) in THF (20 mL) was cooled to −10° C. in a brine bath. N-Bromosuccinimide (441 mg, 2.48 mmol) in THF (5 mL) was added dropwise, and the reaction mixture was stirred at −10° C. for 1 hour. The reaction was subsequently quenched with water (100 mL) and extracted with ethyl acetate (2×100 mL). The organic layers were combined and dried and to give the title compound, which was used without further purification (520 mg). $^1$H NMR (400 MHz, DMSO-d$_6$) δ ppm 3.02-3.05 (m, 2H), 4.17-4.20 (m, 2H), 6.58 (d, J=4.40 Hz, 1H), 6.67 (d, J=3.90 Hz, 1H). ESI-MS m/z [M+H]$^+$calc'd for C$_7$H$_6$BrNO, 200. found, 200.

Step B: 6-(4,4,5,5-Tetramethyl-1,3,2-dioxaborolan-2-yl)-2,3-dihydro-1H-pyrrolizin-1-one A mixture of 6-bromo-2,3-dihydro-1H-pyrrolizin-1-one (520 mg, 2.60 mmol), bis(pinacolato)diboron (1584 mg, 6.24 mmol), PdCl$_2$(dppf) (95 mg, 0.130 mmol), and potassium acetate (765 mg, 7.80 mmol) in DMSO (12 mL) was heated to 80° C. in an oil bath overnight. The solution was extracted with ether (2×20 mL) and water (30 mL). The organic layers were combined, dried over magnesium sulfate, and concentrated to give the title compound, which was used without further purification (1.56 g). $^1$H NMR (400 MHz, DMSO-d$_6$) δ ppm 1.17 (s, 12H), 3.01-3.04 (m, 2H), 4.28-4.30 (m, 2H), 7.51 (s, 1H), 7.92 (s, 1H). ESI-MS m/z [M+H]$^+$calc'd for C$_{13}$H$_{18}$BNO$_3$, 248. found, 248.

Preparation 24 tert-Butyl (1S,2R)-2-aminocyclohexylcarbamate, (S)-mandelic acid salt

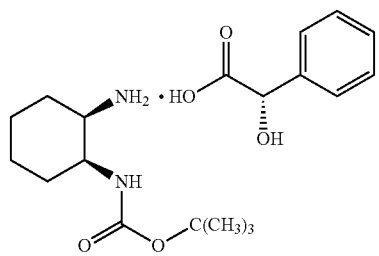

Step A: A. cis-N-(2-Aminocyclohexyl)-2,2,2-trifluoroacetamide

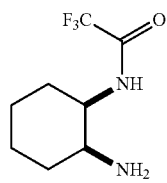

To a 12-L 4-neck cylindrical jacketed vessel equipped with an overhead stirrer, J-KEM thermocouple, and an addition funnel, was charged a solution of cis-cyclohexane-1,2-diamine (500.0 g, 4.378 mole) in EtOH (2.5 L) under nitrogen. The vessel was cooled to −5° C. Ethyl trifluoroacetate (521 mL, 1.00 eq, Acros lot # A0267844) was charged to the addition funnel and was added dropwise to the reaction mixture over a period of 1 hour and 45 minutes to afford the title compound in EtOH, which was carried forward into the next step.

Step B: cis-tert-Butyl 2-(2,2,2-trifluoroacetamido)cyclohexylcarbamate

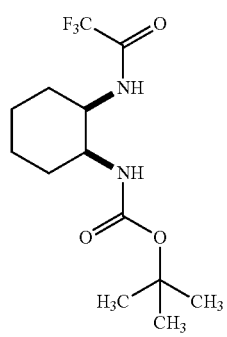 [SMILES: CC(C)(C)OC(=O)N[C@H]1CCCC[C@H]1NC(=O)C(F)(F)F]

A solution of di-tert-butyl dicarbonate (1.00 kg, 4.597 mole, 1.05 eq, Oakwood lot # DO8E) in EtOH (500 mL) was prepared and added dropwise over a period of 35 minutes to the solution of cis-N-(2-aminocyclohexyl)-2,2,2-trifluoroacetamide in EtOH from Step A. During the addition, the reaction temperature was maintained at <15° C. Once the addition was complete, the solution, which turned to a slurry after 1 hour, was stirred for 4 hours to afford the title compound in EtOH, which was carried forward into the next step.

Step C: cis-tert-Butyl 2-aminocyclohexylcarbamate

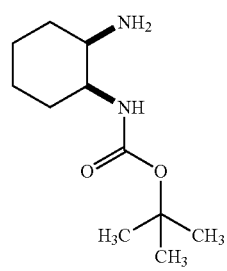

To the mixture of cis-tert-butyl 2-(2,2,2-trifluoroacetamido)cyclohexylcarbamate in EtOH from Step B, was added a solution of NaOH (500.0 g of a 50 wt % solution in water, 1.42 eq) in water (1.0 L) portion wise over a period of 15 minutes, while maintaining a reaction temperature <15° C. Once the addition was complete, the reaction temperature was allowed to rise to room temperature, and the reaction mixture was stirred at RT overnight (16 hours). The batch (6 L) was distilled under reduced pressure (~200 mBar) to a volume of ~3.4 L. Water (2.0 L) was added and the distillation was continued (at ~200 mBar) until the volume of the mixture was about 4.0 L and the solution had turned milky in appearance. The batch was cooled to 25° C., diluted with IPAc (3.5 L) and stirred for 10 minutes. Following phase separation, the aqueous phase was extracted with IPAc (1.5 L) and the phases separated. The combined organic extracts were washed with water (1.5 L) and then with an aqueous solution of NaCl (5 wt %, 1.5 L). The organic phase (5.8 L) was distilled under reduced pressure (~200 mBar) until the volume of the mixture was ~2.0 L. This afforded the title compound as a crude racemic product in IPAc, which was carried forward into the next step. Proton NMR analysis showed the presence of EtOH (2.3 mole %) and KF analysis indicated the presence of water (0.58%).

Step D: tert-Butyl (1S,2R)-2-aminocyclohexylcarbamate, (S)-mandelic acid salt The mixture of cis-tert-butyl 2-aminocyclohexylcarbamate in IPAc from Step C was heated to 80° C. and then a solution of (S)-mandelic acid (333.0 g, 2.189 mole, 0.5 eq) in IPAc (8.0 L) was added over a period of 45 minutes while maintaining the reaction temperature above 70° C. Crystallization began during the addition of the last 0.5 L of mandelic acid solution (no seed was added). Once the addition was complete, the batch was heated to 82° C. and was stirred for 13 hours under nitrogen, resulting in a beige slurry having a dark orange supernatant (visible upon sitting). The batch was cooled to 25° C. and was filtered through a 26 cm diameter Buchner funnel under vacuum over a period of less than 2 minutes. The filter cake was conditioned for 5 minutes and then washed with IPAc (1.5 L), which had been used to rinse the reaction vessel. After additional conditioning for 5 minutes, the filter cake was again washed with an IPAc rinse (1.5 L). The filter cake was conditioned for 30 minutes and then tray dried in a vacuum oven at 40-50° C. for 5 hours to give the title compound (550 g, 34% over 4 steps, 99.1% ee via chiral HPLC analysis following derivatization with 4-methoxy benzoyl chloride and work-up).

Preparation 25 tert-Butyl 6-((1R,2S)-2-(tert-butoxycarbonylamino) cyclohexylamino)-4-chloro-7-fluoro-3-oxo-1H-pyrrolo[3,4-c]pyridine-2(3H)-carboxylate

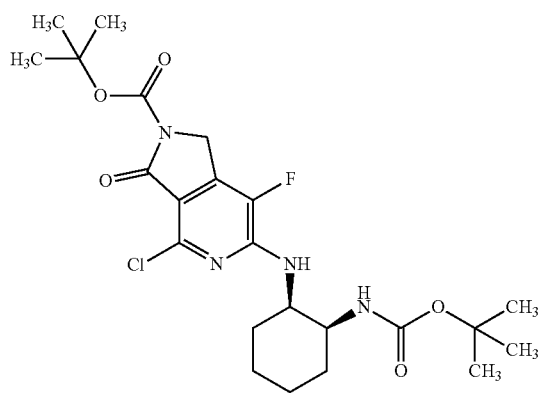 [SMILES: CC(C)(C)OC(=O)N[C@H]1CCCC[C@H]1Nc1nc(Cl)c2c(c1F)CN(C(=O)OC(C)(C)C)C2=O]

Step A: tert-Butyl (1S,2R)-2-aminocyclohexylcarbamate (free base)

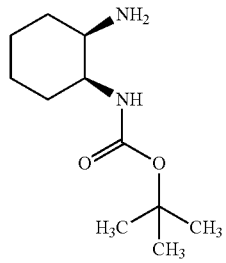

To a 10-L carboy equipped with a magnetic stirrer was charged tert-butyl (1S,2R)-2-aminocyclohexylcarbamate, (S)-mandelic acid salt (570.56 g, 1.5580 mol, 1.25 eq). Water (2.8 L) and MTBE (2.28 L) were added and agitation was begun. To the resulting white slurry was added 2N NaOH solution (1.25 L). The mixture was stirred at room temperature for 30 minutes. The phases were separated in a 22-L separatory funnel. The aqueous layer was extracted with MTBE (2.28 L), and the organic extracts were combined, washed with water (2 L) and brine (2 L), and transferred to a 5-L 4-neck RBF equipped with reduced-pressure distillation apparatus. The mixture was concentrated under reduced pressure (240-245 torr) to a volume of about 2 L over a period of about 5 hours. The mixture was stored at room temperature overnight. Isopropanol (2 L) was added to the mixture, which was distilled under a vacuum of 230-234 torr for 75 minutes and then under a vacuum of 123-125 torr for 2 hours and 40 minutes, resulting in a volume of about 2 L. A second portion of IPA (2 L) was added and the mixture was stored at room temperature overnight. The mixture was subsequently distilled at a pressure of 112-115 torr for 5 hours. Isopropanol (800 mL) was added and the mixture was distilled under a vacuum of 114-116 torr for 3 hours. The residual was stored at room temperature overnight, whereupon distillation was continued under a vacuum of 114-116 torr for 4 hours until about 2 L of the material remained. NMR analysis of the residual indicated that MTBE was not detectable.

Step B: tert-Butyl 6-((1R,2S)-2-(tert-butoxycarbonylamino)cyclohexylamino)-4-chloro-7-fluoro-3-oxo-1H-pyrrolo[3,4-c]pyridine-2(3H)-carboxylate To the 5-L RBF containing tert-butyl (1S,2R)-2-aminocyclohexylcarbamate (STEP A) was added tert-butyl 4,6-dichloro-7-fluoro-3-oxo-1H-pyrrolo[3,4-c]pyridine-2(3H)-carboxylate (400.0 g, 1.246 mol, 1 eq). To this mixture was added IPA (400 mL), DMSO (400 mL) and DIPEA (282 mL, 1.3 eq). The resulting pink slurry was heated up to 78° C. and was stirred for 34 hours. The mixture was then cooled to room temperature and was stirred over the weekend. HPLC analysis indicated the presence of 1.6% of the starting material, 4.63% of the des-Boc side product, 72.38% of the desired product, and 11.23% of an isomer. $^1$H NMR analysis indicated a ratio of 5.49 of the IPA/DMSO. Isopropanol (200 mL) was added to the mixture to adjust the ratio to 6. The slurry was heated up to 78° C. Water (1.6 L) was added over a period of 1 hour at a rate which kept the temperature of the mixture above 64° C. The mixture was then cooled to room temperature and was stirred overnight. The slurry was filtered the next morning through a fritted glass funnel. The filter cake was washed with IPA/water/DMSO (800 mL, 6:4:1) and IPA/water (2×800 mL, 3:2) to give the title compound, which was dried under high vacuum at 40-45° C. until a constant weight was obtained (299.27 g, 48% yield with a 96.6% purity). $^1$H NMR (300 MHz, CDCl$_3$) δ ppm 1.80-1.30 (m, 26 H), 4.04 (m, 1 H), 4.21 (m, 1 H), 4.64 (d, J=0.9 Hz, 1 H), 4.85 (br, 1 H), 6.08 (br, 1 H).

Preparation 26 tert-Butyl 4-chloro-6,7-difluoro-3-oxo-1H-pyrrolo[3,4-c]pyridine-2(3H)-carboxylate

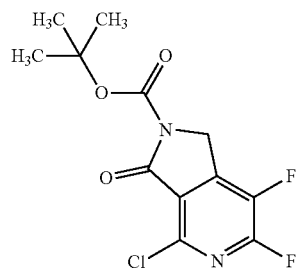 [SMILES: CC(C)(C)OC(=O)N1Cc2c(F)c(F)nc(Cl)c2C1=O]

Step A: 2-Chloro-5,6-difluoronicotinonitrile

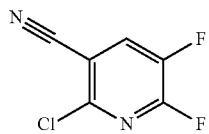 [SMILES: N#Cc1cc(F)c(F)nc1Cl]

To 2,6-dichloro-5-fluoronicotinonitrile (50 g, 262 mmol) was added spray-dried potassium fluoride (30 g, 516 mmol) followed immediately by the addition of anhydrous DMSO (125 mL). The reaction mixture was stirred at 20° C. for 16-20 hours. The progress of the reaction was closely monitored by HPLC. When the product concentration reached maximum (~79%), the reaction was worked up immediately. Ethyl acetate (1000 mL) was added to the reaction mixture followed by the addition of ice (50 g). Water (500 mL) was then slowly added with cooling to ensure the temperature did not exceed 25° C. The organic phase and the aqueous phase were separated. The organic phase was washed with water (400 mL). Active carbon (12 g, Darco G-60, 100 mesh) was added and the mixture was stirred for 2 hours. The mixture was filtered through a pad of Celite. The filtrate was washed with water (400 mL) and concentrated by rotary evaporation to a volume of about 120 mL. The concentrate was diluted with heptane (150 mL) and the resulting solution was concentrated to a volume of about 150 mL, which resulted in precipitation of solid product. The mixture was stirred for 30 minutes at room temperature and filtered. The filter cake was washed with heptane (100 mL) and dried to afford the title compound (29.5 g, 65%). $^1$H NMR (500 MHz, CDCl$_3$) δ ppm 7.92-7.96 (m, 1 H).

Step B: 2-Chloro-5,6-difluoronicotinamide

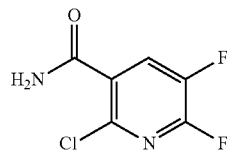 [SMILES: NC(=O)c1cc(F)c(F)nc1Cl]

To a mixture of 2-chloro-5,6-difluoronicotinonitrile (89.66 g, 514 mmol), acetamide (66.8 g, 1130 mmol), THF (337.5 mL), and water (113 mL) was added palladium(II) chloride (1.822 g, 10.27 mmol) with stirring. The reaction mixture was stirred at 60° C. for 18 hours under a nitrogen atmosphere. The reaction mixture was subsequently cooled to room temperature and was added to a stirred mixture of EtOAc (900 mL), hexane (90 mL) and water (180 mL). The layers were allowed to separate and the aqueous layer was removed. The organic layer was washed with water (180 mL) and concentrated on a rotary evaporator at 29° C. to afford an oil that solidified. The solid was suspended in hexanes (270 mL) and filtered after 1 hour. The flask was rinsed forward with hexanes (50 mL). The filter cake was washed with additional hexanes (20 mL) and dried in a vacuum oven at 40° C. to give the title compound as a light tan solid (82.21 g, 83%). $^1$H NMR (400 MHz, DMSO-d$_6$) δ ppm 7.93 (s br, 1H), 8.10 (s br, 1H), 8.32-8.37 (m 1H).

Step C: 4-Chloro-6,7-difluoro-1-hydroxy-1H-pyrrolo[3,4-c]pyridin-3(2H)-one

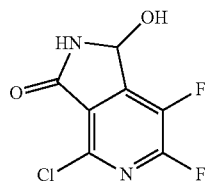 [SMILES: O=C1NC(O)c2c(F)c(F)nc(Cl)c21]

To an inert 250 mL 3-neck round bottom flask with magnetic stirring was added LiHMDS (1M in THF, 57.3 mL, 57.3 mmol). The solution was cooled in an ice/brine bath to achieve an internal temperature of −4° C. To the cooled LiHMDS solution was added dropwise a solution of 2-chloro-5,6-difluoronicotinamide (4.41 g, 22.9 mmol) dissolved in 2-methyltetrahydrofuran (22 mL) and N,N-dimethylformamide (8.87 mL, 115 mmol) while maintaining the internal temperature between +1° C. to −3° C. The reaction mixture was stirred for 30 minutes at a temperature of about 0° C. The reaction was quenched by adding it dropwise to a cooled (0-5° C.) stirred mixture of 2M aqueous HCl (74.4 mL, 149 mmol) and IPAc (75 mL) while maintaining an internal temperature <10° C. Once the transfer was completed, the biphasic solution was transferred to a separatory funnel and the lower aqueous layer was removed and extracted with IPAc (75 mL). The organic layers were combined, washed with water (25 mL), dried over sodium sulfate, and concentrated on a rotary evaporator. The resulting solid was suspended in heptane (20 mL), and the mixture was stirred for 90 minutes and filtered. The filter cake was washed with heptane (20 mL) and dried to give the title compound as an off-white solid (4.442 g, 88%). $^1$H NMR (400 MHz, DMSO-d$_6$) δ ppm 6.11-6.14 (m, 1H), 6.98 (d, J=8 Hz, 1H), 9.5 (s br, 1H).

Step D: 4-Chloro-6,7-difluoro-1H-pyrrolo[3,4-c]pyridin-3(2H)-one

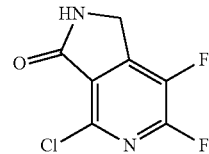 [SMILES: O=C1NCc2c(F)c(F)nc(Cl)c21]

To an inert 50 mL round bottom flask with magnetic stirring was added 4-chloro-6,7-difluoro-1-hydroxy-1H-pyrrolo[3,4-c]pyridin-3(2H)-one (4.39 g, 19.90 mmol) and trifluoroacetic acid (18.40 mL, 239 mmol). The solids were suspended with stirring and triethylsilane (7.95 mL, 49.8 mmol) was added. The reaction mixture was heated to 60° C. and stirred for 30 minutes at that temperature. The reaction mixture was subsequently cooled to room temperature and added dropwise to MTBE (88 mL) to produce a white precipitate. The suspension was cooled to 5° C. for 45 minutes. The solids were filtered, washed with MTBE (20 mL) and air dried on the filter to afford the title compound (3.336 g, 82%). $^1$H NMR (400 MHz, DMSO-d$_6$) δ ppm 4.58 (s, 2H), 9.13 (s br, 1H).

Step E: tert-Butyl 4-chloro-6,7-difluoro-3-oxo-1H-pyrrolo[3,4-c]pyridine-2(3H)-carboxylate To a 50 mL 3-neck round bottom flask with magnetic stirring was added 4-chloro-6,7-difluoro-1H-pyrrolo[3,4-c]pyridin-3(2H)-one (3.25 g, 15.89 mmol) and DCM (23 mL).

75

The suspension was cooled to 5° C. and Et₃N (4.43 mL, 31.8 mmol) was added followed by DMAP (0.019 g, 0.159 mmol). A solution of di-tert-butyl dicarbonate (4.16 g, 19.07 mmol) in DCM (6.5 mL) was added dropwise over a period of 2 minutes during which the reaction mixture turned dark red. The reaction mixture was stirred and allowed to warm slowly to 14° C. over a 4 hour period after which HPLC analysis showed 11% starting material remained. Additional DMAP (0.019 g, 0.159 mmol) was added to provide complete consumption of the starting material within 1 hour. The reaction suspension was then added to IPA (65 mL). The red suspension was cooled to 5° C. for 5 minutes before the solids were filtered, washed with IPA (10 mL), and dried in a vacuum oven at 45° C. overnight to yield the title compound as a reddish solid (3.87 g, 80%). ¹H NMR (400 MHz, DMSO-d₆) δ ppm 1.53 (s, 9H), 4.94 (s, 2H).

Preparation 27 tert-Butyl 6-((3R,4R)-3-(tert-butoxycarbonylamino) tetrahydro-2H-pyran-4-ylamino)-4-chloro-7-fluoro-3-oxo-1H-pyrrolo[3,4-e]pyridine-2(3H)-carboxylate

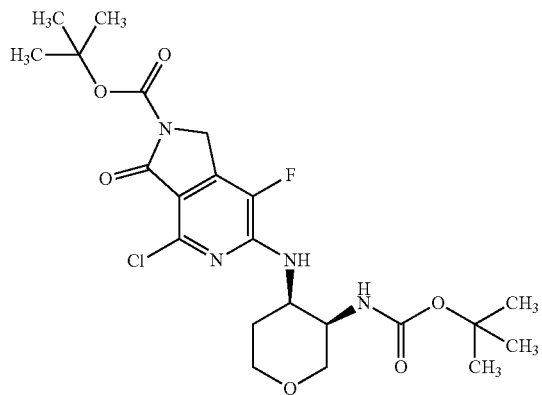 [SMILES: CC(C)(C)OC(=O)N[C@H]1COCC[C@H]1Nc1nc(Cl)c2c(c1F)CN(C(=O)OC(C)(C)C)C2=O]

To a mixture of tert-butyl 4-chloro-6,7-difluoro-3-oxo-1H-pyrrolo[3,4-c]pyridine-2(3H)-carboxylate (42.5 g, 139 mmol) and tert-butyl (3R,4R)-4-aminotetrahydro-2H-pyran-3-ylcarbamate (36.2 g, 167 mmol) was added IPA (425 mL) followed by 4-methylmorpholine (18.40 mL, 167 mmol). The reaction mixture was stirred at 60° C. for 20 hours under a nitrogen atmosphere. HPLC analysis indicated that the reaction was complete. The reaction mixture was subsequently cooled to room temperature and water (890 mL) was added slowly. The suspension was cooled in an ice/water bath to 6° C. and was stirred for 1 hour. The solids were collected by filtration and washed with water (30 mL) used to rinse the reaction vessel. The filter cake was washed with additional water (350 mL) and allowed to dry on the filter. The filter cake was subsequently dried in a vacuum oven at 60° C. over the weekend to afford the title compound (64.78 g, 93%). ¹H NMR (400 MHz, DMSO-d₆) δ ppm 1.36 (s, 9 H), 1.50 (s, 9 H), 1.59-1.61 (m, 1 H), 1.97-1.99 (m, 1 H), 1.97-1.99 (m, 1 H), 3.46-3.49 (m, 2 H), 3.80-3.83 (m, 3 H), 4.31-4.33 (m, 1 H), 4.73 (s, 1 H), 6.59 (d, J=7.30 Hz, 1 H), 7.43 (d, J=7.30 Hz, 1 H). ESI-MS m/z [M+H]⁺calc'd for C₂₂H₃₀ClFN₄O₆, 501. found, 501.

76

Preparation 28 tert-Butyl 6-((1R,2S)-2-(tert-butoxycarbonylamino) cyclohexylamino)-7-fluoro-4-(3-methylisothiazol-5-yl)-3-oxo-1H-pyrrolo[3,4-c]pyridine-2(3H)-carboxylate

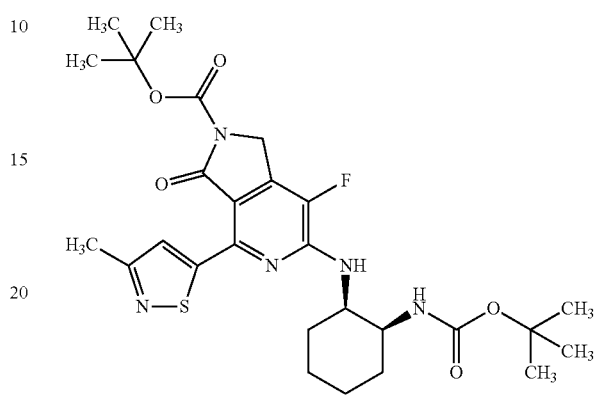

METHOD A: A solution of tert-butyl 6-((1R,2S)-2-(tert-butoxycarbonylamino)cyclohexylamino)-4-chloro-7-fluoro-3-oxo-1H-pyrrolo[3,4-c]pyridine-2(3H)-carboxylate (100 mg, 0.200 mmol), 3-methyl-5-(tributylstannyl)isothiazole (117 mg, 0.301 mmol) and tetrakis(triphenylphosphine) palladium(0) (116 mg, 0.100 mmol) in toluene (10 mL) was heated to 120° C. for 45 minutes via microwave irradiation. The reaction mixture was poured into water and was extracted with EtOAc. The extracts were dried over Na₂SO₄, and concentrated in vacuo. The residue was purified by silica gel chromatography (Flash 60 column) eluting with hexane/EtOAc (4:1) to give the title compound as a yellow solid (84.4 mg, 75%). ¹H NMR (500 MHz, CDCl₃) δ ppm 1.29-1.51 (m, 11 H), 1.53-1.70 (m, 11 H), 1.71-1.88 (m, 3 H), 2.03-2.17 (m, 1 H), 2.58 (s, 3 H), 4.07-4.21 (m, 2 H), 4.72 (s, 2 H), 4.89 (br s, 1 H), 6.36 (br s, 1 H), 8.74 (s, 1 H). ESI-MS m/z [M+H]⁺calc'd for C₂₇H₃₆FN₅O₅S, 562. found, 562.

METHOD B: To a solution of 3-methyl-5-(4,4,5,5-tetramethyl-1,3,2-dioxaborolan-2-yl)isothiazole (24.39 g, 108 mmol) in DMA (110 mL) was added cesium fluoride (10.76 g, 70.1 mmol). During the CsF addition the temperature of the reaction mixture rose to 26° C. The reaction mixture was cooled to 22° C. and was stirred for 90 minutes. The reaction mixture was degassed by successively evacuating and purging the reaction vessel with nitrogen (3×). A portion of the degassed boronate solution (25 mL) was then added to a mixture of tert-butyl 6-((1R,2S)-2-(tert-butoxycarbonylamino)cyclohexylamino)-4-chloro-7-fluoro-3-oxo-1H-pyrrolo[3,4-c]pyridine-2(3H)-carboxylate (21.20 g, 42.5 mmol) and Pd-118 (Johnson-Matthey, 1.448 g, 2.124 mmol) which was suspended in DMA (100 mL) and degassed by nitrogen purging (3×). The reaction mixture was heated to 80° C. over a period of 15 minutes. Once the temperature of the reaction mixture reached about 65° C., the remainder of the boronate solution was added slowly over a period of 60 minutes. The reaction mixture was then heated at 77° C. for 14 hours and was subsequently cooled to room temperature. The reaction mixture was extracted with EtOAc (2×500 mL) and water (500 mL). The organic extracts were combined, dried over sodium sulfate, concentrated, and purified via silica gel flash chromatography, eluting with a gradient of 5-20% EtOAc and hexanes/dichloromethane (1:1). The resulting brown solid was triturated with EtOAc/hexanes (1:9, 200 mL) and was collected via vacuum filtration to give a crude tan solid (ca 19 g). The crude product was dispersed in absolute ethanol (200 mL). The mixture was heated to 60° C. for 1 hour and was allowed to cool to room temperature. The mixture was further cooled to 0° C. in an ice bath. The precipitate was collected and dried to afford the title compound as a tan solid (13.86 g, 58%). $^1$H NMR (400 MHz, DMSO-$d_6$) δ ppm 1.06-1.08 (m, 2H), 1.34 (s, 9H), 1.34-1.36 (m, 2H), 1.53 (s, 9H), 1.55-1.57 (m, 2H), 1.61-1.63 (m, 2H), 2.49 (s, 3H), 3.93-3.94 (m, 1H), 4.10-4.11 (m, 1H), 4.79 (s, 2H), 6.70-6.71 (br s, 1H), 7.16-7.17 (br s, 1H), 8.52 (s, 1H). ESI-MS m/z [M+H]$^+$calc'd for $C_{27}H_{36}FN_5O_5S$, 562. found, 562.

Preparation 29

4,6-Dichloro-7-fluoro-1-hydroxyfuro[3,4-c]pyridin-3(1H)-one

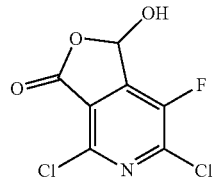 [SMILES: O=C1OC(O)c2c(F)c(Cl)nc(Cl)c21]

To a solution of diisopropylamine (96 g, 0.94 mol) in THF (800 mL) was slowly added n-butyllithium (379 mL, 0.95 mol, 2.5 M) at −78° C. The mixture was stirred at the same temperature for 30 minutes. To the mixture was added 2,6-dichloro-5-fluoronicotinic acid (90 g, 0.43 mol) in THF (500 mL). The solution was stirred for an additional 2 h. To the mixture was added DMF (154 mL, 1.94 mol) dropwise, The mixture was stirred for 1 h, after which 2N HCl (1.54 L) (pH<1) was introduced. The mixture was subsequently extracted with EtOAc and the organic layers were basified with aqueous NaHCO$_3$ (pH >8). The aqueous layer was separated, acidified with 2N HCl (1.2 L) (pH<1), and extracted with EtOAc. The organic layer was washed with water and brine, dried over anhydrous Na$_2$SO$_4$, and filtered. The filtrate was concentrated under reduced pressure and the resulting residue was washed with DCM to give the title compound as a reddish solid (81.6 g, 80%). $^1$H NMR (DMSO-$d_6$, 400 MHz) δ ppm 6.85 (s, 1H), 8.83 (s, 1H). [M+H] calc'd for $C_7H_2Cl_2FNO_3$, 238. found, 238.

Preparation 30

(E)-2,6-Dichloro-4-(((2,4-dimethoxybenzyl)imino)methyl)-5-fluoronicotinic acid

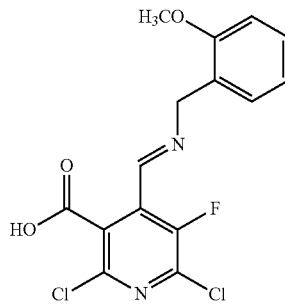

To a solution of (2,4-dimethoxyphenyl)methanamine (40.5 g, 242.0 mmol) in MeOH (250 mL) was added 4,6-dichloro-7-fluoro-1-hydroxyfuro[3,4-c]pyridin-3(1H)-one (55.0 g, 231.0 mmol). The mixture was stirred for 0.5 h, filtered, and washed with petroleum ether to give the title compound as a white solid (73.0 g, 82%). $^1$H NMR (CDCl$_3$, 400 MHz) δ ppm 3.75 (s, 3H), 3.79 (s, 3H), 3.93 (s, 2H), 6.30 (s, 1H), 6.40-6.42 (m, 2H), 7.12 (d, J=8.4 Hz, 1H). [M+H] calc'd for $C_{16}H_{13}Cl_2FN_2O_4$, 387. found, 387.

Preparation 31

4,6-Dichloro-2-(2,4-dimethoxybenzyl)-7-fluoro-1-methyl-1H-pyrrolo[3,4-c]pyridin-3(2H)-one

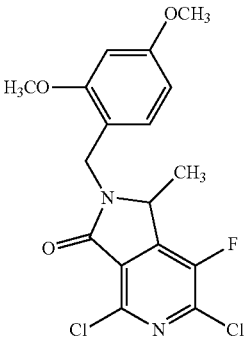 [SMILES: COc1ccc(CN2C(=O)c3c(Cl)nc(Cl)c(F)c3C2C)c(OC)c1]

To a mixture of (E)-2,6-dichloro-4#(2,4-dimethoxybenzyl)imino)methyl)-5-fluoronicotinic acid (72.0 g, 186.5 mmol) in THF (700 mL) was added methyllithium (933.0 mL, 933.0 mmol) dropwise at −78° C. After the addition was complete, the solution was stirred for an additional 2 h. The reaction mixture was then acidified with 1N HCl to pH 6, heated to 50° C. for 7 h, and subsequently extracted with EtOAc. The organic layer was washed with brine and dried over anhydrous Na$_2$SO$_4$. The concentrated crude was purified by silica gel chromatography to give the title compound as a white solid (14 g, 15%). $^1$H NMR (CDCl$_3$, 400 MHz) δ ppm 1.58 (d, J=6.8 Hz, 3H), 3.79 (s, 3H), 3.84 (s, 3H), 4.35 (d, J=14.4 Hz, 1H), 4.52 (q, J=6.8 Hz, 1H), 5.07 (d, J=14.4 Hz, 1H), 6.43-6.45 (m, 2H), 7.28 (d, J=9.2 Hz, 1H). [M+H] calc'd for $C_{12}H_{15}Cl_2FN_2O_3$, 385. found, 385.

Preparation 32

4,6-Dichloro-7-fluoro-1-methyl-1H-pyrrolo[3,4-c]pyridin-1N 3(2H)-one

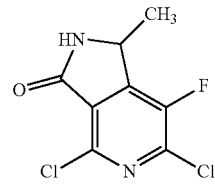

4,6-Dichloro-2-(2,4-dimethoxybenzyl)-7-fluoro-1-methyl-1H-pyrrolo[3,4-c]pyridin-3(2H)-one (14.0 g, 36.4 mmol) was dissolved in TFA (70 mL) and triethylsilane (5.1 g, 43.7 mmol). The mixture was heated to reflux and additional triethylsilane (1.3 g, 10.9 mmol) was added until the red-colored solution became clear. TFA and triethylsilane were removed under reduced pressure. The mixture was basified with aq. NaHCO$_3$ to pH 7 and filtered to give the title compound (7.3 g, 85%). $^1$H NMR (DMSO-d$_6$, 400 MHz) δ ppm 1.42 (d, J=6.8 Hz, 3H), 4.92 (q, J=6.8 Hz, 2H), 9.25 (s, 1H). [M+H] calc'd for C$_8$H$_5$C$_{12}$FN$_2$O, 235. found, 235.

Preparation 33 tert-Butyl 4,6-dichloro-7-fluoro-3-oxo-1H-pyrrolo[3,4-c]pyridine-2(3H)-carboxylate

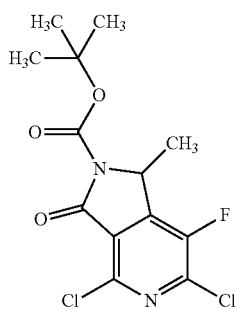 [SMILES: CC1c2c(F)c(Cl)nc(Cl)c2C(=O)N1C(=O)OC(C)(C)C]

To a mixture of 4,6-dichloro-7-fluoro-1-methyl-1H-pyrrolo[3,4-c]pyridin-3(2H)-one (7.3 g, 31.1 mol) in acetonitrile (50 mL) was added di-tert-butyl dicarbonate (7.5 g, 34.2 mol) dropwise while stirring the mixture in an ice bath. After the addition was complete, the mixture was stirred for an additional 0.5 h. The resulting solid was collected by filtration and washed with acetonitrile and ethyl acetate to give a white solid (5.5 g, 53%). $^1$H NMR (DMSO-d$_6$) δ ppm 1.53 (s, 9H), 1.61 (d, J=6.8 Hz, 3H), 5.30 (q, J=6.8 Hz, 2H). [M+H] calc'd for C$_{12}$H$_{11}$C$_{12}$FN$_2$O$_3$, 321. found, 321.

Preparation 34 tert-Butyl 6-(((1R,2S)-2-((tert-butoxycarbonyl)amino)cyclohexyl)amino)-4-chloro-7-fluoro-1-methyl-3-oxo-1H-pyrrolo[3,4-c]pyridine-2(3H)-carboxylate

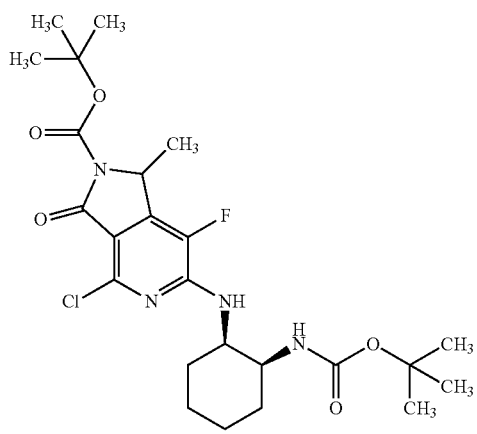 [SMILES: CC1c2c(F)c(N[C@@H]3CCCC[C@@H]3NC(=O)OC(C)(C)C)nc(Cl)c2C(=O)N1C(=O)OC(C)(C)C]

To a flask containing a mixture of tert-butyl 4,6-dichloro-7-fluoro-3-oxo-1H-pyrrolo[3,4-c]pyridine-2(3H)-carboxylate (1 g, 2.98 mmol) in 2-propanol (7 mL) was added tert-butyl ((1S,2R)-2-aminocyclohexyl)carbamate (767 mg, 3.58 mmol) dissolved in DMSO (1.2 mL) followed by DIPEA (0.677 mL, 3.88 mmol). The flask was equipped with a condenser and nitrogen blanket and was lowered into a 90° C. oil bath, where the reaction mixture was allowed to stir for 16 h. The mixture was subsequently purified via preparative HPLC to give the title compound as a white solid (490 mg, 32%). [M+H] calc'd for C$_{19}$H$_{26}$ClFN$_4$O$_3$, 413. found, 413.

Preparation 35 tert-Butyl ((3R,4R)-4-((4-chloro-2-(2,4-dimethoxybenzyl)-7-fluoro-1-methyl-3-oxo-2,3-dihydro-1H-pyrrolo[3,4-c]pyridin-6-yl)amino)tetrahydro-2H-pyran-3-yl)carbamate

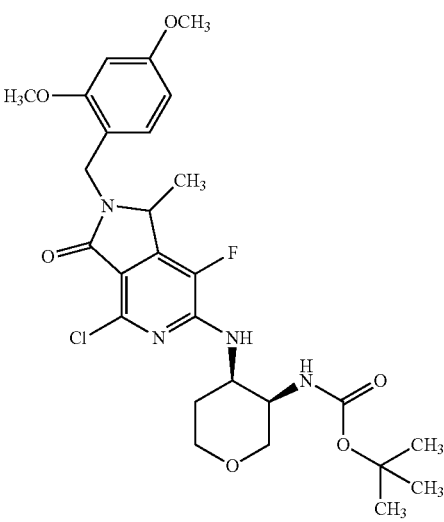 [SMILES: COc1ccc(CN2C(=O)c3c(Cl)nc(N[C@@H]4CCOC[C@@H]4NC(=O)OC(C)(C)C)c(F)c3C2C)c(OC)c1]

To a sealed tube was added 4,6-dichloro-2-(2,4-dimethoxybenzyl)-7-fluoro-1-methyl-1H-pyrrolo[3,4-c]pyridin-3(2H)-one (430 mg, 1.12 mol), tert-butyl ((3R,4R)-4-aminotetrahydro-2H-pyran-3-yl)carbamate (7.5 g, 34.2 mol), and DIPEA (0.97 mL, 5.58 mmol). The mixture was heated in the sealed tube at 95° C. for 72 h. The mixture was purified via preparative HPLC to give the title compound as a yellow solid (100 mg, 16%). [M+H] calc'd for C$_{27}$H$_{34}$ClFN$_4$O$_6$, 565. found, 565.

Example 1

6-((3R,4R)-3-Aminotetrahydro-2H-pyran-4-ylamino)-4-(3-(difluoromethyl)isothiazol-5-yl)-7-fluoro-1H-pyrrolo[3,4-c]pyridin-3(2H)-one

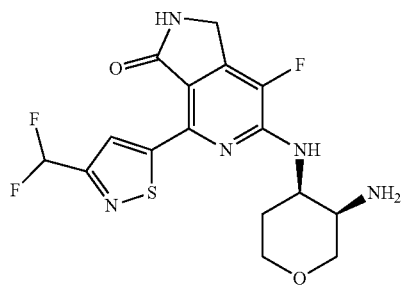 [SMILES: N[C@H]1COCC[C@H]1Nc1nc(-c2cc(C(F)F)ns2)c2c(c1F)CNC2=O]

Step A: tert-Butyl 6-((3R,4R)-3-(tert-butoxycarbonylamino)tetrahydro-2H-pyran-4-ylamino)-4-(3-(difluoromethyl)isothiazol-5-yl)-7-fluoro-3-oxo-1H-pyrrolo[3,4-c]pyridine-2(3H)-carboxylate

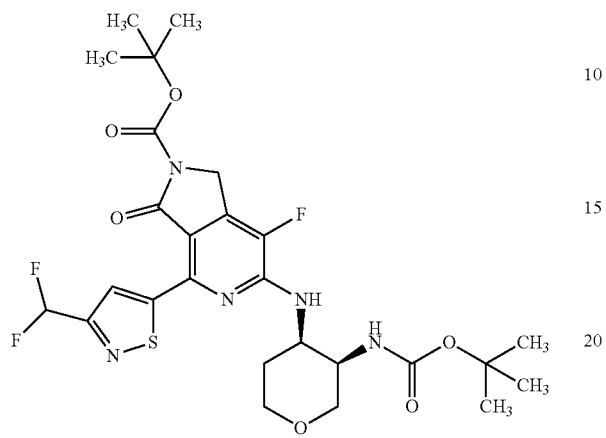

A solution of tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (50 mg, 0.100 mmol), 3-(difluoromethyl)-5-(tributylstannyl)isothiazole (296 mg, 0.699 mmol) and tetrakis(triphenylphosphine)palladium(0) (57.7 mg, 0.050 mmol) in toluene (2.0 mL) was heated to 120° C. for 45 minutes via microwave irradiation. The reaction mixture was poured into water and was extracted with EtOAc. The extracts were dried over Na$_2$SO$_4$ and concentrated in vacuo. The residue was purified by silica gel column chromatography (Flash 60 column) eluting with hexane/EtOAc (1:1) to yield the title compound as a mixture with byproduct. The crude product was used without further purification.

Step B: 6-((3R,4R)-3-Aminotetrahydro-2H-pyran-4-ylamino)-4-(3-(difluoromethyl)isothiazol-5-yl)-7-fluoro-1H-pyrrolo[3,4-c]pyridin-3(2H)-one To a stirred solution of tert-butyl 6-((3R,4R)-3-(tert-butoxycarbonylamino)tetrahydro-2H-pyran-4-ylamino)-4-(3-(difluoromethyl)isothiazol-5-yl)-7-fluoro-3-oxo-1H-pyrrolo[3,4-c]pyridine-2(3H)-carboxylate (59.8 mg, 0.100 mmol) in EtOAc (2.0 mL) and MeOH (10 mL) was added 4N HCl/dioxane (10.0 mL, 40.0 mmol). The reaction mixture was heated to 60° C. for 1 h and then concentrated in vacuo. The resulting crude material was reconstituted in DMF and purified via preparative mass triggered LCMS, eluting with a gradient of 15-40% ACN (0.035% TFA) in H$_2$O (0.05% TFA). The collected fractions were combined and the solvent was removed via rotary evaporation to yield the title compound as a TFA salt (0.5 mg, 1%). $^1$H NMR (500 MHz, CD$_3$OD) δ ppm 1.89-1.96 (m, 1 H), 2.08-2.22 (m, 1 H), 3.68-3.78 (m, 1 H), 3.87-3.96 (m, 1 H), 4.03-4.17 (m, 3 H), 4.40-4.59 (m, 3 H), 6.65-6.95 (m, 1 H), 9.15 (s, 1 H). ESI-MS m/z [M+H]$^+$ calc'd for C$_{16}$H$_{16}$F$_3$N$_5$O$_2$S, 400. found, 400.

Example 2

6-((3R,4R)-3-Aminotetrahydro-2H-pyran-4-ylamino)-4-(3-ethylisothiazol-5-yl)-7-fluoro-1H-pyrrolo[3,4-c]pyridin-3(2H)-one

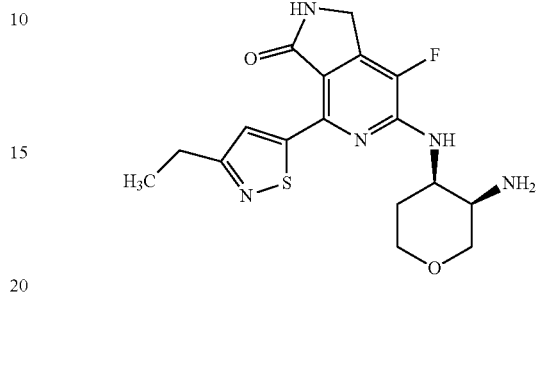

Step A: tert-Butyl 6-((3R,4R)-3-(tert-butoxycarbonylamino)tetrahydro-2H-pyran-4-ylamino)-7-fluoro-3-oxo-4-(3-vinylisothiazol-5-yl)-1H-pyrrolo[3,4-c]pyridine-2(3H)-carboxylate

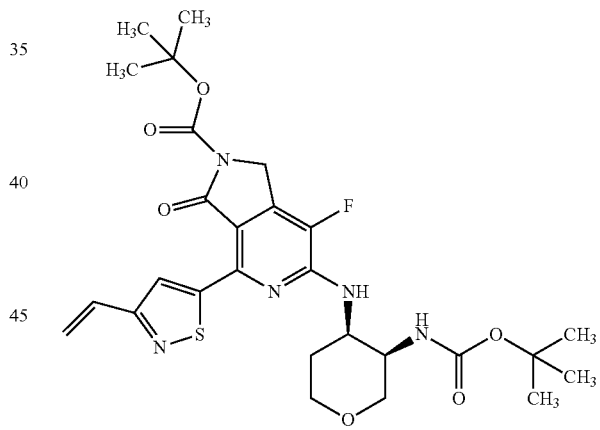

A solution of tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (75 mg, 0.150 mmol), 5-(tributylstannyl)-3-vinylisothiazole (90 mg, 0.225 mmol) and tetrakis(triphenylphosphine)palladium(0) (87 mg, 0.075 mmol) in toluene (4.0 mL) was heated to 120° C. for 45 minutes via microwave irradiation. The reaction mixture was poured into water and was extracted with EtOAc. The extracts were dried over Na$_2$SO$_4$ and concentrated in vacuo. The residue was purified by silica gel chromatography (Flash 60 column) eluting with hexane/EtOAc (1:1) to give the title compound as a yellow solid (59.2 mg, 69%). ESI-MS m/z [M+H]$^+$ calc'd for C$_{27}$H$_{34}$FN$_5$O$_6$S, 576. found, 576.

Step B: tert-Butyl 6-((3R,4R)-3-(tert-butoxycarbonylamino)tetrahydro-2H-pyran-4-ylamino)-4-(3-ethylisothiazol-5-yl)-7-fluoro-3-oxo-1H-pyrrolo[3,4-c]pyridine-2(3H)-carboxylate

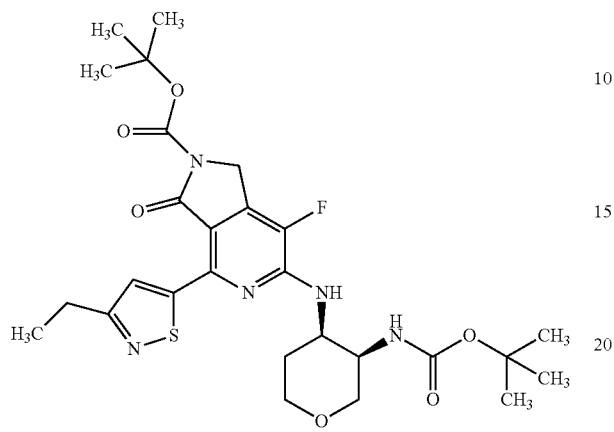

To a stirred solution of tert-butyl 6-((3R,4R)-3-(tert-butoxycarbonylamino)tetrahydro-2H-pyran-4-ylamino)-7-fluoro-3-oxo-4-(3-vinylisothiazol-5-yl)-1H-pyrrolo[3,4-c]pyridine-2(3H)-carboxylate (58 mg, 0.101 mmol) in MeOH (1.0 mL) was added Pd/C (30 mg, 0.282 mmol) under $N_2$ atmosphere. The mixture was stirred at room temperature overnight under $H_2$ atmosphere. The solids were removed by filtration, and the filtrate was concentrated in vacuo. The residue was purified by silica gel chromatography (Flash 60 column) eluting with hexane/EtOAc (1:1) to give the title compound as a yellow solid (54.9 mg, 94%). $^1$H NMR (500 MHz, CDCl$_3$) δ ppm 1.36 (t, J=7.57 Hz, 3 H), 1.48 (br s, 9 H), 1.61 (s, 9 H), 1.71-1.82 (m, 1 H), 2.20-2.33 (m, 1 H), 2.91 (q, J=7.60 Hz, 2 H), 3.64 (t, J=11.72 Hz, 1 H), 3.74 (d, J=11.72 Hz, 1 H), 3.91-3.99 (m, 1 H), 4.01-4.10 (m, 2 H), 4.23-4.34 (m, 1 H), 4.72 (s, 2 H), 5.37 (d, J=6.83 Hz, 1 H), 6.47 (br s, 1 H), 8.78 (s, 1 H). ESI-MS m/z [M+H]$^+$calc'd for $C_{27}H_{36}FN_5O_6S$, 578. found, 578.

Step C: 6-((3R,4R)-3-Aminotetrahydro-2H-pyran-4-ylamino)-4-(3-ethylisothiazol-5-yl)-7-fluoro-1H-pyrrolo[3,4-c]pyridin-3(2H)-one To a stirred solution of tert-butyl 6-((3R,4R)-3-(tert-butoxycarbonylamino)tetrahydro-2H-pyran-4-ylamino)-4-(3-ethylisothiazol-5-yl)-7-fluoro-3-oxo-1H-pyrrolo[3,4-c]pyridine-2(3H)-carboxylate (53 mg, 0.092 mmol) in MeOH (10 mL) was added 4N HCl/dioxane (10.0 mL, 40.0 mmol). The mixture was heated to 60° C. for 1 hour and then concentrated in vacuo. The residue was triturated with EtOAc and filtered. The filter cake was washed with EtOAc to give a yellow solid, which was suspended into EtOH. The mixture was stirred at 80° C. for 30 minutes and then cooled to room temperature. The resulting precipitate was collected by filtration and washed with EtOH to give a hydrochloride salt of the title compound as an off-white solid (26.8 mg, 70%). $^1$H NMR (500 MHz, DMSO-d$_6$) δ ppm 1.26 (t, J=7.57 Hz, 3 H), 1.74-1.83 (m, 1 H), 2.07-2.20 (m, 1 H), 2.81 (q, J=7.60 Hz, 2 H), 3.57-3.67 (m, 1 H), 3.73-3.84 (m, 2 H), 3.96-4.09 (m, 2 H), 4.28-4.36 (m, 1 H), 4.43-4.53 (m, 2 H), 7.46 (d, J=5.37 Hz, 1 H), 8.05 (br s, 3 H), 8.68 (s, 1 H), 8.80 (s, 1 H). ESI-MS m/z [M+H]$^+$calc'd for $C_{12}H_{20}FN_5O_2S$, 378. found, 378.

Example 3

6-((1R,2S)-2-Aminocyclohexylamino)-4-(3-ethylisothiazol-5-yl)-7-fluoro-1H-pyrrolo[3,4-c]pyridin-3(2H)-one

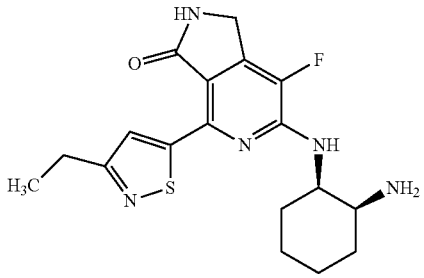 [SMILES: CCc1cc(-c2nc(N[C@@H]3CCCC[C@@H]3N)c(F)c3c2C(=O)NC3)sn1]

Step A: tert-Butyl 6-((1R,2S)-2-(tert-butoxycarbonylamino)cyclohexylamino)-7-fluoro-3-oxo-4-(3-vinylisothiazol-5-yl)-1H-pyrrolo[3,4-c]pyridine-2(3H)-carboxylate

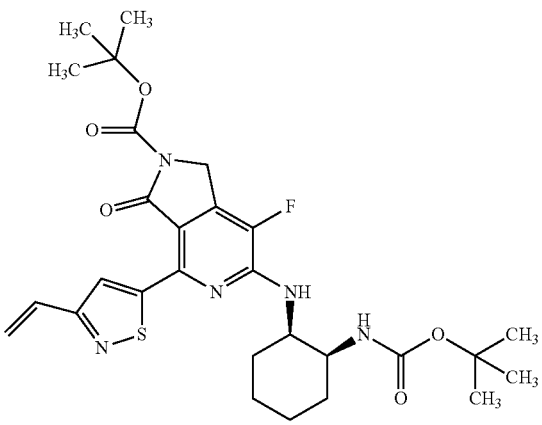 [SMILES: C=Cc1cc(-c2nc(N[C@@H]3CCCC[C@@H]3NC(=O)OC(C)(C)C)c(F)c3c2C(=O)N(C(=O)OC(C)(C)C)C3)sn1]

A solution of tert-butyl 6-((1R,2S)-2-(tert-butoxycarbonylamino)cyclohexylamino)-4-chloro-7-fluoro-3-oxo-1H-pyrrolo[3,4-c]pyridine-2(3H)-carboxylate (80 mg, 0.160 mmol), 5-(tributylstannyl)-3-vinylisothiazole (96 mg, 0.240 mmol), and tetrakis(triphenylphos-phine)palladium(0) (93 mg, 0.080 mmol) in toluene (4.0 mL) was heated to 120° C. for 45 minutes via microwave irradiation. The reaction mixture was subsequently poured into water and was extracted with EtOAc. The extracts were dried over Na$_2$SO$_4$ and were concentrated in vacuo. The residue was purified by silica gel chromatography (Flash 60 column) eluting with hexane/EtOAc (1:1) to give the title compound as a yellow solid, which was used without further purification (81.3 mg, 88%). ESI-MS m/z [M+H]$^+$calc'd for $C_{28}H_{36}FN_5O_5S$, 574. found, 574.

Step B: tert-Butyl 6-((1R,2S)-2-(tert-butoxycarbonylamino)cyclohexylamino)-7-fluoro-3-oxo-4-(3-vinylisothiazol-5-yl)-1H-pyrrolo[3,4-c]pyridine-2(3H)-carboxylate

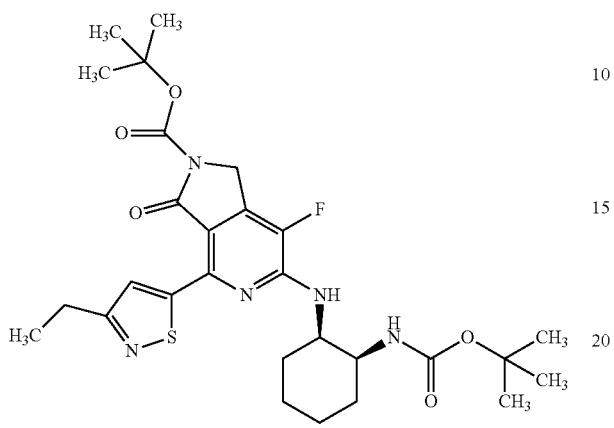

To a stirred solution of tert-butyl 6-((1R,2S)-2-(tert-butoxycarbonylamino)cyclohexylamino)-7-fluoro-3-oxo-4-(3-vinylisothiazol-5-yl)-1H-pyrrolo[3,4-c]pyridine-2(3H)-carboxylate (80 mg, 0.139 mmol) in MeOH (1.0 mL) was added Pd/C (30 mg, 0.282 mmol) under $N_2$ atmosphere. The mixture was stirred at room temperature overnight under $H_2$ atmosphere. The solids were removed by filtration, and the filtrate was concentrated in vacuo. The residue was purified by silica gel chromatography (Flash 60 column) eluting with hexane/EtOAc (1:1) to yield the title compound as a yellow solid. ESI-MS m/z [M+H]$^+$calc'd for $C_{28}H_{38}FN_5O_5S$, 576. found, 576.

Step C: 6-((1R,2S)-2-Aminocyclohexylamino)-4-(3-ethylisothiazol-5-yl)-7-fluoro-1H-pyrrolo[3,4-c]pyridin-3(2H)-one To a stirred solution of tert-butyl 6-((1R,2S)-2-(tert-butoxycarbonylamino)cyclohexylamino)-4-(3-ethylisothiazol-5-yl)-7-fluoro-3-oxo-1H-pyrrolo[3,4-c]pyridine-2(3H)-carboxylate (80 mg, 0.139 mmol) in MeOH (1.0 mL) was added 4N HCl/dioxane (1.0 mL, 4.00 mmol). The mixture was heated to 60° C. for 1 h and was subsequently concentrated in vacuo. The residue was triturated with EtOAc and filtered. The filter cake was washed with EtOAc to give a yellow solid, which was suspended into EtOH. The mixture was stirred at 80° C. for 30 minutes and then cooled to room temperature. The resulting precipitate was collected by filtration and washed with EtOH to give a hydrochloride salt of the title compound as an off-white solid (20.6 mg, 36%). $^1$H NMR (500 MHz, DMSO-d$_6$) δ ppm 1.26 (t, J=7.57 Hz, 3 H), 1.39-1.55 (m, 2 H), 1.56-1.83 (m, 4 H), 1.83-2.04 (m, 2 H), 2.81 (q, J=7.65 Hz, 2 H), 3.77 (br s, 1 H), 4.18-4.30 (m, 1 H), 4.41-4.53 (m, 2 H), 7.16 (d, J=5.86 Hz, 1 H), 7.82 (br s, 3 H), 8.66 (s, 1 H), 8.80 (s, 1 H). ESI-MS m/z [M+H]$^+$calc'd for $C_{18}H_{22}FN_5OS$, 376. found, 376.

Example 4

6-((3R,4R)-3-Aminotetrahydro-2H-pyran-4-ylamino)-7-fluoro-4-(isothiazol-5-yl)-1H-pyrrolo[3,4-c]pyridin-3(2H)-one

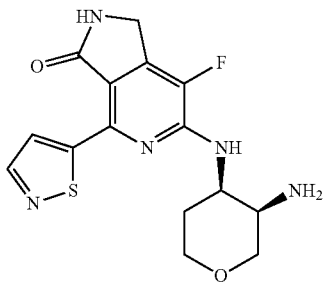 [SMILES: N[C@H]1COCC[C@H]1Nc1nc(-c2ccns2)c2c(c1F)CNC2=O]

Step A: tert-Butyl 6-((3R,4R)-3-(tert-butoxycarbonylamino)tetrahydro-2H-pyran-4-ylamino)-7-fluoro-4-(isothiazol-5-yl)-3-oxo-1H-pyrrolo[3,4-c]pyridine-2(3H)-carboxylate

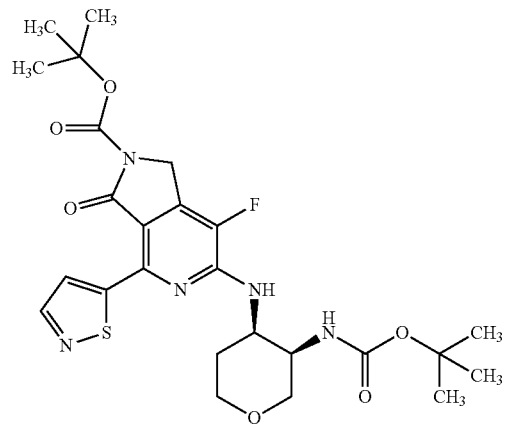 [SMILES: CC(C)(C)OC(=O)N[C@H]1COCC[C@H]1Nc1nc(-c2ccns2)c2c(c1F)CN(C(=O)OC(C)(C)C)C2=O]

A solution of tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (60 mg, 0.120 mmol), 5-(tributylstannyl)isothiazole (67.2 mg, 0.180 mmol) and tetrakis(triphenylphosphine)palladium(0) (69.2 mg, 0.060 mmol) in toluene (2.0 mL) was heated to 120° C. for 45 minutes via microwave irradiation. The reaction mixture was subsequently poured into water and was extracted with EtOAc. The extracts were dried over $Na_2SO_4$ and concentrated in vacuo. The residue was purified by silica gel chromatography (Flash 60 column) eluting with hexane/EtOAc (1:1) to give the title compound as a yellow solid. ESI-MS m/z [M+H]$^+$calc'd for $C_{25}H_{32}FN_5O_6S$, 550. found, 550.

Step B: 6-((3R,4R)-3-Aminotetrahydro-2H-pyran-4-ylamino)-7-fluoro-4-(isothiazol-5-yl)-1H-pyrrolo[3,4-c]pyridin-3(2H)-one To a stirred solution of tert-butyl 6-((3R,4R)-3-(tert-butoxycarbonylamino)tetrahydro-2H-pyran-4-ylamino)-7-fluoro-4-(isothiazol-5-yl)-3-oxo-1H-pyrrolo[3,4-c]pyridine- 2(3H)-carboxylate (65.8 mg, 0.120 mmol) in MeOH (1.0 mL) was added 4N HCl/dioxane (1.0 mL, 4.00 mmol). The reaction mixture was heated to 60° C. for 1 hour and was subsequently concentrated in vacuo. The residue was triturated with EtOAc and filtered. The filter cake was washed with EtOAc to give a yellow solid, which was suspended into EtOH. The mixture was stirred at 80° C. for 30 minutes and allowed to cool to room temperature. The resulting precipitate was collected by filtration and washed with EtOH to give a hydrochloride salt of the title compound as an off-white solid (26.5 mg, 57%). $^1$H NMR (500 MHz, DMSO-d$_6$) δ ppm 1.74-1.85 (m, 1 H), 2.08-2.23 (m, 1 H), 3.56-3.68 (m, 1 H), 3.80 (d, J=11.23 Hz, 2 H), 3.96-4.11 (m, 2 H), 4.29-4.39 (m, 1 H), 4.42-4.55 (m, 2 H), 7.49 (d, J=5.37 Hz, 1 H), 8.08 (br s, 3 H), 8.63 (s, 1 H), 8.71 (s, 1 H), 8.96 (s, 1 H). ESI-MS m/z [M+H]$^+$calc'd for C$_{15}$H$_{16}$FN$_5$O$_2$S, 350. found, 350.

Example 5

6-((1R,2S)-2-Aminocyclohexylamino)-7-fluoro-4-(isothiazol-5-yl)-1H-pyrrolo[3,4-c]pyridin-3 (2H)-one

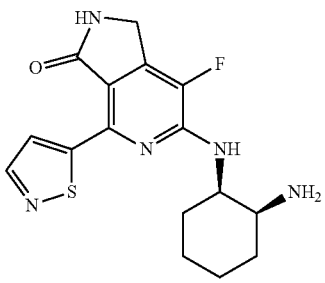 [SMILES: N[C@H]1CCCC[C@H]1Nc1nc(-c2ccns2)c2c(c1F)CNC2=O]

Step A: tert-butyl 6-((1R,2S)-2-(tert-butoxycarbonylamino)cyclohexylamino)-7-fluoro-4-(isothiazol-5-yl)-3-oxo-1H-pyrrolo[3,4-c]pyridine-2(3H)-carboxylate

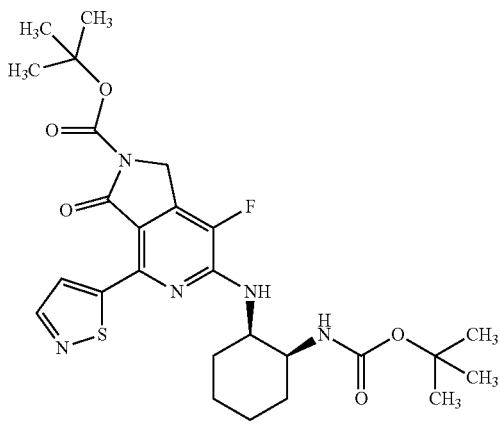 [SMILES: CC(C)(C)OC(=O)N[C@H]1CCCC[C@H]1Nc1nc(-c2ccns2)c2c(c1F)CN(C(=O)OC(C)(C)C)C2=O]

A solution of tert-butyl 6-((1R,2S)-2-(tert-butoxycarbonylamino)cyclohexylamino)-4-chloro-7-fluoro-3-oxo-1H-pyrrolo[3,4-c]pyridine-2(3H)-carboxylate (60 mg, 0.120 mmol), 5-(tributylstannyl)isothiazole (67.5 mg, 0.180 mmol) and tetrakis(triphenylphosphine)palladium(0) (69.5 mg, 0.060 mmol) in toluene (2.0 mL) was heated to 120° C. for 45 minutes via microwave irradiation. The reaction mixture was subsequently poured into water and was extracted with EtOAc. The extracts were dried over Na$_2$SO$_4$ and concentrated in vacuo. The residue was purified by silica gel chromatography (Flash 60 column) eluting with hexane/EtOAc (1:1) to give the title compound as a yellow solid. ESI-MS m/z [M+H]$^+$calc'd for C$_{26}$H$_{34}$FN$_5$O$_5$S, 548. found, 548.

Step B: 6-((1R,2S)-2-Aminocyclohexylamino)-7-fluoro-4-(isothiazol-5-yl)-1H-pyrrolo[3,4-c]pyridin-3(2H)-one To a stirred solution of tert-butyl 6-((1R,2S)-2-(tert-butoxycarbonylamino)cyclohexylamino)-7-fluoro-4-(isothiazol-5-yl)-3-oxo-1H-pyrrolo[3,4-c]pyridine-2(3H)-carboxylate (65.9 mg, 0.120 mmol) in MeOH (1.0 mL) was added 4N HCl/dioxane (1.0 mL, 4.00 mmol). The reaction mixture was heated to 60° C. for 1 hour and was subsequently concentrated in vacuo. The residue was triturated with EtOAc and filtered. The filter cake was washed with EtOAc to give a yellow solid, which was suspended into EtOH. The mixture was stirred at 80° C. for 30 minutes and allowed to cool to room temperature. The resulting precipitate was collected by filtration and washed with EtOH to yield a hydrochloride salt of the title compound as an off-white solid (18.6 mg, 40%). $^1$H NMR (500 MHz, DMSO-d$_6$) δ ppm 1.36-1.55 (m, 2 H), 1.58-2.06 (m, 6 H), 3.77 (br s, 1 H), 4.17-4.33 (m, 1 H), 4.39-4.54 (m, 2H), 7.19 (d, J=5.86 Hz, 1 H), 7.88 (br s, 3 H), 8.62 (d, J=1.95 Hz, 1 H), 8.69 (s, 1 H), 8.97 (d, J=1.95 Hz, 1 H). ESI-MS m/z [M+H]$^+$calc'd for C$_{16}$H$_{18}$FN$_5$OS, 348. found, 348.

Example 6

6-((3R,4R)-3-Aminotetrahydro-2H-pyran-4-ylamino)-4-(3-cyclopropylisothiazol-5-yl)-7-fluoro-1H-pyrrolo[3,4-c]pyridin-3(2H)-one

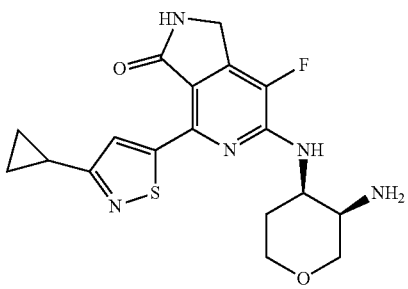 [SMILES: N[C@H]1COCC[C@H]1Nc1nc(-c2cc(C3CC3)ns2)c2c(c1F)CNC2=O]

Step A: tert-Butyl 6-((3R,4R)-3-(tert-butoxycarbonylamino)tetrahydro-2H-pyran-4-ylamino)-4-(3-cyclopropylisothiazol-5-yl)-7-fluoro-3-oxo-1H-pyrrolo[3,4-c]pyridine-2(3H)-carboxylate

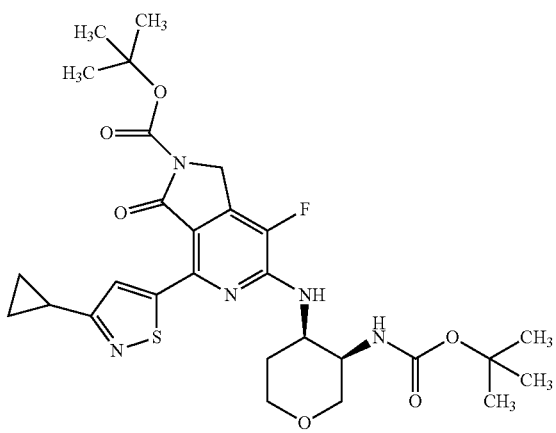 [SMILES: CC(C)(C)OC(=O)N[C@H]1COCC[C@H]1Nc1nc(-c2cc(C3CC3)ns2)c2c(c1F)CN(C(=O)OC(C)(C)C)C2=O]

A solution of tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (50 mg, 0.100 mmol), 3-cyclopropyl-5-(tributylstannyl)isothiazole (62.0 mg, 0.150 mmol) and tetrakis(triphenylphosphine)palladium(0) (34.6 mg, 0.030 mmol) in toluene (10 mL) was heated to 120° C. for 45 minutes via microwave irradiation. The reaction mixture was poured into water and was extracted with EtOAc. The extracts were dried over Na$_2$SO$_4$ and concentrated in vacuo. The residue was purified by silica gel chromatography (Flash 60 column) eluting with hexane/EtOAc (1:1) to give the title compound as a yellow solid, which was used without further purification (58.9 mg, 100%). ESI-MS m/z [M+H]$^+$calc'd for C$_{28}$H$_{36}$FN$_5$O$_6$S, 590. found, 590.

Step B: 6-((3R,4R)-3-Aminotetrahydro-2H-pyran-4-ylamino)-4-(3-cyclopropylisothiazol-5-yl)-7-fluoro-1H-pyrrolo[3,4-c]pyridin-3(2H)-one To a stirred solution of tert-butyl 6-((3R,4R)-3-(tert-butoxycarbonylamino)tetrahydro-2H-pyran-4-ylamino)-4-(3-cyclopropylisothiazol-5-yl)-7-fluoro-3-oxo-1H-pyrrolo[3,4-c]pyridine-2(3H)-carboxylate (58.9 mg, 0.100 mmol) in MeOH (2.0 mL) was added 4N HCl/dioxane (2.0 mL, 8.00 mmol). The reaction mixture was heated to 60° C. for 1 hour and then concentrated in vacuo. The residue was triturated with EtOAc and filtered. The filter cake was washed with EtOAc to give a yellow solid, which was suspended into EtOH. The mixture was stirred at 80° C. for 30 minutes and then cooled to room temperature. The resulting precipitate was collected by filtration and washed with EtOH to give a hydrochloride salt of the title compound as an off-white solid (26.5 mg, 62%). $^1$H NMR (500 MHz, DMSO-d$_6$) δ ppm 0.82-0.92 (m, 2 H), 0.95-1.06 (m, 2 H), 1.70-1.85 (m, 1 H), 2.07-2.17 (m, 1 H), 2.18-2.26 (m, 1 H), 3.56-3.66 (m, 1 H), 3.72-3.84 (m, 2 H), 3.95-4.08 (m, 2 H), 4.26-4.36 (m, 1 H), 4.41-4.53 (m, 2 H), 7.46 (d, J=4.88 Hz, 1 H), 8.02 (br s, 1 H), 8.68 (s, 1 H), 8.72 (s, 1 H). ESI-MS m/z [M+H]$^+$calc'd for C$_{18}$H$_{20}$FN$_5$O$_2$S, 390. found, 390.

Example 7

6-((3R,4R)-3-Aminotetrahydro-2H-pyran-4-ylamino)-7-fluoro-4-(5-fluorobenzo[b]thiophen-2-yl)-1H-pyrrolo[3,4-c]pyridin-3(2H)-one

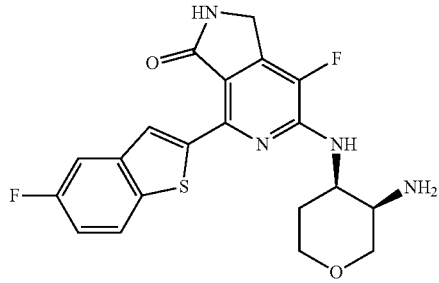 [SMILES: N[C@H]1COCC[C@H]1Nc1nc(-c2cc3cc(F)ccc3s2)c2c(c1F)CNC2=O]

A solution of tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (33 mg, 0.066 mmol), 5-fluorobenzo[b]thiophen-2-ylboronic acid (12.91 mg, 0.066 mmol) and tetrakis(triphenylphosphine)palladium(0) (76 mg, 0.066 mmol) in toluene (3 mL) was heated to 120° C. via microwave irradiation for 30 minutes. The reaction mixture was diluted with EtOAc (50 mL) and saturated aqueous NaHCO$_3$ (100 mL). The organic layer was separated and the aqueous layer was washed with EtOAc (50 mL). The organic layers were combined and dried over Na$_2$SO$_4$, and the solvent was removed in vacuo to give the intermediate, tert-butyl 6-(((3R,4R)-3-((tert-butoxycarbonyl)amino)tetrahydro-2H-pyran-4-yl)amino)-7-fluoro-4-(5-fluorobenzo[b]thiophen-2-yl)-3-oxo-1H-pyrrolo[3,4-c]pyridine-2(3H)-carboxylate. The intermediate was dispersed in TFA and DCM (1:1, 10 mL). The mixture was stirred at room temperature for 60 minutes and then concentrated. The resulting crude material was reconstituted in MeOH and DCM (6.0 mL) and purified via preparative HPLC, eluting with a gradient of 25-30% ACN (0.035% TFA) and H$_2$O (0.05% TFA). The collected fractions were combined and the solvent was stripped to dryness via rotary evaporation to yield a TFA salt of the title compound (12 mg, 44%). $^1$H NMR (500 MHz, DMSO-d$_6$) δ ppm 1.82 (d, J=9.76 Hz, 1 H), 2.15 (d, J=8.30 Hz, 1 H), 3.59-3.70 (m, 1 H), 3.82 (s, 1 H), 3.91 (br s, 1 H), 3.98-4.11 (m, 2 H), 4.38 (br s, 1 H), 4.43-4.55 (m, 2 H), 7.23-7.33 (m, 1 H), 7.42 (d, J=4.88 Hz, 1 H), 7.76 (dd, J=9.76, 2.44 Hz, 1 H), 7.93-8.03 (m, 3 H), 8.62-8.74 (m, 1 H), 9.41 (s, 1H). ESI-MS m/z [M+H]$^+$calc'd for C$_{20}$H$_{18}$F$_2$N$_4$O$_2$S, 417. found, 417.

Example 8

5-(6-((3R,4R)-3-Aminotetrahydro-2H-pyran-4-ylamino)-7-fluoro-3-oxo-2,3-dihydro-1H-pyrrolo[3,4-c]pyridin-4-yl)thiophene-2-carbonitrile

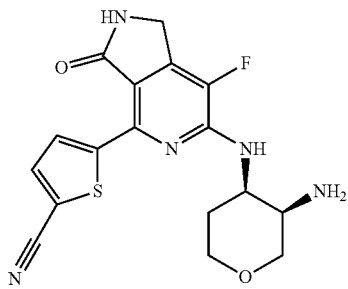 [SMILES: N#Cc1ccc(-c2nc(N[C@@H]3CCOC[C@@H]3N)c(F)c3c2C(=O)NC3)s1]

A solution of tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (30 mg, 0.060 mmol), 5-cyanothiophen-2-ylboronic acid (27.5 mg, 0.180 mmol), tris(dibenzylideneacetone)dipalladium(0) (3.29 mg, 3.59 μmol) and 2-(dicyclohexylphosphino)biphenyl (1.259 mg, 3.59 μmol) in dioxane (2 mL) and DMF (0.500 mL) was heated to 160° C. via microwave irradiation for 60 minutes. The reaction mixture was diluted with EtOAc (50 mL) and saturated aqueous NaHCO$_3$ (100 mL). The organic layer was separated and the aqueous layer was washed with EtOAc (50 mL). The combined organic layers were dried over Na$_2$SO$_4$ and the solvent was removed in vacuo to give the intermediate, tert-butyl 6-(((3R,4R)-3-((tert-butoxycarbonyl)amino)tetrahydro-2H-pyran-4-yl)amino)-4-(5-cyanothiophen-2-yl)-7-fluoro-3-oxo-1H-pyrrolo[3,4-c]pyridine-2(3H)-carboxylate. The intermediate was dispersed in TFA and DCM (10 mL). The mixture was stirred at room temperature for 60 minutes and then concentrated. The resulting crude material was reconstituted in MeOH and DCM (10.0 mL) and was purified via preparative HPLC, eluting with a gradient of 20-25% ACN (0.035% TFA) and H$_2$O (0.05% TFA). The collected fractions were combined and the solvent was stripped to dryness via rotary evaporation to yield a TFA salt of the title compound (3.3 mg, 15%). $^1$H NMR (500 MHz, DMSO-d$_6$) δ ppm 1.78 (d, J=14.16 Hz, 1 H), 2.04-2.21 (m, 1 H), 3.57-3.67 (m, 1 H), 3.73-3.88 (m, 2 H), 4.01 (d, J=10.74 Hz, 2 H), 4.36 (d, J=11.23 Hz, 1 H), 4.48 (br s, 2 H), 7.47 (br s, 1 H), 7.91-8.02 (m, 3 H), 8.73 (br s, 1 H), 9.13 (br s, 1 H). ESI-MS m/z [M+H]$^+$calc'd for C$_{12}$H$_{16}$FN$_5$O$_2$S, 374. found, 374.

Example 9

6-((3R,4R)-3-Aminotetrahydro-2H-pyran-4-ylamino)-7-fluoro-4-(thieno[2,3-c]pyridin-2-yl)-1H-pyrrolo[3,4-c]pyridin-3(2H)-one

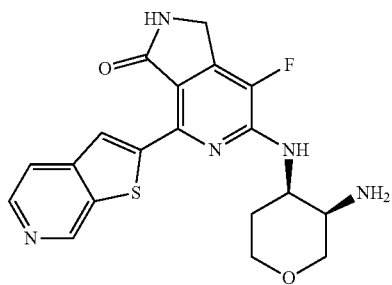 [SMILES: N[C@H]1COCC[C@H]1Nc1nc(-c2cc3ccncc3s2)c2c(c1F)CNC2=O]

A TFA salt of the title compound was prepared in a manner similar to Example 7 using thieno[2,3-c]pyridin-2-ylboronic acid in place of 5-fluorobenzo[b]thiophen-2-ylboronic acid. $^1$H NMR (500 MHz, DMSO-d$_6$) δ ppm 1.74-1.91 (m, 1 H), 2.12-2.26 (m, 1 H), 3.59-3.69 (m, 1 H), 3.77-3.95 (m, 2 H), 4.00-4.13 (m, 2 H), 4.42 (d q, J=12.75, 4.37 Hz, 1 H), 4.53 (d, J=5.37 Hz, 2 H), 7.61 (br s, 1 H), 8.07 (br s, 2 H), 8.21 (br s, 1 H), 8.60 (d, J=5.86 Hz, 1 H), 8.82 (s, 1 H), 9.47 (br s, 1 H), 9.61 (s, 1 H). ESI-MS m/z [M+H]$^+$calc'd for C$_{19}$H$_{18}$FN$_5$O$_2$S, 400. found, 400.

Example 10

6-((3R,4R)-3-Aminotetrahydro-2H-pyran-4-ylamino)-7-fluoro-4-(thieno[2,3-c]pyridin-2-yl)-1H-pyrrolo[3,4-c]pyridin-3(2H)-one

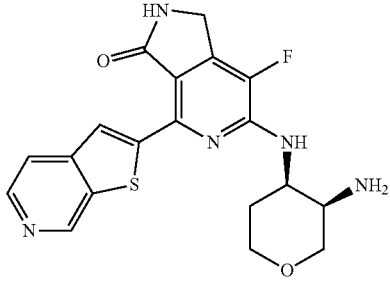 [SMILES: N[C@H]1COCC[C@H]1Nc1nc(-c2cc3ccncc3s2)c2c(c1F)CNC2=O]

A solution of tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (53 mg, 0.106 mmol), 2-(tributylstannyl)thieno[2,3-c]pyridine (44.9 mg, 0.106 mmol) and tetrakis(triphenylphosphine) palladium(0) (122 mg, 0.106 mmol) in toluene (3 mL) was heated to 120° C. in a microwave for 60 minutes. The reaction mixture was diluted with EtOAc (50 mL) and saturated aqueous NaHCO$_3$ (100 mL). The organic layer was separated and the aqueous layer was washed with EtOAc (50 mL). The organic layers were combined and dried over Na$_2$SO$_4$, and the solvent was removed in vacuo to give the intermediate, ten-butyl 6-(((3R,4R)-3-((tert-butoxycarbonyl)amino)tetrahydro-2H-pyran-4-yl)amino)-7-fluoro-3-oxo-4-(thieno[2,3-c]pyridin-2-yl)-1H-pyrrolo[3,4-c]pyridine-2(3H)-carboxylate. The intermediate was dispersed in TFA and DCM (10 mL). The mixture was stirred at room temperature for 60 minutes and then concentrated. The resulting crude material was reconstituted in MeOH and DCM (10.0 mL) and purified via preparative HPLC, eluting with a gradient of 10-25% ACN (0.035% TFA) and H$_2$O (0.05% TFA). The collected fractions were combined and diluted with EtOAc (50 mL) and saturated aqueous NaHCO$_3$ (100 mL). The organic layer was separated and the aqueous layer was extracted with EtOAc (50 mL). The organic layers were combined and dried over Na$_2$SO$_4$, and the solvent was removed in vacuo to give the title compound (5.8 mg, 14%). $^1$H NMR (500 MHz, DMSO-d$_6$) δ ppm 1.83 (d, J=8.79 Hz, 1 H), 2.10-2.27 (m, 1 H), 3.81-3.92 (m, 2 H), 3.98-4.16 (m, 3 H), 4.34-4.48 (m, 1 H), 4.52 (br s, 2 H), 7.55 (d, J=5.37 Hz, 1 H), 7.97-8.08 (m, 3 H), 8.53 (br s, 1 H), 8.75 (s, 1 H), 9.34 (br s, 1 H), 9.53 (s, 1 H). ESI-MS m/z [M+H]$^+$calc'd for C$_{19}$H$_{18}$FN$_5$O$_2$S, 400. found, 400.

Example 11

5-(6-((3R,4R)-3-Aminotetrahydro-2H-pyran-4-ylamino)-7-fluoro-3-oxo-2,3-dihydro-1H-pyrrolo[3,4-c]pyridin-4-yl)thiophene-2-carbonitrile

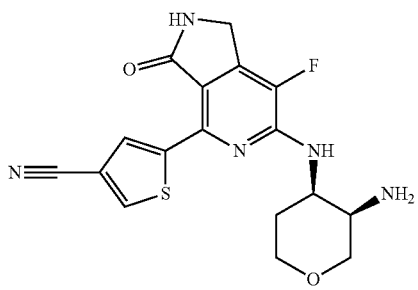 [SMILES: N#Cc1csc(-c2nc(N[C@@H]3CCOC[C@@H]3N)c(F)c3c2C(=O)NC3)c1]

A TFA salt of the title compound was prepared in a manner similar to Example 7 using 5-(4,4,5,5-tetramethyl-1,3,2-dioxaborolan-2-yl)thiophene-3-carbonitrile in place of 5-fluorobenzo[b]thiophen-2-ylboronic acid. $^1$H NMR (500 MHz, DMSO-d$_6$) δ ppm 1.78 (d, J=12.69 Hz, 1 H), 2.03-2.22 (m, 2 H), 3.69-3.87 (m, 2 H), 4.01 (d, J=12.20 Hz, 2 H), 4.26-4.41 (m, 1 H), 4.43-4.53 (m, 2 H), 7.44 (d, J=5.37 Hz, 1 H), 7.96 (br s, 2 H), 8.63-8.68 (m, 1 H), 8.71 (s, 1 H), 9.29 (s, 1 H). ESI-MS m/z [M+H]$^+$calc'd for C$_{17}$H$_{16}$FN$_5$O$_2$S, 374. found, 374.

Example 12

6-((3R,4R)-3-Aminotetrahydro-2H-pyran-4-ylamino)-7-fluoro-4-(5-fluorothiophen-2-yl)-1H-pyrrolo[3,4-c]pyridin-3(2H)-one

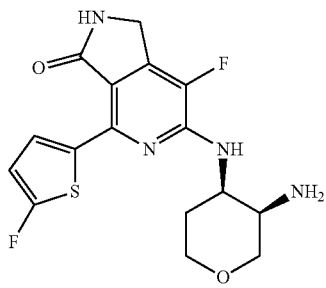 [SMILES: N[C@H]1COCC[C@H]1Nc1nc(-c2ccc(F)s2)c2c(c1F)CNC2=O]

A TFA salt of the title compound was prepared in a manner similar to Example 7 using 2-(5-fluorothiophen-2-yl)-4,4,5,5-tetramethyl-1,3,2-dioxaborolane in place of 5-fluorobenzo[b]thiophen-2-ylboronic acid. $^1$H NMR (500 MHz, DMSO-d$_6$) δ ppm 1.72-1.81 (m, 1 H), 3.56-3.66 (m, 1 H), 3.77 (d, J=11.72 Hz, 2 H), 3.94-4.14 (m, 3 H), 4.25-4.33 (m, 1 H), 4.38-4.52 (m, 2 H), 6.74-6.81 (m, 1 H), 7.32 (s, 1 H), 7.92 (br s, 2 H), 8.55 (s, 1H), 8.80 (t, J=4.15 Hz, 1 H). ESI-MS m/z [M+H]$^+$calc'd for C$_{16}$H$_{16}$F$_2$N$_4$O$_2$S, 367. found, 367.

Example 13

6-((3R,4R)-3-Aminotetrahydro-2H-pyran-4-ylamino)-7-fluoro-4-(thieno[2,3-b]pyridin-2-yl)-1H-pyrrolo[3,4-c]pyridin-3(2H)-one

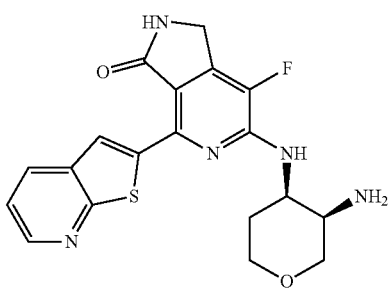 [SMILES: N[C@H]1COCC[C@H]1Nc1nc(-c2cc3cccnc3s2)c2c(c1F)CNC2=O]

The title compound was prepared in a manner similar to Example 10 using 2-(tributylstannyl)thieno[2,3-b]pyridine in place of 2-(tributylstannyl)thieno[2,3-c]pyridine. $^1$H NMR (500 MHz, DMSO-d$_6$) δ ppm 1.82 (d, J=9.76 Hz, 1 H), 2.07-2.23 (m, 1 H), 3.62-3.70 (m, 1 H), 3.83 (d, J=11.23 Hz, 1 H), 3.92 (br s, 2 H), 4.00-4.10 (m, 2 H), 4.34-4.42 (m, 1 H), 4.49 (s, 2 H), 7.37-7.53 (m, 1 H), 7.99 (d, J=4.39 Hz, 2 H), 8.32 (dd, J=8.06, 1.71 Hz, 1 H), 8.51-8.61 (m, 1 H), 8.63-8.76 (m, 1 H), 9.43 (s, 1 H). ESI-MS m/z [M+H]$^+$calc'd for C$_{19}$H$_{18}$FN$_5$O$_2$S, 400. found, 400.

Example 14

6-((1R,2S)-2-Aminocyclohexylamino)-7-fluoro-4-(thieno[2,3-b]pyridin-2-yl)-1H-pyrrolo[3,4-c]pyridin-3(2H)-one

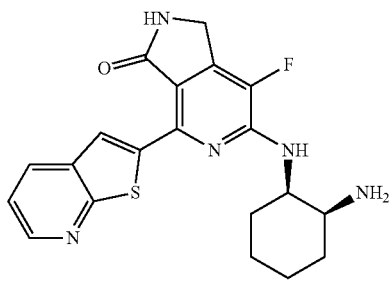 [SMILES: N[C@H]1CCCC[C@H]1Nc1nc(-c2cc3cccnc3s2)c2c(c1F)CNC2=O]

Step A: tert-Butyl 6-(((1R,2S)-2-((tert-butoxycarbonyl)amino)cyclohexyl)amino)-7-fluoro-3-oxo-4-(thieno[2,3-b]pyridin-2-yl)-1H-pyrrolo[3,4-c]pyridine-2(3H)-carboxylate

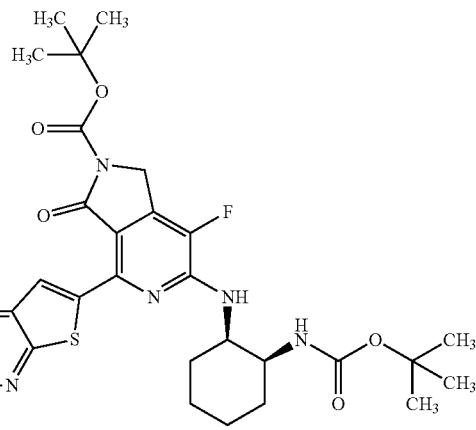

A solution of tert-butyl 6-((1R,2S)-2-(tert-butoxycarbonylamino)cyclohexylamino)-4-chloro-7-fluoro-3-oxo-1H-pyrrolo[3,4-c]pyridine-2(3H)-carboxylate (200 mg, 0.401 mmol), 2-(tributylstannyl)thieno[2,3-b]pyridine (340 mg, 0.802 mmol) and tetrakis(triphenylphosphine)palladium(0) (463 mg, 0.401 mmol) in toluene (3 mL) was heated to 102° C. overnight. The reaction mixture was diluted with EtOAc (50 mL) and saturated aqueous NaHCO$_3$ (100 mL). The organic layer was separated and the aqueous layer was washed with EtOAc (50 mL). The organic layers were combined, dried over Na$_2$SO$_4$, and the solvent was removed in vacuo. The crude product was purified by silica gel column chromatography, eluting with a gradient of 5-50% EtOAc and hexane over a period of 120 minutes. The fractions were collected to give the title compound (85 mg, 35%). ESI-MS m/z [M+H]$^+$calc'd for C$_{30}$H$_{36}$FN$_5$O$_5$S, 598. found, 598.

Step B: 6-((1R,2S)-2-Aminocyclohexylamino)-7-fluoro-4-(thieno[2,3-b]pyridin-2-yl)-1H-pyrrolo[3,4-c]pyridin-3(2H)-one To a solution of tert-butyl 6-(((1R,2S)-2-((tert-butoxycarbonyl)amino)cyclohexyl)amino)-7-fluoro-3-oxo-4-(thieno[2,3-b]pyridin-2-yl)-1H-pyrrolo[3,4-c]pyridine-2(3H)-carboxylate (85 mg, 142 mmol) in DCM (3 mL) was added 4M HCl (10 mL). The reaction mixture was stirred at 60° C. for 1 hour. After removal of the solvent, the resulting crude material was reconstituted in MeOH/DMF/DCM (10.0 mL) and was purified via preparative mass trigger LCMS, eluting with a gradient of 20-25% ACN (0.035% TFA) and H$_2$O (0.05% TFA). The collected fractions were combined and the solvent was stripped to dryness via rotary evaporation to give a TFA salt of the title compound (13 mg, 8% two steps). $^1$H NMR (500 MHz, DMSO-d$_6$) δ ppm 1.39-2.08 (m, 8 H), 3.88 (br s, 1H), 4.31 (d, J=3.91 Hz, 1 H), 4.44-4.56 (m, 2 H), 7.11-7.22 (m, 1 H), 7.38-7.46 (m, 1 H), 7.79 (br s, 2 H), 8.32 (dd, J=8.05, 1.71 Hz, 1 H), 8.57 (dd, J=4.64, 1.71 Hz, 1 H), 8.68 (s, 1H), 9.43 (s, 1 H). ESI-MS m/z [M+H]$^+$calc'd for C$_{20}$H$_{20}$FN$_5$OS, 398. found, 398.

Example 15

6-((1R,2S)-2-Aminocyclohexylamino)-7-fluoro-4-(thieno[2,3-c]pyridin-2-yl)-1H-pyrrolo[3,4-c]pyridin-3(2H)-one

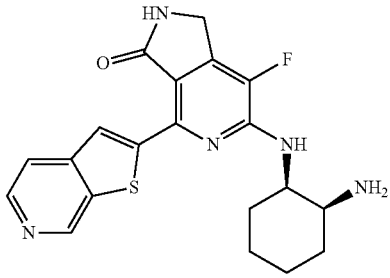 [SMILES: N[C@H]1CCCC[C@H]1Nc1nc(-c2cc3ccncc3s2)c2c(c1F)CNC2=O]

Step A: tert-Butyl 6-(((1R,2S)-2-((tert-butoxycarbonyl)amino)cyclohexyl)amino)-7-fluoro-3-oxo-4-(thieno[2,3-c]pyridin-2-yl)-1H-pyrrolo[3,4-c]pyridine-2(3H)-carboxylate

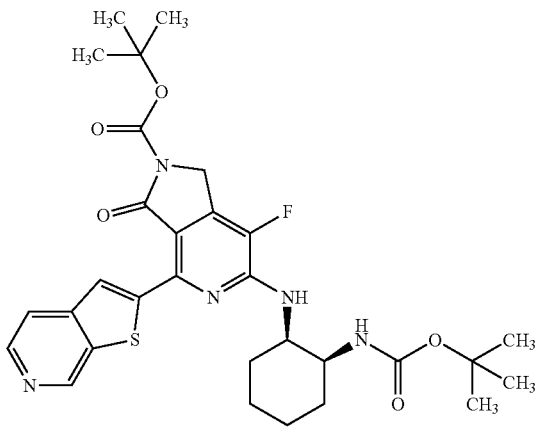 [SMILES: CC(C)(C)OC(=O)N[C@H]1CCCC[C@H]1Nc1nc(-c2cc3ccncc3s2)c2c(c1F)CN(C(=O)OC(C)(C)C)C2=O]

A solution of tert-butyl 6-((1R,2S)-2-(tert-butoxycarbonylamino)cyclohexylamino)-4-chloro-7-fluoro-3-oxo-1H-pyrrolo[3,4-c]pyridine-2(3H)-carboxylate (200 mg, 0.401 mmol), 2-(tributylstannyl)thieno[2,3-c]pyridine (510 mg, 1.202 mmol) and tetrakis(triphenylphosphine)palladium(0) (463 mg, 0.401 mmol) in toluene (3 mL) was heated to 120° C. via microwave irradiation for 30 minutes. The reaction mixture was diluted with EtOAc (50 mL) and saturated aqueous NaHCO$_3$ (100 mL). The organic layer was separated and the aqueous layer was washed with EtOAc (50 mL). The organic layers were combined, dried over Na$_2$SO$_4$, and the solvent was removed in vacuo. The crude product was purified by silica gel column chromatography, eluting with a gradient of 5-50% EtOAc and hexane over a period of 120 minutes. The fractions were collected to give the title compound (135 mg, 56%).

Step B: 6-((1R,2S)-2-Aminocyclohexylamino)-7-fluoro-4-(thieno[2,3-c]pyridin-2-yl)-1H-pyrrolo[3,4-c]pyridin-3(2H)-one To a solution of tert-butyl 6-(((1R,2S)-2-((tert-butoxycarbonyl)amino)cyclohexyl)amino)-7-fluoro-3-oxo-4-(thieno[2,3-c]pyridin-2-yl)-1H-pyrrolo[3,4-c]pyridine-2(3H)-carboxylate (135 mg, 226 mmol) in DCM (3 mL) was added TFA in DCM (1:1, 10 mL). The reaction mixture was stirred at room temperature for 1 hour. After removal of the solvent, the resulting crude material was reconstituted in MeOH/DMF/DCM (10.0 mL) and was purified via preparative mass trigger LCMS, eluting with a gradient of 10-25% ACN (0.035% TFA) and H$_2$O (0.05% TFA). The collected fractions were combined and the solvent was stripped to dryness via rotary evaporation to give a TFA salt of the title compound (76 mg, 48% two steps). $^1$H NMR (400 MHz, DMSO-d$_6$) δ ppm 1.48-2.06 (m, 8 H), 3.83 (br s, 1 H), 4.34 (d, J=3.28 Hz, 1 H), 4.57 (s, 2 H), 7.35 (d, J=6.06 Hz, 1 H), 7.88 (br s, 2 H), 8.20 (d, J=5.81 Hz, 1 H), 8.58 (d, J=5.81 Hz, 1 H), 8.81 (s, 1 H), 9.47 (s, 1 H), 9.61 (s, 1 H). ESI-MS m/z [M+H]$^+$calc'd for C$_{20}$H$_{20}$FN$_5$OS, 398. found, 398.

Example 16

6-(((1R,2S)-2-Aminocyclohexyl)amino)-7-fluoro-4-(5-fluorobenzo[b]thiophen-2-yl)-1H-pyrrolo[3,4-c]pyridin-3(2H)-one

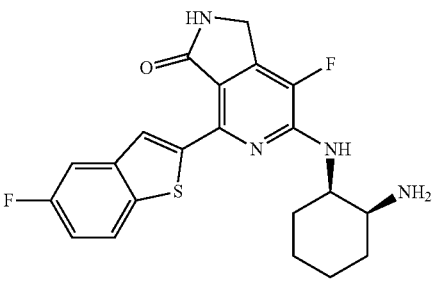 [SMILES: N[C@H]1CCCC[C@H]1Nc1nc(-c2cc3cc(F)ccc3s2)c2c(c1F)CNC2=O]

A solution of tert-butyl 6-((1R,2S)-2-(tert-butoxycarbonylamino)cyclohexylamino)-4-chloro-7-fluoro-3-oxo-1H-pyrrolo[3,4-c]pyridine-2(3H)-carboxylate (300 mg, 0.601 mmol), 5-fluorobenzo[b]thiophen-2-ylboronic acid (236 mg, 1.202 mmol) and tetrakis(triphenylphosphine)palladium(0) (695 mg, 0.601 mmol) in dioxane and saturated aqueous NaHCO$_3$ (1:1, 5 mL) was heated to 120° C. via microwave irradiation for 30 minutes. After the solvent was removed, the crude product was purified by silica gel column chromatography, eluting with a gradient of 10-50% EtOAc and hexane over a period of 60 minutes. The fractions were collected to give the intermediate, tert-butyl 6-(((1R,2S)-2-((tert-butoxycarbonyl)amino)cyclohexyl)amino)-7-fluoro-4-(5-fluorobenzo[b]thiophen-2-yl)-3-oxo-1H-pyrrolo[3,4-c]pyridine-2(3H)-carboxylate. The intermediate was first dissolved in DCM (3 mL) then TFA/DCM (1:1, 10 mL) and the mixture was stirred at 60° C. for 1 hour. After solvent was removed, the resulting crude material was reconstituted in MeOH/DMF/DCM (30.0 mL) and purified via preparative mass trigger LCMS, eluting with gradient of 30-40 ACN (0.035% TFA) and H$_2$O (0.05% TFA). The collected fractions were combined and ACN was removed via rotary evaporation. The mixture was neutralized with saturated aqueous NaHCO$_3$, washed with EtOAc (2×300 mL), dried over Na$_2$SO$_4$, and filtered. The organic phase was stripped to dryness via rotary evaporation to give the title compound (77 mg, 31%). $^1$H NMR (500 MHz, DMSO-d$_6$) δ ppm 1.36-2.09 (m, 8 H), 3.82 (br s, 1 H), 4.31 (d, J=1.95 Hz, 1 H), 4.42-4.53 (m, 2 H), 7.13 (d, J=5.86 Hz, 1 H), 7.27 (td, J=8.91, 2.69 Hz, 1 H), 7.56-7.82 (m, 3 H), 7.94-8.04 (m, 1 H), 8.64 (s, 1 H), 9.41 (s, 1 H). ESI-MS m/z [M+H]$^+$calc'd for C$_{21}$H$_{20}$F$_2$N$_4$OS, 415. found, 415.

Example 17

6-((3R,4R)-3-Aminotetrahydro-2H-pyran-4-ylamino)-7-fluoro-4-(thieno[3,2-c]pyridin-2-yl)-1H-pyrrolo[3,4-c]pyridin-3(2H)-one

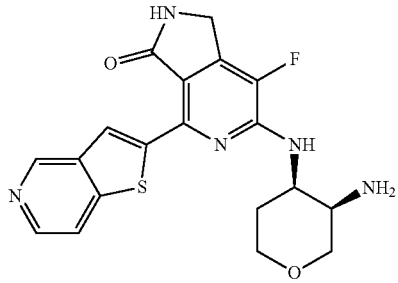 [SMILES: N[C@H]1COCC[C@H]1Nc1nc(-c2cc3cnccc3s2)c2c(c1F)CNC2=O]

The title compound was prepared in a manner similar to Example 10 using 2-(tributylstannyl)thieno[3,2-c]pyridine in place of 2-(tributylstannyl)thieno[2,3-c]pyridine. $^1$H NMR (400 MHz, DMSO-d$_6$) δ ppm 1.82 (d, J=9.35 Hz, 1 H), 2.09-2.27 (m, 1 H), 3.57-3.69 (m, 1 H), 3.80-3.93 (m, 2 H), 3.96-4.17 (m, 2 H), 4.40 (td, J=8.53, 4.42 Hz, 1 H), 4.52 (d, J=2.78 Hz, 2 H), 7.60 (d, J=5.31 Hz, 1 H), 8.09 (d, J=4.29 Hz, 2 H), 8.39 (d, J=5.31 Hz, 1H), 8.58 (d, J=6.06 Hz, 1 H), 8.80 (s, 1 H), 9.46 (s, 1 H), 9.71 (s, 1 H). ESI-MS m/z [M+H]$^+$calc'd for C$_{19}$H$_{18}$FN$_5$O$_2$S, 400. found, 400.

Example 18

6-((1R,2S)-2-Aminocyclohexylamino)-7-fluoro-4-(thieno[3,2-c]pyridin-2-yl)-1H-pyrrolo[3,4-c]pyridin-3(2H)-one

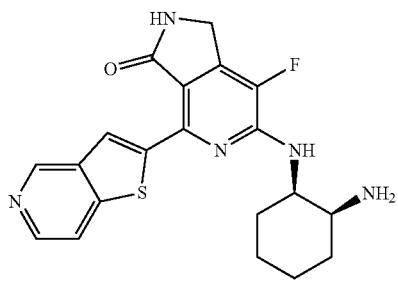 [SMILES: N[C@H]1CCCC[C@H]1Nc1nc(-c2cc3cnccc3s2)c2c(c1F)CNC2=O]

A solution of tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (200 mg, 0.399 mmol), 2-(tributylstannyl)thieno[3,2-c]pyridine (339 mg, 0.798 mmol) and tetrakis(triphenylphosphine)palladium(0) (461 mg, 0.399 mmol) in toluene (3 mL) was heated to 120° C. via microwave irradiation for 30 minutes. After the solvent was removed, the crude product was purified by silica gel column chromatography, eluting with a gradient of 10-50% EtOAc and hexane over a period of 60 minutes. The fractions were collected to give the intermediate, tert-butyl 6-(((1R,2S)-2-((tert-butoxycarbonyl)amino)cyclohexyl)amino)-7-fluoro-3-oxo-4-(thieno[3,2-c]pyridin-2-yl)-1H-pyrrolo[3,4-c]pyridine-2(3H)-carboxylate. The intermediate was first dissolved in DCM (3 mL) and then TFA/DCM (1:1, 10 mL) at 60° C. for 1 hour. After removal of solvent, the resulting crude material was reconstituted in MeOH/DMF/DCM (30.0 mL) and purified via preparative mass triggered LCMS, eluting with a gradient of 30-40% ACN (0.035% TFA) and H$_2$O (0.05% TFA). The collected fractions were combined and the ACN was removed via rotary evaporation. The mixture was neutralized with saturated aqueous NaHCO$_3$, washed with EtOAc (2×300 mL), dried over Na$_2$SO$_4$, and filtered. The organic phase was stripped to dryness via rotary evaporation to give the title compound (30 mg, 19%). $^1$H NMR (400 MHz, DMSO-d$_6$) δ ppm 1.44-2.10 (m, 8 H), 3.82 (br s, 1 H), 4.33 (d, J=3.54 Hz, 1 H), 4.47 (s, 2 H), 7.30 (d, J=6.06 Hz, 1 H), 7.89 (br s, 2 H), 8.39 (d, J=5.05 Hz, 1 H), 8.57 (s, 1 H), 8.77 (s, 1 H), 9.44 (s, 1 H), 9.71 (s, 1 H). ESI-MS m/z [M+H]$^+$calc'd for C$_{20}$H$_{20}$FN$_5$OS, 398. found, 398.

Example 19

6-((3R,4R)-3-Aminotetrahydro-2H-pyran-4-ylamino)-7-fluoro-4-(6-fluorobenzo[b]thiophen-2-yl)-1H-pyrrolo[3,4-c]pyridin-3(2H)-one

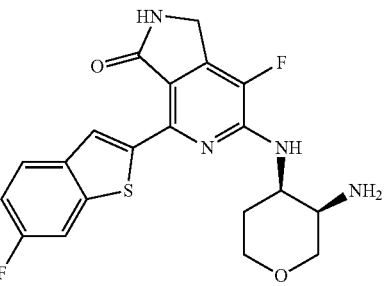

A TFA salt of the title compound was prepared in a manner similar to Example 7 using 6-fluorobenzo[b]thiophen-2-ylboronic acid in place of 5-fluorobenzo[b]thiophen-2-ylboronic acid. $^1$H NMR (500 MHz, DMSO-d$_6$) δ ppm 1.82 (d, J=9.28 Hz, 1 H), 2.15 (qd, J=12.86, 4.88 Hz, 1 H), 3.59-3.69 (m, 1 H), 3.78-3.94 (m, 2 H), 4.00-4.11 (m, 2 H), 4.34-4.42 (m, 1 H), 4.47 (s, 2 H), 7.20-7.30 (m, 1 H), 7.41 (d, J=4.88 Hz, 1 H), 7.81-7.90 (m, 1H), 7.91-8.00 (m, 3 H), 8.62-8.69 (m, 1 H), 9.38-9.50 (m, 1 H). ESI-MS m/z [M+H]$^+$calc'd for C$_{20}$H$_{18}$F$_2$N$_4$O$_2$S, 417. found, 417.

Example 20

6-(((1R,2S)-2-Aminocyclohexylamino)-7-fluoro-4-(6-fluorobenzo[b]thiophen-2-yl)-1H-pyrrolo[3,4-c]pyridin-3(2H)-one

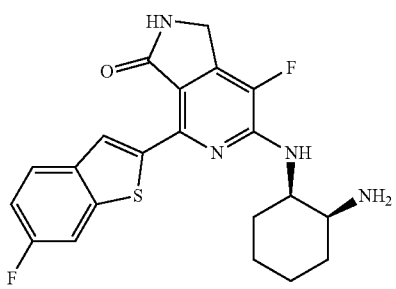 [SMILES: N[C@H]1CCCC[C@H]1Nc1nc(-c2cc3ccc(F)cc3s2)c2c(c1F)CNC2=O]

A TFA salt of the title compound was prepared in a manner similar to Example 16 using 6-fluorobenzo[b]thiophen-2-ylboronic acid in place of 5-fluorobenzo[b]thiophen-2-ylboronic acid. $^1$H NMR (500 MHz, DMSO-$d_6$) δ ppm 1.42-2.07 (m, 8 H), 3.84 (br s, 1 H), 4.32 (d, J=3.42 Hz, 1 H), 4.48 (d, J=4.39 Hz, 2 H), 7.11 (br s, 1 H), 7.25 (td, J=9.03, 2.44 Hz, 1 H), 7.80 (br s, 2 H), 7.88 (dd, J=9.28, 2.44 Hz, 1 H), 7.94 (dd, J=8.79, 5.37 Hz, 1 H), 8.63 (s, 1 H), 9.43 (s, 1 H). ESI-MS m/z [M+H]$^+$calc'd for $C_2H_{20}F_2N_4OS$, 415. found, 415.

Example 21

2-(6-((3R,4R)-3-Aminotetrahydro-2H-pyran-4-ylamino)-7-fluoro-3-oxo-2,3-dihydro-1H-pyrrolo[3,4-c]pyridin-4-yl)benzo[b]thiophene-5-carbonitrile

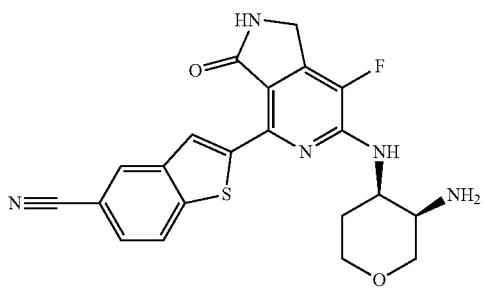 [SMILES: N#Cc1ccc2sc(-c3nc(N[C@@H]4CCOC[C@@H]4N)c(F)c4c3C(=O)NC4)cc2c1]

A solution of tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (100 mg, 0.200 mmol), 5-cyanobenzo[b]thiophen-2-ylboronic acid (40.5 mg, 0.200 mmol) and tetrakis(triphenylphosphine)palladium(0) (231 mg, 0.200 mmol) in dioxane and saturated aqueous $Na_2CO_3$ (3:5, 6 mL) was heated to 120° C. in a microwave for 30 minutes. The reaction mixture was diluted with EtOAc (50 mL) and saturated aqueous NaHCO$_3$ (100 mL). The organic layer was separated and the aqueous layer was washed with EtOAc (50 mL). The organic layers were combined, dried over $Na_2SO_4$, and the solvent was removed in vacuo to give the intermediate, tert-butyl 6-(((3R,4R)-3-((tert-butoxycarbonyl)amino)tetrahydro-2H-pyran-4-yl)amino)-4-(5-cyanobenzo[b]thiophen-2-yl)-7-fluoro-3-oxo-1H-pyrrolo[3,4-c]pyridine-2(3H)-carboxylate.

The intermediate was dispersed in TFA and DCM (1:1, 10 mL) and the mixture was stirred at room temperature for 60 minutes. The mixture was concentrated, reconstituted in MeOH and DCM (10.0 mL) and purified via preparative HPLC eluting with a gradient of 10-25% ACN (0.035% TFA) and H$_2$O (0.05% TFA). The collected fractions were combined and diluted with EtOAc (50 mL) and saturated aqueous NaHCO$_3$ (100 mL). The organic layer was separated and the aqueous layer was washed with EtOAc (50 mL). The organic layers were combined, dried over Na$_2$SO$_4$, and the solvent was removed in vacuo to give the title compound (26 mg, 31%). $^1$H NMR (500 MHz, DMSO-$d_6$) δ ppm 1.78 (dd, J=13.42, 4.15 Hz, 1 H), 1.87-2.05 (m, 1 H), 3.17-3.25 (m, 1 H), 3.45-3.57 (m, 1 H), 3.67 (d, J=10.25 Hz, 1 H), 3.80 (br s, 1 H), 3.91 (d, J=11.23 Hz, 1 H), 4.26 (d, J=4.39 Hz, 1 H), 4.43 (s, 2 H), 7.00 (d, J=6.35 Hz, 1 H), 7.72 (dd, J=8.30, 1.46 Hz, 1 H), 8.20 (d, J=8.30 Hz, 1 H), 8.47 (d, J=1.46 Hz, 1 H), 8.61 (s, 1 H), 9.50 (s, 1 H). ESI-MS m/z [M+H]$^+$calc'd for $C_{21}H_{18}FN_5O_2S$, 424. found, 424.

Example 22

2-(6-((1R,2S)-2-Aminocyclohexylamino)-7-fluoro-3-oxo-2,3-dihydro-1H-pyrrolo[3,4-c]pyridin-4-yl)benzo[b]thiophene-5-carbonitrile

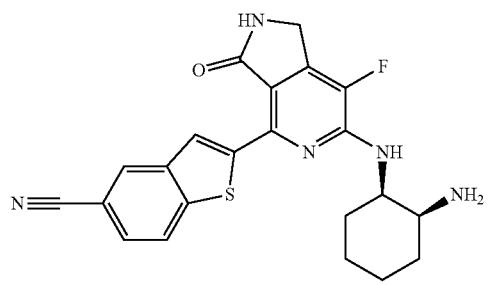 [SMILES: N#Cc1ccc2sc(-c3nc(N[C@@H]4CCCC[C@@H]4N)c(F)c4c3C(=O)NC4)cc2c1]

A TFA salt of the title compound was prepared in a manner similar to Example 16 using 5-cyanobenzo[b]thiophen-2-ylboronic acid in place of 5-fluorobenzo[b]thiophen-2-ylboronic acid. $^1$H NMR (500 MHz, DMSO-$d_6$) δ ppm 1.38-2.07 (m, 8 H), 3.83 (br s, 1 H), 4.33 (d, J=3.42 Hz, 1 H), 4.47-4.56 (m, 2 H), 7.19 (d, J=5.86 Hz, 1 H), 7.72-7.77 (m, 1 H), 7.80 (d, J=4.39 Hz, 2 H), 8.21 (d, J=8.79 Hz, 1 H), 8.49 (d, J=0.98 Hz, 1 H), 8.69 (s, 1 H), 9.51 (s, 1 H). ESI-MS m/z [M+H]$^+$calc'd for $C_{22}H_{20}FN_5OS$, 422. found, 422.

Example 23

6-((3R,4R)-3-Aminotetrahydro-2H-pyran-4-ylamino)-7-fluoro-4-(4-fluorobenzo[b]thiophen-2-yl)-1H-pyrrolo[3,4-c]pyridin-3(2H)-one

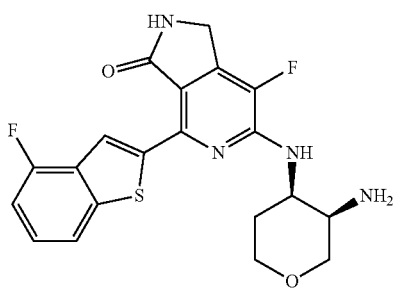 [SMILES: N[C@H]1COCC[C@H]1Nc1nc(-c2cc3c(F)cccc3s2)c2c(c1F)CNC2=O]

A TFA salt of the title compound was prepared in a manner similar to Example 7 using 4-fluorobenzo[b]thiophen-2-ylboronic acid in place of 5-fluorobenzo[b]thiophen-2-ylboronic acid. $^1$H NMR (500 MHz, DMSO-d$_6$) δ ppm 1.82 (d, J=9.76 Hz, 1 H), 2.08-2.24 (m, 1 H), 3.60-3.71 (m, 1 H), 3.81-3.88 (m, 1 H), 3.91 (br s, 1 H), 4.00-4.12 (m, 2 H), 4.34-4.43 (m, 1 H), 4.49 (s, 2 H), 7.17-7.26 (m, 1 H), 7.36-7.50 (m, 2 H), 7.80 (s, 1 H), 7.98 (br s, 2 H), 8.69 (s, 1 H), 9.52-9.63 (m, 1 H). ESI-MS m/z [M+H]$^+$calc'd for C$_{20}$H$_{15}$F$_2$N$_4$O$_2$S, 417. found, 417.

Example 24

6-((1R,2S)-2-Aminocyclohexylamino)-7-fluoro-4-(4-fluorobenzo[b]thiophen-2-yl)-1H-pyrrolo[3,4-c]pyridin-3(2H)-one

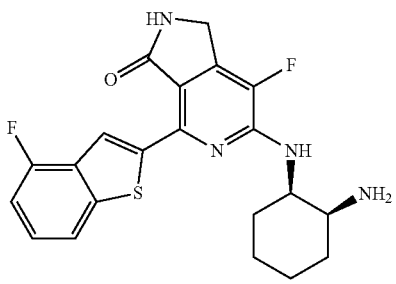 [SMILES: N[C@H]1CCCC[C@H]1Nc1nc(-c2cc3c(F)cccc3s2)c2c(c1F)CNC2=O]

A solution of tert-butyl 6-(((1R,2S)-2-(tert-butoxycarbonylamino)cyclohexylamino)-4-chloro-7-fluoro-3-oxo-1H-pyrrolo[3,4-c]pyridine-2(3H)-carboxylate (152 mg, 0.305 mmol), 4-fluorobenzo[b]thiophen-2-ylboronic acid (149 mg, 0.762 mmol) and tetrakis(triphenylphosphine)palladium(0) (352 mg, 0.305 mmol) in dioxane and saturated aqueous NaHCO$_3$ (1:1, 5 mL) was heated to 120° C. via microwave irradiation for 30 minutes. The reaction mixture was diluted with EtOAc (50 mL) and saturated aqueous NaHCO$_3$ (100 mL). The organic layer was separated and the aqueous layer was washed with EtOAc (50 mL). The organic layers were combined, dried over Na$_2$SO$_4$, and the solvent was removed in vacuo to give the intermediate, tert-butyl 6-((1R,2S)-2-((tert-butoxycarbonyl)amino)cyclohexyl)amino)-7-fluoro-4-(4-fluorobenzo[b]thiophen-2-yl)-3-oxo-1H-pyrrolo[3,4-c]pyridine-2(3H)-carboxylate. The intermediate was dispersed in TFA and DCM (1:1, 10 mL) and stirred at room temperature for 60 minutes. The mixture was concentrated and the resulting crude material was reconstituted in MeOH/DCM (10.0 mL) and was purified via preparative HPLC eluting with a gradient of 30-50% ACN (0.035% TFA) and H$_2$O (0.05% TFA). The combined fractions were neutralized with saturated aqueous NaHCO$_3$, washed with EtOAc (2×200 mL), dried over Na$_2$SO$_4$, and filtered. The organic phase was stripped to dryness via rotary evaporation to give the title compound (83 mg, 66%). $^1$H NMR (500 MHz, DMSO-d$_6$) δ ppm 1.31-1.48 (m, 2 H), 1.55-1.85 (m, 6 H), 3.17 (s, 2 H), 4.10 (dd, J=6.35, 2.93 Hz, 2 H), 4.45 (s, 2 H), 6.79 (d, J=6.35 Hz, 1 H), 7.19 (dd, J=10.25, 7.81 Hz, 1 H), 7.40 (td, J=8.05, 5.37 Hz, 1 H), 7.82 (d, J=8.30 Hz, 1 H), 8.56 (s, 1 H), 9.56 (s, 1 H). ESI-MS m/z [M+H]$^+$calc'd for C$_{21}$H$_{20}$F$_2$N$_4$OS, 415. found, 415.

Example 25

6-((3R,4R)-3-Aminotetrahydro-2H-pyran-4-ylamino)-7-fluoro-4-(thieno[3,2-b]pyridin-2-yl)-1H-pyrrolo[3,4-c]pyridin-3(2H)-one

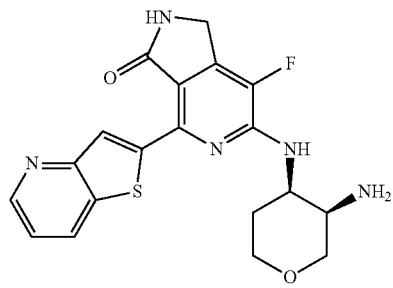 [SMILES: N[C@H]1COCC[C@H]1Nc1nc(-c2cc3ncccc3s2)c2c(c1F)CNC2=O]

The title compound was prepared in a manner similar to Example 21 using thieno[3,2-b]pyridin-2-ylboronic acid in place of 5-cyanobenzo[b]thiophen-2-ylboronic acid. $^1$H NMR (500 MHz, DMSO-d$_6$) δ ppm 1.62-2.06 (m, 4 H), 3.09 (d, J=1.95 Hz, 1 H), 3.43-3.53 (m, 1 H), 3.63 (dd, J=11.72, 1.95 Hz, 1 H), 3.76 (dd, J=11.72, 2.44 Hz, 1 H), 3.89 (dt, J=11.35, 3.60 Hz, 1 H), 4.20-4.29 (m, 1 H), 4.47 (s, 2 H), 6.89 (d, J=6.83 Hz, 1 H), 7.36 (dd, J=8.05, 4.64 Hz, 1 H), 8.39-8.49 (m, 1 H), 8.55-8.71 (m, 2 H), 9.58 (s, 1 H). ESI-MS m/z [M+H]$^+$calc'd for C$_{19}$H$_{18}$FN$_5$O$_2$S, 400. found, 400.

Example 26

6-((1R,2S)-2-Aminocyclohexylamino)-7-fluoro-4-(thieno[3,2-b]pyridin-2-yl)-1H-pyrrolo[3,4-c]pyridin-3(2H)-one

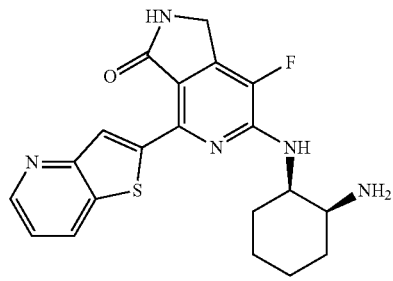 [SMILES: N[C@H]1CCCC[C@H]1Nc1nc(-c2cc3ncccc3s2)c2c(c1F)CNC2=O]

The title compound was prepared in a manner similar to Example 24 using thieno[3,2-b]pyridin-2-ylboronic acid in place of 4-fluorobenzo[b]thiophen-2-ylboronic acid. $^1$H NMR (500 MHz, DMSO-d$_6$) δ ppm 1.24 (s, 1 H), 1.40 (br s, 3 H), 1.55-1.87 (m, 7 H), 3.21 (d, J=2.93 Hz, 1 H), 4.08 (d, J=3.42 Hz, 1 H), 4.37-4.52 (m, 2 H), 6.75 (br s, 1 H), 7.25-7.38 (m, 1 H), 8.39-8.48 (m, 1 H), 8.58 (s, 1 H), 8.65 (dd, J=4.39, 1.46 Hz, 1 H), 9.54 (s, 1H). ESI-MS m/z [M+H]$^+$calc'd for C$_{20}$H$_{20}$FN$_5$OS, 398. found, 398.

Example 27

6-((3R,4R)-3-Aminotetrahydro-2H-pyran-4-ylamino)-7-fluoro-4-(4-fluorothiophene-2-yl)-1H-pyrrolo[3,4-c]pyridin-3(2H)-one

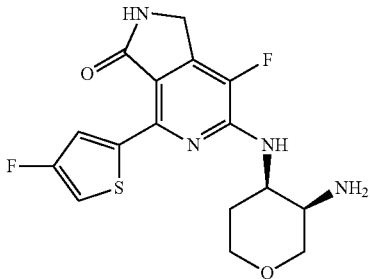 [SMILES: N[C@H]1COCC[C@H]1Nc1nc(-c2cc(F)cs2)c2c(c1F)CNC2=O]

To a 30 mL sealed cap glass vessel containing tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (200 mg, 0.399 mmol) and 2-(4-fluorothiophene-2-yl)-4,4,5,5-tetramethyl-1,3,2-dioxaborolane (137 mg, 0.599 mmol) dissolved in DME and water (4:1) was added tetrakis(triphenylphosphine)palladium(0) (105 mg, 0.399 mmol) and potassium phosphate, tribasic (212 mg, 1 mmol). The cap was sealed, and the reaction mixture was heated at 85° C. for 1 hour and then cooled to room temperature. The mixture was diluted with water (10 mL) and extracted with EtOAc (2×25 mL). The organic layers were combined, dried over sodium sulfate, and solvent removed via rotary evaporation to give the intermediate, tert-butyl 6-(((3R,4R)-3-((tert-butoxycarbonyl)amino)tetrahydro-2H-pyran-4-yl)amino)-7-fluoro-4-(4-fluorothiophene-2-yl)-3-oxo-1H-pyrrolo[3,4-c]pyridine-2(3H)-carboxylate. The intermediate was dissolved in TFA (5 mL) and the resulting mixture was stirred at room temperature for 1 hour to give crude product, which was purified via preparative HPLC, eluting with a gradient of 15-50% ACN (0.035% TFA) and H$_2$O (0.05% TFA). The pure fractions were combined, evaporated to minimal volume, and lyophilized to give a TFA salt of the title compound (86 mg, 59%). $^1$H NMR (400 MHz, DMSO-d$_6$) δ ppm 1.78 (d, J=9.60 Hz, 1 H), 2.03-2.18 (m, 1 H), 3.53-3.68 (m, 1 H), 3.75 (d, J=11.62 Hz, 1H), 3.85 (br s, 1 H), 4.01 (d, J=12.38 Hz, 2 H), 4.32 (td, J=8.53, 4.17 Hz, 1 H), 4.45 (s, 2 H), 7.32 (t, J=1.64 Hz, 1 H), 7.40 (d, J=5.31 Hz, 1 H), 7.95 (br s, 3 H), 8.65 (s, 1 H), 8.98 (d, J=1.77 Hz, 1 H). ESI-MS m/z [M+H]$^+$calc'd for C$_{16}$H$_{16}$F$_2$N$_4$O$_2$S, 367. found, 367.

Example 28

6-((1R,2S)-2-Aminocyclohexylamino)-7-fluoro-4-(4-fluorothiophene-2-yl)-1H-pyrrolo[3,4-c]pyridin-3(2H)-one

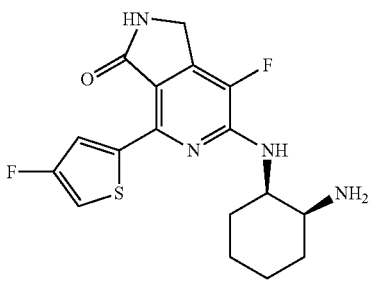 [SMILES: N[C@H]1CCCC[C@H]1Nc1nc(-c2cc(F)cs2)c2c(c1F)CNC2=O]

To a 30 mL sealed cap glass vessel containing tert-butyl 6-((1R,2S)-2-(tert-butoxycarbonylamino)cyclohexylamino)-4-chloro-7-fluoro-3-oxo-1H-pyrrolo[3,4-c]pyridine-2(3H)-carboxylate (200 mg, 0.401 mmol) and 2-(4-fluorothiophen-2-yl)-4,4,5,5-tetramethyl-1,3,2-dioxaborolane (137 mg, 0.601 mmol) dissolved in DME and water (4:1) was added tetrakis(triphenylphosphine)palladium(0) (105 mg, 0.401 mmol) and potassium phosphate, tribasic (212 mg, 1 mmol). The cap was sealed, and the reaction mixture was heated at 85° C. for 4 hours and then cooled to room temperature. The mixture was diluted with water and extracted with EtOAc (2×25 mL). The organic layers were combined, dried over sodium sulfate, and evaporated to give the intermediate, tert-butyl 6-(((1R,2S)-2-((tert-butoxycarbonyl)amino)cyclohexyl)amino)-7-fluoro-4-(4-fluorothiophen-2-yl)-3-oxo-1H-pyrrolo[3,4-c]pyridine-2(3H)-carboxylate. The intermediate was dissolved in TFA (5 mL) and stirred at room temperature for 2 hours. The mixture was evaporated and purified by preparative HPLC, eluting with a gradient of 15-50% ACN (0.035% TFA) and H$_2$O (0.05% TFA). The pure fractions were combined, evaporated to minimal volume, and lyophilized to give a TFA salt of the title compound as a white solid (112 mg, 77%). $^1$H NMR (400 MHz, DMSO-d$_6$) δ ppm 1.29-1.54 (m, 2 H), 1.60 (d, J=12.88 Hz, 2 H), 1.66-1.81 (m, 2 H), 1.83-1.99 (m, 2 H), 3.81 (br s, 1 H), 4.24 (br s, 1 H), 4.45 (d, J=2.27 Hz, 2 H), 7.14 (d, J=5.31 Hz, 1 H), 7.31 (t, J=1.39 Hz, 1 H), 7.79 (br s, 3 H), 8.62 (s, 1 H), 8.97 (d, J=1.77 Hz, 1 H). ESI-MS m/z [M+H]$^+$calc'd for C$_{12}$H$_{18}$F$_2$N$_4$OS, 365. found, 365.

Example 29

6-((1R,2S)-2-Aminocyclohexylamino)-7-fluoro-4-(1-methyl-1H-thieno[3,2-c]pyrazol-5-yl)-1H-pyrrolo[3,4-c]pyridin-3(2H)-one

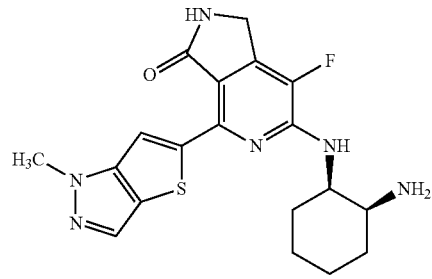 [SMILES: Cn1ncc2sc(-c3nc(N[C@@H]4CCCC[C@@H]4N)c(F)c4c3C(=O)NC4)cc21]

In a 30 mL sealed cap glass vessel, tert-butyl 6-((1R,2S)-2-(tert-butoxycarbonylamino)cyclohexylamino)-4-chloro-7-fluoro-3-oxo-1H-pyrrolo[3,4-c]pyridine-2(3H)-carboxylate (102 mg, 0.205 mmol), 1-methyl-5-(tributylstannyl)-1H-thieno[3,2-c]pyrazole (175 mg, 0.410 mmol) and tetrakis(triphenylphosphine) palladium(0) (118 mg, 0.102 mmol) were dissolved in toluene (5 mL). The cap was sealed and the reaction mixture was heated at 90° C. in an oil bath for 2 hours. The reaction mixture was concentrated to give the intermediate, tert-butyl 6-(((1R,2S)-2-((tert-butoxycarbonyl)amino)cyclohexyl)amino)-7-fluoro-4-(1-methyl-1H-thieno[3,2-c]pyrazol-5-yl)-3-oxo-1H-pyrrolo[3,4-c]pyridine-2(3H)-carboxylate. The intermediate was dissolved in TFA (5 mL) and the reaction mixture was stirred for 1 hour. The mixture was concentrated, dissolved in DMSO (5 mL), and purified via preparative HPLC, eluting with a gradient of 15-65% ACN (0.035% TFA) and H₂O (0.05% TFA). The pure fractions were combined, evaporated to a minimal volume, and lyophilized to give a TFA salt of the title compound as a white solid (75 mg, 91%). ¹H NMR (400 MHz, DMSO-d₆) δ ppm 1.28-1.55 (m, 2 H), 1.60 (d, J=14.15 Hz, 1 H), 1.67-1.93 (m, 3 H), 1.98 (dd, J=13.64, 4.29 Hz, 2 H), 3.85 (br s, 1 H), 3.99 (s, 2 H), 4.24 (d, J=3.54 Hz, 1H), 4.38-4.54 (m, 2 H), 7.14 (d, J=5.81 Hz, 1 H), 7.62-7.88 (m, 3 H), 8.62 (s, 1 H), 9.27 (s, 1 H). ESI-MS m/z [M+H]⁺calc'd for C₁₉H₂₁FN₆OS, 401. found, 401.

Example 30

6-((3R,4R)-3-Aminotetrahydro-2H-pyran-4-ylamino)-7-fluoro-4-(1-methyl-1H-thieno[3,2-c]pyrazol-5-yl)-1H-pyrrolo[3,4-c]pyridin-3(2H)-one

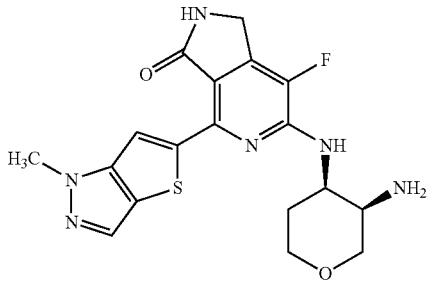 [SMILES: Cn1ncc2sc(-c3nc(N[C@@H]4CCOC[C@@H]4N)c(F)c4c3C(=O)NC4)cc21]

In a 30 mL sealed cap glass vessel, tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (119 mg, 0.238 mmol), 1,3-dimethyl-5-(tributylstannyl)-1H-thieno[3,2-c]pyrazole (210 mg, 0.476 mmol) and tetrakis(triphenylphosphine)palladium(0) (137 mg, 0.119 mmol) were dissolved in toluene (5 mL). The cap was sealed and the reaction mixture was heated at 90° C. in an oil bath for 2 hours. The mixture was concentrated to give the intermediate, tert-butyl 6-(((3R,4R)-3-((tert-butoxycarbonyl)amino)tetrahydro-2H-pyran-4-yl)amino)-7-fluoro-4-(1-methyl-1H-thieno[3,2-c]pyrazol-5-yl)-3-oxo-1H-pyrrolo[3,4-c]pyridine-2(3H)-carboxylate. The intermediate was dissolved in TFA (5 mL) and the reaction mixture was stirred for 1 hour. The mixture was concentrated, dissolved in DMSO (5 mL), and purified via preparatory HPLC eluting with a gradient of 15-50% ACN (0.035% TFA) and H₂O (0.05% TFA). The pure fractions were combined, evaporated to a minimal volume, and lyophilized to give a TFA salt of the title compound as a white solid (65 mg, 68%). ¹H NMR (400 MHz, DMSO-d₆) δ ppm 1.79 (d, J=10.86 Hz, 1 H), 2.04-2.26 (m, 1 H), 3.55-3.68 (m, 2 H), 3.80 (d, J=11.62 Hz, 1 H), 3.89 (br s, 1 H), 3.99 (s, 3 H), 4.02-4.06 (m, 1 H), 4.33 (td, J=8.27, 4.67 Hz, 1 H), 4.45 (s, 2 H), 7.40 (d, J=5.05 Hz, 1 H), 7.74 (d, J=0.76 Hz, 1 H), 7.96 (d, J=4.55 Hz, 2 H), 8.65 (s, 1 H), 9.28 (d, J=0.76 Hz, 1 H). ESI-MS m/z [M+H]⁺calc'd for C₁₈H₁₉FN₆O₂S, 403. found, 403.

Example 31

6-(((1R,2S)-2-Aminocyclohexylamino)-4-(1,3-dimethyl-1H-thieno[3,2-c]pyrazol-5-yl)-7-fluoro-1H-pyrrolo[3,4-c]pyridin-3(2H)-one

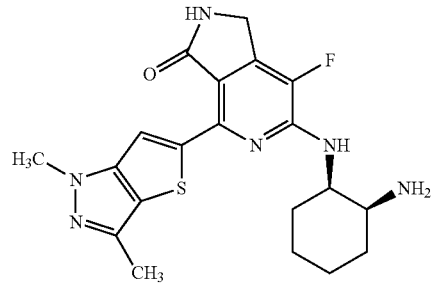 [SMILES: Cc1nn(C)c2cc(-c3nc(N[C@@H]4CCCC[C@@H]4N)c(F)c4c3C(=O)NC4)sc12]

In a 30 mL sealed cap glass tube, tert-butyl 6-((1R,2S)-2-(tert-butoxycarbonylamino)cyclohexylamino)-4-chloro-7-fluoro-3-oxo-1H-pyrrolo[3,4-c]pyridine-2(3H)-carboxylate (150 mg, 0.301 mmol), 1,3-dimethyl-5-(tributylstannyl)-1H-thieno[3,2-c]pyrazole (265 mg, 0.601 mmol) and tetrakis(triphenylphosphine) palladium(0) (174 mg, 0.150 mmol) were dissolved in toluene (5 mL). The cap was sealed and the reaction mixture was heated at 90° C. in an oil bath for 2 hours. The mixture was concentrated to give the intermediate, tert-butyl 6-(((1R,2S)-2-((tert-butoxycarbonyl)amino)cyclohexyl)amino)-4-(1,3-dimethyl-1H-thieno[3,2-c]pyrazol-5-yl)-7-fluoro-3-oxo-1H-pyrrolo[3,4-c]pyridine-2(3H)-carboxylate. The intermediate was dissolved in TFA (5 mL) and the reaction mixture was stirred for 2 hours. The mixture was concentrated, dissolved in DMSO (5 mL), and purified via preparatory HPLC eluting with a gradient of 15-65% ACN (0.035% TFA) and H₂O (0.05% TFA). The pure fractions were combined, evaporated to a minimal volume, and lyophilized to give a TFA salt of the title compound as a white solid (95 mg, 72%). ¹H NMR (400 MHz, DMSO-d₆) δ ppm 1.48 (br s, 2 H), 1.43-2.03 (m, 6 H), 2.33 (s, 3 H), 3.83 (br s, 1 H), 3.90 (s, 3 H), 4.28 (br s, 1 H), 4.39-4.51 (m, 2 H), 7.09 (d, J=5.81 Hz, 1 H), 7.79 (br s, 3 H), 8.61 (s, 1 H), 9.22 (s, 1 H). ESI-MS m/z [M+H]⁺calc'd for C₂₀H₂₃FN₆OS, 415. found, 415.

Example 32

6-((3R,4R)-3-Aminotetrahydro-2H-pyran-4-ylamino)-4-(1,3-dimethyl-1H-thieno[3,2-c]pyrazol-5-yl)-7-fluoro-1H-pyrrolo[3,4-c]pyridin-3(2H)-one

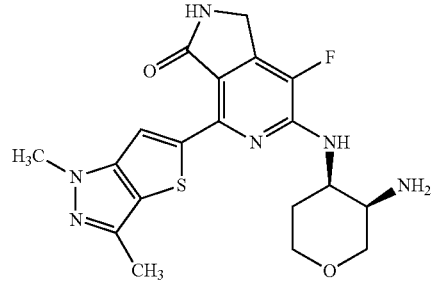 [SMILES: Cc1nn(C)c2cc(-c3nc(N[C@@H]4CCOC[C@@H]4N)c(F)c4c3C(=O)NC4)sc12]

In a 30 mL sealed cap glass tube, tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (119 mg, 0.238 mmol), 1,3-dimethyl-5-(tributylstannyl)-1H-thieno[3,2-c]pyrazole (210 mg, 0.476 mmol) and tetrakis(triphenylphosphine)palladium(0) (137 mg, 0.119 mmol) were dissolved in toluene (5 mL). The cap was sealed and the reaction mixture was heated at 90° C. in an oil bath for 2 hours. The mixture was concentrated to give the intermediate, tert-butyl 6-(((3R,4R)-3-((tert-butoxycarbonyl)amino)tetrahydro-2H-pyran-4-yl)amino)-4-(1,3-dimethyl-1H-thieno[3,2-c]pyrazol-5-yl)-7-fluoro-3-oxo-1H-pyrrolo[3,4-c]pyridine-2(3H)-carboxylate. The intermediate was dissolved in TFA (5 mL) and the reaction mixture was stirred for 2 hours. The mixture was concentrated, dissolved in DMSO (5 mL), and purified via preparatory HPLC eluting with a gradient of 15-65% ACN (0.035% TFA) and H$_2$O (0.05% TFA). The pure fractions were combined, evaporated to a minimal volume, and lyophilized to give a TFA salt of the title compound as a white solid (101 mg, 76%). $^1$H NMR (400 MHz, DMSO-d$_6$) δ ppm 1.79 (d, J=9.60 Hz, 1 H), 2.02-2.22 (m, 1 H), 2.33 (br s, 3 H), 3.55-3.71 (m, 1H), 3.82 (d, J=11.62 Hz, 1 H), 3.90 (br s, 3 H), 3.97-4.13 (m, 2 H), 4.27-4.40 (m, 1 H), 4.41-4.53 (m, 2 H), 7.24-7.44 (m, 1 H), 7.84-8.04 (m, 3 H), 8.63 (br s, 1 H), 9.22 (br s, 1H). ESI-MS m/z [M+H]$^+$calc'd for C$_{19}$H$_{21}$FN$_6$O$_2$S, 417. found, 417.

Example 33

6-((1R,2S)-2-Aminocyclohexylamino)-4-(2,3-dimethyl-2H-thieno[3,2-c]pyrazol-5-yl)-7-fluoro-1H-pyrrolo[3,4-c]pyridin-3(2H)-one

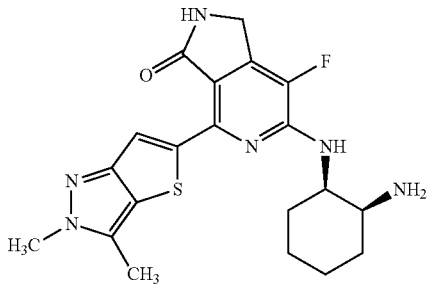 [SMILES: Cc1c2sc(-c3nc(N[C@@H]4CCCC[C@@H]4N)c(F)c4c3C(=O)NC4)cc2nn1C]

In a 30 mL sealed cap glass tube, tert-butyl 6-(((1R,2S)-2-(tert-butoxycarbonylamino)cyclohexylamino)-4-chloro-7-fluoro-3-oxo-1H-pyrrolo[3,4-c]pyridine-2(3H)-carboxylate (150 mg, 0.301 mmol), 2,3-dimethyl-5-(tributylstannyl)-2H-thieno[3,2-c]pyrazole (265 mg, 0.601 mmol) and tetrakis(triphenylphosphine)palladium(0) (174 mg, 0.150 mmol) were dissolved in toluene (5 mL). The cap was sealed and the reaction mixture was heated at 90° C. in an oil bath for 2 hours. The mixture was concentrated to give the intermediate, tert-butyl 6-(((1R,2S)-2-((tert-butoxycarbonyl)amino)cyclohexyl)amino)-4-(2,3-dimethyl-2H-thieno[3,2-c]pyrazol-5-yl)-7-fluoro-3-oxo-1H-pyrrolo[3,4-c]pyridine-2(3H)-carboxylate. The intermediate was dissolved in TFA (5 mL) and the reaction mixture was stirred for 90 minutes. The mixture was concentrated, dissolved in DMSO (5 mL), and purified via preparatory HPLC eluting with a gradient of 20-30% ACN (0.035% TFA) and H$_2$O (0.05% TFA). The pure fractions were combined, evaporated to a minimal volume, and lyophilized to give a TFA salt of the title compound as a white solid (108 mg, 68.0%). $^1$H NMR (400 MHz, DMSO-d$_6$) ppm 1.49-2.04 (m, 8 H), 2.45 (s, 3 H), 3.84 (br s, 1 H), 3.92 (s, 3 H), 4.27 (br s, 1 H), 4.35-4.51 (m, 2 H), 7.08 (d, J=6.06 Hz, 1 H), 7.78 (br s, 3 H), 8.60 (s, 1 H), 9.25 (s, 1 H). ESI-MS m/z [M+H]$^+$calc'd for C$_{20}$H$_{23}$FN$_6$OS, 415. found, 415.

Example 34

6-((3R,4R)-3-Aminotetrahydro-2H-pyran-4-ylamino)-4-(2,3-dimethyl-2H-thieno[3,2-c]pyrazol-5-yl)-7-fluoro-1H-pyrrolo[3,4-c]pyridin-3(2H)-one

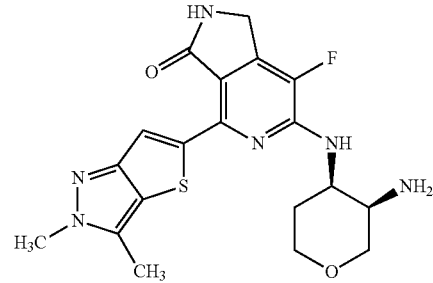 [SMILES: Cc1c2sc(-c3nc(N[C@@H]4CCOC[C@@H]4N)c(F)c4c3C(=O)NC4)cc2nn1C]

In a 30 mL sealed cap glass tube, tert-butyl 6-(((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (100 mg, 0.200 mmol), 2,3-dimethyl-5-(tributylstannyl)-2H-thieno[3,2-c]pyrazole (176 mg, 0.399 mmol) and tetrakis(triphenylphosphine)palladium(0) (115 mg, 0.100 mmol) were dissolved in toluene (5 mL). The cap was sealed and the reaction mixture was heated at 90° C. in an oil bath for 2 hours. The mixture was concentrated to give the intermediate, tert-butyl 6-(((3R,4R)-3-((tert-butoxycarbonyl)amino)tetrahydro-2H-pyran-4-yl)amino)-4-(2,3-dimethyl-2H-thieno[3,2-c]pyrazol-5-yl)-7-fluoro-3-oxo-1H-pyrrolo[3,4-c]pyridine-2(3H)-carboxylate. The intermediate was dissolved in TFA (5 mL) and the reaction mixture was stirred for 2 hours. The mixture was concentrated, dissolved in DMSO (5 mL), and purified via preparatory HPLC eluting with a gradient of 10-60% ACN (0.035% TFA) and H$_2$O (0.05% TFA). The pure fractions were combined, evaporated to a minimal volume, and lyophilized to give a TFA salt of the title compound as a white solid (65 mg, 61%). $^1$H NMR (400 MHz, DMSO-d$_6$) δ ppm 1.80 (d, J=12.38 Hz, 1 H), 1.96-2.25 (m, 1 H), 2.46 (s, 3 H), 3.55-3.71 (m, 1 H), 3.82 (d, J=11.87 Hz, 1 H), 3.92 (s, 3 H), 4.05 (d, J=11.12 Hz, 3 H), 4.28-4.38 (m, 1 H), 4.40-4.51 (m, 2 H), 7.37 (d, J=4.80 Hz, 1 H), 7.96 (d, J=4.80 Hz, 3 H), 8.63 (s, 1 H), 9.26 (s, 1H). ESI-MS m/z [M+H]$^+$ calc'd for C$_{19}$H$_{21}$FN$_6$O$_2$S, 417. found, 417.

Example 35

6-((1R,2S)-2-Aminocyclohexylamino)-4-(3,4-dihydro-1H-pyrrolo[2,1-c][1,4]oxazin-7-yl)-7-fluoro-1H-pyrrolo[3,4-c]pyridin-3(2H)-one

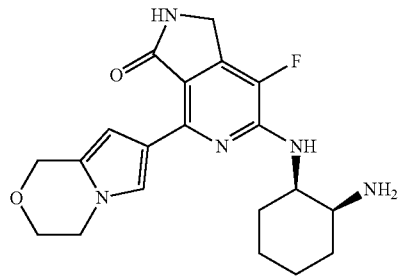 [SMILES: N[C@H]1CCCC[C@H]1Nc1nc(-c2cc3n(c2)CCOC3)c2c(c1F)CNC2=O]

In a 30 mL sealed cap glass tube, tert-butyl 6-((1R,2S)-2-(tert-butoxycarbonylamino)cyclohexylamino)-4-chloro-7-fluoro-3-oxo-1H-pyrrolo[3,4-c]pyridine-2(3H)-carboxylate (150 mg, 0.301 mmol), 7-(tributylstannyl)-3,4-dihydro-1H-pyrrolo[2,1-c][1,4]oxazine (124 mg, 0.301 mmol) and tetrakis(triphenylphosphine)palladium(0) (174 mg, 0.150 mmol) were dissolved in toluene (5 mL). The cap was sealed and the reaction mixture was heated at 90° C. in an oil bath for 2 hours. Following work-up, the intermediate, tert-butyl 6-(((1R,2S)-2-((tert-butoxycarbonyl)amino)cyclohexyl)amino)-4-(3,4-dihydro-1H-pyrrolo[2,1-c][1,4]oxazin-7-yl)-7-fluoro-3-oxo-1H-pyrrolo[3,4-c]pyridine-2(3H)-carboxylate, was purified by preparative HPLC eluting with a gradient of 55-95% ACN (0.035% TFA) and H$_2$O (0.05% TFA). The pure fractions were combined and the solvent stripped by rotary evaporation to give a solid intermediate. The intermediate was subsequently dissolved in TFA (3 mL) and the reaction mixture was stirred for 1 hour. The mixture was concentrated, dissolved in DMSO (5 mL), and purified via preparatory HPLC eluting with a gradient of 20-50% ACN (0.035% TFA) and H$_2$O (0.05% TFA). The pure fractions were combined, evaporated to a minimal volume, and lyophilized to give a TFA salt of the title compound as a pale yellow solid (7.3 mg, 6.3%). $^1$H NMR (400 MHz, DMSO-d$_6$) δ ppm 1.44 (d, J=7.33 Hz, 2 H), 1.59 (br s, 1 H), 1.63-1.92 (m, 4 H), 3.98 (d, J=1.77 Hz, 3 H), 4.26-4.46 (m, 3H), 4.74 (s, 2 H), 6.54-6.71 (m, 2 H), 7.74 (br s, 3 H), 8.17-8.36 (m, 2 H). ESI-MS m/z [M+H]$^+$calc'd for C$_{20}$H$_{24}$FN$_5$O$_2$, 386. found, 386.

Example 36

6-((1R,2S)-2-Aminocyclohexylamino)-4-(1,3-dimethyl-1H-thieno[2,3-c]pyrazol-5-yl)-7-fluoro-1H-pyrrolo[3,4-c]pyridin-3(2H)-one

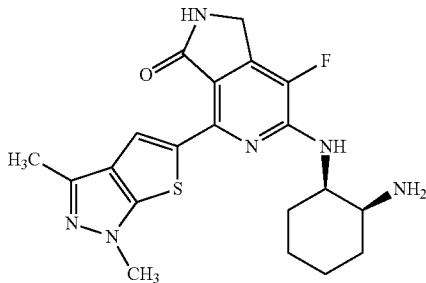 [SMILES: Cc1nn(C)c2sc(-c3nc(N[C@@H]4CCCC[C@@H]4N)c(F)c4c3C(=O)NC4)cc12]

A mixture of tert-butyl 6-((1R,2S)-2-(tert-butoxycarbonylamino)cyclohexylamino)-4-chloro-7-fluoro-3-oxo-1H-pyrrolo[3,4-c]pyridine-2(3H)-carboxylate (120 mg, 0.240 mmol), 1,3-dimethyl-5-(tributylstannyl)-1H-thieno[2,3-c]pyrazole (212 mg, 0.481 mmol) and tetrakis(triphenylphosphine)palladium(0) (139 mg, 0.120 mmol) in toluene (3 mL) was heated to 120° C. in a Biotage Initiator microwave for 30 minutes. The mixture was concentrated to give the intermediate, tert-butyl 6-(((1R,2S)-2-((tert-butoxycarbonyl)amino)cyclohexyl)amino)-4-(1,3-dimethyl-1H-thieno[2,3-c]pyrazol-5-yl)-7-fluoro-3-oxo-1H-pyrrolo[3,4-c]pyridine-2(3H)-carboxylate, which was subsequently dissolved in DCM (5 mL) and TFA (5 mL). The resulting solution was stirred at room temperature for 20 minutes, concentrated, and purified by preparatory HPLC, eluting with a gradient of 10-40% ACN (0.035% TFA) and water (0.05% TFA). The collected fractions were combined and dried to give a TFA salt of the title compound as a white solid (89 mg, 89%). $^1$H NMR (400 MHz, DMSO-d$_6$) δ ppm 1.48-1.73 (m, 5H), 1.83-1.97 (m, 3H), 2.35 (s, 3H), 3.78-3.79 (m, 1H), 3.86 (s, 3H), 4.26-4.27 (m, 1H), 4.43 (d, J=4.88 Hz, 2H), 7.02-7.04 (m, 1H), 7.81-7.82 (m, 2H), 8.51 (s, 1H), 9.16 (s, 1H). ESI-MS m/z [M+H]$^+$calc'd for C$_{20}$H$_{23}$FN$_6$OS, 415. found, 415.

Example 37

6-((3R,4R)-3-Aminotetrahydro-2H-pyran-4-ylamino)-4-(1,3-dimethyl-1H-thieno[2,3-c]pyrazol-5-yl)-7-fluoro-1H-pyrrolo[3,4-c]pyridin-3(2H)-one

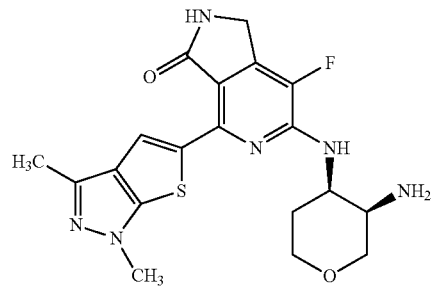 [SMILES: Cc1nn(C)c2sc(-c3nc(N[C@@H]4CCOC[C@@H]4N)c(F)c4c3C(=O)NC4)cc12]

A mixture of tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (200 mg, 0.399 mmol), 1,3-dimethyl-5-(tributylstannyl)-1H-thieno[2,3-c]pyrazole (352 mg, 0.798 mmol) and tetrakis(triphenylphosphine)palladium(0) (231 mg, 0.200 mmol) in toluene (3 mL) was heated to 120° C. in a Biotage Initiator microwave for 30 minutes. The mixture was concentrated to give the intermediate, tert-butyl 6-(((3R,4R)-3-((tert-butoxycarbonyl)amino)tetrahydro-2H-pyran-4-yl)amino)-4-(1,3-dimethyl-1H-thieno[2,3-c]pyrazol-5-yl)-7-fluoro-3-oxo-1H-pyrrolo[3,4-c]pyridine-2(3H)-carboxylate, which was subsequently dissolved in DCM (5 mL) and TFA (5 mL). The resulting solution was stirred at room temperature for 20 minutes, concentrated, and purified by preparatory HPLC, eluting with a gradient of 10-30% ACN (0.035% TFA) and water (0.05% TFA). The collected fractions were combined and dried to give a TFA salt of the title compound as a white solid (85 mg, 51%). $^1$H NMR (400 MHz, DMSO-d$_6$) δ ppm 1.79-1.81 (m, 1H), 2.13-2.14 (m, 1H), 2.53 (s, 3H), 3.61-3.63 (m, 1H), 3.85-3.87 (m, 2H), 3.87 (s, 3H), 4.01-4.07 (m, 2H), 4.33-4.35 (m, 1H), 4.44 (d, J=7.80 Hz, 2H), 7.33-47.34 (m, 1H), 8.01-8.02 (m, 2H), 8.53 (s, 1H), 9.16 (s, 1H). ESI-MS m/z [M+H]$^+$calc'd for C$_{19}$H$_{21}$FN$_6$O$_2$S, 417. found, 417.

Example 38

6-((3R,4R)-3-Aminotetrahydro-2H-pyran-4-ylamino)-4-(1-ethyl-1H-pyrazol-4-yl)-7-fluoro-1H-pyrrolo[3,4-c]pyridin-3(2H)-one

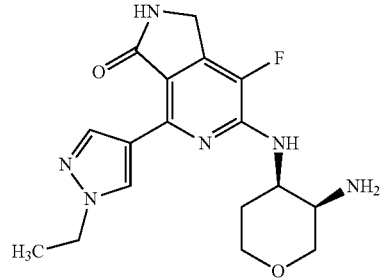 [SMILES: CCn1cc(-c2nc(N[C@@H]3CCOC[C@@H]3N)c(F)c3c2C(=O)NC3)cn1]

A mixture of bis(triphenylphosphine)palladium chloride (14.01 mg, 0.020 mmol), tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (200 mg, 0.399 mmol), and 1-ethyl-4-(4,4,5,5-tetramethyl-1,3,2-dioxaborolan-2-yl)-1H-pyrazole (177 mg, 0.798 mmol) in dioxane (4 mL) and saturated aqueous NaHCO$_3$ (1 mL) was heated to 100° C. in a Biotage Initiator microwave for 1 hour. The mixture was concentrated to give the intermediate, tert-butyl 6-(((3R,4R)-3-((tert-butoxycarbonyl)amino)tetrahydro-2H-pyran-4-yl)amino)-4-(1-ethyl-1H-pyrazol-4-yl)-7-fluoro-3-oxo-1H-pyrrolo[3,4-c]pyridine-2(3H)-carboxylate, which was subsequently dissolved in DCM (5 mL) and TFA (5 mL). The resulting solution was stirred at room temperature for 20 minutes, concentrated, and purified by preparatory HPLC, eluting with a gradient of 10-25% ACN (0.035% TFA) and water (0.05% TFA). The collected fractions were combined and dried to give a TFA salt of the title compound as a white solid (87 mg, 60%). $^1$H NMR (400 MHz, DMSO-d$_6$) δ ppm 1.40 (t, J=7.3 Hz, 3H), 1.75-1.77 (m, 1H), 2.10-2.11 (m, 1H), 3.61-3.63 (m, 1H), 3.85-3.86 (m, 1H), 3.93-3.94 (m, 1H), 3.96-3.98 (m, 2H), 4.18 (q, J=7.32, 2H), 4.47-4.48 (m, 1H), 7.04-7.05 (m, 1H), 7.89-7.91 (m, 2H), 8.30 (s, 1H), 8.37 (s, 1H), 8.88 (s, 1H). ESI-MS m/z [M+H]$^+$calc'd for C$_{12}$H$_{21}$FN$_6$O$_2$, 361. found, 361.

Example 39

Ethyl 2-(6-((3R,4R)-3-Aminotetrahydro-2H-pyran-4-ylamino)-7-fluoro-3-oxo-2,3-dihydro-1H-pyrrolo[3,4-c]pyridin-4-yl)indolizine-7-carboxylate

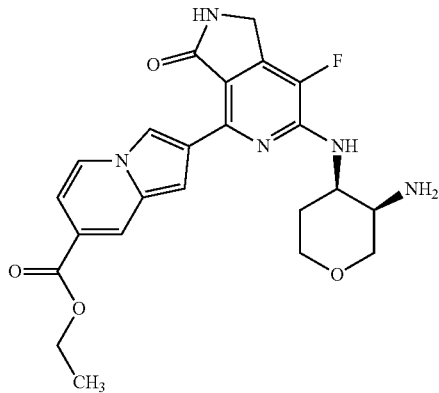 [SMILES: CCOC(=O)c1ccn2cc(-c3nc(N[C@@H]4CCOC[C@@H]4N)c(F)c4c3C(=O)NC4)cc2c1]

A mixture of bis(triphenylphosphine)palladium chloride (13.09 mg, 0.019 mmol), tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (187 mg, 0.373 mmol), and ethyl 2-(4,4,5,5-tetramethyl-1,3,2-dioxaborolan-2-yl)indolizine-7-carboxylate (118 mg, 0.373 mmol) in dioxane (4 mL) and saturated aqueous NaHCO$_3$ (1 mL) were heated to 100° C. in a Biotage Initiator microwave for 1 hour. The mixture was concentrated to give the intermediate, tert-butyl 6-(((3R,4R)-3-((tert-butoxycarbonyl)amino)tetrahydro-2H-pyran-4-yl)amino)-4-(7-(ethoxycarbonyl)indolizin-2-yl)-7-fluoro-3-oxo-1H-pyrrolo[3,4-c]pyridine-2(3H)-carboxylate, which was subsequently dissolved in DCM (5 mL) and TFA (5 mL). The resulting solution was stirred at room temperature for 20 minutes, concentrated, and purified by preparatory HPLC, eluting with a gradient of 10-40% ACN (0.035% TFA) and water (0.05% TFA). The collected fractions were combined and dried to give a TFA salt of the title compound as a tan solid (31 mg, 18%). $^1$H NMR (400 MHz, DMSO-d$_6$) δ ppm 1.34 (t, J=6.80 Hz, 3H), 1.78-1.81 (m, 1H), 2.11-2.12 (m, 1H), 3.62-3.65 (m, 1H), 3.89-3.91 (m, 1H), 3.94-4.28 (m, 3H), 4.31 (q, J=6.83 Hz, 2H), 4.43 (d, J=8.3 Hz, 2H), 4.53-4.54 (m, 1H), 6.96 (dd, J=1.46, 7.32 Hz, 1H), 7.15 (d, J=4.88 Hz, 1H), 7.71 (s, 1H), 7.92-7.93 (m, 2H), 8.21 (s, 1H), 8.36 (d, J=7.32 Hz, 1H), 8.48 (s, 1H), 9.03 (s, 1H). ESI-MS m/z [M+H]$^+$calc'd for C$_{23}$H$_{24}$FN$_5$O$_4$, 454. found, 454.

Example 40

2-(6-((3R,4R)-3-Aminotetrahydro-2H-pyran-4-ylamino)-7-fluoro-3-oxo-2,3-dihydro-1H-pyrrolo[3,4-c]pyridin-4-yl)indolizine-7-carboxylic acid

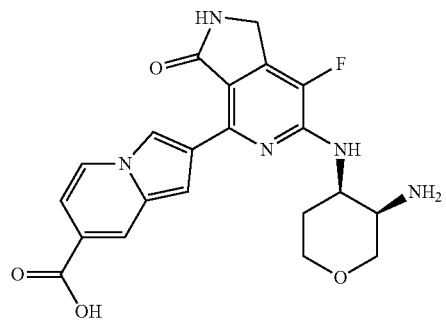 [SMILES: N[C@H]1COCC[C@H]1Nc1nc(-c2cc3cc(C(=O)O)ccn3c2)c2c(c1F)CNC2=O]

A mixture of ethyl 2-(6-((3R,4R)-3-aminotetrahydro-2H-pyran-4-ylamino)-7-fluoro-3-oxo-2,3-dihydro-1H-pyrrolo[3,4-c]pyridin-4-yl)indolizine-7-carboxylate (20 mg, 0.044 mmol) in dioxane (3 mL) and 1N NaOH (1 mL) was heated to 150° C. in a Biotage Initiator microwave for 1 hour. The mixture was concentrated under reduced pressure and purified by preparatory HPLC, eluting with a gradient of 10-30% ACN (0.035% TFA) and water (0.05% TFA). The collected fractions were combined and dried to give a TFA salt of the title compound as a yellow solid (8 mg, 43%). $^1$H NMR (400 MHz, DMSO-d$_6$) δ ppm 1.79-1.81 (m, 1H), 2.11-2.12 (m, 1H), 3.65-3.67 (m, 1H), 3.93-4.04 (m, 4H), 4.43 (d, J=7.8 Hz, 2H), 4.52-4.53 (m, 1H), 6.95 (dd, J=1.46, 7.32 Hz, 1H), 7.14 (d, J=4.88 Hz, 1H), 7.67 (s, 1H), 7.92-7.93 (m, 2H), 8.16 (s, 1H), 8.34 (d, J=7.32 Hz, 1H), 8.47 (s, 1H), 9.00 (s, 1H). ESI-MS m/z [M+H]$^+$calc'd for C$_{21}$H$_{20}$FN$_5$O$_4$, 426. found, 426.

Example 41

6-((3R,4R)-3-Aminotetrahydro-2H-pyran-4-ylamino)-7-fluoro-4-(1-oxo-2,3-dihydro-1H-pyrrolizin-6-yl)-1H-pyrrolo[3,4-c]pyridin-3(2H)-one

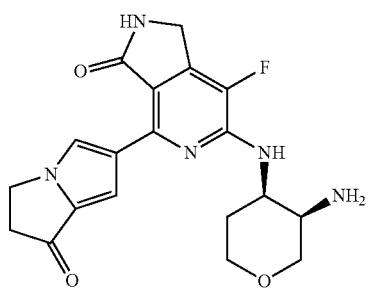 [SMILES: N[C@H]1COCC[C@H]1Nc1nc(-c2cc3n(c2)CCC3=O)c2c(c1F)CNC2=O]

A mixture of bis(triphenylphosphine)palladium chloride (10.51 mg, 0.015 mmol), tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (150 mg, 0.299 mmol), and 6-(4,4,5,5-tetramethyl-1,3,2-dioxaborolan-2-yl)-2,3-dihydro-1H-pyrrolizin-1-one (148 mg, 0.599 mmol) in dioxane (4 mL) and saturated aqueous NaHCO$_3$ (1 mL) was heated to 100° C. in a Biotage Initiator microwave for 1 hour. The mixture was concentrated to give the intermediate, tert-butyl 6-(((3R,4R)-3-((tert-butoxycarbonyl)amino)tetrahydro-2H-pyran-4-yl)amino)-7-fluoro-3-oxo-4-(1-oxo-2,3-dihydro-1H-pyrrolizin-6-yl)-1H-pyrrolo[3,4-c]pyridine-2(3H)-carboxylate, which was subsequently dissolved in DCM (5 mL) and TFA (5 mL). The resulting solution was stirred at room temperature for 20 minutes, concentrated, and purified by preparatory HPLC, eluting with a gradient of 10-40% ACN (0.035% TFA) and water (0.05% TFA). The collected fractions were combined and dried to give a TFA salt of the title compound as a white solid (7 mg, 6%). $^1$H NMR (400 MHz, DMSO-d$_6$) δ ppm 1.75-1.78 (m, 1H), 2.10-2.11 (m, 1H), 3.01-3.04 (m, 2H), 3.34-3.34 (m, 1H), 3.66-3.67 (m, 1H), 3.76-3.78 (m, 1H), 3.84-3.86 (m, 1H), 3.95-3.97 (m, 1H), 4.37-4.39 (m, 4H), 4.50-4.51 (m, 1H), 7.05 (d, J=6.35 Hz, 1H), 7.60 (s, 1H), 7.90-7.92 (m, 2H), 8.43 (s, 1H), 8.56 (s, 1H). ESI-MS m/z [M+H]$^+$calc'd for C$_{19}$H$_{20}$FN$_5$O$_3$, 386. found, 386.

Example 42

6-((1R,2S)-2-Aminocyclohexylamino)-7-fluoro-4-(3-methylisothiazol-5-yl)-1H-pyaolo[3,4-c]pyridine-3(2H)-one

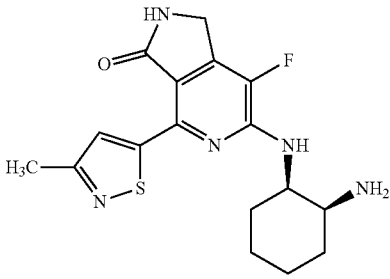 [SMILES: Cc1cc(-c2nc(N[C@@H]3CCCC[C@@H]3N)c(F)c3c2C(=O)NC3)sn1]

To a stirred solution of tert-butyl 6-((1R,2S)-2-(tert-butoxycarbonylamino)cyclohexylamino)-7-fluoro-4-(3-methylisothiazol-5-yl)-3-oxo-1H-pyrrolo[3,4-c]pyridine-2(3H)-carboxylate (82 mg, 0.146 mmol) in MeOH (2.0 mL) was added 4N HCl/dioxane (2.0 mL, 8.00 mmol). The reaction mixture was heated to 60° C. for 1 hour. Following reaction, the mixture was concentrated in vacuo. The residue was triturated with EtOAc and filtered. The filter cake was washed with EtOAc to yield crude desired compound as a yellow solid. The crude product was recrystallized from MeOH-Et$_2$O to give a hydrochloride salt of the title compound as a white solid. $^1$H NMR (500 MHz, DMSO-d$_6$) δ ppm 1.37-1.56 (m, 2 H), 1.58-1.83 (m, 4 H), 1.84-2.04 (m, 2 H), 2.46 (s, 3 H), 3.73 (br. s., 1 H), 4.17-4.29 (m, 1 H), 4.47 (s, 2 H), 7.17 (d, J=5.37 Hz, 1 H), 7.84 (br. s., 3 H), 8.66 (s, 1H), 8.76 (s, 1 H). ESI-MS m/z [M+H]$^+$calc'd for C$_{17}$H$_{20}$FN$_5$OS, 362. found, 362.

Example 43

6-((1R,2S)-2-Aminocyclohexylamino)-7-fluoro-4-(phenylethynyl)-1H-pyrrolo[3,4-c]pyridin-3(2H)-one

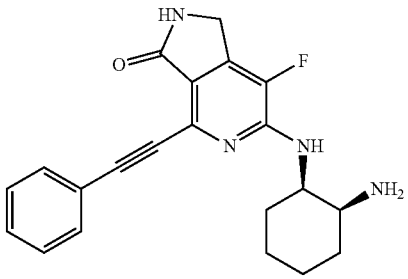 [SMILES: N[C@H]1CCCC[C@H]1Nc1nc(C#Cc2ccccc2)c2c(c1F)CNC2=O]

In a 30 mL glass vial, tert-butyl 6-((1R,2S)-2-(tert-butoxycarbonylamino)cyclohexylamino)-4-chloro-7-fluoro-3-oxo-1H-pyrrolo[3,4-c]pyridine-2(3H)-carboxylate (150 mg, 0.301 mmol), 4,4,5,5-tetramethyl-2-(phenylethynyl)-1,3,2-dioxaborolane (103 mg, 0.451 mmol) and PdCl$_2$(PPh$_3$)$_2$ (105 mg, 0.150 mmol) were dissolved in dioxane (5 mL). To the reaction mixture was added 2N aqueous sodium carbonate solution (2 mL). The vessel was sealed with a cap and the reaction mixture was heated at 90° C. for 2 hours. The reaction mixture was subsequently diluted with water (10 mL) and was extracted with EtOAc (2×50 mL). The combined organic phase was dried over sodium sulfate and evaporated to give the intermediate, tert-butyl 6-(((1R,2S)-2-((tert-butoxycarbonyl)amino)cyclohexyl)amino)-7-fluoro-3-oxo-4-(phenylethynyl)-1H-pyrrolo[3,4-c]pyridine-2(3H)-carboxylate. The intermediate was dissolved in dichloromethane (3 mL), TFA (3 mL) was added, and the mixture was stirred for 1 hour. The volatiles were subsequently evaporated and the residual material was dissolved in DMSO (5 mL) and purified by preparative HPLC, eluting with a gradient of 15-50% ACN (0.035% TFA) and water (0.05% TFA). The pure product fractions were combined, evaporated to a minimal volume, and lyophilized to give a TFA salt of the title compound as a pale yellow solid (32 mg, 29%). $^1$H NMR (400 MHz, DMSO-d$_6$) δ ppm 1.43 (br s, 3 H), 1.66-1.91 (m, 5 H), 3.63 (br s, 1 H), 4.34-4.52 (m, 3 H), 6.87 (d, J=7.07 Hz, 1 H), 7.41-7.52 (m, 3 H), 7.56-7.65 (m, 2 H), 7.74 (br s, 3 H), 8.48 (s, 1 H). ESI-MS m/z [M+H]$^+$ calc'd for C$_{21}$H$_{21}$FN$_4$O, 365. found, 365.

Example 44

6-((3R,4R)-3-Aminotetrahydro-2H-pyran-4-ylamino)-7-fluoro-4-(phenylethynyl)-1H-pyrrolo[3,4-c]pyridin-3(2H)-one

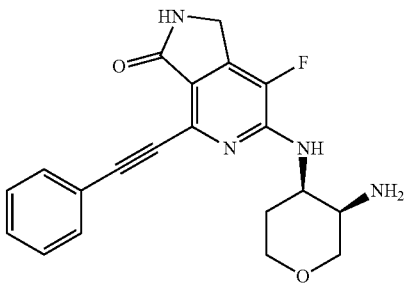 [SMILES: N[C@H]1COCC[C@H]1Nc1nc(C#Cc2ccccc2)c2c(c1F)CNC2=O]

In a 30 mL glass vial, tert-butyl 6-((3R,4R)-3-(tert-butoxycarbonylamino)tetrahydro-2H-pyran-4-ylamino)-4- chloro-7-fluoro-3-oxo-1H-pyrrolo[3,4-c]pyridine-2(3H)-carboxylate (150 mg, 0.299 mmol), 4,4,5,5-tetramethyl-2-(phenylethynyl)-1,3,2-dioxaborolane (75 mg, 0.329 mmol) and PdCl$_2$(PPh$_3$)$_2$ (105 mg, 0.150 mmol) were dissolved in dioxane (5 mL). To the reaction mixture was added 2N aqueous sodium carbonate solution (2 mL). The vessel was sealed with a cap and the reaction mixture was heated to 90° C. in an oil bath for 2 hours. The reaction mixture was subsequently diluted with water (10 mL) and extracted with EtOAc (2×25 mL). The combined organic phase was dried over sodium sulfate and evaporated to give the intermediate, tert-butyl 6-(((3R,4R)-3-((tert-butoxycarbonyl)amino)tetrahydro-2H-pyran-4-yl)amino)-7-fluoro-3-oxo-4-(phenylethynyl)-1H-pyrrolo[3,4-c]pyridine-2(3H)-carboxylate. The intermediate was dissolved in dichloromethane (3 mL), TFA (3 mL) was added, and the mixture was stirred for 1 hour. The volatiles were subsequently evaporated and the residual material was dissolved in DMSO (5 mL) and purified by preparative HPLC, eluting with a gradient of 15-50% ACN (0.035% TFA) and water (0.05% TFA). The pure product fractions were combined, evaporated to a minimal volume, and lyophilized to give the TFA salt of the title compound as a pale yellow solid (14.5 mg, 13%). $^1$H NMR (400 MHz, DMSO-d$_6$) δ ppm 1.72 (m, 1 H), 2.05-2.12 (m, 1 H), 3.49-3.66 (m, 2 H), 3.76 (d, J=11.62 Hz, 1 H), 3.84-4.04 (m, 2 H), 4.31-4.51 (m, 3 H), 7.16-7.29 (m, 1 H), 7.42-7.53 (m, 3 H), 7.53-7.67 (m, 2 H), 7.92 (br s, 3H), 8.50 (s, 1 H). ESI-MS m/z [M+H]$^+$calc'd for C$_{20}$H$_{19}$FN$_4$O$_2$, 367. found, 367.

Example 45

6-((1R,2S)-2-Aminocyclohexylamino)-7-fluoro-4-(4-fluorostyryl)-1H-pyrrolo[3,4-c]pyridin-3(2H)-one

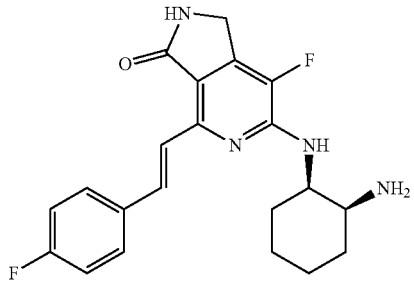 [SMILES: N[C@H]1CCCC[C@H]1Nc1nc(/C=C/c2ccc(F)cc2)c2c(c1F)CNC2=O]

In a 30 mL sealed cap glass vial, tert-butyl 6-((1R,2S)-2-(tert-butoxycarbonylamino)cyclohexylamino)-4-chloro-7-fluoro-3-oxo-1H-pyrrolo[3,4-c]pyridine-2(3H)-carboxylate (150 mg, 0.301 mmol), (E)-4-fluorostyrylboronic acid (49.9 mg, 0.301 mmol) and PdCl$_2$(PPh$_3$)$_2$ (42.2 mg, 0.060 mmol) were dissolved in dioxane (5 mL). To the reaction mixture was added 2N aqueous sodium carbonate solution (2 mL). The cap was sealed and the reaction mixture was heated at 85° C. for 2 hours. The reaction mixture was subsequently diluted with water (5 mL) and was extracted into EtOAc (2×30 mL). The combined organic phase was dried over sodium sulfate and evaporated to give the intermediate, tert-butyl 6-(((1R,2S)-2-((tert-butoxycarbonyl)amino)cyclohexyl)amino)-7-fluoro-4-((E)-4-fluorostyryl)-3-oxo-1H-pyrrolo[3,4-c]pyridine-2(3H)-carboxylate, which was treated with TFA (4 mL) for 1.5 hours to remove the protecting groups. TFA was subsequently evaporated from the reaction mixture. The residual material was dissolved in DMSO (8 mL) and purified by preparative HPLC, eluting with a gradient of 10-30% ACN (0.035% TFA) and water (0.05% TFA). The pure product fractions were combined, evaporated to a minimal volume, and lyophilized to give a TFA salt of the title compound as a tan solid (58 mg, 50%). $^1$H NMR (400 MHz, DMSO-d$_6$) δ ppm 1.42-1.92 (m, 8 H), 3.74 (br s, 1 H), 4.40 (d, J=2.53 Hz, 2 H), 4.51 (br s, 1 H), 6.86 (d, J=6.57 Hz, 1 H), 7.27 (t, J=8.84 Hz, 1 H), 7.56-7.73 (m, 3 H), 7.82 (br s, 3 H), 8.14 (d, J=15.92 Hz, 1 H), 8.49 (s, 1H). ESI-MS m/z [M+H]$^+$calc'd for C$_{21}$H$_{22}$F$_2$N$_4$O, 385. found, 385.

Example 46

6-((3R,4R)-3-Aminotetrahydro-2H-pyran-4-ylamino)-7-fluoro-4-(4-fluorostyryl)-1H-pyrrolo[3,4-c]pyridin-3(2H)-one

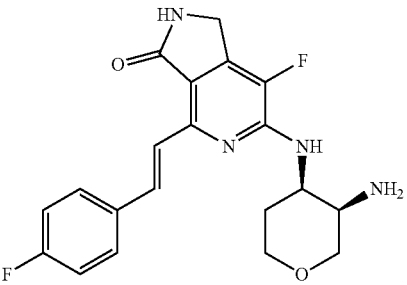 [SMILES: N[C@H]1COCC[C@H]1Nc1nc(/C=C/c2ccc(F)cc2)c2c(c1F)CNC2=O]

In a 30 mL sealed cap glass vial, tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (150 mg, 0.299 mmol), (E)-4-fluorostyrylboronic acid (49.7 mg, 0.299 mmol) and PdCl$_2$(PPh$_3$)$_2$ (42.0 mg, 0.060 mmol) were dissolved in dioxane (5 mL). To the reaction mixture was added 2N aqueous sodium carbonate solution (2.0 mL). The cap was sealed and the reaction mixture was heated at 85° C. for 2 hours. The reaction mixture was subsequently diluted with water (5 mL) and extracted with EtOAc (2×30 mL). The combined organic phase was dried over sodium sulfate and evaporated to give the intermediate, tert-butyl 6-(((3R,4R)-3-((tert-butoxycarbonyl)amino)tetrahydro-2H-pyran-4-yl)amino)-7-fluoro-4-((E)-4-fluorostyryl)-3-oxo-1H-pyrrolo[3,4-c]pyridine-2(3H)-carboxylate, which was treated with TFA (4 mL) at room temperature for 1 hour to remove the protecting groups. TFA was subsequently evaporated from the reaction mixture. The residual material was dissolved in DMSO (8 mL) and purified by preparative HPLC, eluting with a gradient of 20-50% ACN (0.035% TFA) and water (0.05% TFA). The pure product fractions were combined, evaporated to a minimal volume, and lyophilized to give a TFA salt of the title compound as a light yellow solid (32 mg, 28%). $^1$H NMR (400 MHz, DMSO-d$_6$) δ ppm 1.77 (d, J=16.17 Hz, 1 H), 2.00-2.21 (m, 1 H), 3.55-3.71 (m, 2 H), 3.79-3.93 (m, 2H), 3.93-4.10 (m, 1 H), 4.33-4.46 (m, 2 H), 4.54 (d, J=8.84 Hz, 1 H), 7.15 (d, J=5.05 Hz, 1 H), 7.28 (t, J=8.84 Hz, 1 H), 7.58-7.74 (m, 3 H), 7.93 (br s, 3 H), 8.15 (d, J=15.92 Hz, 1 H), 8.51 (s, 1 H). ESI-MS m/z [M+H]$^+$ calc'd for C$_{20}$H$_{20}$F$_2$N$_4$O$_2$, 387. found, 387.

Example 47

6-((1R,2S)-2-Aminocyclohexylamino)-7-fluoro-4-phenethyl-1H-pyrrolo[3,4-c]pyridin-3 (2H)-one

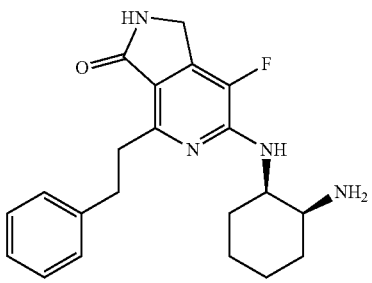 [SMILES: N[C@H]1CCCC[C@H]1Nc1nc(CCc2ccccc2)c2c(c1F)CNC2=O]

In a 30 mL sealed cap glass vial, tert-butyl 6-((1R,2S)-2-(tert-butoxycarbonylamino)cyclohexylamino)-4-chloro-7-fluoro-3-oxo-1H-pyrrolo[3,4-c]pyridine-2(3H)-carboxylate (150 mg, 0.301 mmol), potassium trifluoro(phenethyl)borate (76 mg, 0.361 mmol) and $PdCl_2(PPh_3)_2$ (42.2 mg, 0.060 mmol) were dissolved in dioxane (5 mL). To the reaction mixture was added 2N aqueous sodium carbonate solution (2 mL). The cap was sealed and the reaction mixture was heated at 85° C. for 2 hours. The reaction mixture was subsequently diluted with water (5 mL) and extracted with EtOAc (2×30 mL). The combined organic phase was dried over sodium sulfate and evaporated to give the intermediate, tert-butyl 6-(((1R,2S)-2-((tert-butoxycarbonyl)amino)cyclohexyl)amino)-7-fluoro-3-oxo-4-phenethyl-1H-pyrrolo[3,4-c]pyridine-2(3H)-carboxylate, which was treated with TFA (4 mL) at room temperature for 1 hour to remove the protecting groups. TFA was subsequently evaporated from the reaction mixture. The residual material was dissolved in DMSO (8 mL) and purified by preparative HPLC, eluting with a gradient of 25-40% ACN (0.035% TFA) and water (0.05% TFA). The pure product fractions were combined, evaporated to a minimal volume, and lyophilized to give a TFA salt of the title compound as a white solid (21 mg, 19%). $^1$H NMR (400 MHz, DMSO-$d_6$) δ ppm 1.41 (br s, 2 H), 1.65 (br s, 2 H), 1.68-1.81 (m, 2 H), 1.84 (br s, 2 H), 2.83-3.04 (m, 2 H), 3.14-3.41 (m, 2 H), 4.22-4.43 (m, 3 H), 6.65 (d, J=6.82 Hz, 1 H), 7.08-7.33 (m, 4 H), 7.37 (br s, 1 H), 7.54 (br s, 1H), 7.70 (br s, 3 H), 8.31 (s, 1 H). ESI-MS m/z [M+H]$^+$calc'd for $C_{21}H_{25}FN_4O$, 369. found, 369.

Example 48

6-((1R,2S)-2-Aminocyclohexylamino)-7-fluoro-4-phenethyl-1H-pyrrolo[3,4-c]pyridin-3(2H)-one

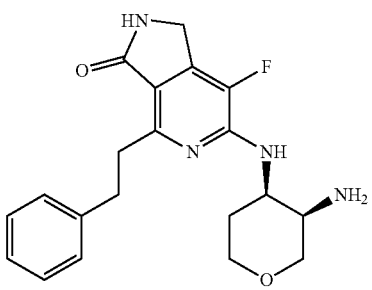 [SMILES: N[C@H]1COCC[C@H]1Nc1nc(CCc2ccccc2)c2c(c1F)CNC2=O]

In a 30 mL sealed cap glass vial, tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (150 mg, 0.299 mmol), potassium trifluoro(phenethyl)borate (76 mg, 0.359 mmol) and $PdCl_2(PPh_3)_2$ (42.0 mg, 0.060 mmol) were dissolved in dioxane (5 mL). To the reaction mixture was added 2N aqueous sodium carbonate solution (2.0 mL). The cap was sealed and the reaction mixture was heated at 85° C. for 3 hours. The reaction mixture was subsequently diluted with water (5 mL) and extracted with EtOAc (2×30 mL). The combined organic phase was dried over sodium sulfate and evaporated to give the intermediate, tert-butyl 6-(((3R,4R)-3-((tert-butoxycarbonyl)amino)tetrahydro-2H-pyran-4-yl)amino)-7-fluoro-3-oxo-4-phenethyl-1H-pyrrolo[3,4-c]pyridine-2(3H)-carboxylate, which was treated with TFA (4 mL) at room temperature for 1 hour to remove the protecting groups. TFA was subsequently evaporated from the reaction mixture. The residual material was dissolved in DMSO (8 mL) and purified by preparative HPLC, eluting with a gradient of 20-55% ACN (0.035% TFA) and water (0.05% TFA). The pure product fractions were combined, evaporated to a minimal volume, and lyophilized to give a TFA salt of the title compound as a light yellow solid (42 mg, 38%). $^1$H NMR (400 MHz, DMSO-$d_6$) δ ppm 1.58-1.75 (m, 1 H), 1.95-2.17 (m, 1 H), 2.83-3.04 (m, 2 H), 3.16-3.32 (m, 1 H), 3.32-3.46 (m, 1 H), 3.47-3.61 (m, 1 H), 3.66 (d, J=11.37 Hz, 1 H), 3.83-4.03 (m, 2 H), 4.22-4.39 (m, 3 H), 6.99 (d, J=5.05 Hz, 1 H), 7.09-7.33 (m, 5 H), 7.93 (br s, 2 H), 8.32 (s, 1 H). ESI-MS m/z [M+H]$^+$calc'd for $C_{20}H_{23}FN_4O_2$, 371. found, 371.

Example 49

6-((3R,4R)-3-Aminotetrahydro-2H-pyran-4-ylamino)-4-(4-chlorophenethyl)-7-fluoro-1H-pyrrolo[3,4-c]pyridin-3(2H)-one

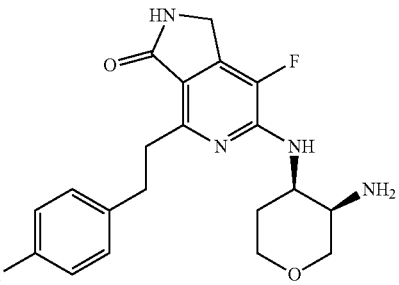

In a 30 mL sealed cap glass vial, tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (150 mg, 0.299 mmol), 2-(4-chlorophenethyl)-4,4,5,5-tetramethyl-1,3,2-dioxaborolane (88 mg, 0.329 mmol) and $PdCl_2(PPh_3)_2$ (63.1 mg, 0.090 mmol) were dissolved in dioxane (5 mL). To the reaction mixture was added 2N aqueous sodium carbonate solution (2 mL). The cap was sealed and the reaction mixture was heated at 85° C. for 2 hours. The reaction mixture was subsequently diluted with water (5 mL) and extracted with EtOAc (2×30 mL). The combined organic phase was dried over sodium sulfate and evaporated to give the intermediate, tert-butyl 6-(((3R,4R)-3-((tert-butoxycarbonyl)amino)tetrahydro-2H-pyran-4-yl)amino)-4-(4-chlorophenethyl)-7- fluoro-3-oxo-1H-pyrrolo[3,4-c]pyridine-2(3H)-carboxylate. The intermediate was dissolved in dichloromethane (3 mL) and treated with TFA (3 mL) at room temperature for 1 hour to remove the protecting groups. The volatiles were subsequently evaporated from the reaction mixture and the residual material was dissolved in DMSO (8 mL) and purified by preparative HPLC, eluting with a gradient of 20-65% ACN (0.035% TFA) and water (0.05% TFA). The pure product fractions were combined, evaporated to a minimal volume, and lyophilized to give a TFA salt of the title compound as a white solid (43 mg, 36%). $^1$H NMR (400 MHz, DMSO-d$_6$) δ ppm 1.68 (d, J=9.60 Hz, 1 H), 1.90-2.15 (m, 1 H), 2.86-3.02 (m, 2 H), 3.19-3.38 (m, 2 H), 3.47-3.61 (m, 1 H), 3.61-3.75 (m, 2 H), 3.81-4.03 (m, 2 H), 4.13-4.41 (m, 3 H), 6.99 (d, J=5.31 Hz, 1 H), 7.22 (m, J=8.34 Hz, 2 H), 7.32 (m, J=8.34 Hz, 2 H), 7.91 (br s, 3 H), 8.33 (s, 1 H). ESI-MS m/z [M+H]$^+$calc'd for C$_{20}$H$_{22}$ClFN$_4$O$_2$, 405. found, 405.

Example 50

6-((1R,2S)-2-Aminocyclohexylamino)-4-(4-chlorostyryl)-7-fluoro-1H-pyrrolo[3,4-c]pyridin-3(2H)-one

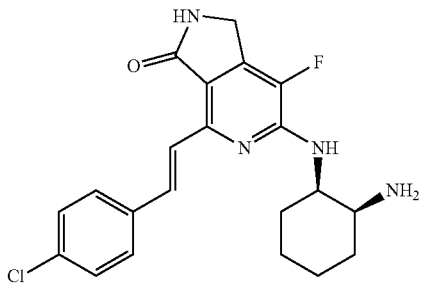 [SMILES: N[C@H]1CCCC[C@H]1Nc1nc(/C=C/c2ccc(Cl)cc2)c2c(c1F)CNC2=O]

In a 30 mL sealed cap glass vial, tert-butyl 6-((1R,2S)-2-(tert-butoxycarbonylamino)cyclohexylamino)-4-chloro-7-fluoro-3-oxo-1H-pyrrolo[3,4-c]pyridine-2(3H)-carboxylate (150 mg, 0.301 mmol), (E)-4-chlorostyrylboronic acid (54.8 mg, 0.301 mmol) and PdCl$_2$(PPh$_3$)$_2$ (42.2 mg, 0.060 mmol) were dissolved in dioxane (5 mL). To the reaction mixture was added 2N aqueous sodium carbonate solution (2.0 mL). The cap was sealed and the reaction mixture was heated at 85° C. for 3 hours. The reaction mixture was subsequently diluted with water (5 mL) and extracted with EtOAc (2×30 mL). The combined organic phase was dried over sodium sulfate and evaporated to give the intermediate, tert-butyl 6-(((1R,2S)-2-((tert-butoxycarbonyl)amino)cyclohexyl)amino)-4-(4-chlorophenethyl)-7-fluoro-3-oxo-1H-pyrrolo[3,4-c]pyridine-2(3H)-carboxylate, which was treated with TFA (4 mL) at room temperature for 1 hour to remove the protecting groups. TFA was subsequently evaporated from the reaction. The residual material was dissolved in DMSO (8 mL) and purified by preparative HPLC, eluting with a gradient of 10-30% ACN (0.035% TFA) and water (0.05% TFA). The pure product fractions were combined, evaporated to a minimal volume, and lyophilized to give a TFA salt of the title compound as a pale yellow solid (31 mg, 26%). $^1$H NMR (400 MHz, DMSO-d$_6$) δ ppm 1.48 (d, J=6.82 Hz, 2 H), 1.62 (d, J=7.58 Hz, 1 H), 1.66-1.80 (m, 3 H), 1.80-2.02 (m, 2 H), 3.74 (br s, 1 H), 4.41 (d, J=2.27 Hz, 1 H), 4.50 (br s, 1 H), 6.86 (d, J=5.56 Hz, 1 H), 7.50 (d, J=8.59 Hz, 1 H), 7.56-7.68 (m, 2 H), 7.69 (s, 1 H), 7.76 (br s, 3 H), 8.21 (d, J=15.92 Hz, 1 H), 8.51 (s, 1 H). ESI-MS m/z [M+H]$^+$calc'd for C$_{21}$H$_{22}$ClFN$_4$O, 401. found, 401.

Example 51

6-(3R,4R)-3-Aminotetrahydro-2H-pyran-4-ylamino)-4-(4-chlorostyryl)-7-fluoro-1H-pyrrolo[3,4-c]pyridin-3(2H)-one

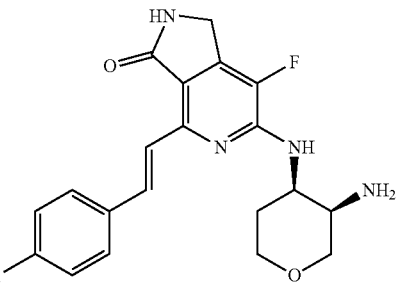

In a 30 mL sealed cap glass vial, tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (150 mg, 0.299 mmol), (E)-4-chlorostyrylboronic acid (54.6 mg, 0.299 mmol) and PdCl$_2$(PPh$_3$)$_2$ (42.0 mg, 0.060 mmol) were dissolved in dioxane (5 mL). To the reaction mixture was added 2N aqueous sodium carbonate solution (2 mL). The cap was sealed and the reaction mixture was heated at 85° C. for 2 hours. The reaction mixture was subsequently diluted with water (5 mL) and extracted with EtOAc (2×30 mL). The combined organic phase was dried over sodium sulfate and evaporated to give the intermediate, tert-butyl 6-(((3R,4R)-3-((tert-butoxycarbonyl)amino)tetrahydro-2H-pyran-4-yl)amino)-4-((E)-4-chlorostyryl)-7-fluoro-3-oxo-1H-pyrrolo[3,4-c]pyridine-2(3H)-carboxylate. The intermediate was diluted with dichloromethane (3.0 mL) and treated with TFA (3 mL) for 1.5 hours to remove the protecting groups. The volatiles were subsequently evaporated from the reaction mixture, and the residual material was dissolved in DMSO (8 mL) and purified by preparative HPLC, eluting with 20-60% ACN (0.035% TFA) and water (0.05% TFA). The pure product fractions were combined, evaporated to a minimal volume, and lyophilized to give a TFA salt of the title compound as a pale yellow solid (42 mg, 35%). $^1$H NMR (400 MHz, DMSO-d$_6$) δ ppm 1.77 (d, J=15.66 Hz, 1 H), 1.98-2.22 (m, 1 H), 3.50-3.73 (m, 2 H), 3.79-4.08 (m, 3 H), 4.32-4.51 (m, 2 H), 4.55 (br s, 1 H), 7.17 (d, J=5.05 Hz, 1 H), 7.50 (d, J=8.59 Hz, 2 H), 7.55-7.73 (m, 2 H), 7.92 (d, J=4.55 Hz, 3 H), 8.22 (d, J=16.17 Hz, 1 H), 8.53 (s, 1 H). ESI-MS m/z [M+H]$^+$calc'd for C$_{20}$H$_{20}$ClFN$_4$O$_2$, 403. found, 403.

Example 52

(R)-6-(((1R,2S)-2-Aminocyclohexyl)amino)-7-fluoro-4-(5-fluoropyrazolo[1,5-a]pyridin-3-yl)-1-methyl-1H-pyrrolo[3,4-c]pyridin-3(2H)-one

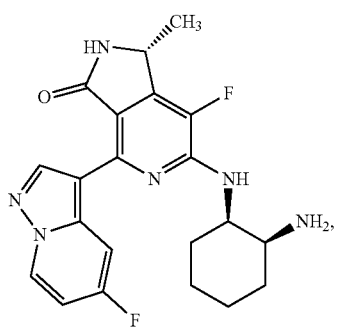 [SMILES: C[C@H]1NC(=O)c2c(-c3cnn4ccc(F)cc34)nc(N[C@@H]3CCCC[C@@H]3N)c(F)c21]

and

Example 53

(S)-6-(((1R,2S)-2-Aminocyclohexyl)amino)-7-fluoro-4-(5-fluoropyrazolo[1,5-a]pyridin-3-yl)-1-methyl-1H-pyrrolo[3,4-c]pyridin-3(2H)-one

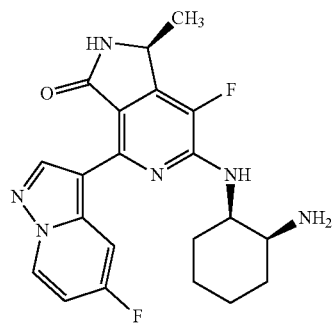 [SMILES: C[C@@H]1NC(=O)c2c(-c3cnn4ccc(F)cc34)nc(N[C@@H]3CCCC[C@@H]3N)c(F)c21]

A mixture tert-butyl 6-(((1R,2S)-2-((tert-butoxycarbonyl)amino)cyclohexyl)amino)-4-chloro-7-fluoro-1-methyl-3-oxo-1H-pyrrolo[3,4-c]pyridine-2(3H)-carboxylate (200 mg, 0.390 mmol), 5-fluoro-3-(4,4,5,5-tetramethyl-1,3,2-dioxaborolan-2-yl)pyrazolo[1,5-a]pyridine (153 mg, 0.585 mmol), potassium carbonate (108 mg, 0.780 mmol), Pd-118 (10 mg, 0.016 mmol) in DMA (10 mL) and water (0.67 mL) was stirred at 80° C. for 20 h. The solution was worked up and treated with TFA (3 mL) and DCM (6 mL) at room temperature for 1 h and was subsequently purified via preparative HPLC to give TFA salts of the title compounds as tan (40 mg, 25%) and white solids (35 mg, 22%), respectively.

EXAMPLE 52: $^1$H NMR (500 MHz, DMSO-d$_6$) δ ppm 1.35-1.56 (m, 5 H), 1.67-1.80 (m, 2 H), 1.84-2.00 (m, 1 H), 3.74 (br s, 1H), 4.48 (br s, 1 H), 4.77 (q, J=6.65 Hz, 1 H), 6.87 (d, J=6.28 Hz, 1 H), 7.08 (td, J=7.31, 2.65 Hz, 1 H), 7.82 (br s, 2H), 8.06 (dd, J=9.92, 2.59 Hz, 1 H), 8.51 (s, 1 H), 8.88 (dd, J=7.44, 5.37 Hz, 1 H), 9.46 (s, 1 H). [M+H] calc'd for $C_{21}H_{22}F_2N_6O$, 413. found, 413.

EXAMPLE 53: $^1$H NMR (500 MHz, DMSO-d$_6$) δ ppm 1.36-1.60 (m, 4 H), 1.60-1.83 (m, 3 H), 1.90-2.06 (m, 1 H), 3.73 (br s, 1H), 4.46 (br s, 1 H), 4.76 (q, J=6.39 Hz, 1 H), 6.93 (d, J=6.35 Hz, 1 H), 7.02-7.15 (m, 1 H), 7.90-8.14 (m, 3 H), 8.51 (s, 1 H), 8.88 (dd, J=7.29, 5.46 Hz, 1 H), 9.47 (s, 1 H). [M+H] calc'd for $C_{21}H_{22}F_2N_6O$, 413. found, 413.

Example 54

(R)-6-(((1R,2S)-2-Aminocyclohexyl)amino)-7-fluoro-1-methyl-4-(5-methylpyrazolo[1,5-a]pyridin-3-yl)-1H-pyrrolo[3,4-c]pyridin-3(2H)-one

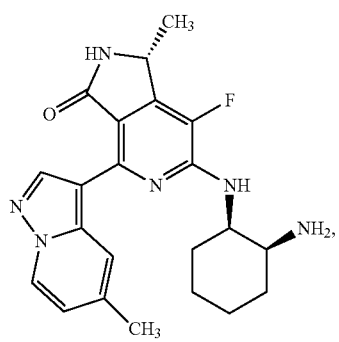 [SMILES: Cc1ccn2ncc(-c3nc(N[C@@H]4CCCC[C@@H]4N)c(F)c4c3C(=O)N[C@@H]4C)c2c1]

and

Example 55

(S)-6-(((1R,2S)-2-Aminocyclohexyl)amino)-7-fluoro-1-methyl-4-(5-methylpyrazolo[1,5-a]pyridin-3-yl)-1H-pyrrolo[3,4-c]pyridin-3(2H)-one

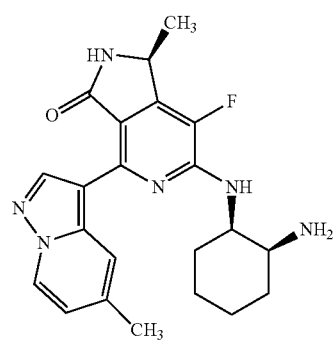 [SMILES: Cc1ccn2ncc(-c3nc(N[C@@H]4CCCC[C@@H]4N)c(F)c4c3C(=O)N[C@H]4C)c2c1]

A mixture of tert-butyl 6-(((1R,2S)-2-((tert-butoxycarbonyl)amino)cyclo-hexyl)amino)-4-chloro-7-fluoro-1-methyl-3-oxo-1H-pyrrolo[3,4-c]pyridine-2(3H)-carboxylate (100 mg, 0.195 mmol), 5-methyl-3-(4,4,5,5-tetramethyl-1,3,2-dioxaborolan-2-yl)pyrazolo[1,5-a]pyridine (75 mg, 0.292 mmol), potassium carbonate (54 mg, 0.390 mmol), Pd-118 (5 mg, 0.008 mmol) in DMA (6 mL) and water (0.33 mL) was stirred at 80° C. for 20 h. The solution was worked up and treated with TFA (3 mL) and DCM (6 mL) at room temperature for 1 h. The mixture was purified via preparative HPLC to give TFA salts of the title compounds as white solids (24 mg, 30% and 18 mg, 23%, respectively).

EXAMPLE 54: $^1$H NMR (500 MHz, DMSO-d$_6$) δ ppm 1.34-1.53 (m, 5 H), 1.61 (d, J=12.39 Hz, 1 H), 1.66-1.84 (m, 3 H), 1.88 (d, J=9.58 Hz, 1 H), 1.96 (dd, J=13.64, 4.55 Hz, 1 H), 2.46 (s, 3 H), 3.76 (br s, 1 H), 4.16-4.29 (m, 1 H), 4.81

(q, J=6.39 Hz, 1 H), 7.17 (d, J=5.74 Hz, 1 H), 7.81 (br s, 2 H), 8.71-8.80 (m, 2 H). [M+H] calc'd for $C_{22}H_{25}FN_6O$, 409. found, 409.

EXAMPLE 55: $^1$H NMR (500 MHz, DMSO-$d_6$) δ ppm 1.17-1.32 (m, 3 H), 1.32-1.54 (m, 4 H), 1.61-1.82 (m, 3 H), 1.84-2.01 (m, 1 H), 2.37-2.46 (m, 2 H), 3.67-3.82 (m, 1 H), 4.52 (br s, 1 H), 4.75 (q, J=6.61 Hz, 1 H), 6.80 (d, J=6.65 Hz, 1 H), 6.88 (dd, J=7.02, 1.77 Hz, 1 H), 7.68-7.85 (m, 2 H), 8.18 (s, 1 H), 8.46 (s, 1 H), 8.65 (d, J=7.02 Hz, 1 H), 9.30 (s, 1 H). [M+H] calc'd for $C_{22}H_{25}FN_6O$, 409. found, 409.

Example 56

(R)-6-(((3R,4R)-3-Aminotetrahydro-2H-pyran-4-yl)amino)-7-fluoro-1-methyl-4-(3-methylisothiazol-5-yl)-1H-pyrrolo[3,4-c]pyridin-3(2H)-one

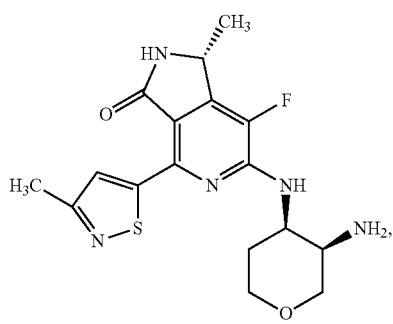 [SMILES: Cc1cc(-c2nc(N[C@@H]3CCOC[C@@H]3N)c(F)c3c2C(=O)N[C@@H]3C)sn1]

and

Example 57

(S)-6-(((3R,4R)-3-Aminotetrahydro-2H-pyran-4-yl)amino)-7-fluoro-1-methyl-4-(3-methylisothiazol-5-yl)-1H-pyrrolo[3,4-c]pyridin-3(2H)-one

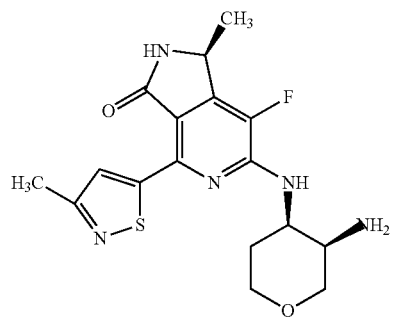

A mixture of tert-butyl ((3R,4R)-4-((4-chloro-2-(2,4-dimethoxybenzyl)-7-fluoro-1-methyl-3-oxo-2,3-dihydro-1H-pyrrolo[3,4-c]pyridin-6-yl)amino)tetrahydro-2H-pyran-3-yl)carbamate (75 mg, 0.133 mmol), 3-methyl-5-(tributylstannyl)isothiazole (77 mg, 0.199 mmol), tetrakis(triphenylphosphine)palladium(0) (31 mg, 0.027 mmol) in toluene (5 mL) was heated at 140° C. in a microwave for 8 h. The reaction mixture was diluted with EtOAc (200 mL) and washed with brine (200 mL). The organics were dried and concentrated. The resulting material was dissolved in TFA (5 mL) and stirred at 60° C. for 3 h. The mixture was purified via preparative HPLC to give TFA salts of the title compounds (12 mg, 24% and 9 mg, 18%, respectively).

EXAMPLE 56: $^1$H NMR (500 MHz, DMSO-$d_6$) δ ppm 0.88 (t, J=5.62 Hz, 2H), 1.43 (d, J=10.0 Hz, 3H), 2.36 (m, 1H), 2.52 (m, 3H), 2.64 (m, 1H), 3.29 (m, 1H), 3.62 (m, 1H), 3.78 (d, J=10 Hz, 1H), 4.00 (m, 1H), 4.43 (d, J=10.0 Hz, 1H), 6.52 (s, 1H), 5.62 (d, J=5.62 Hz, 1H), 8.75 (s, 1H), 8.78 (s, 1H). [M+H] calc'd for $C_{17}H_{20}FN_5O_2S$, 378. found, 378.

EXAMPLE 57: $^1$H NMR (500 MHz, DMSO-$d_6$) δ ppm 0.88 (t, J=10.0 Hz, 2H), 1.43 (d, J=10.0 Hz, 3H), 2.07 (m, 1H), 2.36 (m, 1H), 2.49 (m, 3H), 2.63 (m, 1H), 3.62 (m, 1H), 3.78 (m, 1H), 4.00 (m, 1H), 4.82 (d, J=10.0 Hz, 1H), 6.52 (s, 1H), 7.43 (d, J=5.0 Hz, 1H), 8.75 (s, 1H), 8.79 (s, 1H). [M+H] calc'd for $C_{17}H_{20}FN_5O_2S$, 378. found, 378.

Example 58

6-(((3R,4R)-3-Aminotetrahydro-2H-pyran-4-yl)amino)-7-fluoro-4-(5-methylpyrazolo[1,5-a]pyridin-3-yl)-1H-pyrrolo[3,4-c]pyridin-3 (2H)-one

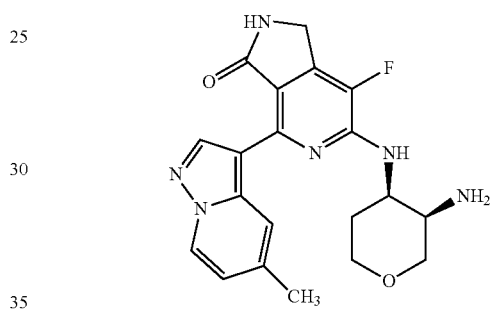

Step A: tert-Butyl 6-(((3R,4R)-3-((tert-butoxycarbonyl)amino)tetrahydro-2H-pyran-4-yl)amino)-7-fluoro-4-(5-methylpyrazolo[1,5-a]pyridin-3-yl)-3-oxo-1H-pyrrolo[3,4-c]pyridine-2(3H)-carboxylate

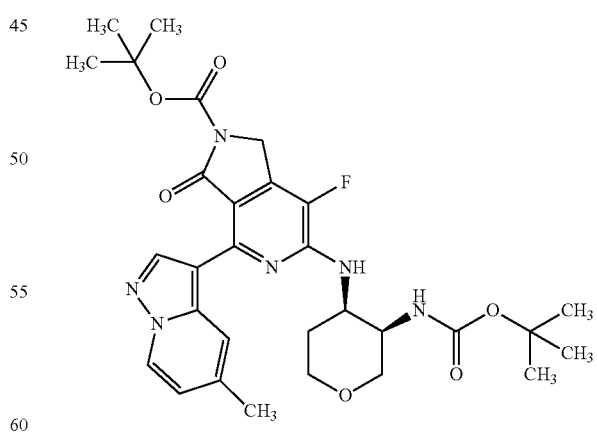

To a 25 mL reaction flask equipped with magnetic stir bar and thermometer was added tert-butyl 6-(((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (200 mg, 0.399 mmol) and 5-methyl-3-(4,4,5,5-tetramethyl-1,3,2-dioxaborolan-2-yl)pyrazolo[1,5-a]

pyridine (124 mg, 0.479 mmol), followed by potassium carbonate (325 mesh powder) (110 mg, 0.798 mmol), DMA (10 mL), and water (0.667 mL). The mixture was stirred at room temperature for 3 min before degassing with vacuum and $N_2$ back-fill (5×). To the resulting deep purple mixture was added Pd-118 (10.89 mg, 0.016 mmol). The reaction mixture was degassed again with vacuum and $N_2$ back-fill (5×). The flask was wrapped tightly with plastic film, placed in an oil bath, and the reaction mixture was stirred at 80° C. for 18 hours. Solid N-acetyl cysteine (65.2 mg, 0.399 mmol) was added and the mixture was stirred at 70° C. for 2 h. The mixture was subsequently diluted with water and extracted with EtOAc (200 mL). The organic layer was dried and concentrated to give a residue, which was purified by preparative HPLC, eluting with a gradient of 45-70% ACN (0.035% TFA) and water (0.05% TFA). The fractions were collected to give, upon basic work-up, the title compound as a light yellow solid (50 mg, 21%).

Step B: 6-(((3R,4R)-3-Aminotetrahydro-2H-pyran-4-yl)amino)-7-fluoro-4-(5-methylpyrazolo[1,5-a]pyridin-3-yl)-1H-pyrrolo[3,4-c]pyridin-3(2H)-one To a solution of tert-butyl 6-(((3R,4R)-3-((tert-butoxycarbonyl)amino)tetrahydro-2H-pyran-4-yl)amino)-7-fluoro-4-(5-methylpyrazolo[1,5-a]pyridin-3-yl)-3-oxo-1H-pyrrolo[3,4-c]pyridine-2(3H)-carboxylate (45 mg, 0.075 mmol) in isopropanol (5 mL) at 65° C. was added concentrated HCl (0.268 mL, 3.21 mmol) dropwise. The reaction mixture was stirred at 65° C. overnight and then slowly cooled. The solids were filtered and dried to give an HCl salt of the title compound as a pale yellow solid (30 mg, 92%). $^1$H NMR (500 MHz, DMSO-$d_6$) δ ppm 1.84 (d, J=9.88 Hz, 1 H), 2.08-2.22 (m, 1 H), 2.46 (s, 3 H), 3.55-3.67 (m, 2H), 3.94-4.09 (m, 2 H), 4.35-4.47 (m, 2 H), 6.88 (dd, J=7.08, 1.83 Hz, 1 H), 7.12 (d, J=5.98 Hz, 1 H), 8.03 (d, J=3.97 Hz, 2 H), 8.15 (s, 1 H), 8.39 (s, 1 H), 8.66 (d, J=7.08 Hz, 1 H), 9.24 (s, 1 H). [M+H] calc'd for $C_{20}H_{21}FN_6O_2$, 397. found, 397.

Example 59

6-(((1R,2S)-2-Aminocyclohexyl)amino)-7-fluoro-4-(5-methylpyrazolo[1,5-a]pyridin-3-yl)-1H-pyrrolo[3,4-c]pyridine-3(2H)-one

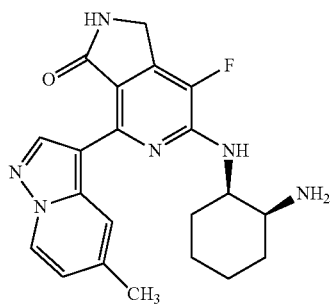 [SMILES: Cc1ccn2ncc(-c3nc(N[C@@H]4CCOC[C@@H]4N)c(F)c4c3C(=O)NC4)c2c1]

Step A: tert-Butyl 6-(((1R,2S)-2-((tert-butoxycarbonyl)amino)cyclohexyl)amino)-7-fluoro-4-(5-methylpyrazolo[1,5-a]pyridin-3-yl)-3-oxo-1H-pyrrolo[3,4-c]pyridine-2(3H)-carboxylate

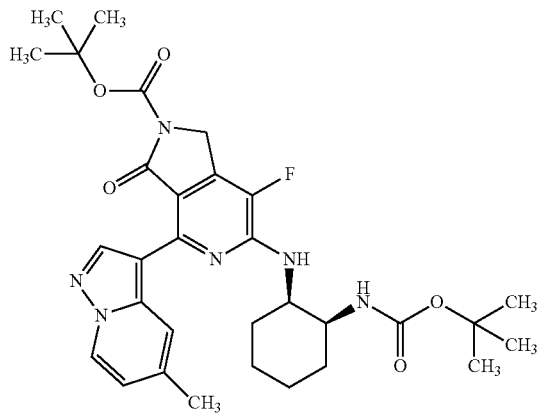 [SMILES: Cc1ccn2ncc(-c3nc(N[C@@H]4CCCC[C@@H]4NC(=O)OC(C)(C)C)c(F)c4c3C(=O)N(C(=O)OC(C)(C)C)C4)c2c1]

To a 25 mL reaction flask equipped with magnetic stir bar and thermometer was added tert-butyl 6-((1R,2S)-2-(tert-butoxycarbonylamino)cyclohexylamino)-4-chloro-7-fluoro-3-oxo-1H-pyrrolo[3,4-c]pyridine-2(3H)-carboxylate (200 mg, 0.401 mmol) and 5-methyl-3-(4,4,5,5-tetramethyl-1,3,2-dioxaborolan-2-yl)pyrazolo[1,5-a]pyridine (124 mg, 0.481 mmol), followed by potassium carbonate (325 mesh powder) (111 mg, 0.802 mmol), DMA (6 mL), and water (0.400 mL). The mixture was stirred at room temperature for 3 min before degassing with vacuum and $N_2$ back-fill (5×). To the resulting deep purple mixture was added Pd-118 (10.93 mg, 0.016 mmol). The reaction mixture was degassed again with vacuum and $N_2$ back-fill (5×). The flask was wrapped tightly with plastic film, placed in an oil bath, and the reaction mixture was stirred at 80° C. for 18 hours. Solid N-acetyl cysteine (65.4 mg, 0.401 mmol) was added and the mixture was stirred at 70° C. for 2 h. The mixture was subsequently diluted with water and extracted with EtOAc (200 mL). The organic layer was dried and concentrated to give a residue, which was purified by preparative HPLC, eluting with a gradient of 55-80% ACN (0.035% TFA) and water (0.05% TFA). The fractions were collected to give, upon basic work-up, the title compound as a light yellow solid (110 mg, 46%).

Step B: 6-(((1R,2S)-2-Aminocyclohexyl)amino)-7-fluoro-4-(5-methylpyrazolo[1,5-a]pyridin-3-yl)-1H-pyrrolo[3,4-c]pyridin-3(2H)-one To a solution of tert-butyl 6-(((1R,2S)-2-((tert-butoxycarbonyl)amino)cyclo-hexyl)amino)-7-fluoro-4-(5-methylpyrazolo[1,5-a]pyridin-3-yl)-3-oxo-1H-pyrrolo[3,4-c]pyridine-2(3H)-carboxylate (110 mg, 0.185 mmol) in isopropanol (10 mL) at 65° C. was added concentrated HCl (0.268 mL, 3.21 mmol) dropwise. The reaction mixture was stirred at 65° C. overnight and then slowly cooled. The solids were filtered and dried to give an HCl salt of the title compound as a pale yellow solid (75 mg, 94%). $^1$H NMR (500 MHz, DMSO-$d_6$) δ ppm 1.49 (br s, 1 H) 1.61-1.82 (m, 1 H) 1.96 (d, J=8.79 Hz, 1 H) 2.44 (s, 3 H), 4.33-4.45 (m, 2 H) 6.81 (d, J=6.35 Hz, 1 H) 6.88 (dd, J=7.02, 1.83 Hz, 1 H) 7.90 (br s, 2 H) 8.20 (s, 1 H) 8.37 (s, 1 H) 8.66 (d, J=7.02 Hz, 1 H) 9.33 (s, 1 H). [M+H] calc'd for $C_{21}H_{23}FN_6O$, 395. found, 395.

Table 1, below, lists compounds that can be made in a manner similar to Example 39 (Examples 60-67), Example 24 (Examples 68-76), Example 41 (Example 77), Example 29 (Examples 78-84), and Example 35 (Examples 85-91).

TABLE 1

EXAMPLES 60-91

| Example | Structure |
|---|---|
| 60 | 6-(((3R,4R)-3-aminotetrahydro-2H-pyran-4-yl)amino)-7-fluoro-4-(indolizin-2-yl)-1H-pyrrolo[3,4-c]pyridin-3(2H)-one |
| 61 | 2-(6-(((3R,4R)-3-aminotetrahydro-2H-pyran-4-yl)amino)-7-fluoro-3-oxo-2,3-dihydro-1H-pyrrolo[3,4-c]pyridin-4-yl)indolizine-7-carbonitrile |
| 62 | 6-(((3R,4R)-3-aminotetrahydro-2H-pyran-4-yl)amino)-7-fluoro-4-(7-fluoroindolizin-2-yl)-1H-pyrrolo[3,4-c]pyridin-3(2H)-one |
| 63 | 6-(((3R,4R)-3-aminotetrahydro-2H-pyran-4-yl)amino)-7-fluoro-4-(1-oxo-1,2,3,4-tetrahydropyrrolo[1,2-a]pyrazin-7-yl)-1H-pyrrolo[3,4-c]pyridin-3(2H)-one |
| 64 | 6-(((3R,4R)-3-aminotetrahydro-2H-pyran-4-yl)amino)-7-fluoro-4-(1-methyl-1H-pyrrolo[1,2-b]pyrazol-5-yl)-1H-pyrrolo[3,4-c]pyridin-3(2H)-one |
| 65 | 6-(((3R,4R)-3-aminotetrahydro-2H-pyran-4-yl)amino)-7-fluoro-4-(3-oxo-1,2,3,4-tetrahydro-pyrrolo[1,2-a]pyrazin-7-yl)-1H-pyrrolo[3,4-c]pyridin-3(2H)-one |
| 66 | 6-(((3R,4R)-3-aminotetrahydro-2H-pyran-4-yl)amino)-7-fluoro-4-(1-methyl-1H-pyrrolo[1,2-a]imidazol-6-yl)-1H-pyrrolo[3,4-c]pyridin-3(2H)-one |

TABLE 1-continued

EXAMPLES 60-91

| Example | Structure |
|---|---|
| 67 | 6-(((3R,4R)-3-aminotetrahydro-2H-pyran-4-yl)amino)-7-fluoro-4-(pyrrolo[2,1-b]oxazol-6-yl)-1H-pyrrolo[3,4-c]pyridin-3(2H)-one |
| 68 | 6-(((1R,2S)-2-aminocyclohexyl)amino)-7-fluoro-4-(indolizin-2-yl)-1H-pyrrolo[3,4-c]pyridin-3(2H)-one |
| 69 | 6-(((1R,2S)-2-aminocyclohexyl)amino)-7-fluoro-3-oxo-2,3-dihydro-1H-pyrrolo[3,4-c]pyridin-4-yl)indolizine-7-carbonitrile |
| 70 | 6-(((1R,2S)-2-aminocyclohexyl)amino)-7-fluoro-4-(7-fluoroindolizin-2-yl)-1H-pyrrolo[3,4-c]pyridin-3(2H)-one |
| 71 | 6-(((1R,2S)-2-aminocyclohexyl)amino)-7-fluoro-4-(1-oxo-1,2,3,4-tetrahydropyrrolo[1,2-a]pyrazin-7-yl)-1H-pyrrolo[3,4-c]pyridin-3(2H)-one |
| 72 | 6-(((1R,2S)-2-aminocyclohexyl)amino)-7-fluoro-4-(1-methyl-1H-pyrrolo[1,2-b]pyrazol-5-yl)-1H-pyrrolo[3,4-c]pyridin-3(2H)-one |
| 73 | 6-(((1R,2S)-2-aminocyclohexyl)amino)-7-fluoro-4-(3-oxo-1,2,3,4-tetrahydropyrrolo[1,2-a]pyrazin-7-yl)-1H-pyrrolo[3,4-c]pyridin-3(2H)-one |
| 74 | 6-(((1R,2S)-2-aminocyclohexyl)amino)-7-fluoro-4-(1-methyl-1H-pyrrolo[1,2-a]imidazol-6-yl)-1H-pyrrolo[3,4-c]pyridin-3(2H)-one |

TABLE 1-continued

EXAMPLES 60-91

| Example | Structure |
|---|---|
| 75 | 6-(((1R,2S)-2-aminocyclohexyl)amino)-7-fluoro-4-(pyrrolo[2,1-b]oxazol-6-yl)-1H-pyrrolo[3,4-c]pyridin-3(2H)-one |
| 76 | 6-(((1R,2S)-2-aminocyclohexyl)amino)-7-fluoro-4-(8-oxo-5,6,7,8-tetrahydroindolizin-2-yl)-1H-pyrrolo[3,4-c]pyridin-3(2H)-one |
| 77 | 6-(((3R,4R)-3-aminotetrahydro-2H-pyran-4-yl)amino)-7-fluoro-4-(8-oxo-5,6,7,8-tetrahydro-indolizin-2-yl)-1H-pyrrolo[3,4-c]pyridin-3(2H)-one |
| 78 | 6-(((3R,4R)-3-aminotetrahydro-2H-pyran-4-yl)amino)-7-fluoro-4-(3-methyl-3,4-dihydro-1H-pyrrolo[2,1-c][1,4]oxazin-7-yl)-1H-pyrrolo[3,4-c]pyridin-3(2H)-one |
| 79 | 6-(((3R,4R)-3-aminotetrahydro-2H-pyran-4-yl)amino)-4-(3,3-dimethyl-3,4-dihydro-1H-pyrrolo[2,1-c][1,4]oxazin-7-yl)-7-fluoro-1H-pyrrolo[3,4-c]pyridin-3(2H)-one |
| 80 | 6-(((3R,4R)-3-aminotetrahydro-2H-pyran-4-yl)amino)-4-(3-ethyl-3,4-dihydro-1H-pyrrolo[2,1-c][1,4]oxazin-7-yl)-7-fluoro-1H-pyrrolo[3,4-c]pyridin-3(2H)-one |
| 81 | 6-(((3R,4R)-3-aminotetrahydro-2H-pyran-4-yl)amino)-7-fluoro-4-(3-isopropyl-3,4-dihydro-1H-pyrrolo[2,1-c][1,4]oxazin-7-yl)-1H-pyrrolo[3,4-c]pyridin-3(2H)-one |
| 82 | 6-(((3R,4R)-3-aminotetrahydro-2H-pyran-4-yl)amino)-7-fluoro-4-(1,2,3,4-tetrahydropyrrolo[1,2-a]pyrazin-7-yl)-1H-pyrrolo[3,4-c]pyridin-3(2H)-one |

TABLE 1-continued

EXAMPLES 60-91

| Example | Structure |
|---------|-----------|
| 83 | 6-(((3R,4R)-3-aminotetrahydro-2H-pyran-4-yl)amino)-7-fluoro-4-(2-methyl-1,2,3,4-tetrahydropyrrolo[1,2-a]pyrazin-7-yl)-1H-pyrrolo[3,4-c]pyridin-3(2H)-one |
| 84 | 6-(((3R,4R)-3-aminotetrahydro-2H-pyran-4-yl)amino)-4-(2-ethyl-1,2,3,4-tetrahydropyrrolo[1,2-a]pyrazin-7-yl)-7-fluoro-1H-pyrrolo[3,4-c]pyridin-3(2H)-one |
| 85 | 6-(((1R,2S)-2-aminocyclohexyl)amino)-7-fluoro-4-(3-methyl-3,4-dihydro-1H-pyrrolo[2,1-c][1,4]oxazin-7-yl)-1H-pyrrolo[3,4-c]pyridin-3(2H)-one |
| 86 | 6-(((1R,2S)-2-aminocyclohexyl)amino)-4-(3,3-dimethyl-3,4-dihydro-1H-pyrrolo[2,1-c][1,4]oxazin-7-yl)-7-fluoro-1H-pyrrolo[3,4-c]pyridin-3(2H)-one |
| 87 | 6-(((1R,2S)-2-aminocyclohexyl)amino)-4-(3-ethyl-3,4-dihydro-1H-pyrrolo[2,1-c][1,4]oxazin-7-yl)-7-fluoro-1H-pyrrolo[3,4-c]pyridin-3(2H)-one |
| 88 | 6-(((1R,2S)-2-aminocyclohexyl)amino)-7-fluoro-4-(3-isopropyl-3,4-dihydro-1H-pyrrolo[2,1-c][1,4]oxazin-7-yl)-1H-pyrrolo[3,4-c]pyridin-3(2H)-one |
| 89 | 6-(((1R,2S)-aminocyclohexyl)amino)-7-fluoro-4-(1,2,3,4-tetrahydropyrrolo[1,2-a]pyrazin-7-yl)-1H-pyrrolo[3,4-c]pyridin-3(2H)-one |
| 90 | 6-(((1R,2S)-2-aminocyclohexyl)amino)-7-fluoro-4-(2-methyl-1,2,3,4-tetrahydropyrrolo[1,2-a]pyrazin-7-yl)-1H-pyrrolo[3,4-c]pyridin-3(2H)-one |

TABLE 1-continued

EXAMPLES 60-91

| Example | Structure |
|---|---|
| 91 | 6-(((1R,2S)-2-aminocyclohexyl)amino)-4-(2-ethyl-1,2,3,4-tetrahydropyrrolo[1,2-a]pyrazin-7-yl)-7-fluoro-1H-pyrrolo[3,4-c]pyridin-3(2H)-one |

Table 2, below, lists SYK inhibition data for many of the compounds described in the examples, where larger $pIC_{50}$ values represent higher potency. The compounds were tested in accordance with the specification.

TABLE 2

SYK Inhibition ($pIC_{50}$) for Example Compounds

| Example # | $pIC_{50}$ |
|---|---|
| 1 | 7.3 |
| 2 | 8.4 |
| 3 | 8.9 |
| 4 | 7.9 |
| 5 | 8.4 |
| 6 | 9.1 |
| 7 | 9.7 |
| 8 | 7.7 |
| 9 | 9.7 |
| 10 | 9.2 |
| 11 | 8.0 |
| 12 | 7.9 |
| 13 | 9.6 |
| 14 | 9.8 |
| 15 | 9.8 |
| 16 | 9.5 |
| 17 | 9.6 |
| 18 | 9.5 |
| 19 | 9.8 |
| 20 | 9.6 |
| 21 | 9.5 |
| 22 | 9.9 |
| 23 | 9.4 |
| 24 | 9.4 |
| 25 | 7.9 |
| 26 | 8.3 |
| 27 | 8.3 |
| 28 | 8.8 |
| 29 | 10.0 |
| 30 | 10.0 |
| 31 | 9.9 |
| 32 | 9.7 |
| 33 | 9.2 |
| 34 | 8.9 |
| 35 | 8.0 |
| 36 | 9.9 |
| 37 | 9.5 |
| 38 | 7.7 |
| 39 | 8.7 |
| 40 | 9.7 |
| 41 | 7.7 |
| 42 | 9.2 |
| 43 | 7.2 |
| 44 | 7.2 |
| 45 | 8.6 |
| 46 | 8.3 |
| 47 | 7.0 |
| 48 | 7.0 |
| 49 | 7.2 |
| 50 | 8.7 |
| 51 | 8.7 |
| 52 | 7.4 |
| 53 | 6.4 |
| 54 | 7.3 |
| 55 | 6.6 |
| 56 | 7.8 |
| 57 | 7.0 |
| 58 | 7.9 |
| 59 | 8.6 |

As used in this specification and the appended claims, singular articles such as "a," "an," and "the," may refer to a single object or to a plurality of objects unless the context clearly indicates otherwise. Thus, for example, reference to a composition containing "a compound" may include a single compound or two or more compounds. It is to be understood that the above description is intended to be illustrative and not restrictive. Many embodiments will be apparent to those of skill in the art upon reading the above description. Therefore, the scope of the invention should be determined with reference to the appended claims and includes the full scope of equivalents to which such claims are entitled. The disclosures of all articles and references, including patents, patent applications and publications, are herein incorporated by reference in their entirety and for all purposes.

What is claimed is:

1. A compound of the formula,

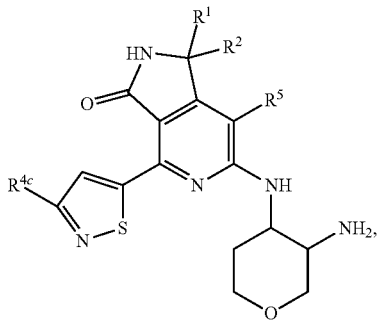

or a pharmaceutically acceptable salt thereof, wherein:
$R^1$ and $R^2$ are each independently selected from hydrogen, halo, $C_{1-3}$ alkyl, and $C_{1-3}$ haloalkyl; or
$R^1$ and $R^2$, together with the atom to which they are attached, form a $C_{3-6}$ cycloalkylidene;
$R^{4c}$ is selected from hydrogen, halo, —CN, $C_{1-4}$ alkyl, and $C_{3-8}$ cycloalkyl, wherein the $C_{1-4}$ alkyl moiety is optionally substituted with from one to five substituents independently selected from halo and provided $R^{4c}$ is not unsubstituted methyl; and
$R^5$ is selected from hydrogen, halo, and $C_{1-4}$ alkyl.

2. A compound or pharmaceutically acceptable salt according to claim 1, wherein $R^1$ and $R^2$ are both hydrogen.

3. A compound or pharmaceutically acceptable salt according to claim 1, wherein $R^5$ is selected from hydrogen and halo.

4. A compound according to claim 1, which is selected from the following compounds:
- 6-((3R,4R)-3-Aminotetrahydro-2H-pyran-4-ylamino)-4-(3-(difluoromethyl)isothiazol-5-yl)-7-fluoro-1H-pyrrolo[3,4-c]pyridin-3(2H)-one;
- 6-((3R,4R)-3-Aminotetrahydro-2H-pyran-4-ylamino)-4-(3-ethylisothiazol-5-yl)-7-fluoro-1H-pyrrolo[3,4-c]pyridin-3(2H)-one;
- 6-((3R,4R)-3-Aminotetrahydro-2H-pyran-4-ylamino)-7-fluoro-4-(isothiazol-5-yl)-1H-pyrrolo[3,4-c]pyridin-3(2H)-one;
- 6-((3R,4R)-3 -Aminotetrahydro-2H-pyran-4-ylamino)-4-(3 -cyclopropylisothiazol-5 -yl)-7-fluoro-1H-pyrrolo[3,4-c]pyridin-3(2H)-one;
- (R)-6-(((3R,4R)-3-Aminotetrahydro-2H-pyran-4-yl)amino)-7-fluoro-1-methyl-4-(3-methylisothiazol-5-yl)-1H-pyrrolo[3,4-c]pyridin-3(2H)-one;
- (S)-6-(((3R,4R)-3-Aminotetrahydro-2H-pyran-4-yl)amino)-7-fluoro-1-methyl-4-(3-methylisothiazol-5-yl)-1H-pyrrolo[3,4-c]pyridin-3(2H)-one;

a stereoisomer of any of the aforementioned compounds; and a pharmaceutically acceptable salt of any of the aforementioned compounds or stereoisomers.

5. A pharmaceutical composition comprising:
a compound or pharmaceutically acceptable salt as defined in claim 1; and
a pharmaceutically acceptable excipient.

* * * * *

SEQUENCE LISTING

```
<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: Synthetic Peptide Substrate

<400> SEQUENCE: 1

Lys Lys Lys Lys Glu Glu Ile Tyr Phe Phe Phe Gly
1               5                   10
```